US00RE44599E

(19) United States
(12) Reissued Patent
Fowler et al.

(10) Patent Number: US RE44,599 E
(45) Date of Reissued Patent: Nov. 12, 2013

(54) QUINAZOLINONES AS INHIBITORS OF HUMAN PHOSPHATIDYLINOSITOL 3-KINASE DELTA

(71) Applicant: ICOS Corporation, Indianapolis, IN (US)

(72) Inventors: Kerry W. Fowler, Seattle, WA (US); Danwen Huang, Sammamish, WA (US); Edward A. Kesicki, Bothell, WA (US); Hua Chee Ooi, Kirkland, WA (US); Amy Oliver, Bothell, WA (US); Fuqiang Ruan, Bellevue, WA (US); Jennifer Treiberg, Redmond, WA (US); Kamal Deep Puri, Lynnwood, WA (US)

(73) Assignee: ICOS Corporation, Indianapolis, IN (US)

(21) Appl. No.: 13/730,276

(22) Filed: Dec. 28, 2012

Related U.S. Patent Documents

Reissue of:
(64) Patent No.: 8,207,153
Issued: Jun. 26, 2012
Appl. No.: 12/732,128
Filed: Mar. 25, 2010

U.S. Applications:
(62) Division of application No. 11/596,092, filed as application No. PCT/US2005/016778 on May 12, 2005, now Pat. No. 7,932,260.

(60) Provisional application No. 60/570,784, filed on May 13, 2004.

(51) Int. Cl.
*A01N 43/54* (2006.01)
*A01N 43/00* (2006.01)
*C07D 473/00* (2006.01)
*C07D 239/72* (2006.01)

(52) U.S. Cl.
USPC ..... 514/183; 514/266.1; 544/277; 544/287

(58) Field of Classification Search
None
See application file for complete search history.

(56) References Cited

U.S. PATENT DOCUMENTS

| | | | |
|---|---|---|---|
| 3,322,756 | A | 5/1967 | Ruschig et al. |
| 3,691,016 | A | 9/1972 | Patel |
| 3,897,432 | A | 7/1975 | Shen et al. |
| 3,969,287 | A | 7/1976 | Jaworek et al. |
| 3,984,555 | A | 10/1976 | Amschler et al. |
| 4,179,337 | A | 12/1979 | Davis et al. |
| 4,183,931 | A | 1/1980 | Wolfe et al. |
| 4,195,128 | A | 3/1980 | Hildebrand et al. |
| 4,225,489 | A | 9/1980 | Rolf et al. |
| 4,229,537 | A | 10/1980 | Hodgins et al. |
| 4,247,642 | A | 1/1981 | Hirohara et al. |
| 4,289,872 | A | 9/1981 | Denkewalter et al. |
| 4,301,144 | A | 11/1981 | Iwashita et al. |
| 4,330,440 | A | 5/1982 | Ayers et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,925,673 | A | 5/1990 | Steiner et al. |
| 5,013,556 | A | 5/1991 | Woodle et al. |
| 5,225,347 | A | 7/1993 | Goldberg et al. |
| 5,229,490 | A | 7/1993 | Tam |
| 5,378,725 | A | 1/1995 | Bonjouklian et al. |
| 5,480,906 | A | 1/1996 | Creemer et al. |
| RE35,862 | E | 7/1998 | Steiner et al. |
| 5,858,753 | A | 1/1999 | Chantry et al. |
| 5,882,910 | A | 3/1999 | Chantry et al. |
| 5,948,664 | A | 9/1999 | Williams et al. |
| 5,985,589 | A | 11/1999 | Chantry et al. |
| 6,046,049 | A | 4/2000 | Monia et al. |
| 6,048,970 | A | 4/2000 | Lal et al. |
| 6,277,981 | B1 | 8/2001 | Tu et al. |
| 6,291,220 | B1 | 9/2001 | Williams et al. |
| 6,369,038 | B1 | 4/2002 | Blumenfeld et al. |
| 6,410,224 | B1 | 6/2002 | Stinchcomb et al. |
| 6,426,337 | B1 | 7/2002 | Cox et al. |
| 6,482,623 | B1 | 11/2002 | Vanhaesebroeck et al. |
| 6,518,227 | B2 | 2/2003 | Sadhu et al. |
| 6,518,277 | B1 | 2/2003 | Sadhu et al. |
| 6,667,300 | B2 | 12/2003 | Sadhu et al. |
| 6,696,250 | B1 | 2/2004 | Cech et al. |
| 6,800,620 | B2 | 10/2004 | Sadhu et al. |
| 6,949,535 | B2 | 9/2005 | Sadhu et al. |
| 7,932,260 | B2 | 4/2011 | Fowler et al. |

(Continued)

FOREIGN PATENT DOCUMENTS

| | | |
|---|---|---|
| EP | 0 525 960 | 2/1993 |
| EP | 0 525 960 A1 | 2/1993 |

(Continued)

OTHER PUBLICATIONS

"Acute Congestive Heart Failure", Thomas N. Levin, Postgraduate Medicine, vol. 101, No. 1, 1997.

Sutton, A. (Jun. 9, 2006). "Baylor, St. Luke's study uses gene therapy as pancreatic cancer", located at <http: //www.bcm.edu/news/item.cfm?newsID=640>, last visited on Sep. 2, 2006, 2 pages.

Anonymous (2006). "Cardiovascular Disease: Treatment for Stroke", Stanford Hospital & Clinics, located at <http://www.stanfordhospital.com/healthLib/atoz/cardiac/stktreat.html>, last visited on Sep. 19, 2006, 2 pages.

Marchione, M. et al. (2006). "Drugs hold promise in kidney cancer fight", located at <http://www.ledger-enquirer.com/mld/ledgerenquirer/living/health/14744763.htm>, last visited on Sep. 2, 2006, 3 pages.

Anonymous (2006). "Heart Disease", WebMD, located at <http://www.webmd.com/content/pages/9/1675_57842.htm> as retrieved on Sep. 14, 2006, 1 page.

(Continued)

*Primary Examiner* — Anna Pagonakis
(74) *Attorney, Agent, or Firm* — Morrison & Foerster LLP

(57) ABSTRACT

Compounds that inhibit P13Kδ activity, including compounds that selectively inhibit P13Kδ activity, are disclosed. Methods of inhibiting phosphatidylinositol 3-kinase delta isoform (P13Kδ) activity, and methods of treating diseases, such as disorders of immunity and inflammation in which P13Kδ plays a role in leukocyte function, using the compounds also are disclosed.

6 Claims, No Drawings

(56) References Cited

U.S. PATENT DOCUMENTS

| | | | |
|---|---|---|---|
| 8,138,195 | B2 | 3/2012 | Sadhu et al. |
| 8,207,153 | B2 | 6/2012 | Fowler et al. |
| 2002/0161014 | A1 | 10/2002 | Sadhu et al. |
| 2003/0195211 | A1 | 10/2003 | Sadhu et al. |
| 2004/0023390 | A1 | 2/2004 | Davidson et al. |
| 2004/0092561 | A1 | 5/2004 | Ruckle et al. |
| 2004/0121996 | A1 | 6/2004 | Barvian et al. |
| 2004/0138199 | A1 | 7/2004 | Gogliotti et al. |
| 2004/0242631 | A1 | 12/2004 | Garlich et al. |
| 2004/0248953 | A1 | 12/2004 | Gogliotti et al. |
| 2004/0248954 | A1 | 12/2004 | Gogliotti et al. |
| 2004/0259926 | A1 | 12/2004 | Bruendle et al. |
| 2004/0266780 | A1 | 12/2004 | Sadhu et al. |
| 2005/0004195 | A1 | 1/2005 | Para et al. |
| 2005/0020630 | A1 | 1/2005 | Connolly et al. |
| 2005/0020631 | A1 | 1/2005 | Gogliotti et al. |
| 2005/0043239 | A1 | 2/2005 | Douangpanya et al. |
| 2005/0054614 | A1 | 3/2005 | Diacovo et al. |
| 2005/0239809 | A1 | 10/2005 | Watts et al. |
| 2005/0261317 | A1 | 11/2005 | Sadhu et al. |
| 2006/0079538 | A1 | 4/2006 | Hallahan et al. |
| 2006/0106038 | A1 | 5/2006 | Bouscary et al. |
| 2008/0275067 | A1 | 11/2008 | Fowler et al. |
| 2008/0287469 | A1 | 11/2008 | Diacovo et al. |
| 2010/0029693 | A1 | 2/2010 | Douangpanya et al. |
| 2010/0152211 | A1 | 6/2010 | Sadhu et al. |
| 2010/0168139 | A1 | 7/2010 | Sadhu et al. |
| 2010/0202963 | A1 | 8/2010 | Gallatin et al. |
| 2010/0249155 | A1 | 9/2010 | Evarts et al. |
| 2010/0256167 | A1 | 10/2010 | Fowler et al. |
| 2010/0256168 | A1 | 10/2010 | Fowler et al. |
| 2011/0044942 | A1 | 2/2011 | Puri et al. |
| 2011/0230465 | A1 | 9/2011 | Stammers et al. |
| 2012/0015964 | A1 | 1/2012 | Fowler et al. |
| 2012/0040980 | A1 | 2/2012 | Huggins et al. |
| 2012/0135994 | A1 | 5/2012 | Sadhu et al. |
| 2012/0172591 | A1 | 7/2012 | Sadhu et al. |

FOREIGN PATENT DOCUMENTS

| | | | |
|---|---|---|---|
| EP | 0 525 960 | B1 | 10/1995 |
| EP | 0 675 124 | | 10/1995 |
| EP | 0 675 124 | A2 | 10/1995 |
| EP | 0 675 124 | A3 | 10/1995 |
| EP | 0 716 857 | | 6/1996 |
| EP | 0 716 857 | A1 | 6/1996 |
| EP | 0 716 857 | B1 | 6/1996 |
| EP | 0 884 310 | | 12/1998 |
| EP | 0 884 310 | A1 | 12/1998 |
| EP | 0 884 310 | B1 | 12/1998 |
| EP | 0 900 568 | | 3/1999 |
| EP | 0 900 568 | A2 | 3/1999 |
| EP | 0 900 568 | A3 | 3/1999 |
| GB | 1356763 | | 6/1974 |
| GB | 1356763 | A | 6/1974 |
| GB | 2 017 097 | A | 10/1979 |
| GB | 2017097 | | 10/1979 |
| JP | 55-118917 | | 9/1980 |
| JP | 55 118917 | A2 | 9/1980 |
| JP | 55-118918 | | 9/1980 |
| JP | 55 118918 | A2 | 1/1981 |
| JP | 56-002322 | | 1/1981 |
| JP | 56 002322 | A2 | 1/1981 |
| WO | WO-93/21259 | | 10/1993 |
| WO | WO-93/21259 | A1 | 10/1993 |
| WO | WO-94/17090 | | 8/1994 |
| WO | WO-94/17090 | A1 | 8/1994 |
| WO | WO-95/24379 | | 9/1995 |
| WO | WO-95/24379 | A1 | 9/1995 |
| WO | WO-96/04923 | | 2/1996 |
| WO | WO-96/04923 | A1 | 2/1996 |
| WO | WO-96/25488 | | 8/1996 |
| WO | WO-96/25488 | A1 | 8/1996 |
| WO | WO-96/32478 | | 10/1996 |
| WO | WO-96/32478 | A1 | 10/1996 |
| WO | WO-97/34631 | | 9/1997 |
| WO | WO-97/34631 | A1 | 9/1997 |
| WO | WO-97/41097 | | 11/1997 |
| WO | WO-97/41097 | A2 | 11/1997 |
| WO | WO-97/43276 | | 11/1997 |
| WO | WO-97/43276 | A1 | 11/1997 |
| WO | WO-97/46688 | | 12/1997 |
| WO | WO-97/46688 | A1 | 12/1997 |
| WO | WO-98/33802 | | 8/1998 |
| WO | WO-98/33802 | A1 | 8/1998 |
| WO | WO-98/38173 | | 9/1998 |
| WO | WO-98/38173 | A1 | 9/1998 |
| WO | WO-99/08501 | | 2/1999 |
| WO | WO-99/08501 | A2 | 2/1999 |
| WO | WO-99/08501 | A3 | 2/1999 |
| WO | WO-99/34804 | | 7/1999 |
| WO | WO-99/34804 | A1 | 7/1999 |
| WO | WO-01/00881 | | 1/2001 |
| WO | WO-01/00881 | A1 | 1/2001 |
| WO | WO-01/30768 | | 5/2001 |
| WO | WO-01/30768 | A1 | 5/2001 |
| WO | WO-01/30768 | C2 | 5/2001 |
| WO | WO-01/81346 | | 5/2001 |
| WO | WO-01/53266 | | 7/2001 |
| WO | WO-01/53266 | A1 | 7/2001 |
| WO | WO-01/57034 | | 8/2001 |
| WO | WO-01/57034 | A1 | 8/2001 |
| WO | WO-01/81346 | A2 | 11/2001 |
| WO | WO-01/81346 | A3 | 11/2001 |
| WO | WO-03/035075 | | 5/2003 |
| WO | WO-03/035075 | A1 | 5/2003 |
| WO | WO-03/106622 | | 12/2003 |
| WO | WO-03/106622 | A2 | 12/2003 |
| WO | WO-03/106622 | A3 | 12/2003 |
| WO | WO-2004/007491 | | 1/2004 |
| WO | WO-2004/007491 | A1 | 1/2004 |
| WO | WO-2004/012768 | | 2/2004 |
| WO | WO-2004/012768 | A1 | 2/2004 |
| WO | WO-2004/026285 | | 4/2004 |
| WO | WO-2004/026285 | A2 | 4/2004 |
| WO | WO-2004/026285 | A3 | 4/2004 |
| WO | WO-2004/029055 | | 4/2004 |
| WO | WO-2004/029055 | A1 | 4/2004 |
| WO | WO-2004/052373 | | 6/2004 |
| WO | WO-2004/052373 | A1 | 6/2004 |
| WO | WO-2004/056820 | | 7/2004 |
| WO | WO-2004/056820 | A1 | 7/2004 |
| WO | WO-2004/089925 | | 10/2004 |
| WO | WO-2004/089925 | A1 | 10/2004 |
| WO | WO-2004/108708 | | 12/2004 |
| WO | WO-2004/108708 | A1 | 12/2004 |
| WO | WO-2004/108709 | | 12/2004 |
| WO | WO-2004/108709 | A1 | 12/2004 |
| WO | WO-2004/108713 | | 12/2004 |
| WO | WO-2004/108713 | A1 | 12/2004 |
| WO | WO-2004/108713 | C1 | 12/2004 |
| WO | WO-2004/108715 | | 12/2004 |
| WO | WO-2004/108715 | A1 | 12/2004 |
| WO | WO-2004/108715 | C1 | 12/2004 |
| WO | WO-2005/016348 | | 2/2005 |
| WO | WO-2005/016348 | A1 | 2/2005 |
| WO | WO-2005/016349 | | 2/2005 |
| WO | WO-2005/016349 | A1 | 2/2005 |
| WO | WO-2005/067901 | | 7/2005 |
| WO | WO-2005/067901 | A2 | 7/2005 |
| WO | WO-2005/067901 | A3 | 7/2005 |
| WO | WO-2005/120511 | | 12/2005 |
| WO | WO-2005/120511 | A1 | 12/2005 |
| WO | WO-2009/058361 | | 5/2009 |
| WO | WO-2009/058361 | A1 | 5/2009 |
| WO | WO-2010/065923 | | 6/2010 |
| WO | WO-2010/065923 | A2 | 6/2010 |
| WO | WO-2010/065923 | A2 | 6/2010 |
| WO | WO-2010/065923 | A3 | 6/2010 |
| WO | WO-2010/123931 | A1 | 10/2010 |

OTHER PUBLICATIONS

Anonymous, (2010). "Multiple Sclerosis", located at <http://www.health.nytimes.com/health/guides/disease/multiple-sclerosis/over-

(56) References Cited

OTHER PUBLICATIONS view.html>, last visited Aug. 1, 2010, 4 pages.
Anonymous, (2004). "NIH Heart Disease & Stroke Research: Fact Sheet", American Heart Association, located at <http://www.americanheart.org/presenter.jhtml?identifier=3010188>, last visited Feb. 17, 2004, 1 page.
Anonymous (2010). "Spinal Cord Injury", located at <http://www.medicinenet.com/spinal_cord_injury/page.htm>, last visited on Aug. 1, 2010, 3 pages.
Anonymous (2010) "Systemic Lupus Erythematosus", located at <http://www.nlm.nih.gov/medlineplus/ency/article/000435.htm>, last visited Aug. 1, 2010, 4 pages.
"Chemia Lekow", ed. E. Pawelczyk, PZWL, Warszawa 1986, see, part 1.2.2.
"Preparatyka Organiczna", ed. A.I. Vogel, WNT, Warszawa 1984, page, e.g. 83.
Abu-Duhier et al., Br. J. Haematol. (2001) 113:983-988.
Adamkiewicz, "Tumor Angiogenesis: Mechanisms" IMT Marburg—Research Group, retrieved from the internet on Apr. 13, 2004, located at: <http://www.imt.uni-marburg.de/~adamkiew/mechanism.html> 2 pages.
Advisory Action from U.S. Appl. No. 11/596,092, mailed on Jul. 27, 2010.
Ager et al., J. Med. Chem. (1977) 20:379-386.
Ali et al., Nature (2004) 431:1007-1011.
Amendment from U.S. Appl. 09/841,341, filed Aug. 21, 2002.
Amendment from U.S. Appl. No. 10/027,591, filed Jun. 3, 2003.
Amendment in Response to Final Office Action from U.S. Appl. No. 11/596,092, filed Jul. 19, 2010.
Amendment in Response to Non-Final Office Action / Restriction Requirement from U.S. Appl. No. 11/884,566, filed Jun. 7, 2010.
Amendment in Response to Non-Final Office Action from U.S. Appl. No. 10/918,803, filed Oct. 1, 2008.
Amendment in Response to Non-Final Office Action from U.S. Appl. No. 10/918,803, filed Sep. 4, 2009.
Amendment in Response to Non-Final Office Action from U.S. Appl. No. 11/110,204, filed Dec. 31, 2008.
Amendment in Response to Non-Final Office Action from U.S. Appl. No. 11/110,204, filed Sep. 4, 2009.
Amendment in Response to Non-Final Office Action from U.S. Appl. No. 11/110,204, filed Jun. 4, 2010.
Amendment in Response to Non-Final Office Action from U.S. Appl. No. 11/596,092, filed Nov. 10, 2009.
Amendment in Response to Non-Final Office Action from U.S. Appl. No. 11/596,092, filed Mar. 24, 2010.
Amendment Under 37 C.F.R. § 1.111 from U.S. Appl. No. 11/129,006, filed Apr. 12, 2010.
Amendment Under 37 C.F.R. § 1.111/Restriction Requirement from U.S. Appl. No. 11/110,204, filed Apr. 10, 2008.
Amendment with Request for Continued Examination from U.S. Appl. No. 11/596,092, filed Sep. 1, 2010.
Amin et al., Circ Res (2003) 93(4):321-329.
Angel, Activities of Phosphoinositide Kinase-3 (PI3K) (1999) retrieved from the internet on May 22, 2003, URL: http://www.chem.csustan.edu/chem4400/SJBR/angel99.htm.
Angio World, "How Angiogenesis Complicates Psoriasis" (2001) retrieved from the internet on Apr. 13, 2004, located at <http://www.angioworld.com/psoriasis.htm>, 1 page.
Annabi et al., J. Cell. Biochem. (2004) 91:1146-1158.
Aoki et al., PNAS USA (2001) 98:136-141.
Aoudjit et al., J. Immunol. (1998) 161:2333-2338.
Arcaro et al., Biochem. J. (1994) 298:517-520.
Asti et al., Pulm. Pharmacol. Ther. (2000) 13:61-69.
Ausprunk et al., Microvasc. Res. (1977) 14:53-65.
Bader, A.G. et al. (2005). "Oncogenic P13K Deregulates Transcription and Translation," *Nature Reviews Cancer* 5(12):921-922 (abstract and introduction).
Barakat et al., Chemical Abstracts (1996) 124(21):1334.
Barakat, S.E-S. et al. (Dec. 1994). "Synthesis and CNS Depressant Activity of Some New Quinazoline Derivatives," *Az. J. Pharm. Sci.* 14:239-246.
Bardet et al., 9th Congress of the European Hematology Association Geneva Palexpo, Switzerland, Jun. 10-13, 2004, View Abstract data, Abstract nr.: 620.
Barker, Lancet (1991) 338:227-230.
Benekli et al., Blood (2002) 99:252-257.
Benekli et al., Blood (2003) 101:2940-2954.
Bennett et al., Ann. Intern. Med. (1985) 103:620-625.
Bennett et al., J. Pharmacol. Exp. Ther. (1997) 280:988-1000.
Bergers et al., Science (1999) 284:808-812.
Bharadwaj et al., J. Immunol. (2001) 166:6735-6741.
Binetruy-Tournaire et al., EMBO J. (2000) 19:1525-1533.
Bloemen et al., Am. J. Respir. Crit. Care Med. (1996) 153:521-529.
Boehm et al., Nature (1997) 390:404-407.
Borregaard et al., Blood (1997) 89:3503-3521.
Boudewijn et al., Nature (1995) 376:599-602.
Bouscary et al., Blood (2003) 101:3436-3443.
Bouscary et al., Oncogene (2001) 20:2197-2204.
Bowes et al., Exp. Neurol. (1993) 119:215-219.
Brennan et al., Arthritis Res. (2002) 4(Suppl. 3):S177-S182.
Brown et al., 44th Annual Meeting of the American Society of Hematology, Philadelphia, PA, Dec. 6-10, 2002, Abstract No. 3012, p. 761A.
Brown, J. et al. (2010). "Clinical Activity in a Phase 1 Study of Cal-101, an Isoform-Selective Inhibitor of Phosphatidylinositol 3-Kinase P110Delta, in Patients with B-Cell Malignancies," *Haematologica* 95(s2):466, Abstract No. 1130.
Brunn et al., EMBO J. (1996) 15:5256-5267.
Burgering et al., Nature (1995) 376:599-602.
Butcher et al., Science (1996) 272:60-66.
Cadwallader et al., J. Immunol. (2002) 169:3336-3344.
Cantley et al., PNAS USA (1999) 96:4240-4245.
Cantley et al., Science (2002) 296:1655-1657.
Cardone et al., Science (1998) 282:1318-1321.
Carnero et al., FEB Letters (1998) 422:155-159.
CAS Abstract, Accession No. DN 86:83505 [1977] pp. 112-118.
Cebon et al., Cancer Immun. (2003) 3:7-25.
Chang et al., Exp. Opin. Ther. Patents (2001) 11:45-59.
Chang, BioMed. Eng. Online (2003) 2:12.
Chantry et al., J. Biol. Chem. (1997) 272:19236-19241.
Chen et al., Blood (2000) 96:3181-3187.
Chern et al., Chem. Pharm. Bull. (1998) 46(6):928-933.
Chern et al., Chemical Abstracts (1998) 129(16):676.
Chopp et al., Stroke (1994) 25:869-876.
Choy et al., Arthritis & Rheumatism (2002) 46:3143-3150.
Clark et al., J. Neurosurg. (1991) 75:623-627.
Clavel et al., Joint Bone Spine (2003) 70:321-326.
Clayton et al., J. Exp. Med. (2002) 196:753-763.
Cleary, J.M. et al. (2010). "Development of Phosphoinositide-3 Kinase Pathway Inhibitors for Advanced Cancer," *Curr. Oncol. Rep.* 12:87-94.
Coligan et al., Current Protocols in Protein Science (2002) 3:15-20.
Constantin et al., Immunity (2000) 13:759-769.
Cosimi et al., J. Immunol. (1990) 144:4604-4612.
Coxon, Immunity (1996) 5:653-666.
Creamer et al., Angiogenesis (2002) 5:231-236.
Cross et al., Inflamm. Res. (1999) 48:255-261.
Curnock et al., Immunology (2002) 105:125-136.
Dahia et al., Hum. Mol. Genet. (1999) 8:185-193.
Dallegri et al., Inflamm. Res. (1997) 46:382-391.
Das et al., Prog. Retin. Eye Res. (2003) 22:721-748.
Datta et al., Cell (1997) 91:231-241.
Datta et al., Genes & Dev. (1999) 13:2905-2927.
Davies et al., Biochem. J. (2000) 351:95-105.
De Benedetti et al., Clin. Exper. Reheum. (1992) 10:493-498.
Deininger et al., Blood (2000) 96:3343-3356.
Demeester et al., Transplantation (1996) 62:1477-1485.
Descamps et al., J. Immunol. (2004) 173:4953-4959.
Doggett et al., Biophys. J. (2002) 83:194-205.

(56) References Cited

OTHER PUBLICATIONS

Dorland's Illustrated Medical Dictionary (2003), retrieved Oct. 21, 2005 from Xreferplus, http://www.xreferplus.com/entry/4196914.
Downward, Nature (1995) 376:553-554.
Drakesmith et al., Immunol. Today (2000) 21:214-217.
Druker et al., New England Journal of Medicine (2001) 344:1038-1042.
Dunne et al., Blood (2002) 99:336-341.
Edwards et al., Canc. Res. (2002) 62:4671-4677.
Eichholtz et al., J. Biol. Chem. (1993) 268:1982-1986.
El-Fattah et al., Indian J Hetercyclic Chemistry (1995) 4:199-202.
El-Feky, S.A. et al. (1985). "Synthesis of Certain New Sulfur-Containing Quinazolinone Derivatives Likely to Possess CNS Depressant Action," *Egyptian Journal of Pharmaceutical Sciences* 24(1-4):39-47.
El-Feky et al., Chemical Abstracts (1987) 106(13):650.
El-Feky et al., Chemical Abstracts (1999) 131(23):497.
El-Feky, S.A. (Aug. 1998). "Novel Quinazolinones From 2-Cyanomethyl-3-Phenyl-4(3H) Quinazolinone," *Bollettino Chimico Farmaceutico* 137(7):286-289.
Engelman et al., Nature Reviews (2006) 7:606-619.
Environmental Protection Agency, EPA-Radiation Information (EPA's Radiation Protection Program:Information) "Ionizing Radiation Fact Sheet Series No. 1" (May 1998) Retrieved on Apr. 21, 2004: http://www.epa.gov/radiation/docs/ionize/ionize.htm.
Erbagci et al., Clin. Biochem. (2001) 34:645-650.
Estey, Cancer (2001) 92:1059-1073.
Etzioni, Pediatr. Res. (1996) 39:191-198.
European Search Report mailed Mar. 29, 2011, for EP Patent Application No. 10163434.3, filed on Apr. 24, 2001, 9 pages.
Faffe et al., Eur. Respir. J. (2000) 15:85-91.
Fantl et al., Ann. Rev. Biochem. (1993) 62:453-481.
Faust et al., Blood (2000) 96:719-726.
Final Office Action from U.S. Appl. No. 10/918,803, mailed on Jan. 8, 2009.
Final Office Action from U.S. Appl. No. 11/129,006, mailed on Oct. 5, 2010.
Final Office Action from U.S. Appl. No. 11/596,092, mailed on May 18, 2010.
Final Office Action mailed on Oct. 24, 2011, for U.S. Appl. No. 12/732,128, filed Mar. 25, 2010, 8 pages.
Final Office Action mailed on Feb. 15, 2012, for U.S. Appl. No. 12/732,124, filed Mar. 25, 2010, 12 pages.
Final Office Action mailed on Jun. 7, 2012, for U.S. Appl. No. 11/129,006, filed May 12, 2005, 14 pages.
First Preliminary Amendment from U.S. Appl. No. 12/538,748, filed Apr. 1, 2010.
Flinn, I.W. et al. (2009). "Preliminary Evidence of Clinical Activity in a Phase 1 Study of CAL-101, a Selective Inhibitor of the p1108 Isoform of Phosphatidylinositol 3-Kinase (P13K), in Patients with Select Hematologic Malignancies," Journal of Clinical Oncology 27:156s, Abstract 3543.
Flinn, I.W. et al. (Nov. 20, 2009). "Evidence of Clinical Activity in a Phase 1 Study of CAL-101, an Oral P110Δ Isoform-Selective Inhibitor of Phosphatidylinositol 3-Kinase, in Patients with Relapsed or Refractory B-Cell Malignancies," *Blood* 1 14(22):380, Abstract 922.
Flinn, W. et al. (Jun. 4-7, 2009). "Preliminary Evidence of Clinical Activity in a Phase 1 Study of CAL-101, A Potent Selective Inhibitor of the P110Delta Isoform of Phosphatidylinositol 3-Kinase, in Patients with B-Cell Maglignancies," Haematologica 94(s2):303, Abstract 0744.
Folkman, Curr. Mol. Med. (2003) 3:643-651.
Folkman, Nat. Med. (1995) 1:27-31.
Fraser et al., Science (1991) 251:313-316.
Frey et al., Lancet (2008) 372(9643):1088-1099 (abstract).
Freyssinier et al., Br. J. Haematol. (1999) 106:912-922.
Fruman et al., Ann. Rev. Biochem. (1998) 67:481-507.
Fruman et al., Semin. Immunol. (2002) 14:7-18.
Furman, R.R. (Jul. 2010). "New Agents in Early Clinical Trials for CLL Therapy," *Clinical Advances in Hematology & Oncology* 8(7):475-476.
Garcia-Barros et al., Science (2003) 300:1155-1159.
Genbank Accession No. AK040867, last updated Sep. 19, 2008, located at <http://www.ncbi.n1m.nih.gov.nuccore/26334014>, last visited on Apr. 16, 2010, 6 pages.
GenBank Accession No. AR255866, last updated Dec. 20, 2002, located at <http://www.ncbi.n1m.nih.gov.nuccore/27305059>, last visited on Apr. 16, 2010, 2 pages.
GenBank Accession No. BC035203, last updated Aug. 11, 2006, located at <http://www.ncbi.n1m.nih.gov/nuccore/23270986>, last visited on Apr. 16, 2010, 5 pages.
GenBank Accession No. NM_005026, last updated Apr. 11, 2010, located at <http://www.ncbi.n1m.nih.gov/nuccore/15654404>, last visited Apr. 16, 2010, 7 pages.
GenBank Accession No. NM_008840, last updated on Mar. 5, 2010, located at <http://www.ncbi.n1m.nih.gov/nuccore/255708435>, last visited on Apr. 16, 2010, 5 pages.
GenBank Accession No. U57843, last updated on May 9, 1997, located at <http://www.ncbi.n1m.nih.gov/nuccore/U57843>, last visited on Aug. 9, 2011, 2 pages.
GenBank Accession No. U86453, last updated on Jul. 7, 1998, located at <http://www.ncbi.n1m.nih.gov/nuccore/2317893>, last visited on Apr. 16, 2010, 3 pages.
GenBank Accession No. U86587, last updated Jul. 7, 1998, located at <http://www.ncbi.n1m.nih.gov/nuccore/2331237>, last visited on Apr. 16, 2010, 3 pages.
GenBank Accession No. XM_345606, last updated Jun. 22, 2006, located at <http://www.ncbi.n1m.nih.gov/nuccore/109475856?report=genbank>, last visited on Apr. 16, 2010, 3 pages.
GenBank Accession No. Y10055, last updated Oct. 7, 2008, located at <http://www.ncbi.n1m.nih.gov/nuccore/37496958>, last visited on Apr. 16, 2010, 3 pages.
Geng et al., Cancer Research (2001) 61:2413-19.
Geng et al., Cancer Research (2004) 64:4893-4899.
Geng et al., Cancer Research (2004) 64:8130-8133.
Gibson, (ed.), Antisense and Ribozyme Methodology, "Laboratory Companion" (1997) Table of Contents.
Gilliland et al., Blood (2002) 100:1532-1542.
Gilliland et al., Cancer Cell (2002) 1:417-420.
Gingras et al., Genes Dev. (2001) 15:2852-2864.
Gingras et al., Genes Dev. (2001) 15:807-826.
Glenjen et al., Int. J. Cancer (2002) 101:86-94.
Gorczynski et al., J. Immunol. (1994) 152:2011-2019.
Gorski et al., Cancer Research (1999) 59:3374-3378.
Gouilleux-Gruart et al., Blood (1996) 87:1692-1697.
Grant et al., Drugs of Today (2002) 38:783-791.
Gross et al., Science (1998) 281:703-706.
Gu et al., Mol. Cell. Biol. (2000) 20:7109-7120.
Gupta et al., Int'l J Radiation Oncology Biology Physics (2003) 56(3):846-853.
Gute et al., Mol. Cell. Biochem. (1998) 179:169-187.
Guzman et al., Blood (2001) 98:2301-2307.
Guzman et al., Proc. Natl. Acad. Sci. (USA) (2002) 99:16220-16225.
Hadden, Int. Immunopharmacol. (2003) 3:1061-1071.
Hallahan et al., Proc. Natl. Acad. Sci (USA) (1997) 94:6432-6437.
Halloran et al., Arthritis Rheum. (1996) 39:810-819.
Hanamoto et al., Am. J. Pathol. (2004) 164(3):997-1006.
Hannigan et al., Proc. Natl. Acad. Sci. U.S.A. (2002) 99:3603-3608.
Hardma et al. (eds.), Goodman and Gilman's The Pharmacological Basis of Therapeutics (1996) 9th ed., pp. 11-16.
Harlan, Haematology 96, the Education Program Book of the 26th Congress of the International Society of Haematology. Singapore, 1996.
Harning et al., Transplantation (1991) 52:842-845.
Hartley et al., Cell (1995) 82:849-856.
Hartman et al., Cardiovasc. Res. (1995) 30:47-54.
Hasagawa et al., Int. Immunol. (1994) 6:831-838.
Hassan et al., Chinese Journal of Chemistry (1991) 9:262-269.
He et al., Opthalmol. Vis. Sci. (1994) 35:3218-3225.
Healy et al., Hum. Reprod. Update (1998) 4:736-740.
Healy et al., Pharma. Res. (Dec. 2004) 21:2234-2246.

(56) References Cited

OTHER PUBLICATIONS

Heit et al., J. Cell Biol. (2002) 159:91-102.
Hellman, Cancer: Principles and Practice of Oncology (1993) 4th ed., vol. 1:248-275.
Herman, S.E.M. et al. (Sep. 23, 2010). "Phosphatidylinositol 3-Kinase-δ Inhibitor CAL-101 Shows Promising Preclinical Activity in Chronic Lymphocytic Leukemia by Antagonizing Intrinsic and Extrinsic Cellular Survival Signals," *Blood* 116(12):2078-2088.
Herold et al., Cell Immunol. (1994) 157:489-500.
Higuchi, Prodrugs as Novel Delivery Systems, vol. 14, ASCD Symposium Series, and in Roche (ed.), Bioreversible Carriers in Drug Design, American Pharmaceutical Association and Pergamon Press (1987) Chapter 1, pp. 1-12.
Hilbert et al., J. Exper. Med. (1995) 182:243-248.
Hiles et al., Cell (1992) 70:419-429.
Hilmas et al., Rad. Res. (1975) 61:128-143.
Hirsch et al., Science (2000) 287:1049-1053.
Horgan et al., Am. J. Physiol. (1991) 261:H1578-H1584.
Hsieh, S.N. (2003). "Identification of PI3Ky in Endothelial Cells and Its Involvement in Sphingosine 1-Phosphate Mediated Endothelial Cell Migration," Dissertation, Friedrick Schiller University, Jena, Germany, 104 pages.
Hu et al., Mol. Cell. Biol. (1993) 13:7677-7688.
Hu et al., Science (1995) 268:100-102.
Hunter, Cell (1995) 83:1-4.
Hussong et al., Blood (2000) 95:309-313.
Ikeda, H. et al. (Feb. 2009). "CAL-101: a Selective Inhibitor of P13K p11δ for the Treatment of Multiple Myeloma," *Clinical Lymphoma and Myeloma* 9(Supp. 1):S98-S99.
Ikeda, H. et al. (Nov. 16, 2008). "CAL-101, a Specific Inhibitor of the p110δ Isoform of Phosphatidylinositide 3-Kinase Induces Cytotoxicity in Multiple Myeloma (MM)," *Blood* 112(11):950, Abstract No. 2753.
Ikeda, H. et al. (Sep. 2, 2010). "PI3K/p110δ is a Novel Therapeutic Target in Multiple Myeloma," *Blood* 116(9):1460-1468.
International Preliminary Report on Patentability for PCT/US2006/005621, issued on Aug. 21, 2007, 8 pages.
International Search Report for International (PCT) Patent Application Serial No. PCT/US2004/026436, dated Dec. 2, 2004.
International Search Report for International (PCT) Patent Application Serial No. PCT/US2004/029561, dated May 25, 2005.
International Search Report for International (PCT) Patent Application Serial No. PCT/US2004/026834, dated Nov. 29, 2004.
International Search Report for International (PCT) Patent Application Serial No. PCT/US2004/037860, dated May 6, 2005.
International Search Report mailed on Aug. 29, 2005, for PCT Application No. PCT/US2005/016778, filed on May 12, 2005, 4 pages.
International Search Report mailed on Sep. 15, 2006 for PCT Application No. PCT/US2006/005621, filed on Feb. 16, 2006, 4 pages.
Interview Summary from U.S. Appl. No. 10/918,825, mailed on Jun. 14, 2006.
Ismail and Sayed, Indian Journal of Chemistry (1982) 21B(5):461-462.
Ismail et al., Chemical Abstracts (1983) vol. 98, No. 1, p. 406.
Isobe et al., Science (1992) 255:1125-1127.
Johnson et al., Intl. J. Rad. One. Biol. Phys. (1976) 1:659-670.
Johnson et al., J. Endourol. (2003) 17:557-562.
Jordan, Nature Reviews: Drug Discovery (2003) 2:205.
Jou et al., Mol. Cell. Biol. (2002) 22:8580-8591.
Kahl, B.S. (May 2010). "Novel Agents for Non-Hodgkin Lymphoma," *Clinical Advances in Hematology & Oncology* 8(5)(Suppl. 10):10-15.
Kakimoto et al., Cell. Immunol. (1992) 142:326-337.
Kallman et al., Canc. Res. (1972) 32:483-490.
Kandel et al., Exp. Cell Res. (1999) 253:210-229.
Kawasaki et al., J. Immunol. (1993) 150:1074-1083.
Kim et al., Endocrin. (2000) 141:1846-1853.
Kim, Retrieved from the Internet on Apr. 13, 2004: URL: http://www.math.umn.edu/~yjkim/biopaper/timy.html.
Kishimoto et al., Cell (1987) 50:193-202.
Klein et al., Cell. Signal. (2001) 13:335-343.
Klippel et al., Mol. Cell. Biol. (1994) 14:2675-2685.
Knall et al., Proc. Natl. Acad. Sci. (USA) (1997) 94:3052-3057.
Knight and Shokat, Chemistry and Biology (2005) 12:621-637.
Knight et al., Bioorganic & Medicinal Chemistry (Jul. 2004) 12:4749-4759.
Knoerzer et al., Toxicol. Pathol. (1997) 25:13-19.
Kolonin et al., Nature Medicine (2004) 10:625-632.
Kong et al., J. Biol. Chem. (2000) 275:36035-36042.
Kopf et al., Nature (1994) 368:339-342.
Krugmann et al., J. Biol. Chem. (1999) 274:17152-17158.
Kumar et al., Blood (2003) 101(10):3960-3968.
Kunkel et al., Circ. Res. (1996) 79:1196-1204.
Lannutti, B.J. et al. (Apr. 2009). "CAL-101, a Specific PI3K p110δ Inhibitor for the Treatment of Hematological Maglignancies," *Proceedings of the American Association for Cancer Research* 50:1400, Abstract No. #SY32-2.
Lannutti, B.J. et al. (Nov. 16, 2008). "CAL-101, a Potent Selective Inhibitor of the p110d Isoform of Phosphatidylinositol 3-Kinase, Attenuates PI3K Signaling and Inhibitos Proliferation and Survival of Acure Lumpoblastic Leukemia in Addition to a Range of Other Hematological Malignancies," *Blood* 112(11):12, Abstract No. 16.
Lannutti, B.J. et al. (Nov. 20, 2009). "CAL-101, An Oral P110δ Selective Phosphatidylinositol-3-Kinase (PI3K) Inhibitor for the Treatment of B Cell Malignancies Inhibits PI3K Signaling, Cellular Viability and Protective Signals of the Microenvironment," *Blood* 114(22):120-121, Abstract No. 286.
Lannutti, J. et al. (2010). "Demonstration of Pharmacodynamic Target Inhibition and Chemokine Modulation in Patients with CLL Following Treatment with CAL-101, a Selective Inhibitor of the P110 Delta Isoform of PI3K," *Haematologica* 95(52):45-46, Abstract No. 0113.
Lannutti, J. et al. (Jun. 4-7, 2009). "CAL-101, A Specific Inhibitor of the P11-Delta Isoform of Phosphatidylinositide 3-Kinase, for the Treatment of Non-Hodgkins Lymphomas," *Haematologica* 94(S2):272-273, Abstract No. 0668.
Lecoq-Lafon et al., Blood (1999) 93:2578-2585.
Lemmon et al., Trends Cell. Biol. (1997) 7:237-242.
Letter from Polish Patent Law Firm "Patpol" translating Office Action from Polish Patent Application No. P-358590, dated Feb. 27, 2008.
Li et al., Trends Biochem. Sci. (Jan. 2004) 29:32-38.
Liang et al., Molecular Cancer Therapeutics (2003) 2(4):353-360.
Liekens et al., Biochem. Pharmacol. (2001) 61:253-270.
Liu et al., J. Immunol. (Jan. 2004) 172 :7-13.
Lowell et al., J. Cell Biol. (1996) 133:895-910.
Luo et al., Cancer Cell (2003) 4:257-262.
Luo et al., Leukemia (2003) 17:1-8.
Luster, N. Engl. J. Med. (1998) 338:436-445.
Madge et al., J. Biol. Chem. (2000) 275:15458-15465.
Manning et al., Mol. Cell (2002) 10:151-162.
Marley et al., Br. J. Haematol. (May 2004) 125:500-511.
May, S.E. et al. (Nov. 16, 2008). "CAL-101, a Selective Inhibitor of the p110δ Isoform of Phosphatidylinositol 3-Kinase, Effectively Induces Apoptosis in Primary Chronic Lumphocytic Leukemia Cells Providing a Novel Therapeutic Strategy for the Treatment of this Disease," *Blood* 112(11):1085-1086, Abstract No. 3165.
Meneses et al., Gene Ther. (2001) 8:646-648.
Milella et al., J. Clin. Invest. (2001) 108:851-859.
Miller et al., Nucleic Acids Res. (1988) 16:1215.
Moehler et al., Ann. Hematol. (2001) 80:695-705.
Moore, J. Clin. Invest. (2002) 109:313-315.
Moulton et al., Circ. (1999) 99:1726-1732.
Mulligan et al., J. Immunol. (1995) 154:1350-1363.
Mulligan et al., Proc. Natl. Acad. Sci. (USA) (1993) 90:11523-11527.
Nagase et al., Am. J. Respir. Crit. Care Med. (1996) 154:504-510.
Nakao et al., Leukemia (1996) 10:1911-1918.
Nakao et al., Muscle Nerve (1995) 18:93-102.
Neshat et al., Proc. Natl. Acad. Sci. (USA) (2001) 98:10314-10319.
Ninomiya et al., J. Biol. Chem. (1994) 269:22732-22737.
Non Final Office Action from U.S. Appl. No. 11/596,092, mailed on Dec. 24, 2009.

(56) References Cited

OTHER PUBLICATIONS

Non-Final Office Action from U.S. Appl. No. 09/841,341, mailed on Apr. 25, 2002.
Non-Final Office Action from U.S. Appl. No. 10/027,591, mailed on Feb. 26, 2003.
Non-Final Office Action from U.S. Appl. No. 10/918,803, mailed on Apr. 1, 2008.
Non-Final Office Action from U.S. Appl. No. 10/918,803, mailed on Mar. 16, 2010.
Non-Final Office Action from U.S. Appl. No. 10/918,825, mailed on Nov. 7, 2005.
Non-Final Office Action from U.S. Appl. No. 11/110,204, mailed on Aug. 5, 2008.
Non-Final Office Action from U.S. Appl. No. 11/110,204, mailed on Feb. 4, 2010.
Non-Final Office Action from U.S. Appl. No. 11/110,204, mailed on Jun. 17, 2009.
Non-Final Office Action from U.S. Appl. No. 11/129,006, mailed on Dec. 15, 2009.
Non-Final Office Action mailed on Jan. 20, 2012 for U.S. Appl. No. 13/163,597, filed Jun. 17, 2011, 14 pages.
Non-Final Office Action mailed on Oct. 17, 2011 for U.S. Appl. No. No. 12/732,124, filed Mar. 25, 2010, 8 pages.
Non-Final Office Action from U.S. Appl. No. 11/596,092, mailed on Jun. 10, 2009.
Non-Final Office Action from U.S. Appl. No. 11/884,566, mailed on Aug. 3, 2010.
Non-Final Office Action mailed on Jun. 28, 2011, for U.S. Appl. No. 12/732,124, filed Mar. 25, 2010, 11 pages.
Non-Final Office Action mailed on Aug. 2, 2012 for U.S. Appl. No. 12/575,277, filed Oct. 7, 2009, 8 pages.
Non-Final Office Action mailed on Aug. 7, 2012 for U.S. Appl. No. 12/575,367, filed Oct. 7, 2009, 9 pages.
Notice of Allowance from U.S. Appl. No. 09/841,341, mailed on Oct. 7, 2002.
Notice of Allowance from U.S. Appl. No. 10/027,591, mailed on Jul. 29, 2003.
Notice of Allowance from U.S. Appl. No. 10/337,192, mailed on Mar. 11, 2004.
Notice of Allowance from U.S. Appl. No. 10/697,912, mailed on Dec. 30, 2004.
Notice of Allowance mailed on Nov. 8, 2010, for U.S. Appl. No. 11/110,204, filed Apr. 20, 2005, 6 pages.
Notice of Allowance mailed on Jun. 26, 2012 for U.S. Appl. No. 12/732,124, filed Mar. 25, 2010, 11 pages.
Notice of Allowance mailed on Nov. 13, 2012 for U.S. Appl. No. 12/732,124, filed Mar. 25, 2010, 11 pages.
Notice of Reexamination for Chinese Patent Application No. 0811654.X, mailed Nov. 5, 2009; 7 pages.
Notice Regarding Non-Compliant Amendment from U.S. Appl. No. 10/918,803, mailed on Nov. 19, 2009.
Notification of Reasons for Rejection for Japanese Patent Application No. 2003-537642, mailed on May 26, 2009, 4 pages.
Office Action for European Patent Application No. 04 816 855.3, mailed on Oct. 21, 2008, 4 pages.
Office Action for European Patent Application No. 01 928 855.4, mailed on Feb. 26, 2009, 3 pages.
Office Action for European Patent Application No. 01 928 855.4, mailed on Nov. 15, 2007, 4 pages.
Office Action for European Patent Application No. 01 928 855.4, mailed on Mar. 29, 2006, 6 pages.
Office Action for European Patent Application No. 01 928 855.4, mailed on Jul. 13, 2004, 5 pages.
Office Action for European Patent Application No. 02 757 407.8, mailed on Oct. 6, 2009, 3 pages.
Office Action for European Patent Application No. 02 757 407.8, mailed on Jul. 1, 2009, 2 pages.
Office Action for European Patent Application No. 02 757 407.8, mailed on Oct. 21, 2008, 3 pages.
Office Action for European Patent Application No. 02 757 407.8, mailed on Jun. 6, 2007, 2 pages.
Office Action for European Patent Application No. 02 757 407.8, mailed on Jan. 24, 2006, 3 pages.
Office Action for European Patent Application No. 04 816 855.3, mailed on Feb. 2, 2011, 4 pages.
Office Action for European Patent Application No. 05 752 122.1, mailed on Dec. 28, 2010, 4 pages.
Office Action for European Patent Application No. 04 810 878.1, mailed on Sep. 10, 2010, 4 pages.
Ohno-Matsui et al., Invest. Ophthalmol. Vis: Sci. (2003) 44:5370-5375.
Okkenhaug et al., Science (2002) 297:1031-1034.
Oppenheimer-Marks et al., J. Clin. Invest. (1998) 101:1261-1272.
Oshiro et al., Stroke (1997) 28:2031-2038.
Otsu et al., Cell (1991) 65:91-104.
Paez et al., Frank (ed.), Cancer Treatment and Research (2003) 115:146 Kluwer Academic Publishers.
Pages et al., Nature (1994) 369:327-329.
Palanki, Curr. Med. Chem. (2002) 9:219-227.
Paleolog et al., Angiogenesis (1998/1999) 2:295-307.
Panayotou et al., Trends in Cell Biol. (1992) 2:358-360.
Panes et al., Gastroenterology (1995) 108:1761-1769.
Parasharya and Parikh, J. Inst. Chemists (1992) 64(5):184-185.
Parasharya et al., Chemical Abstracts (1994) vol. 121, No. 9, p. 1065.
Park, S. et al. (2010). "Role of the PI3K/AKT and mTOR Signaling Pathways in Acute Myeloid Leukemia," *Haematologica* 95(5):819-829.
Parker, Current Biology (1995) 5:577-579.
Passegue et al., Proc. Natl. Acad. Sci., (USA) (2003) 100 Supp. 1:11842-11849.
Patani, G.A. et al. (1996), "Bioisosterism: a Rational Approach in Drug Design," *Chem Rev.* 96(8):3147-3176.
Pierce et al., J. Biol. Chem. (1997) 272:21096-21103.
Plows et al., J. Immunol. (1999) 162(2):1018-1023.
Podsypanina et al., Proc. Natl. Acad. Sci. (USA) (2001) 98:10320-10325.
Psychoyos et al., J. Immunol. Methods (1991) 137:37-46.
Puri et al., Blood (2005) 106(1):150-157, 144.
Puri et al., Blood (May 2004) 103:3448-3456.
Puri, K. et al. (Jul. 18-23, 2004). "A Role for Phosphoinositide 3-Kinase δ in Neutrophil Trafficking," Immunology 2004: Cytokine Network, Regulatory Cells, Signaling, and Apoptosis: Collection of Free Papers Presented at the *12th International Congress of Immunology and 4th Annual Conference of FOCIS Medimond International Proceedings in Montreal, Canada* on Jul. 18, 23, 2004, pp. 303-307.
Quirici et al., Br. J. Haematol. (2001) 115:186-194.
Rameh et al., Cell (1995) 83:821-830.
Rameh et al., J. Biol. Chem. (1999) 274:8347-8350.
Rathman et al., J. Org. Chem. (1980) 45:2169-2176.
Remington'S Pharmaceutical Sciences (1990) 18th Ed., Chapter 89, pp. 1435-1712 Table of Contents Only.
Ren et al., Curr. Drug Targets Inflamm. Allergy (2003) 2(3):242-256.
Request for Continued Examination and Amendment Under 37 C.F. R. § 1.116 from U.S. Appl. No. 10/918,803, filed May 7, 2009.
Response to Election of Species Requirement from U.S. Appl. No. 10/918,803, filed Jun. 27, 2007.
Response to Non-Final Office Action from U.S. Appl. No. 10/918,803, filed Dec. 18, 2009.
Response to Non-Final Office Action filed on Sep. 16, 2010, for U.S. Appl. No. 10/918,803, filed Aug. 13, 2004, 25 pages.
Response to Restriction Requirement from U.S. Appl. No. 10/918,803, filed Jan. 4, 2008.
Response to Restriction Requirement from U.S. Appl. No. 11/129,006, filed May 12, 2009.
Response to Restriction Requirement from U.S. Appl. No. 11/137,901, filed Feb. 6, 2008.
Response to Restriction Requirement from U.S. Appl. No. 11/596,092, filed May 27, 2009.
Restriction Requirement from U.S. Appl. No. 10/918,803, mailed on Jun. 12, 2009.

(56) References Cited

OTHER PUBLICATIONS

Restriction Requirement from U.S. Appl. No. 10/918,803, mailed on Mar. 13, 2007.
Restriction Requirement from U.S. Appl. No. 10/918,803, mailed on Sep. 7, 2007.
Restriction Requirement from U.S. Appl. No. 11/110,204, mailed on Mar. 10, 2008.
Restriction Requirement from U.S. Appl. No. 11/129,006, mailed on Nov. 12, 2008.
Restriction Requirement from U.S. Appl. No. 11/137,901, mailed on Aug. 6, 2007.
Restriction Requirement from U.S. Appl. No. 11/137,901, mailed on May 23, 2008.
Restriction Requirement from U.S. Appl. No. 11/596,092, mailed on Jan. 28, 2009.
Restriction Requirement from U.S. Appl. No. 11/884,566, mailed on Apr. 5, 2010.
Restriction Requirement mailed on Oct. 14, 2010, for U.S. Appl. No. 12/732,124, filed Mar. 25, 2010, 9 pages.
Restriction Requirement mailed on Dec. 1, 2011, for U.S. Appl. No. 13/163,597, filed Jun. 17, 2011, 7 pages.
Restriction Requirement mailed on Jun. 7, 2012, for U.S. Appl. No. 13/399,828, filed Feb. 17, 2012, 5 pages.
Restriction Requirement mailed on Jul. 17, 2012, for U.S. Appl. No. 13/247,962, filed Sep. 28, 2011, 27 pages.
Restriction Requirement mailed on Sep. 11, 2012, for U.S. Appl. No. 13/399,828, filed Feb. 17, 2012, 7 pages.
Reyes et al., J. Clin. Invest. (2002) 109:337-346.
Rickert et al., Trends Cell Biol. (2000) 10:466-473.
Riesterer, Int'l J Radiation Oncology Biology Physics (2004) 361-368.
Roberts et al., Immunity (1999) 10:183-196.
Rodrigues et al., Mol. Cell. Biol. (2000) 20:1448-1459.
Rodriguez-Viciana et al., Embo J. (1996) 15:2442-2451.
Roth et al., J. Immunol. Methods (1995) 188:97-116.
Rudd, Immunity (1996) 4:527-534.
Rupnick et al., Proc. Nat'l. Acad. Sci. (USA) (2002) 99:10730-35.
Sadhu et al., J. Immunol. (2003) 170:2647-2654.
Salven et al., Blood (1999) 94:3334-3339.
Salvesen et al., Cell (1997) 91:443-446.
Sasaki et al., Science (2000) 287:1040-1046.
Sauder et al., J. Am. Acad. Dermatol. (2002) 47:535-541.
Schuch et al., Blood (2002) 100:4622-4628.
Schueneman et al., Canc. Res. (2003) 63:4009-4016.
Second Preliminary Amendment and Response to Notice to File Missing Parts of Nonprovisional Application from U.S. Appl. No. 12/575,277, filed Jan. 20, 2010.
Second Preliminary Amendment and Response to Notice to File Missing Parts of Nonprovisional Application from U.S. Appl. No. 12/575,367, filed Jan. 20, 2010.
Second Preliminary Amendment from U.S. Appl. No. 11/110,204, filed Aug. 24, 2007.
Second Preliminary Amendment from U.S. Appl. No. 11/884,566, filed May 13, 2008.
Sengupta et al., Circulation (2003) 107:2955-2961.
Shimamoto et al., Leukemia Res. (2003) 27:783-788.
Shiojima et al., Circ. Res. (2002) 90:1243-1250.
Shvidel et al., Hematol. J. (2002) 3:32-37.
Smith et al., Am. J. Respir. Cell Mol. Biol. (1996) 15(6):693-702.
Song et al., Canc. Res. (1974) 34:2344-2350.
Springer, Cell (1994) 76:301-314.
Stein et al., Mol. Med. Today (2000) 6:347-357.
Stenmark et al., J. Cell. Sci. (1999) 112:4175-4183.
Stennicke et al., Biochim. Biophys. Acta. (2000) 1477:299-306.
Stephens et al., Current Biology (1994) 4:203-214.
Stirewalt et al., Nat. Rev. Cancer (2003) 3:650-665.
Stoyanov et al., Science (1995) 269:690-693.
Su et al., Cancer Research (2003) 63:3585-3592.
Sumariwalla et al., Arthritis Res. Ther. (2002) 5:R32-R39.
Sunil et al., Respir. Res. (2002) 3:21.
Supplemental Amendment from U.S. Appl. No. 11/110,204, filed Oct. 27, 2009.
Supplemental Notice of Allowance from U.S. Appl. No. 10/337,192, mailed on Jun. 29, 2004.
Tager et al., J. Exp. Med. (2000) 192:439-446.
Talento et al., Transplantation (1993) 55:418-422.
Tamiya et al., Immunopharmacology (1995) 29:53-63.
Tan et al., Cancer Research (2003) 63:7663-7667.
Tan et al., J. Immunol. Meths. (2000), 238:59-68.
Tanaka et al., J. Immunol. (1993) 151:5088-5095.
Tang et al., J. Biol. Chem. (1999) 274:16741-16746.
Taylor et al., Curr. Opin. Rheumatol. (2005) 17(3):293-298.
Tesar et al., Med. Sc. Monit. (2002) 8:BR24-BR29.
The Merck Manual on "arthritis" (2008).
The Merck Manual on "rheumatoid arthritis" (2008).
The Merck Manual, 17th ed, (1999) p. 1001.
Thelan et al., Proc. Natl. Acad. Sci. (USA) (1994) 91:4960-4964.
Ting et al., Int. J. Rad. Biol. (1991) 60:335-339.
Vacca et al., Blood (1999) 9:3064-3073.
Van Dijk et al., Blood (2000) 96:3406-3413.
Vanhaesebroeck et al., Faseb J. (1996) 10:A1395, Abst. No. 2280.
Vanhaesebroeck et al., Proc. Natl. Acad. Sci., (USA) (1997) 94:4330-4335.
Vanhaesebroeck et al., TIBS (1997) 22:267-272.
Vermes et al., J. Immunol. Meth. (1995) 184:39-51.
Vippagunta, S.R. et al. (2001). "Crystalline Solids," *Advanced Drug Delivery* 48:3-26.
Vivanco et al., Nat. Rev. Cancer (2002) 2:489-501.
Vlahos et al., J. Immunol. (1995) 154:2413-2422.
Volinia et al., Embo J. (1995) 14:3339-3348.
Volinia et al., Genomics (1994) 24:472-477.
Volinia et al., Oncogene (1992) 7:789-793.
Webb, H.K. et al. (Apr. 2009). "CAL-101, a Potent and Selective Inhibitor of the Class 1 Phosphatidylinositol 3 Kinase (PI3K) p110δ: Preclinical Summary," *Proceedings of the American Association for Cancer Research* 50:894-895, Abstract No. #3703.
Wegner et al., Lung (1992) 170:267-279.
Wegner et al., Science (1990) 247:456-459.
Weiner et al., Nat. Cell Biol. (1999) 1:75-81.
Weyand et al., Arthritis & Rheumatism (2000) 43:1041-1048.
Williams, D.A. et al. (2002). *Foye's Principles of Medicinal Chemistry*, Lippincott, Williams & Wilkins, Baltimore MD, Fifth Edition, pp. 50 and 59-61.
Williams, Methods Mol. Med. (2004) 98:207-216.
Williams et al., Chem. Biol. (2010) 17:123-134.
Wolff, ed., Burger's Medicinal Chemistry and Drug Discovery, 5th edition (1996) vol. 1, New York: John Wiley & Sons, pp. 975-977.
Wymann et al., Biochem. Biophys. Acta. (1998) 1436:127-150.
Wymann et al., Biochem. J. (1994) 298:517-520.
Wymann et al., Trends Immunol. Today (2000) 21:260-264.
Xing et al., Am. J. Pathol. (1993) 143:1009-1015.
Xu et al., Blood (2003) 102:972-980.
Yamasawa et al., Inflammation (1999) 23:263-274.
Yamaura et al., Int. J. Rad. Biol. (1976) 30:179-187.
Yao et al., Science (1995) 267:2003-2006.
Yum et al., J. Immunol. (2001) 167:6601-6608.
Zeng et al., Transplantation (1994) 58:681-689.
Zhao et al., Leukemia (2004) 18:267-75.
Williams et al. (Foye's Principles of Medicinal Chemistry, 5th Edition, pp. 50 and 59-61, 2002).*
Patani et al. (Chem. Rev., 1996, 96, 3146-76).*
"Preparatyka Organiczna", ed. A.I. Vogel, WNT, Warszawa 1984, p. e.g. 83.
Brown et al., Haematoligica (2010) 95(S2):466.
Cleary and Shapiro, Curr. Oncol. Rep. (2010) 12:87-94.
Flinn et al., Blood (2009) 114(22):380.
Flinn et al., Haematologica (2010) 94(S2):303.
Flinn et al., Journal of Clinical Oncology (2009) 27(15S):156s.
Furman, Clinical Advances in Hematology & Oncology (2010) 8(7):475-476.
Herman et al., Blood (2010) 116(12):2078-2088.
Ikeda et al., Blood (2010) 116(9):1460-1468.
Ikeda et al., Blood (2008) 112(11):950.

(56) References Cited

OTHER PUBLICATIONS

Ikeda et al., Lymphoma and Myeloma (2009) 9(Suppl. 1):S98-S99.
Kahl, Clinical Advances in Hematology & Oncology (2010) 8(5):10-15.
Lannutti et al. Blood (2008) 112(11):12.
Lannutti et al. Proceedings of the American Association for Cancer Research (2009) 50:1400.
Lannutti et al., Blood (2009) 114(22):120-121.
Lannutti et al., Haematologica (2009) 94(S2):272-273.
Lannutti et al., Haematologica (2010) 95(S2):45-46.
May et al., Blood (2008) 112(11):1085-1086.
Park et al., Haematologoca (2010) 95(5):819-829.
Puri et al., Immunology 2004: Cytokine Network, Regulatory Cells, Signaling, and Apoptosis Collection of Free Papers Presented at the 12th International Congress of Immunology and 4th Annual Conference of FOCIS (2004) Medimond International Proceedings, pp. 303-307.
Webb et al., Proceedings of the American Association for Cancer Research (2009) 50:894-895.
Restriction Requirement from U.S. Appl. No. 12/732,124, mailed on Oct. 14, 2010.
Notice of Allowance from U.S. Appl. No. 11/110,204, mailed on Nov. 8, 2010.
Amendment in Response to Final Office Actions from U.S. Appl. No. 11/596,092, filed Jul. 19, 2010.
"NIH Heart Disease & Stroke Research: Fact Sheet", American Heart Association, 2004.
"Cardiovascular Disease: Treatment for Stroke", Stanford Hospital & Clinics, 2003.
"Heart Disease", Charlotte E. Grayson, WebMD, 2004.
"Acute Congenstive Heart Failure", Thomas N. Levin, Postgraduate Medicine, vol. 101, No. 1, 1997.
"Baylor, St. Luke's study uses gene therapy as pancreatic cancer", April Sutton, www.bcm.edu, 2006.
"Drugs hold promise in kidney cancer fight", Marchione et al., www.ledger-enquireer.com, 2006.
"Multiple Sclerosis", www.health.nytimes.com, 2010.
"Systemic Lupus Erythematosus", www.nlm.nih.gov, 2010.
"Spinal Cord Injury", www.medicinenet.com, 2010.
Response to Non-Final Office Action from U.S. Appl. No. 10/918,803, filed Sep. 16, 2010.
Hattori, H. et al. (May/Jun. 2010), "Reactive Oxygen Species as Signaling Molecules in Neutrophil Chemotaxis," *Communicative and Integrative Biology* 3(3):278-281.
International Search Report mailed on Aug. 29, 2005, for PCT Application No. PCT/US2005/016778, filed May 12, 2005, 4 pages.
International Search Report mailed on Sep. 15, 2006 for PCT Application No. PCT/US2006/005621, filed Feb. 16, 2006, 4 pages.
Non-Final Office Action mailed on Oct. 17, 2011 for U.S. Appl. No. 12/732,124, filed Mar. 25, 2010, 8 pages.
Tan, J. et al. (Sep. 1, 2004), "A Specific Antagonist of the p110-Delta Catalytic Component of P13 Kinase, IC486068, Enhances Radiation-Induced Tumor Vascular Destruction," *International Journal of Radiation: Oncology Biology Physics* 60(1):S195.
Adamkiewicz, "Tumor Angiogenesis: Mechanisms" IMT Marburg—Research Group, retrieved from the internet on Apr. 13, 2004, URL: http://www.imt.tuni-marburg.de/_adamkiew/mechanism.html.
Alon et al., "The molecular basis of leukocytes adhesion to and migration through vascular endothelium," Mirelman et al. (eds.), Life Sciences Open Day Book 2002, Weizmann Institute of Science, Life Sciences Department, Chapter 8, vol. 2:206-207 (2002), retrieved from the internet on Sep. 2, 2005, URL: http://www.weizmann.ac.il/Biology/open_day_2002/book/ronen_alon.pdf.
Angio World, "How Angiogenesis Complicates Psoriasis" (2001) retrieved from the internet on Apr. 13, 2004, URL: http://www.angioworld.com/psoriasis.htm.
Bader et al., Nature Reviews Cancer (2005) 5(12):921-922 (abstract and introduction).
CAS Abstract, Accession No. DN 86:83505 [1977] pp. 111-118.
Chemical Abstracts 106:102196, 1985.
Computer Search (8 pages), Cart Navigator, retrieved from the internet on Mar. 22, 2001, URL: http://www.chemnavigator.com/members/CartNavigator.asp#sample1.
El-Feky, Bollettino Chimico Farmaceutico (1998) 137:286-289.
El-Feky et al., Egypt. J. Pharm. Sci. (1983) 24(1-4):39-47.
GenBank Accession No. AK040867 (Caninci et al.), 2008.
GenBank Accession No. AR255866 (Vanhaesebroeck and Waterfield), 2002.
GenBank Accession No. BC035203 (Strausberg et al.), 2006.
GenBank Accession No. NM_005026 (Papakonstanti et al.), 2010.
GenBank Accession No. NM_008840 (Kim et al.), 2010.
GenBank Accession No. U57843, May 10, 1997.
GenBank Accession No. U86453 (Chantry et al.), 1998.
GenBank Accession No. U86587 (Chantry et al.), 1998.
GenBank Accession No. XM_345606 (2006).
GenBank Accession No. Y10055 (Vanhaesebroeck et al.), 2008.
Schimmer et al., J. Immunol. (1998) 160:1466-1477.
Vippagunta et al., Advanced Drug Delivery (2001) 48:3-26.
Wolff, ed., Burger's Medicinal Chemistry and Drug Discovery, 5th edition (1996) vol. 1, New York: John Wiley & Sons, pp. 975-976.
International Search Report for PCT/US2005/016778, mailed on Aug. 29, 2005, 4 pages.
International Search Report for PCT/US2006/005621, mailed on Sep. 15, 2006, 4 pages.
Amendment from U.S. Appl. No. 09/841,341, filed Aug. 21, 2002.
Hsieh, Friedrick Schiller University, Jena, Germany (2003).
U.S. Appl. No. 12/732,124, filed Mar. 25, 2010, by Fowler et al.
U.S. Appl. No. 12/732,128, filed Mar. 25, 2010, by Fowler et al.

* cited by examiner

QUINAZOLINONES AS INHIBITORS OF HUMAN PHOSPHATIDYLINOSITOL 3-KINASE DELTA

Matter enclosed in heavy brackets [ ] appears in the original patent but forms no part of this reissue specification; matter printed in italics indicates the additions made by reissue.

CROSS-REFERENCE TO RELATED APPLICATIONS

This application is a Divisional of U.S. National Phase Application Ser. No. 11/596,092, filed Dec. 14, 2007, now U.S. Pat. No. 7,932,260, which is a U.S. National Phase Application of International Application No. PCT/US2005/016778, filed May 12, 2005, which claims priority to and the benefit of U.S. provisional application No. 60/570,784 filed on May 13, 2004, each of which is incorporated herein by reference in its entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 616082000810Seqlist.txt | May 10, 2010 | 27,987 bytes |

FIELD OF THE INVENTION

The present invention relates generally to phosphatidylinositol 3-kinase (PI3K) enzymes, and more particularly to selective inhibitors of PI3K activity and methods of using such inhibitors.

BACKGROUND OF THE INVENTION

Cell signaling via 3'-phosphorylated phosphoinositides has been implicated in a variety of cellular processes, e.g., malignant transformation, growth factor signaling, inflammation, and immunity (see Rameh et al., J. Biol. Chem., 274:8347-8350 (1999) for a review). The enzyme responsible for generating these phosphorylated signaling products is phosphatidylinositol 3-kinase (PI 3-kinase; PI3K). PI3K originally was identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., Trends Cell Biol 2:358-60 (1992)).

Levels of phosphatidylinositol-3,4,5-triphosphate (PIP3), the primary product of PI 3-kinase activation, increase upon treatment of cells with a variety of agonists. PI 3-kinase activation, therefore, is believed to be involved in a range of cellular responses including cell growth, differentiation, and apoptosis (Parker et al., Curr. Biol., 5:577-99 (1995); Yao et al., Science, 267:2003-05 (1995)). Though the downstream targets of phosphorylated lipids generated following PI 3-kinase activation have not been well characterized, emerging evidence suggests that pleckstrin-homology domain- and FYVE-finger domain-containing proteins are activated when binding to various phosphatidylinositol lipids (Sternmark et al., J. Cell. Sci., 112:4175-83 (1999); Lemmon et al., Trends Cell Biol., 7:237-42 (1997)). In vitro, some isoforms of protein kinase C (PKC) are directly activated by PIP3, and the PKC-related protein kinase, PKB, has been shown to be activated by PI 3-kinase (Burgering et al., Nature, 376:599-602 (1995)).

Presently, the PI 3-kinase enzyme family is divided into three classes based on their substrate specificities. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate, whereas Class III PI3Ks can only phosphorylate PI.

The initial purification and molecular cloning of PI 3-kinase revealed that it was a heterodimer consisting of p85 and p110 subunits (Otsu et al., Cell, 65:91-104 (1991); Hiles et al., Cell, 70:419-29 (1992)). Since then, four distinct Class I PI3Ks have been identified, designated PI3K α, β, δ, and γ, each consisting of a distinct 110 kDa catalytic subunit and a regulatory subunit. More specifically, three of the catalytic subunits, i.e., p110α, p110β, and p110γ, each interact with the same regulatory subunit, i.e., p85, whereas p110γ interacts with a distinct p101 regulatory subunit. As described below, the patterns of expression of each of these PI3Ks in human cells and tissues also are distinct. Though a wealth of information has been accumulated on the cellular functions of PI 3-kinases in general, the roles played by the individual isoforms are largely unknown.

Cloning of bovine p110α has been described. This protein was identified as related to the Saccharomyces cerevisiae protein: Vps34p, a protein involved in vacuolar protein processing. The recombinant p110α product was also shown to associate with p85α, to yield a PI3K activity in transfected COS-1 cells. See Hiles et al., Cell, 70, 419-29 (1992).

The cloning of a second human p110 isoform, designated p110β, is described in Hu et al., Mol. Cell. Biol., 13:7677-88 (1993). This isoform is said to associate with p85 in cells, and to be ubiquitously expressed, as p110β mRNA has been found in numerous human and mouse tissues, as well as in human umbilical vein endothelial cells, Jurkat human leukemic T cells, 293 human embryonic kidney cells, mouse 3T3 fibroblasts, HeLa cells, and NBT2 rat bladder carcinoma cells. Such wide expression suggests that the p110β isoform is broadly important in signaling pathways.

Identification of the p110δ isoform of PI 3-kinase is described in Chantry et al., J. Biol. Chem., 272:19236-41 (1997). It was observed that the human p110δ isoform is expressed in a tissue-restricted fashion. It is expressed at high levels in lymphocytes and lymphoid tissues, suggesting that the protein might play a role in PI 3-kinase-mediated signaling in the immune system. Details concerning the p110δ isoform also can be found in U.S. Pat. Nos. 5,858,753; 5,822,910; and 5,985,589, each incorporated herein by reference. See also, Vanhaesebroeck et al., Proc. Natl. Acad. Sci. USA, 94:4330-5 (1997), and International Publication No WO 97/46688.

In each of the PI3Kα, β, and δ subtypes, the p85 subunit acts to localize PI 3-kinase to the plasma membrane by the interaction of its SH2 domain with phosphorylated tyrosine residues (present in an appropriate sequence context) in target proteins (Rameh et al., Cell, 83:821-30 (1995)). Two isoforms of p85 have been identified, p85α, which is ubiquitously expressed, and p85β, which is primarily found in the brain and lymphoid tissues (Volinia et al., Oncogene, 7:789-93 (1992)). Association of the p85 subunit to the PI 3-kinase p110α, β, or δ catalytic subunits appears to be required for the catalytic activity and stability of these enzymes. In addition, the binding of Ras proteins also upregulates PI 3-kinase activity.

The cloning of p110γ revealed still further complexity within the PI3K family of enzymes (Stoyanov et al., Science, 269:690-93 (1995)). The p110γ isoform is closely related to p110α and p110β (45-48% identity in the catalytic domain), but as noted does not make use of p85 as a targeting subunit. Instead, p110γ contains an additional domain termed a "pleckstrin homology domain" near its amino terminus. This domain allows interaction of p110γ with the βγ subunits of heterotrimeric G proteins and this interaction appears to regulate its activity.

The p101 regulatory subunit for PI3 Kgamma was originally cloned in swine, and the human ortholog identified subsequently (Krugmann et al., J. Biol. Chem., 274:17152-8 (1999)). Interaction between the N-terminal region of p101 with the N-terminal region of p110γ appears to be critical for the PI3Kγ activation through Gβγ mentioned above.

A constitutively active PI3K polypeptide is described in International Publication No. WO 96/25488. This publication discloses preparation of a chimeric fusion protein in which a 102-residue fragment of p85 known as the inter-SH2 (iSH2) region is fused through a linker region to the N-terminus of murine p110. The p85 iSH2 domain apparently is able to activate PI3K activity in a manner comparable to intact p85 (Klippel et al., Mol. Cell. Biol., 14:2675-85 (1994)).

Thus, PI 3-kinases can be defined by their amino acid identity or by their activity. Additional members of this growing gene family include more distantly related lipid and protein kinases including Vps34 TOR1, TOR2 of Saccharomyces cerevisiae (and their mammalian homologs such as FRAP and mTOR), the ataxia telangiectasia gene product (ATR), and the catalytic subunit of DNA-dependent protein kinase (DNA-PK). See generally, Hunter, Cell, 83:1-4 (1995).

PI 3-kinase also appears to be involved in a number of aspects of leukocyte activation. A p85-associated PI 3-kinase activity has been shown to physically associate with the cytoplasmic domain of CD28, which is an important costimulatory molecule for the activation of T-cells in response to antigen (Pages et al., Nature, 369:327-29 (1994); Rudd, Immunity, 4:527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., Science, 251:313-16 (1991)). Mutation of CD28 such that it can no longer interact with PI 3-kinase leads to a failure to initiate IL2 production, suggesting a critical role for PI 3-kinase in T cell activation.

Specific inhibitors against individual members of a family of enzymes provide invaluable tools for deciphering functions of each enzyme. Two compounds, LY294002 and wortmannin, have been widely used as PI 3-kinase inhibitors. These compounds, however, are nonspecific PI3K inhibitors, as they do not distinguish among the four members of Class I PI 3-kinases. For example, the $IC_{50}$ values of wortmannin against each of the various Class I PI 3-kinases are in the range of 1-10 nM. Similarly, the $IC_{50}$ values for LY294002 against each of these PI 3-kinases is about 1 μM (Fruman et al., Ann. Rev. Biochem., 67:481-507 (1998)). Hence, the utility of these compounds in studying the roles of individual Class I PI 3-kinases is limited.

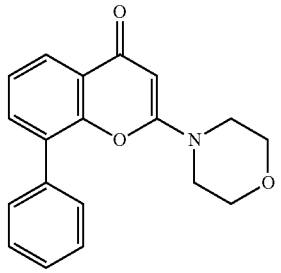

LY294002

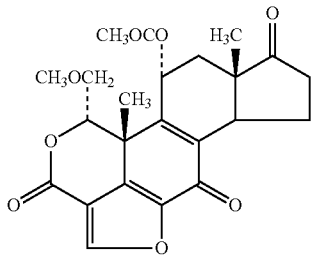

wortmannin

Based on studies using wortmannin, evidence exists that PI 3-kinase function also is required for some aspects of leukocyte signaling through G-protein coupled receptors (Thelen et al., Proc. Natl. Acad. Sci. USA, 91:4960-64 (1994)). Moreover, it has been shown that wortmannin and LY294002 block neutrophil migration and superoxide release. However, because these compounds do not distinguish among the various isoforms of PI3K, it remains unclear which particular PI3K isoform or isoforms are involved in these phenomena.

In view of the above considerations, it is clear that existing knowledge is lacking with respect to structural and functional features of the PI 3-kinase enzymes, including subcellular localization, activation states, substrate affinities, and the like. Moreover, the functions that these enzymes perform in both normal and diseased tissues remains to be elucidated. In particular, the function of PI3Kδ in leukocytes has not been characterized previously, and knowledge concerning its function in human physiology remains limited. The coexpression in these tissues of other PI3K isoforms has heretofore confounded efforts to segregate the activities of each enzyme. Furthermore, separation of the activities of the various PI3K isozymes may not be possible without identification of inhibitors that demonstrate selective inhibition characteristics. Indeed, applicants presently are not aware that such selective, or better, specific, inhibitors of PI3K isozymes have been demonstrated.

Thus, a need exists in the art for further structural characterization of the PI3Kδ polypeptide. A need also exists for functional characterization of PI3Kδ. Furthermore, understanding of PI3Kδ requires further elaboration of the structural interactions of p110δ, both with its regulatory subunit and with other proteins in the cell. A need also remains for selective or specific inhibitors of PI3K isozymes, such that the functions of each isozyme can be better characterized. In particular, selective or specific inhibitors of PI3Kδ are desirable for exploring the role of this isozyme and for development of pharmaceuticals to modulate activity of the isozyme.

SUMMARY OF THE INVENTION

One aspect of the present invention is to provide compounds capable of inhibiting the biological activity of human PI3Kδ. Another aspect of the present invention is to provide compounds that inhibit PI3Kδ selectively compared to the other PI3K isoforms. Still another aspect of the invention is to provide a method of selectively modulating human PI3Kδ activity, and thereby promote medical treatment of diseases mediated by PI3Kδ dysfunction. Yet another aspect of the invention is to provide a method of characterizing the function of human PI3Kδ.

Another aspect of the present invention is to provide a method of disrupting leukocyte function comprising contacting leukocytes with a compound that selectively inhibits phosphatidylinositol 3-kinase delta (PI3Kδ) activity in the leukocytes. The leukocytes can comprise cells selected from the group consisting of neutrophils, B lymphocytes, T lymphocytes, and basophils.

For example, in cases wherein the leukocytes comprise neutrophils, the method comprises disrupting at least one neutrophil function selected from the group consisting of stimulated superoxide release, stimulated exocytosis, and chemotactic migration. Preferably, the method does not substantially disrupt bacterial phagocytosis or bacterial killing by the neutrophils. In cases wherein the leukocytes comprise B lymphocytes, the method comprises disrupting proliferation of the B lymphocytes or antibody production by the B lymphocytes. In cases wherein the leukocytes comprise T lymphocytes, the method comprises disrupting proliferation of the T lymphocytes. In cases wherein the leukocytes comprise basophils, the method comprises disrupting histamine release by the basophils.

In the present method, it is preferred that the PI3Kδ inhibitor is selective. It is preferred that the PI3Kδ inhibitor is at least about 100-fold selective for inhibition of p110δ relative to p110α, at least about 40-fold selective relative to p110β, and at least about 10-fold selective relative to p110γ in a biochemical assay.

Compounds of the present invention are capable of inhibiting PI3Kδ activity and have a structural formula (I):

(I)

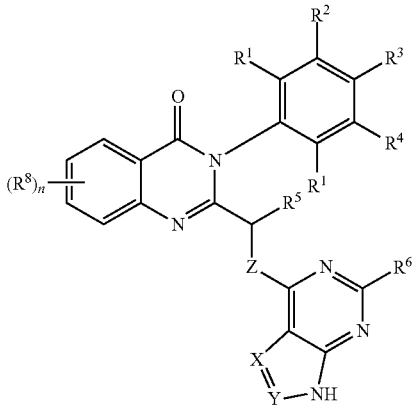

wherein

X and Y, independently, are N or $CR^c$;

Z is N—$R^7$ or O;

$R^1$ are the same and are hydrogen, halo, or $C_{1-3}$alkyl;

$R^2$ and $R^3$, independently, are hydrogen, halo, or $C_{1-3}$alkyl;

$R^4$ is hydrogen, halo, $OR^a$, CN, $C_{2-6}$alkynyl, $C(=O)R^a$, $C(=O)NR^aR^b$, $C_{3-6}$heterocycloalkyl, $C_{1-3}$alkylene$C_{3-6}$heterocycloalkyl, $OC_{1-3}$alkylene$OR^a$, $OC_{1-3}$alkylene$NR^aR^b$, $OC_{1-3}$alkylene$C_{3-6}$cycloalkyl, $OC_{3-6}$heterocycloalkyl, $OC_{1-3}$alkylene$C{\equiv}CH$, or $OC_{1-3}$alkylene$C(=O)NR^aR^b$;

$R^5$ is $C_{1-3}$alkyl, $CH_2CF_3$, phenyl, $CH_2C{\equiv}CH$, $C_{1-3}$alkylene$OR^e$, $C_{1-4}$alkylene$NR^aR^b$, or $C_{1-4}$alkylene$NHC(=O)OR^a$, $R^6$ is hydrogen, halo, or $NR^aR^b$;

$R^7$ is hydrogen or $R^5$ and $R^7$ are taken together with the atoms to which they are attached to form a five- or six-membered saturated ring;

$R^8$ is $C_{1-3}$alkyl, halo, $CF_3$, or $CH_2C_{3-6}$heterocycloalkyl;

n is 0, 1, or 2;

$R^a$ is hydrogen, $C_{1-4}$alkyl, or $CH_2C_6H_5$;

$R^b$ is hydrogen or $C_{1-3}$alkyl; and $R^c$ is hydrogen, $C_{1-3}$alkyl, or halo, wherein when the $R^1$ groups are different from hydrogen, $R^2$ and $R^4$ are the same;

or a pharmaceutically acceptable salt, or prodrug, or solvate (e.g., hydrate) thereof.

Another aspect of the present invention is to provide compounds of structural formula (II) and capable of inhibiting PI3Kδ activity:

(II)

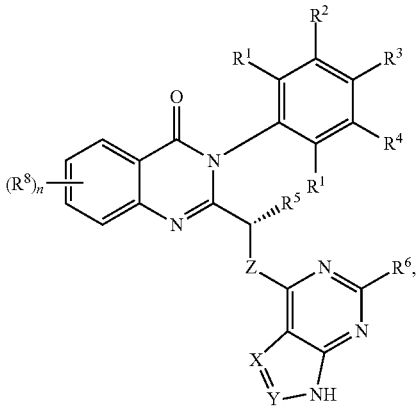

wherein X, Y, Z, $R^1$ through $R^8$, $R^a$, $R^b$, $R^c$, and n are as defined above, or a pharmaceutically acceptable salt, or prodrug, or solvate (e.g., hydrate) thereof.

Another aspect of the present invention is to provide a method of treating a medical condition mediated by neutrophils comprising administering to a mammal in need thereof a therapeutically effective amount of a compound of structural formulae (I) or (II). Exemplary medical conditions that can be treated according to the method include those conditions characterized by an undesirable neutrophil function selected from the group consisting of stimulated superoxide release, stimulated exocytosis, and chemotactic migration. Preferably, according to the method, phagocytic activity or bacterial killing by neutrophils is substantially uninhibited.

Still another aspect of the present invention is to provide a method of disrupting a function of osteoclasts comprising contacting osteoclasts with a compound of structural formulae (I) or (II).

Another aspect of the present invention is to provide a method of ameliorating a bone-resorption disorder in a mammal in need thereof comprising administering to the mammal a therapeutically effective amount of a compound of structural formulae (I) or (II). A preferred bone-resorption disorder amenable to treatment according to the method is osteoporosis.

Yet another aspect of the present invention is to provide a method of inhibiting the growth or proliferation of cancer cells of hematopoietic origin comprising contacting the cancer cells with a compound of structural formulae (I) or (II). The method can be advantageous in inhibiting the growth or proliferation of cancers selected from the group consisting of lymphomas, multiple myelomas, and leukemias.

Another aspect of the present invention is to provide a method of inhibiting kinase activity of a PI3Kδ polypeptide comprising contacting the PI3Kδ polypeptide with a compound of structural formulae (I) or (II).

Still another aspect of the present invention is to provide a method of disrupting leukocyte function comprising contacting leukocytes with a compound of structural formulae (I) or (II).

Another aspect of the present invention is to provide compounds of structural formulae (I) or (II) that inhibit PI3Kδ activity in biochemical and cell-based assays, and exhibit a therapeutic benefit in treating medical conditions wherein PI3Kδ activity is excessive or undesirable.

Another aspect of the present invention is to provide pharmaceutical compositions comprising one or more compounds of structural formulae (I) or (II), and use of the compositions in a therapeutic treatment, wherein inhibition of the PI3Kδ polypeptide, in vivo or ex vivo, provides a therapeutic benefit or is of research or diagnostic interest.

Another aspect of the present invention is to provide an article of manufacture for human pharmaceutical use comprising:

(a) a pharmaceutical composition comprising a compound of structural formulae (I) or (II); and, (b) a container, optionally further comprising a package insert providing that the composition is useful in the treatment of a disease or disorder mediated by PI3Kδ activity.

Another aspect of the present invention is to provide:

(a) pharmaceutical composition comprising a compound of structural formulae (I) or (II); and, (b) a container, optionally further comprising a package insert providing that the composition is useful in the treatment of a bone-resorption disorder or a cancer of a hematopoietic origin.

These and other aspects and advantages of the present invention will become apparent from the following detailed description of the preferred embodiments, which are provided to enhance the understanding of the invention without limiting the scope of the invention.

DETAILED DESCRIPTION OF THE PREFERRED EMBODIMENTS

The present invention provides compounds that selectively inhibit the activity of PI3Kδ. The present invention further provides methods of using the compounds for inhibiting PI3Kδ activity, including methods of selectively modulating the activity of the PI3Kδ isozyme in cells, especially leukocytes, osteoclasts, and cancer cells. The methods include in vitro, in vivo, and ex vivo applications.

Of particular benefit are methods of using the compounds of the invention for selectively modulating PI3Kδ activity in clinical settings to ameliorate diseases or disorders mediated by PI3Kδ activity. Thus, treatment of diseases or disorders characterized by excessive or inappropriate PI3Kδ activity can be treated through administration of selective modulators of PI3Kδ.

Moreover, the invention provides pharmaceutical compositions comprising a selective PI3Kδ inhibitor of structural formulae (I) or (II). Also provided are articles of manufacture comprising a selective PI3Kδ inhibitor compound (or a pharmaceutical composition comprising the compound) and instructions for using the compound. Other methods of the invention include enabling the further characterization of the physiological role of the isozyme.

The methods described herein benefit from the use of compounds that selectively inhibit, and preferably specifically inhibit, the activity of PI3Kδ in cells, including cells in vitro, in vivo, or ex vivo. Cells treated by methods of the present invention include those that express endogenous PI3Kδ, wherein endogenous indicates that the cells express PI3Kδ absent recombinant introduction into the cells of one or more polynucleotides encoding a PI3Kδ polypeptide or a biologically active fragment thereof. The present methods also encompass use of cells that express exogenous PI3Kδ, wherein one or more polynucleotides encoding PI3Kδ or a biologically active fragment thereof have been introduced into the cell using recombinant procedures.

The cells can be in vivo, i.e., in a living subject, e.g., a mammal, including humans, wherein a PI3Kδ inhibitor can be used therapeutically to inhibit PI3Kδ activity in the subject. Alternatively, the cells can be isolated as discrete cells or in a tissue, for ex vivo or in vitro methods. In vitro methods encompassed by the invention can comprise the step of contacting a PI3Kδ enzyme or a biologically active fragment thereof with an inhibitor compound of the invention. The PI3Kδ enzyme can include a purified and isolated enzyme, wherein the enzyme is isolated from a natural source (e.g., cells or tissues that normally express a PI3Kδ polypeptide absent modification by recombinant technology) or isolated from cells modified by recombinant techniques to express exogenous enzyme.

Compounds of the invention potently inhibit p110δ. Potency typically is expressed as the concentration of a compound required to achieve a certain result. The greater the potency, the less compound required to perform its intended function. In vitro potency typically is expressed in terms of $IC_{50}$ values measured using a dose-response assay. $IC_{50}$ values can be measured by contacting a sensitive assay system with a compound of interest over a range of concentrations, including concentrations at which no or minimal effect is observed, through higher concentrations at which partial effect is observed, to saturating concentrations at which a maximum effect is observed. Theoretically, such assays of the dose-response effect of inhibitor compounds can be described as a sigmoidal curve expressing a degree of inhibition as a function of concentration when plotted on a log scale. The curve also theoretically passes through a point at which the concentration is sufficient to reduce activity of the p110δ enzyme to a level that is 50% that of the difference between minimal and maximal enzyme activity observed in the assay. This concentration is defined as the Inhibitory Concentration at 50% inhibition or $IC_{50}$ value.

$IC_{50}$ values can be determined using either conventional biochemical (acellular) assay techniques or cell-based assay techniques well known to those of ordinary skill in the art. An example of such an assay is provided in the examples below. Preferably, $IC_{50}$ values are obtained by performing the relevant assay at least twice, with the $IC_{50}$ value expressed as the average (arithmetic means, or "mean") of the individual values obtained. More preferably, the assay is repeated from 3 to 10 (or more) times, with the $IC_{50}$ value expressed as the mean of the values obtained. Still more preferably, the assay is performed a number of times sufficient to generate a statistically reliable mean $IC_{50}$ value, using statistical methods known to those of ordinary skill in the art.

Compounds of formulae (I) and (II) exhibit unexpectedly low $IC_{50}$ values relative to PI3Kδ, corresponding to unexpectedly high in vitro potency. In various embodiments, compounds of formulae (I) and (II), when assayed as described in Example 14 below, exhibit PI3Kδ $IC_{50}$ values of less than about 250 nM, less than about 200 nM, less than about 150 nM, less than about 125 nM, less than about 100 nM, less than about 75 nM, less than about 50 nM, less than about 25 nM, less than about 10 nM, and in others less than about 5 nM. In other embodiments, the compounds of the invention exhibit $IC_{50}$ values from about 0.1 nM to about 5 nM.

The compounds of formulae (I) and (II) are selective PI3Kδ inhibitors. The term "selective PI3Kδ inhibitor" as used herein refers to a compound that inhibits the PI3Kδ isozyme more effectively than other isozymes of the PI3K family. A "selective PI3Kδ inhibitor" compound is understood to be more selective for PI3Kδ than compounds conventionally and generically designated PI3K inhibitors, e.g., wortmannin or LY294002. Concomitantly, wortmannin and LY294002 are deemed "nonselective PI3K inhibitors." Moreover, compounds of the present invention selectively negatively regulate PI3Kδ expression or activity and possess acceptable pharmacological properties for use in the therapeutic methods of the invention.

Accordingly, a selective inhibitor alternatively can be understood to refer to at least one compound that exhibits a 50% inhibitory concentration ($IC_{50}$) with respect to PI3Kδ that is at least about 50-fold, at least about 100-fold, at least about 150-fold, at least about 200-fold, at least about 250-fold, at least about 300-fold, at least about 350-fold, at least about 400-fold, at least about 500-fold, at least about 600-fold, at least about 700-fold, at least about 800-fold, at least about 900-fold, or at least about 1000-fold lower than the $IC_{50}$ value for PI3Kα. In alternative embodiments, the term selective inhibitor can be understood to refer to at least one compound that exhibits an $IC_{50}$ with respect to PI3Kδ that is at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold lower than the $IC_{50}$ for PI3Kγ. In further embodiments, the term selective inhibitor can be understood to refer to at least one compound that exhibits an $IC_{50}$ with respect to PI3Kδ that is at least about 5-fold, at least about 10-fold, at least about 20-fold, at least about 30-fold, at least about 40-fold, at least about 50-fold, at least about 75-fold, at least about 100-fold, at least about 125-fold, at least about 150-fold, at least about 175-fold, at least about 200-fold, at least about 250-fold, at least about 300-fold, or at least about 350-fold lower than the $IC_{50}$ for PI3Kβ. The selective inhibitors are typically administered in an amount such that they selectively inhibit PI3Kδ, as described above.

The most preferred compounds of the present invention, therefore, have a low $IC_{50}$ value vs. PI3Kδ (i.e., the compound is a potent inhibitor), and are selective with respect to inhibiting PI3Kδ relative to at least one of PI3Kα, PI3Kβ, and PI3Kγ.

"In vivo" means within a living subject, as within an animal or human. In this context, agents can be used therapeutically in vivo to retard or eliminate the proliferation of aberrantly replicating cells. The agents also can be used in vivo as a prophylactic to prevent aberrant cell proliferation or the manifestation of symptoms associated therewith.

"Ex vivo" means outside a living subject. Examples of ex vivo cell populations include cell cultures and biological samples such as fluid or tissue samples from humans or animals. Such samples can be obtained by methods well known in the art. Exemplary biological fluid samples include blood, cerebrospinal fluid, urine, saliva. Exemplary tissue samples include tumors and biopsies. In this context, the present compounds can be in numerous applications, both therapeutic and experimental.

The term "container" means any receptacle and closure therefor suitable for storing, shipping, dispensing, and/or handling a pharmaceutical product.

The term "package insert" means information accompanying the product that provides a description of how to administer the product, along with the safety and efficacy data required to allow the physician, pharmacist, or patient to make an informed decision regarding use of the product. For a pharmaceutical product approved for use in humans or animals, the approving authority may specify the content of the package insert, and such a package insert may be referred to informally as the "label" for the product. as the "label" for the product.

In one embodiment, the present invention provides a method of inhibiting leukocyte function. More particularly, the present invention provides methods of inhibiting or suppressing functions of neutrophils and T and B lymphocytes. With respect to neutrophils, it unexpectedly has been found that inhibition of PI3Kδ activity inhibits functions of neutrophils. For example, it has been observed that the compounds of the present invention elicit inhibition of classical neutrophil functions, such as stimulated superoxide production, stimulated exocytosis, and chemotactic migration. However, it further has been observed that a method of the present invention permits suppression of certain functions of neutrophils, while not substantially affecting other functions of these cells. For example, it has been observed that phagocytosis of bacteria by neutrophils is not substantially inhibited by the selective PI3Kδ inhibitor compounds of the present invention.

Thus, the present invention includes methods of inhibiting neutrophil functions, without substantially inhibiting phagocytosis of bacteria. Neutrophil functions suitable for inhibition according to the present method include any function mediated by PI3Kδ activity or expression. Such functions include, without limitation, stimulated superoxide release, stimulated exocytosis or degranulation, chemotactic migration, adhesion to vascular endothelium (e.g., tethering/rolling of neutrophils, triggering of neutrophil activity, and/or latching of neutrophils to endothelium), transmural diapedesis, or emigration through the endothelium to peripheral tissues. In general, these functions can be collectively termed "inflammatory functions," as they are typically related to neutrophil response to inflammation. The inflammatory functions of neutrophils can be distinguished from the bacterial killing functions exhibited by these cells, e.g., phagocytosis and killing of bacteria. Accordingly, the present invention further includes methods of treating disease states in which one or more of the inflammatory functions of neutrophils are abnormal or undesirable.

The compounds of the present invention may be used to inhibit an endogenous immune response stimulated by at least one endogenous factor without substantially inhibiting an exogenous immune response stimulated by at least one exogenous factor as disclosed in US 2005/0043239 A1, which is incorporated herein by reference. The compounds of the present invention may also be used to inhibit an endogenous immune response stimulated by at least one endogenous factor without substantially inhibiting immune responsiveness, as disclosed in US 2005/0043239 A1. Accordingly, the compounds of the invention advantageously permit treatment of conditions associated with an undesirable endogenous immune response stimulated by at least one endogenous factor without compromising the ability to fight infection.

The compounds of the present invention may also be used to inhibit leukocyte accumulation as disclosed in US 2005/0054614 A1. The compounds may also be used to inhibit leukocyte tethering to endothelial cells and to inhibit leukocyte transmigration into inflamed tissue, as disclosed in US 2005/0043239 A1. Accordingly, the compounds of the invention advantageously permit treatment of individuals having an inflammatory condition where leukocytes are found to be accumulating at the site of insult or inflamed tissue.

It further has been established that PI3Kδ plays a role in the stimulated proliferation of lymphocytes, including B cells and T cells. Moreover, PI3Kδ appears to play a role in stimulated secretion of antibodies by B cells. Selective PI3Kδ inhibitor compounds of the present invention have been employed to establish that these phenomena can be abrogated by inhibition of PI3Kδ. Thus, the present invention includes methods of using compounds of structural formulae (I) or (II) for inhibiting lymphocyte proliferation, or for inhibiting antibody production by B lymphocytes. Other methods enabled by the present invention include methods of treating disease states in which one or more of these lymphocyte functions are abnormal or undesirable.

The methods of this invention can be practiced using compounds of structural formulae (I) or (II). The methods can be practiced using a racemic mixture of the compounds or a specific enantiomer. In preferred embodiments, the S-enantiomer of the compounds are utilized in the present methods.

The methods can be practiced using, for example, the following compounds of the invention, but the invention is not limited to these compounds. Exemplary compounds include 5-methyl-3-phenyl-2-[1-(9H-purin-6-ylamino)-propyl]-3H-quinazolin-4-one; 2-[1-(2-fluoro-9H-purin-6-ylamino)-ethyl]-5-methyl-3-phenyl-3H-quinazolin-4-one; 3-(2,6-difluoro-phenyl)-5-methyl-2-[1-(9H-purin-6-ylamino)-ethyl]-3H-quinazolin-4-one; 2-[1-(2-amino-9H-purin-6-ylamino)-ethyl]-3-(2,6-difluoro-phenyl)-5-methyl-3H-quinazolin-4-one; 3-(2,6-difluoro-phenyl)-2-[1-(2-fluoro-9H-purin-6-ylamino)-ethyl]-5-methyl-3H-quinazolin-4-one; 3-(2,6-difluoro-phenyl)-5-methyl-2-[1-(7H-pyrrolo[2,3-d]pyrimidin-4-ylamino)-ethyl]-3H-quinazolin-4-one; 2-[1-(2-amino-9H-purin-6-ylamino)-propyl]-5-methyl-3-phenyl-3H-quinazolin-4-one; 5-methyl-3-phenyl-2-[1-(7H-pyrrolo[2,3-d]pyrimidin-4-ylamino)-propyl]-3H-quinazolin-4-one; 2-[1-(2-fluoro-9h-purin-6-ylamino)-propyl]-5-methyl-3-phenyl-3h-quinazolin-4-one; 5-methyl-3-phenyl-2-[1-(9H-purin-6-ylamino)-ethyl]-3H-quinazolin-4-one; 2-[1-(2-amino-9H-purin-6-ylamino)-ethyl]-5-methyl-3-phenyl-3H-quinazolin-4-one; 2-[2-benzyloxy-1-(9H-purin-6-ylamino)-ethyl]-5-methyl-3-phenyl-3H-quinazolin-4-one; 2-[1-(2-amino-9H-purin-6-ylamino)-2-benzyloxy-ethyl]-5-methyl-3-phenyl-3H-quinazolin-4-one; 2-[2-benzyloxy-1-(7H-pyrrolo[2,3-d]pyrimidin-4-ylamino)-ethyl]-5-methyl-3-phenyl-3H-quinazolin-4-one; 2-[2-benzyloxy-1-(2-fluoro-9H-purin-6-ylamino)-ethyl]-5-methyl-3-phenyl-3H-quinazolin-4-one; 3-(4-fluoro-phenyl)-5-methyl-2-[1-(9H-purin-6-ylamino)-ethyl]-3H-quinazolin-4-one; 2-[1-(2-amino-9H-purin-6-ylamino)-ethyl]-3-(4-fluoro-phenyl)-5-methyl-3H-quinazolin-4-one; 3-(4-fluoro-phenyl)-2-[1-(2-fluoro-9H-purin-6-ylamino)-ethyl]-5-methyl-3H-quinazolin-4-one; 3-(4-fluoro-phenyl)-5-methyl-2-[1-(7H-pyrrolo[2,3-d]pyrimidin-4-ylamino)-ethyl]-3H-quinazolin-4-one; 5-methyl-3-phenyl-2-[1-(7H-pyrrolo[2,3-d]pyrimidin-4-ylamino)-ethyl]-3H-quinazolin-4-one; 3-(3-fluoro-phenyl)-5-methyl-2-[1-(9H-purin-6-ylamino)-ethyl]-3H-quinazolin-4-one; 2-[1-(2-amino-9H-purin-6-ylamino)-ethyl]-3-(3-fluoro-phenyl)-5-methyl-3H-quinazolin-4-one; 3-(3-fluoro-phenyl)-5-methyl-2-[1-(7H-pyrrolo[2,3-d]pyrimidin-4-ylamino)-ethyl]-3H-quinazolin-4-one; 5-methyl-3-phenyl-2-[1-(9H-purin-6-yl)-pyrrolidin-2-yl]-3H-quinazolin-4-one; 2-[2-hydroxy-1-(9H-purin-6-ylamino)-ethyl]-5-methyl-3-phenyl-3H-quinazolin-4-one; 5-methyl-3-phenyl-2-[phenyl-(9H-purin-6-ylamino)-methyl]-3H-quinazolin-4-one; 2-[(2-amino-9H-purin-6-ylamino)-phenyl-methyl]-5-methyl-3-phenyl-3H-quinazolin-4-one; 2-[(2-fluoro-9H-purin-6-ylamino)-phenyl-methyl]-5-methyl-3-phenyl-3H-quinazolin-4-one; 5-methyl-3-phenyl-2-[phenyl-(7H-pyrrolo[2,3-d]pyrimidin-4-ylamino)-methyl]-3H-quinazolin-4-one; 5-fluoro-3-phenyl-2-[1-(9H-purin-6-ylamino)-ethyl]-3H-quinazolin-4-one; 2-[1-(2-amino-9H-purin-6-ylamino)-ethyl]-5-fluoro-3-phenyl-3H-quinazolin-4-one; 2-[1-(2-amino-9H-purin-6-ylamino)-ethyl]-5-chloro-3-phenyl-3H-quinazolin-4-one; [5-(5-methyl-4-oxo-3-phenyl-3,4-dihydro-quinazolin-2-yl)-5-(9H-purin-6-ylamino)-pentyl]-carbamic acid benzyl ester; [5-(2-amino-9H-purin-6-ylamino)-5-(5-methyl-4-oxo-3-phenyl-3,4-dihydro-quinazolin-2-yl)-pentyl]-carbamic acid benzyl ester; [4-(5-methyl-4-oxo-3-phenyl-3,4-dihydro-quinazolin-2-yl)-4-(9H-purin-6-ylamino)-butyl]-carbamic acid benzyl ester; [4-(2-amino-9H-purin-6-ylamino)-4-(5-methyl-4-oxo-3-phenyl-3,4-dihydro-quinazolin-2-yl)-butyl]-carbamic acid benzyl ester; 3-phenyl-2-[1-(9H-purin-6-ylamino)-ethyl]-3H-quinazolin-4-one; 2-[5-amino-1-(9H-purin-6-ylamino)-pentyl]-5-methyl-3-phenyl-3H-quinazolin-4-one); 2-[5-amino-1-(2-amino-9H-purin-6-ylamino)-pentyl]-5-methyl-3-phenyl-3H-quinazolin-4-one; 2-[1-(2-amino-9H-purin-6-ylamino)-ethyl]-3-(2,6-Dimethyl-phenyl)-5-methyl-3H-quinazolin-4-one; 3-(2,6-dimethyl-phenyl)-5-methyl-2-[1-(9H-purin-6-ylamino)-ethyl]-3H-quinazolin-4-one; 5-morpholin-4-ylmethyl-3-phenyl-2-[1-(9H-purin-6-ylamino)-ethyl]-3H-quinazolin-4-one; 2-[1-(2-amino-9H-purin-6-ylamino)-ethyl]-5-morpholin-4ylmethyl-3-phenyl-3H-quinazolin-4-one; 2-[4-amino-1-(2-amino-9H-purin-6-ylamino)-butyl]-5-methyl-3-phenyl-3H-quinazolin-4-one; 6-fluoro-3-phenyl-2-[1-(9H-purin-6-ylamino)-ethyl]-3H-quinazolin-4-one; 2-[1-(2-amino-9H-purin-6-ylamino)-ethyl]-6-fluoro-3-phenyl-3H-quinazolin-4-one; 2-[2-tert-butoxy-1-(9H-purin-6-ylamino)-ethyl]-5-methyl-3-phenyl-3H-quinazolin-4-one; 3-(3-methyl-phenyl)-5-methyl-2-[1-(9H-purin-6-ylamino)-ethyl]-3H-quinazolin-4-one; 2-[1-(2-amino-9H-purin-6-ylamino)-ethyl]-3-(3-methyl-phenyl)-5-methyl-3H-quinazolin-4-one; 3-(3-chloro-phenyl)-5-methyl-2-[1-(9H-purin-6-ylamino)-ethyl]-3H-quinazolin-4-one; 2-[1-(2-amino-9H-purin-6-ylamino)-ethyl]-3-(3-chloro-phenyl)-5-methyl-3H-quinazolin-4-one; 2-[1-(2-amino-9H-purin-6-ylamino)-2-hydroxy-ethyl]-5-methyl-3-phenyl-3H-quinazolin-4-one; 2-[1-(2-amino-9H-purin-6-ylamino)-ethyl]-3-(3-fluoro-phenyl)-3H-quinazolin-4-one; 2-[1-(2-amino-9H-purin-6-ylamino)-ethyl]-3-(2,6-difluoro-phenyl)-3H-quinazolin-4-one; 2-[1-(2-amino-9H-purin-6-ylamino)-propyl]-5-fluoro-3-phenyl-3H-quinazolin-4-one; 5-chloro-3-(3-fluoro-phenyl)-2-[1-(9H-purin-6-ylamino)-ethyl]-3H-quinazolin-4-one; 2-[1-(2-amino-9H-purin-6-ylamino)-ethyl]-5-chloro-3-(3-fluoro-phenyl)-3H-quinazolin-4-one; 3-phenyl-2-[1-(9H-purin-6-ylamino)-ethyl]-5-trifluoromethyl-3H-quinazolin-4-one; 3-(2,6-difluoro-phenyl)-5-methyl-2-[1-(9H-purin-6-ylamino)-propyl]-3H-quinazolin-4-one; 3-(2,6-difluoro-phenyl)-5-methyl-2-[1-(9H-purin-6-ylamino)-ethyl]-3H-quinazolin-4-one; 2-[1-(2-amino-9H-purin-6-ylamino)-propyl]-3-(2,6-difluoro-phenyl)-5-methyl-3H-quinazolin-4-one; 2-[1-(2-amino-9H-purin-6-ylamino)-ethyl]-3-(2,6-difluoro-phenyl)-5-methyl-3H-quinazolin-4-one; 3-(3,5-dichloro-phenyl)-5-methyl-2-[1-(9H-purin-6-ylamino)-ethyl]-3H-quinazolin-4-one; 3-(2,6-dichloro-phenyl)-5-methyl-2-[1-(9H-purin-6-ylamino)-ethyl]-3H-quinazolin-4-one; 2-[1-(2-amino-9H-purin-6-ylamino)-ethyl]-3-(2,6-dichloro-phenyl)-5-methyl-3H-quinazolin-4-one; 5-chloro-3-phenyl-2-[1-(9H-purin-6-ylamino)-propyl]-3H-quinazolin-4-one; 2-[1-(2-amino-9H-purin-6-ylamino)-propyl]-5-chloro-3-phenyl-3H-quinazolin-4-one; 5-methyl-3-phenyl-2-[1-(9H-purin-6-ylamino)-butyl]-3H-quinazolin-4-one; 2-[1-(2-amino-9H-purin-6-ylamino)-butyl]-5-methyl-3-phenyl-3H-quinazolin-4-one; 2-[1-(2-amino-9H-purin-6-ylamino)-ethyl]-3-(3,5-dichloro-phenyl)-5-methyl-3H-quinazolin-4-one; 5-methyl-3-(3-morpholin-4-ylmethyl-phenyl)-2-[1-(9H-purin-6-ylamino)-ethyl]-3H-quinazolin-4-one; 2-[1-(2-amino-9H-purin-6-ylamino)-ethyl]-5-methyl-3-(3-morpholin-4-ylmethyl-phenyl)-3H-quinazolin-4-one; 2-[1-(5-bromo-7H-pyrrolo[2,3-d]pyrimidin-4-ylamino)-ethyl]-5-methyl-3-phenyl-3H-quinazolin-4-one; 5-methyl-2-[1-(5-methyl-7H-pyrrolo[2,3-d]pyrimidin-4-ylamino)-ethyl]-3-phenyl-3H-quinazolin-4-one; 2-[1-(5-fluoro-7H-pyrrolo[2,3-d]pyrimidin-4-ylamino)-ethyl]-5-methyl-3-phenyl-3H-quinazolin-4-one; 2-[2-hydroxy-1-(9H-purin-6-ylamino)-ethyl]-3-phenyl-3H-quinazolin-4-one; 3-(3,5-difluoro-phenyl)-5-methyl-2-[1-(9H-purin-6-ylamino)-propyl]-3H-quinazolin-4-one; 2-[1-(2-amino-9H-purin-6-ylamino)-propyl]-3-(3,5-difluoro-phenyl)-5-methyl-3H-quinazolin-4-one; 3-(3,5-difluoro-phenyl)-2-[1-(9H-purin-6-ylamino)-ethyl]-3H-quinazolin-4-one; 2-[1-(5-bromo-7H-pyrrolo[2,3-d]pyrimidin-4-ylamino)-ethyl]-3-(3-fluoro-phenyl)-5-methyl-3H-quinazolin-4-one; 3-(3-fluoro-phenyl)-5-methyl-2-[1-(5-methyl-7H-pyrrolo[2,3-d]pyrimidin-4-ylamino)-ethyl]-3H-quinazolin-4-one; 3-phenyl-2-[1-(9H-purin-6-ylamino)-propyl]-3H-quinazolin-4-one; 2-[1-(2-amino-9H-purin-6-ylamino)-ethyl]-3-(3,5-difluoro-phenyl)-3H-quinazolin-4-one; 2-[1-(2-amino-9H-purin-6-ylamino)-propyl]-3-phenyl-3H-quinazolin-4-one; 6,7-difluoro-3-phenyl-2-[1-(9H-purin-6-ylamino)-ethyl]-3H-quinazolin-4-one; 6-fluoro-3-(3-fluoro-phenyl)-2-[1-(9H-purin-6-ylamino)-ethyl]-3H-quinazolin-4-one; 2-[4-diethylamino-1-(9H-purin-6-ylamino)-butyl]-5-methyl-3-phenyl-3H-quinazolin-4-one; 5-fluoro-3-phenyl-2-[1-(9H-purin-6-ylamino)-propyl]-3H-quinazolin-4-one; 3-phenyl-2-[1-(9H-purin-6-ylamino)-ethyl]-3H-quinazolin-4-one; 6-fluoro-3-phenyl-2-[1-(9H-purin-6-ylamino)-ethyl]-3H-quinazolin-4-one; 3-(3,5-difluoro-phenyl)-5-methyl-2-[1-(9H-purin-6-ylamino)-ethyl]-3H-quinazolin-4-one; 5-fluoro-2-[1-(2-fluoro-9H-purin-6-ylamino)-ethyl]-3-phenyl-3H-quinazolin-4-one; 3-(3-fluoro-phenyl)-2-[1-(9H-purin-6-ylamino)-ethyl]-3H-quinazolin-4-one; 5-chloro-3-(3,5-difluoro-phenyl)-2-[1-(9H-purin-6-ylamino)-propyl]-3H-quinazolin-4-one; 3-(2,6-difluoro-phenyl)-5-methyl-2-[1-(9H-purin-6-ylamino)-ethyl]-3H-quinazolin-4-one; 3-(2,6-difluoro-phenyl)-2-[1-(9H-purin-6-ylamino)-ethyl]-3H-quinazolin-4-one; 5-Methyl-3-phenyl-2-[3,3,3-trifluoro-1-(9H-purin-6-ylamino)-propyl]-3H-quinazolin-4-one; 3-(3-hydroxy-phenyl)-5-methyl-2-[1-(9H-purin-6-ylamino)-ethyl]-3H-quinazolin-4-one; 3-(3-methoxy-phenyl)-5-methyl-2-{1-[9H-purin-6-ylamino]-ethyl}-3H-quinazolin-4-one; 3-[3-(2-dimethylamino-ethoxy)-phenyl]-5-methyl-2-{1-[9H-purin-6-ylamino]-ethyl}-3H-quinazolin-4-one; 3-(3-cyclopropylmethoxy-phenyl)-5-methyl-2-{1-[9H-purin-6-ylamino]-ethyl}-3H-quinazolin-4-one; 5-methyl-3-(3-prop-2-ynyloxy-phenyl)-2-{1-[9H-purin-6-ylamino]-ethyl}-3H-quinazolin-4-one; 2-{1-[2-amino-9H-purin-6-ylamino]ethyl}-3-(3-hydroxyphenyl)-5-methyl-3H-quinazolin-4-one; 2-{1-[2-amino-9H-purin-6-ylamino]ethyl}-3-(3-methoxyphenyl)-5-methyl-3H-quinazolin-4-one; 2-{1-[2-amino-9H-purin-6-ylamino]ethyl}-3-(3-cyclopropylmethoxy-phenyl)-5-methyl-3H-quinazolin-4-one; 2-{1-[2-amino-9H-purin-6-ylamino]ethyl}-5-methyl-3-(3-prop-2-ynyloxy-phenyl)-3H-quinazolin-4-one; 3-(3-ethynyl-phenyl)-5-methyl-2-[1-(9H-purin-6-ylamino)-ethyl]-3H-quinazolin-4-one; 3-{5-methyl-4-oxo-2-[1-(9H-purin-6-ylamino)-ethyl]-4H-quinazolin-3-yl}-benzonitrile; 3-{5-methyl-4-oxo-2-{1-[9H-purin-6-ylamino)-ethyl]-4H-quinazolin-3-yl}-benzamide; 3-(3-acetyl-phenyl)-5-methyl-2-{1-[9H-purin-6-ylamino]-ethyl}-3H-quinazolin-4-one; 2-(3-(5-methyl-4-oxo-2-{1-[9H-purin-6-ylamino]-ethyl}-4H-quinazolin-3-yl-phenoxy acetamide; 5-methyl-2-{1-[9H-purin-6-ylamino]-ethyl}-3-[3-(tetrahydropuran-4-yloxy)-phenyl]-3H-quinazolin-4-one; 3-[3-(2-methoxy-ethoxy)-phenyl]-5-methyl-2-[1-(9H-purin-6-ylamino)-ethyl]-3H-quinazolin-4-one; 6-fluoro-2-[1-(9H-purin-6-ylamino)ethyl]-3-[3-(tetrahydro-pyran-4-yloxy)-phenyl]-3H-quinazolin-4-one; 3-[3-(3-dimethylamino-propoxy)-phenyl]-5-methyl-2-[1-(9H-purin-6-ylamino)-ethyl]-3H-quinazolin-4-one; 2-[1-(2-amino-9H-purin-6-ylamino)-ethyl]-3-(3-ethynyl-phenyl)-5-methyl-3H-quinazolin-4-one; 3-{2-[1-(2-amino-9H-purin-6-ylamino)-ethyl]-5-methyl-4-oxo-4H-quinazolin-3-yl}-benzonitrile; 3-{2-[1-(2-amino-9H-purin-6-ylamino)-ethyl]-5-methyl-4-oxo-4H-quinazolin-3-yl}-benzamide; 3-{2-[1-(2-amino-9H-purin-6-ylamino)-ethyl]-5-methyl-4-oxo-4H-quinazolin-3-yl}-benzamide; 5-methyl-3-(3-morpholin-4-yl-phenyl)-2-[1-(9H-purin-6-ylamino)-ethyl]-3H-quinazolin-4-one; 2-[1-(2-amino-9H-purin-6-ylamino)-ethyl]-5-methyl-3-(3-morpholin-4-yl-phenyl)-3H-quinazolin-4-one; 2-[1-(2-amino-9H-purin-6-ylamino)-ethyl]-3-[3-(2-methoxy-ethoxy)-phenyl]-5-methyl-3H-quinazolin-4-one; 2-[1-(2-amino-9H-purin-6-ylamino)-ethyl]-3-[3-(2-dimethylamino-ethoxy)-phenyl]-5-methyl-3H-quinazolin-4-one; 2-[1-(2-amino-9H-purin-6-ylamino)-but-3-ynyl]-5-methyl-3-phenyl-3H-quinazolin-4-one; 2-[1-(2-amino-9H-purin-6-ylamino)-but-3-ynyl]-5-methyl-3-phenyl-3H-quinazolin-4-one; 5-chloro-3-(3,5-difluoro-phenyl)-2-[1-(9H-purin-6-ylamino)-ethyl]-3H-quinazolin-4-one; 2-[1-(2-amino-9H-purin-6-ylamino)-propyl]-5-chloro-3-(3,5-difluoro-phenyl)-3H-quinazolin-4-one; 2-[1-(2-amino-9H-purin-6-ylamino)-ethyl]-5-chloro-3-(3,5-difluoro-phenyl)-3H-quinazolin-4-one; 3-(3,5-difluoro-phenyl)-6-fluoro-2-[1-(9H-purin-6-ylamino)-ethyl]-3H-quinazolin-4-one; 5-chloro-3-(2,6-difluoro-phenyl)-2-[1-(9H-purin-6-ylamino)-propyl]-3H-quinazolin-4-one; 2-[1-(2-amino-9H-purin-6-ylamino)-propyl]-5-chloro-3-(2,6-difluoro-phenyl)-3H-quinazolin-4-one; 5-methyl-3-phenyl-2-[1-(9H-purin-6-yloxy)-ethyl]-3H-quinazolin-4-one.

The methods of the invention can be practiced using compounds that exhibit PI3Kδ inhibitory activity. In particular, the methods of the invention can be practiced using compounds having the general structural formula (I):

(I)

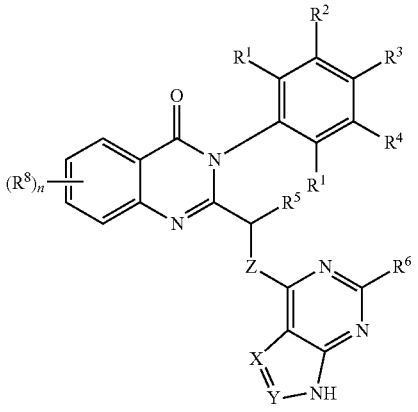

wherein

X and Y, independently, are N or CRC;

Z is N—$R^7$ or O;

$R^1$ are the same and are hydrogen, halo, or $C_{1-3}$alkyl;

$R^2$ and $R^3$, independently, are hydrogen, halo, or $C_{1-3}$alkyl;

$R^4$ is hydrogen, halo, $OR^a$, CN, $C_{2-6}$alkynyl, C(═O)$R^a$, C(═O)$NR^aR^b$, $C_{3-6}$heterocycloalkyl, $C_{1-3}$alkylene$C_{3-6}$heterocycloalkyl, $OC_{1-3}$alkylene$OR^a$, $OC_{1-3}$alkylene$NR^aR^b$, $OC_{1-3}$alkylene$C_{3-6}$cycloalkyl, $OC_{3-6}$heterocycloalkyl, $OC_{1-3}$alkyleneC═CH, or $OC_{1-3}$alkyleneC(═O)$NR^aR^b$;

$R^5$ is $C_{1-3}$alkyl, $CH_2CF_3$, phenyl, $CH_2$C═CH, $C_{1-3}$alkylene$OR^e$, $C_{1-4}$alkylene$NR^aR^b$, or $C_{1-4}$alkyleneNHC(═O)$OR^a$, $R^6$ is hydrogen, halo, or $NR^aR^b$;

$R^7$ is hydrogen or $R^5$ and $R^7$ are taken together with the atoms to which they are attached to form a five- or six-membered saturated ring;

$R^8$ is $C_{1-3}$alkyl, halo, $CF_3$, or $CH_2C_{3-6}$heterocycloalkyl;

n is 0, 1, or 2;

$R^a$ is hydrogen, $C_{1-4}$alkyl, or $CH_2C_6H_5$;

$R^b$ is hydrogen or $C_{1-3}$alkyl; and $R^c$ is hydrogen, $C_{1-3}$alkyl, or halo, wherein when the $R^1$ groups are different from hydrogen, $R^2$ and $R^4$ are the same;

or a pharmaceutically acceptable salt, or prodrug, or solvate (e.g., hydrate) thereof.

Compounds of the present invention are selective inhibitors of PI3Kδ activity. The compounds exhibit inhibition of PI3Kδ in biochemical assays, and selectively disrupt function of PI3Kδ-expressing cells in cell-based assays. As described herein, the present compounds have demonstrated an ability to inhibit certain functions in neutrophils and other leukocytes, as well as functions of osteoclasts.

In general, compounds of the present invention have the general structural formulae (I) or (II), or a pharmaceutically acceptable salt thereof, or prodrug, or solvate thereof:

(I)

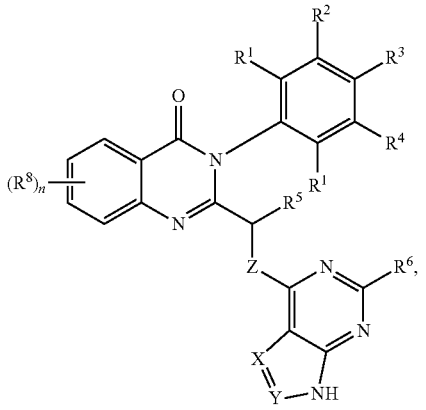

-continued (II)

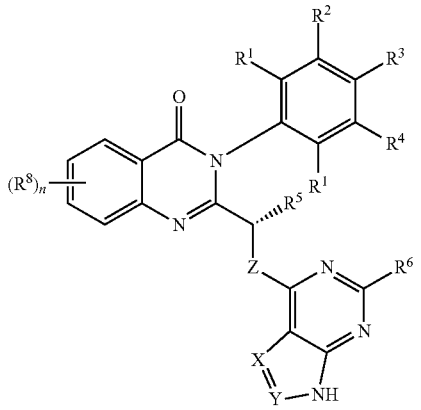

wherein X, Y, Z, $R^1$ through $R^8$, $R^a$, $R^b$, $R^c$, and n are as defined above.

In various embodiments exhibiting increased potency relative to other compounds in accordance with the invention, $R^8$ is $C_{1-3}$alkyl, F, Cl, or $CF_3$. Alternatively, in such embodiments, n is 0 (such that there is no $R^8$ substituent).

In other embodiments exhibiting such increased potency, X and Y, independently, are N or CH. In further embodiment exhibiting increased potency, X is N and Y is CH. Alternatively, X and Y may also both be CH. In further embodiments exhibiting increased potency, $R^6$ is hydrogen, halo, or $NH_2$.

Unexpectedly, potency against PI3Kδ is conserved when $R^1$ is the same. In structural formulae (I) and (II), $R^2$ and $R^4$ may differ provided that $R^1$ is H. When $R^1$ is H, free rotation is unexpectedly permitted about the bond connecting the phenyl ring substituent to the quinazoline ring, and the compounds advantageously do not exhibit atropisomerism (i.e., multiple diasteromer formation is avoided). Alternatively, $R^2$ and $R^4$ can be the same such that the compounds advantageously do not exhibit atropisomerism.

As used herein, the term "alkyl" is defined as straight chained and branched hydrocarbon groups containing the indicated number of carbon atoms, e.g., methyl, ethyl, and straight chain and branched propyl and butyl groups.

The terms "$C_{1-3}$alkylene" and "$C_{1-4}$alkylene" are defined as hydrocarbon groups containing the indicated number of carbon atoms and one less hydrogen than the corresponding alkyl group.

The term "$C_{2-6}$alkynyl" is defined as a hydrocarbon group containing the indicated number of carbon atoms and a carbon-carbon triple bond.

The term "$C_{3-6}$cycloalkyl" is defined as a cyclic hydrocarbon group containing the indicated number of carbon atoms.

The term "$C_{2-6}$heterocycloalkyl" is defined similarly as cycloalkyl except the ring contains one or two heteroatoms selected from the group consisting of O, $NR^a$, and S.

The term "halo" is defined as fluoro, bromo, chloro, and iodo.

In preferred embodiments, Z is N—$R^7$, and the bicyclic ring system containing X and Y is

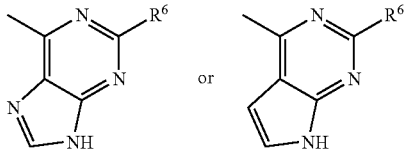

In other preferred embodiments, $R^1$ is hydrogen, fluoro, chloro, methyl, or

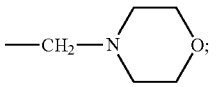

$R^2$ is hydrogen, methyl, chloro, or fluoro; $R^3$ is hydrogen or fluoro; $R^6$ is $NH_2$, hydrogen, or fluoro; $R^7$ is hydrogen or $R^5$ and $R^7$ are taken together to form

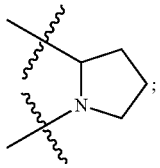

$R^8$ is methyl, trifluoromethyl, chloro, or fluoro; $R^4$ is hydrogen, fluoro, chloro, OH, $OCH_3$, $OCH_2C{=}CH$, $O(CH_2)_2N(CH_3)_2$, $C({=}O)CH_3$, $C{=}CH$, CN, $C({=}O)NH_2$, $OCH_2C({=}O)NH_2$, $O(CH_2)_2OCH_3$, $O(CH_2)_2N(CH_3)_2$,

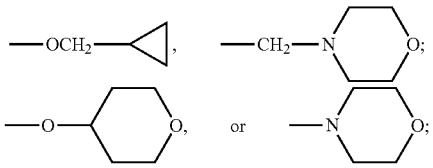

and $R^5$ is methyl, ethyl, propyl, phenyl, $CH_2OH$, $CH_2OCH_2C_6H_5$, $CH_2CF_3$, $CH_2OC(CH_3)_3$, $CH_2C{=}CH$, $(CH_2)_3N(C_2H_5)_2$, $(CH_2)_3NH_2$, $(CH_2)_4NH_2$, $(CH_2)_3NHC({=}O)OCH_2C_6H_5$, or $(CH_2)_4NHC({=}O)OCH_2C_6H_5$; $R^c$ is hydrogen, methyl, fluoro, or bromo; and n is 0 or 1.

It is generally accepted that biological systems can exhibit responses that are very sensitive to the absolute stereochemical nature of compounds to which they are exposed. See, E. J. Ariens, Medicinal Research Reviews, 6:451-66 (1986); E. J. Ariens, Medicinal Research Reviews, 7:367-87 (1987); K. W. Fowler, Handbook of Stereoisomers: Therapeutic Drugs, CRC Press, edited by Donald P. Smith, pp. 35-63 (1989); and S. C. Stinson, Chemical and Engineering News, 75:38-70 (1997).

Therefore, the compounds of the present invention include all possible stereoisomers and geometric isomers of compounds of structural formula (I), and include not only racemic compounds, but also the optically active isomers as well. In preferred embodiments, a compound of the present invention is the S-enantiomer of a compound (I), as depicted in structural formula (II).

When a compound of structural formula (I) is desired as a single enantiomer, it can be obtained either by resolution of the final product or by stereospecific synthesis from either isomerically pure starting material or use of a chiral auxiliary reagent. For example, see Z. Ma et al., Tetrahedron: Asymmetry, 8(6), pages 883-88 (1997). Resolution of the final product, an intermediate, or a starting material can be achieved by any suitable method known in the art. Specific stereoisomers, in particular, S-enantiomers of the compounds of the invention, exhibit an excellent ability to inhibit kinase activity of PI3Kδ.

The term "prodrug" as used herein refers to compounds that are rapidly transformed in vivo to a compound having structural formulae (I) or (II), for example, by hydrolysis. Prodrug design is discussed generally in Hardma et al. (Eds.), Goodman and Gilman's The Pharmacological Basis of Therapeutics, 9th ed., pp. 11-6 (1996). A thorough discussion of prodrugs is provided in Higuchi et al., Prodrugs as Novel Delivery Systems, Vol. 14, ASCD Symposium Series, and in Roche (ed.), "Bioreversible Carriers in Drug Design," American Pharmaceutical Association and Pergamon Press (1987).

Briefly, administration of a drug is followed by elimination from the body or some biotransformation whereby biological activity of the drug is reduced or eliminated. Alternatively, a biotransformation process can lead to a metabolic by-product, which is itself more active or equally active as compared to the drug initially administered. Increased understanding of these biotransformation processes permits the design of so-called "prodrugs," which, following a biotransformation, become more physiologically active in their altered state. Prodrugs, therefore, encompass pharmacologically inactive compounds that are converted to biologically active metabolites.

To illustrate, prodrugs can be converted into a pharmacologically active form through hydrolysis of, for example, an ester or amide linkage, thereby introducing or exposing a functional group on the resultant product. Prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

Methods for Identifying Negative Regulators of PI3Kδ Activity

The PI3Kδ protein, as well as fragments thereof possessing biological activity, can be used for screening putative inhibitor compounds in any of a variety of drug screening techniques. A inhibitor of PI3Kδ is a compound that diminishes or abolishes the ability of PI3Kδ to perform any of its biological functions. An example of such compounds is an agent that decreases the ability of a PI3Kδ polypeptide to phosphorylate phosphatidylinositol or to target appropriate structures within a cell. The selectivity of a compound that negatively regulates PI3Kδ activity can be evaluated by comparing its activity on the PI3Kδ to its activity on other proteins. Selective inhibitors include, for example, antibodies and other proteins or peptides that specifically bind to a PI3Kδ polypeptide, oligonucleotides that specifically bind to PI3Kδ polypeptides, and other nonpeptide compounds (e.g., isolated or synthetic organic molecules) that specifically interact with PI3Kδ polypeptides. Inhibitors also include compounds as described above, but which interact with a specific binding partner of PI3Kδ polypeptides.

Presently preferred targets for the development of selective inhibitors of PI3Kδ include, for example:

(1) cytoplasmic regions of PI3Kδ polypeptides that contact other proteins and/or localize PI3Kδ within a cell;

(2) regions of PI3Kδ polypeptides that bind specific binding partners;

(3) regions of the PI3Kδ polypeptides that bind substrate;

(4) allosteric regulatory sites of the PI3Kδ polypeptides that can or cannot interact directly with the active site upon regulatory signal;

(5) regions of the PI3Kδ polypeptides that mediate multimerization.

For example, one target for development of modulators is the identified regulatory interaction of p85 with p110δ, which can be involved in activation and/or subcellular localization of the p110δ moiety. Still other selective modulators include those that recognize specific regulatory or PI3Kδ-encoding nucleotide sequences. Modulators of PI3Kδ activity can be therapeutically useful in treatment of a wide range of diseases and physiological conditions in which aberrant PI3Kδ activity is involved.

Accordingly, the invention provides methods of characterizing the potency of a test compound as an inhibitor of PI3Kδ polypeptide, said method comprising the steps of (a) measuring activity of a PI3Kδ polypeptide in the presence of a test compound; (b) comparing the activity of the PI3Kδ polypeptide in the presence of the test compound to the activity of the PI3Kδ polypeptide in the presence of an equivalent amount of a reference compound (e.g., a compound having a known potency against PI3Kδ), wherein a lower activity of the PI3Kδ polypeptide in the presence of the test compound than in the presence of the reference indicates that the test compound is a more potent inhibitor than the reference compound, and a higher activity of the PI3Kδ polypeptide in the presence of the test compound than in the presence of the reference indicates that the test compound is a less potent inhibitor than the reference compound.

The invention further provides methods of characterizing the potency of a test compound as an inhibitor of PI3Kδ polypeptide, comprising the steps of (a) determining an amount of a reference compound (e.g., a PI3Kδ inhibitor compound of the present invention) that inhibits an activity of a PI3Kδ polypeptide by a reference percentage of inhibition, thereby defining a reference inhibitory amount for the reference compound; (b) determining an amount of a test compound that inhibits an activity of a PI3Kδ polypeptide by a reference percentage of inhibition, thereby defining a reference inhibitory amount for the test compound; (c) comparing the reference inhibitory amount for the test compound to the reference inhibitory amount for the reference compound, wherein a lower reference inhibitory amount for the test compound than for the reference compound indicates that the test compound is a more potent inhibitor than the reference compound, and a higher reference inhibitory amount for the test compound than for the reference compound indicates that the test compound is a less potent inhibitor than the reference compound. In one aspect, the method uses a reference inhibitory amount which is the amount of the compound than inhibits the activity of the PI3Kδ polypeptide by 50%, 60%, 70%, or 80%. In another aspect, the method employs a reference inhibitory amount that is the amount of the compound that inhibits the activity of the PI3Kδ polypeptide by 90%, 95%, or 99%. These methods comprise determining the reference inhibitory amount of the compounds in an in vitro biochemical assay, in an in vitro cell-based assay, or in an in vivo assay.

The invention further provides methods of identifying a inhibitor of PI3Kδ activity, comprising the steps of (i) measuring activity of a PI3Kδ polypeptide in the presence and absence of a test compound, and (ii) identifying as a inhibitor a test compound that decreases PI3Kδ activity and that competes with a compound of the invention for binding to PI3Kδ. Furthermore, the invention provides methods for identifying compounds that inhibit PI3Kδ activity, comprising the steps of (i) contacting a PI3Kδ polypeptide with a compound of the present invention in the presence and absence of a test compound, and (ii) identifying a test compound as a inhibitor of PI3Kδ activity wherein the compound competes with a compound of the invention for binding to PI3Kδ. The invention therefore provides a method for screening for candidate inhibitors of PI3Kδ activity and/or to confirm the mode of action of candidate such inhibitors. Such methods can be employed against other PI3K isoforms in parallel to establish comparative activity of the test compound across the isoforms and/or relative to a compound of the invention.

In these methods, the PI3Kδ polypeptide can be a fragment of p110δ that exhibits kinase activity, i.e., a fragment comprising the catalytic site of p110δ. Alternatively, the PI3Kδ polypeptide can be a fragment from the p110δ-binding domain of p85 and provides a method to identify allosteric modulators of PI3Kδ. The methods can be employed in cells expressing cells expressing PI3Kδ or its subunits, either endogenously or exogenously. Accordingly, the polypeptide employed in such methods can be free in solution, affixed to a solid support, modified to be displayed on a cell surface, or located intracellularly. The modulation of activity or the formation of binding complexes between the PI3Kδ polypeptide and the agent being tested then can be measured.

Human PI3K polypeptides are amenable to biochemical or cell-based high throughput screening (HTS) assays according to methods known and practiced in the art, including melanophore assay systems to investigate receptor-ligand interactions, yeast-based assay systems, and mammalian cell expression systems. For a review, see Jayawickreme et al., Curr Opin Biotechnol, 8:629-34 (1997). Automated and miniaturized HTS assays also are comprehended as described, for example, in Houston et al., Curr Opin Biotechnol, 8:734-40 (1997).

Such HTS assays are used to screen libraries of compounds to identify particular compounds that exhibit a desired property. Any library of compounds can be used, including chemical libraries, natural product libraries, and combinatorial libraries comprising random or designed oligopeptides, oligonucleotides, or other organic compounds. Chemical libraries can contain known compounds, proprietary structural analogs of known compounds, or compounds that are identified from natural product screening.

Natural product libraries are collections of materials isolated from naturals sources, typically, microorganisms, animals, plants, or marine organisms. Natural products are isolated from their sources by fermentation of microorganisms followed by isolation and extraction of the fermentation broths or by direct extraction from the microorganisms or tissues (plants or animal) themselves. Natural product libraries include polyketides, nonribosomal peptides, and variants (including nonnaturally occurring variants) thereof. For a review, see Cane et al., Science, 282:63-68 (1998).

Combinatorial libraries are composed of large numbers of related compounds, such as peptides, oligonucleotides, or other organic compounds as a mixture. Such compounds are relatively straightforward to design and prepare by traditional automated synthesis protocols, PCR, cloning, or proprietary synthetic methods. Of particular interest are peptide and oligonucleotide combinatorial libraries.

Still other libraries of interest include peptide, protein, peptidomimetic, multiparallel synthetic collection, recombinatorial, and polypeptide libraries. For a review of combinatorial chemistry and libraries created thereby, see Myers, Curr Opin Biotechnol, 8:701-07 (1997).

Therapeutic Uses of Inhibitors of PI3Kδ Activity

The invention provides a method for selectively or specifically inhibiting PI3Kδ activity therapeutically or prophylactically using compounds of the invention. The method comprises administering a selective or specific inhibitor of PI3Kδ activity to an individual in need thereof in an amount sufficient to inhibit PI3Kδ activity. The method can be employed to treat humans or animals suffering from, or subject to, a condition whose symptoms or pathology is mediated by PI3Kδ expression or activity.

"Treating" as used herein refers to preventing a disorder from occurring in an animal that can be predisposed to the disorder, but has not yet been diagnosed as having it; inhibiting the disorder, i.e., arresting its development; relieving the disorder, i.e., causing its regression; or ameliorating the disorder, i.e., reducing the severity of symptoms associated with the disorder. "Disorder" is intended to encompass medical disorders, diseases, conditions, syndromes, and the like, without limitation.

The methods of the invention embrace various modes of treating an animal subject, preferably a mammal, more preferably a primate, and still more preferably a human. Among the mammalian animals that can be treated are, for example, humans; companion animals (pets), including dogs and cats; farm animals, including cattle, horses, sheep, pigs, and goats; laboratory animals, including rats, mice, rabbits, guinea pigs, and nonhuman primates; and zoo specimens. Nonmammalian animals include, for example, birds, fish, reptiles, and amphibians.

A method of the present invention can be employed to treat subjects, therapeutically or prophylactically, suffering from, or subject to, an inflammatory disorder. One aspect of the present invention derives from the involvement of PI3Kδ in mediating aspects of the inflammatory process. Without intending to be bound by any theory, it is theorized that, because inflammation involves processes typically mediated by leukocyte (e.g., neutrophils or lymphocyte) activation and chemotactic transmigration, and because PI3Kδ can mediate such phenomena, antagonists of PI3Kδ can be used to suppress injury associated with inflammation.

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is associated with an influx of leukocytes and/or neutrophil chemotaxis. Inflammation can result from infection with pathogenic organisms and viruses, and from noninfectious means such as trauma or reperfusion following myocardial infarction or stroke, immune response to foreign antigen, and autoimmune responses. Accordingly, inflammatory disorders amenable to the invention encompass disorders associated with reactions of the specific defense system as well as with reactions of the nonspecific defense system.

As used herein, the term "specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents. "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia.

The therapeutic methods of the present invention include methods for the treatment of disorders associated with inflammatory cell activation. "Inflammatory cell activation" refers to the induction by a stimulus (including, but not limited to, cytokines, antigens, or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that activation of one or a combination of these phenotypes in these cells can contribute to the initiation, perpetuation, or exacerbation of an inflammatory disorder.

Compounds of the present invention have been found to inhibit superoxide release by neutrophils. Superoxide is released by neutrophils in response to any of a variety of stimuli, including signals of infection, as a mechanism of cell killing. For example, superoxide release is known to be induced by tumor necrosis factor alpha (TNFα), which is released by macrophages, mast cells, and lymphocytes upon contact with bacterial cell wall components such as lipopolysaccharide (LPS). TNFα is an extraordinarily potent and promiscuous activator of inflammatory processes, being involved in activation of neutrophils and various other cell types, induction of leukocyte/endothelial cell adhesion, pyrexia, enhanced MHC class I production, and stimulation of angiogenesis. Alternatively, superoxide release can be stimulated by formyl-Met-Leu-Phe (fMLP) or other peptides blocked at the N-terminus by formylated methionine. Such peptides normally are not found in eukaryotes, but are fundamentally characteristic of bacteria, and signal the presence of bacteria to the immune system. Leukocytes expressing the fMLP receptor, e.g., neutrophils and macrophages, are stimulated to migrate up gradients of these peptides (i.e., chemotaxis) toward loci of infection. As demonstrated herein, compounds of the present invention inhibit stimulated superoxide release by neutrophils in response to either TNFα or fMLP. Other functions of neutrophils, including stimulated exocytosis and directed chemotactic migration, also have been shown to be inhibited by the PI3Kδ inhibitors of the invention. Accordingly, compounds of the present invention can be expected to be useful in treating disorders, such as inflammatory disorders, that are mediated by any or all of these neutrophil functions.

The present invention enables methods of treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders, such as allergic conjunctivitis, vernal conjunctivitis, uveitis, and thyroid-associated opthalmopathy; eosinophilic granuloma; pulmonary or respiratory disorders, such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis, such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; transplant rejection disorders such as GVHD and allograft rejection; chronic glomerulonephritis; inflammatory bowel diseases, such as chronic inflammatory bowel disease (CIBD), Crohn's disease, ulcerative colitis, and necrotizing enterocolitis; inflammatory dermatoses, such as contact dermatitis, atopic dermatitis, psoriasis, or urticaria; fever and myalgias due to infection; central or peripheral nervous system inflammatory disorders, such as meningitis, encephalitis, and brain or spinal cord injury due to minor trauma; Sjögren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

The method can have utility in treating subjects suffering from, or subject to, reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of PI3Kδ activity will result in reduced amounts of reperfusion injury in such situations.

With respect to the nervous system, global ischemia occurs when blood flow to the entire brain ceases for a period. Global ischemia can result from cardiac arrest. Focal ischemia occurs when a portion of the brain is deprived of its normal blood supply. Focal ischemia can result from thromboembolytic occlusion of a cerebral vessel, traumatic head injury, edema, or brain tumor. Even if transient, both global and focal ischemia can cause widespread neuronal damage. Although nerve tissue damage occurs over hours or even days following the onset of ischemia, some permanent nerve tissue damage can develop in the initial minutes following the cessation of blood flow to the brain.

Ischemia also can occur in the heart in myocardial infarction and other cardiovascular disorders in which the coronary arteries have been obstructed as a result of atherosclerosis, thrombus, or spasm. Accordingly, the invention is believed to be useful for treating cardiac tissue damage, particularly damage resulting from cardiac ischemia or caused by reperfusion injury in mammals.

In another aspect, selective PI3Kδ inhibitors of the present invention can be employed in methods of treating diseases of bone, especially diseases in which osteoclast function is abnormal or undesirable. As shown below, compounds of the present invention inhibit osteoclast function in vitro. Accordingly, the use of such compounds and other PI3Kδ selective inhibitors can be of value in treating osteoporosis, Paget's disease, and related bone resorption disorders.

In a further aspect, the present invention includes methods of using PI3Kδ inhibitory compounds to inhibit the growth or proliferation of cancer cells of hematopoietic origin, preferably cancer cells of lymphoid origin, and more preferably cancer cells related to or derived from B lymphocytes or B lymphocyte progenitors. Cancers amenable to treatment using the method of the invention include, without limitation, lymphomas, e.g., malignant neoplasms of lymphoid and reticuloendothelial tissues, such as Burkitt's lymphoma, Hodgkins' lymphoma, non-Hodgkins lymphomas, lymphocytic lymphomas and the like; multiple myelomas; leukemias, such as lymphocytic leukemias, chronic myeloid (myelogenous) leukemias, and the like. In a preferred embodiment, the present PI3Kδ inhibitory compounds can be used to inhibit or control the growth or proliferation of chronic myeloid (myelogenous) leukemia cells. Other cancer cells, of hematopoietic origin or otherwise, that express p110δ also can be treated by administration of a PI3Kδ inhibitor of the present invention (C. Sawyer et al., Cancer Research, 63(7), 1667-75 (2003)).

In another aspect, the invention includes a method of suppressing a function of basophils and/or mast cells, thereby enabling treatment of diseases or disorders characterized by excessive or undesirable basophil and/or mast cell activity.

According to the method, a present compound can be used to selectively inhibit the expression or activity of PI3Kδ in the basophils and/or mast cells. Preferably, the method employs a PI3Kδ inhibitor in an amount sufficient to inhibit stimulated histamine release by the basophils and/or mast cells. Accordingly, the use of a present selective PI3Kδ inhibitors can be of value in treating diseases characterized by histamine release, i.e., allergic disorders, including disorders such as chronic obstructive pulmonary disease (COPD), asthma, ARDS, emphysema, and related disorders.

Pharmaceutical Compositions of Inhibitors of PI3Kδ Activity

A compound of the present invention can be administered as the neat chemical, but it is typical, and preferable, to administer the compound in the form of a pharmaceutical composition or formulation. Accordingly, the present invention also provides pharmaceutical compositions that comprise a present modulator of PI3Kδ activity and a biocompatible pharmaceutical carrier, adjuvant, or vehicle. The composition can include the PI3Kδ activity modulation either as the sole active agent or in combination with other agents, such as oligo- or polynucleotides, oligo- or polypeptides, drugs, or hormones mixed with an excipient or other pharmaceutically acceptable carriers. Carriers and other ingredients can be deemed pharmaceutically acceptable insofar as they are compatible with other ingredients of the formulation and not deleterious to the recipient thereof.

Techniques for formulation and administration of pharmaceutical compositions can be found in Remington's Pharmaceutical Sciences, 18th Ed., Mack Publishing Co, Easton, Pa., 1990. The pharmaceutical compositions of the present invention can be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation can be determined by one of skill in the art depending on the route of administration and the desired dosage. Such formulations can influence the physical state, stability, rate of in vivo release, and rate of in vivo clearance of the administered agent. Depending on the condition being treated, these pharmaceutical compositions can be formulated and administered systemically or locally.

The pharmaceutical compositions are formulated to contain suitable pharmaceutically acceptable carriers, and optionally can comprise excipients and auxiliaries that facilitate processing of the active compounds into preparations that can be used pharmaceutically. The mode of administration generally determines the nature of the carrier. For example, formulations for parenteral administration can comprise aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art. For preparations comprising proteins, the formulation can include stabilizing materials, such as polyols (e.g., sucrose) and/or surfactants (e.g., nonionic surfactants), and the like.

Alternatively, formulations for parenteral use can comprise dispersions or suspensions of the active compounds prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxymethylcellulose, sorbitol, dextran, and mixtures thereof. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers, such as the EUDRAGIT® series available from Röhm America Inc. (Piscataway, N.J.). Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethlyene sorbitol and sorbitan esters, microcrystalline cellulose, aluminum metahydroxide, bentonite, agar-agar, gum tragacanth, and mixtures thereof.

Liposomes containing the active agent also can be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines (lecithins), both natural and synthetic. Methods of forming liposomes are known in the art. See, e.g., Prescott (Ed.), Methods in Cell Biology, Vol. XIV, p. 33, Academic Press, New York (1976).

Pharmaceutical compositions comprising the agent in dosages suitable for oral administration can be formulated using pharmaceutically acceptable carriers well known in the art. Preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragee cores. Oral formulations can employ liquid carriers similar in type to those described for parenteral use, e.g., buffered aqueous solutions, suspensions, and the like.

Preferred oral formulations include tablets, dragees, and gelatin capsules. These preparations can contain one or excipients, which include, without limitation:

a) diluents, such as sugars, including lactose, dextrose, sucrose, mannitol, or sorbitol;

b) binders, such as magnesium aluminum silicate, starch from corn, wheat, rice, potato, etc.;

c) cellulose materials, such as methylcellulose, hydroxypropylmethyl cellulose, and sodium carboxymethylcellulose, polyvinylpyrrolidone, gums, such as gum arabic and gum tragacanth, and proteins, such as gelatin and collagen;

d) disintegrating or solubilizing agents such as cross-linked polyvinyl pyrrolidone, starches, agar, alginic acid or a salt thereof, such as sodium alginate, or effervescent compositions;

e) lubricants, such as silica, talc, stearic acid or its magnesium or calcium salt, and polyethylene glycol;

f) flavorants and sweeteners;

g) colorants or pigments, e.g., to identify the product or to characterize the quantity (dosage) of active compound; and h) other ingredients, such as preservatives, stabilizers, swelling agents, emulsifying agents, solution promoters, salts for regulating osmotic pressure, and buffers.

Gelatin capsules include push-fit capsules made of gelatin, as well as soft, sealed capsules made of gelatin and a coating such as glycerol or sorbitol. Push-fit capsules can contain the active ingredient(s) mixed with fillers, binders, lubricants, and/or stabilizers, etc. In soft capsules, the active compounds can be dissolved or suspended in suitable fluids, such as fatty oils, liquid paraffin, or liquid polyethylene glycol with or without stabilizers.

Dragee cores can be provided with suitable coatings such as concentrated sugar solutions, which also can contain gum arabic, talc, polyvinyl pyrrolidone, carbopol gel, polyethylene glycol, and/or titanium dioxide, lacquer solutions, and suitable organic solvents or solvent mixtures.

The pharmaceutical composition can be provided as a salt of the active agent. Salts are more soluble in aqueous or other protonic solvents than the corresponding free acid or base forms. Pharmaceutically acceptable salts are well known in the art. Compounds that contain acidic moieties can form pharmaceutically acceptable salts with suitable cations. Suitable pharmaceutically acceptable cations include, for example, alkali metal (e.g., sodium or potassium) and alkaline earth (e.g., calcium or magnesium) cations.

Compounds of structural formula (I) and (II) that contain basic moieties can form pharmaceutically acceptable acid addition salts with suitable acids. For example, Berge et al., J. Pharm. Sci., 66:1 (1977), describe pharmaceutically acceptable salts in detail. The salts can be prepared in situ during the final isolation and purification of the compounds of the invention or separately by reacting a free base function with a suitable acid.

Pharmaceutically acceptable salts of compounds of the invention generally are preferred in the methods of the invention. As used herein, the term "pharmaceutically acceptable salts" refers to salts or zwitterionic forms of the compounds of structural formulae (I) or (II). Suitable pharmaceutically acceptable cations include alkali metal (e.g., sodium or potassium) and alkaline earth metal (e.g., calcium or magnesium) cations. In addition, the pharmaceutically acceptable salts of compounds of structural formulae (I) or (II) that contain a basic center are acid addition salts formed with pharmaceutically acceptable acids. Examples of acids which can be employed to form pharmaceutically acceptable salts include inorganic acids such as hydrochloric, hydrobromic, sulfuric, and phosphoric, and organic acids such as oxalic, maleic, succinic, malonic, and citric. Nonlimiting examples of salts of compounds of the invention include, but are not limited to, hydrochloride, hydrobromide, hydroiodide, sulfate, bisulfate, 2-hydroxyethansulfonate, phosphate, hydrogen phosphate, acetate, adipate, alginate, aspartate, benzoate, butyrate, camphorate, camphorsulfonate, citrate, digluconate, glycerolphosphate, hemisulfate, heptanoate, hexanoate, formate, succinate, malonate, fumarate, maleate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, glutamate, bicarbonate, paratoluenesulfonate, undecanoate, lactate, citrate, tartrate, gluconate, benzene sulphonate, and p-toluenesulphonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phnethyl bromides.

In light of the foregoing, any reference to compounds of the present invention appearing herein is intended to include compounds of structural formulae (I) and (II), as well as pharmaceutically acceptable salts, solvates, quaternary derivatives, and prodrugs, thereof.

Compositions comprising a compound of the invention formulated in a pharmaceutically acceptable carrier can be prepared, placed in an appropriate container, and labeled for treatment of an indicated condition. Accordingly, there also is contemplated an article of manufacture, such as a container comprising a dosage form of a compound of the invention and a label containing instructions for use of the compound. Kits also are contemplated. For example, a kit can comprise a dosage form of a pharmaceutical composition and a package insert containing instructions for use of the composition in treatment of a medical condition. In either case, conditions indicated on the label can include treatment of inflammatory disorders, cancer, and the like.

Methods of Administration of Inhibitors of PI3Kδ Activity

Pharmaceutical compositions comprising an inhibitor of PI3Kδ activity can be administered to the subject by any conventional method, including parenteral and enteral techniques. Parenteral administration modalities include those in which the composition is administered by a route other than through the gastrointestinal tract, for example, intravenous, intraarterial, intraperitoneal, intramedullary, intramuscular, intraarticular, intrathecal, and intraventricular injections. Enteral administration modalities include, for example, oral, buccal, sublingual, and rectal administration. Transepithelial administration modalities include, for example, transmucosal administration and transdermal administration. Transmucosal administration includes, for example, enteral administration as well as nasal, inhalation, and deep lung administration; vaginal administration; and buccal and sublingual administration. Transdermal administration includes passive or active transdermal or transcutaneous modalities, including, for example, patches and iontophoresis devices, as well as topical application of pastes, salves, or ointments. Parenteral administration also can be accomplished using a high-pressure technique, e.g., POWDERJECT®.

Surgical techniques include implantation of depot (reservoir) compositions, osmotic pumps, and the like. A preferred route of administration for treatment of inflammation can be local or topical delivery for localized disorders such as arthritis, or systemic delivery for distributed disorders, e.g., intravenous delivery for reperfusion injury or for systemic conditions such as septicemia. For other diseases, including those involving the respiratory tract, e.g., chronic obstructive pulmonary disease, asthma, and emphysema, administration can be accomplished by inhalation or deep lung administration of sprays, aerosols, powders, and the like.

For the treatment of neoplastic diseases, especially leukemias and other distributed cancers, parenteral administration is typically preferred. Formulations of the compounds to optimize them for biodistribution following parenteral administration would be desirable. The PI3Kδ inhibitor compounds can be administered before, during, or after administration of chemotherapy, radiotherapy, and/or surgery.

Moreover, the therapeutic index of the PI3Kδ inhibitor compounds can be enhanced by modifying or derivatizing the compounds for targeted delivery to cancer cells expressing a marker that identifies the cells as such. For example, the compounds can be linked to an antibody that recognizes a marker that is selective or specific for cancer cells, so that the compounds are brought into the vicinity of the cells to exert their effects locally, as previously described (see for example, Pietersz et al., Immunol. Rev., 129:57 (1992); Trail et al., Science, 261:212 (1993); and Rowlinson-Busza et al., Curr. Opin. Oncol., 4:1142 (1992)). Tumor-directed delivery of these compounds enhances the therapeutic benefit by, inter alia, minimizing potential nonspecific toxicities that can result from radiation treatment or chemotherapy. In another aspect, PI3Kδ inhibitor compounds and radioisotopes or chemotherapeutic agents can be conjugated to the same antitumor antibody.

For the treatment of bone resorption disorders or osteoclast-mediated disorders, the PI3Kδ inhibitors can be delivered by any suitable method. Focal administration can be desirable, such as by intraarticular injection. In some cases, it can be desirable to couple the compounds to a moiety that can target the compounds to bone. For example, a PI3Kδ inhibitor can be coupled to compounds with high affinity for hydroxyapatite, which is a major constituent of bone. This can be accomplished, for example, by adapting a tetracycline-coupling method developed for targeted delivery of estrogen to bone (Orme et al., Bioorg. Med. Chem. Lett., 4(11):1375-80 (1994)).

To be effective therapeutically in modulating central nervous system targets, the agents used in the methods of the invention should readily penetrate the blood brain barrier when peripherally administered. Compounds that cannot penetrate the blood brain barrier, however, can still be effectively administered by an intravenous route.

As noted above, the characteristics of the agent itself and the formulation of the agent can influence the physical state, stability, rate of in vivo release, and rate of in vivo clearance of the administered agent. Such pharmacokinetic and pharmacodynamic information can be collected through preclinical in vitro and in vivo studies, later confirmed in humans during the course of clinical trials. Thus, for any compound used in the method of the invention, a therapeutically effective dose can be estimated initially from biochemical and/or cell-based assays. Then, dosage can be formulated in animal models to achieve a desirable circulating concentration range that modulates PI3Kδ expression or activity. As human studies are conducted further information will emerge regarding the appropriate dosage levels and duration of treatment for various diseases and conditions.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index," which typically is expressed as the ratio $LD_{50}/ED_{50}$. Compounds that exhibit large therapeutic indices, i.e., the toxic dose is substantially higher than the effective dose, are preferred. The data obtained from such cell culture assays and additional animal studies can be used in formulating a range of dosage for human use. The dosage of such compounds lies preferably within a range of circulating concentrations that include the $ED_{50}$ with little or no toxicity.

In accordance with the present invention, any effective administration regimen regulating the timing and sequence of doses can be used. Compounds and pharmaceutical compositions suitable for use in the present invention include those wherein the active ingredient is administered in an effective amount to achieve its intended purpose. More specifically, a "therapeutically effective amount" means an amount sufficient to modulate PI3Kδ expression or activity, and thereby treat an individual suffering an indication, or to alleviate the existing symptoms of the indication. Determination of a therapeutically effective amount is well within the capability of those skilled in the art, especially in light of the detailed disclosure provided herein.

Exemplary dosage levels for a human subject are of the order of from about 0.001 milligram of active agent per kilogram body weight (mg/kg) to about 1000 mg/kg. Typically, dosage units of the active agent comprise from about 0.01 mg to about 1000 mg, preferably from about 0.1 mg to about 100 mg, depending upon the indication, route of administration, and severity of the condition, for example. Depending on the route of administration, a suitable dose can be calculated according to body weight, body surface area, or organ size. The final dosage regimen is determined by the attending physician in view of good medical practice, considering various factors that modify the action of drugs, e.g., the specific activity of the compound, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing depends on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be used for continuous infusion.

The following examples are provided to further aid in understanding the invention, and presuppose an understanding of conventional methods well known to those persons having ordinary skill in the art to which the examples pertain, e.g., the construction of vectors and plasmids, the insertion of genes encoding polypeptides into such vectors and plasmids, or the introduction of vectors and plasmids into host cells. Such methods are described in detail in numerous publications including, for example, Sambrook et al., Molecular Cloning: A Laboratory Manual, Cold Spring Harbor Laboratory Press (1989), Ausubel et al. (Eds.), Current Protocols in Molecular Biology, John Wiley & Sons, Inc. (1994); and Ausubel et al. (Eds.), Short Protocols in Molecular Biology, 4th ed., John Wiley & Sons, Inc. (1999). The particular materials and conditions described hereunder are intended to exemplify particular aspects of the invention and should not be construed to limit the reasonable scope thereof.

EXAMPLE 1

Preparation and Purification of Recombinant PI3Kα, β, and δ

Recombinant PI3K heterodimeric complexes consisting of a p110 catalytic subunit and a p85 regulatory subunit were overexpressed using the BAC-TO-BAC® HT baculovirus expression system (GIBCO/BRL), and then purified for use in biochemical assays. The four Class I PI 3-kinases were cloned into baculovirus vectors as follows:

p110δ: A FLAG®-tagged version of human p110δ (SEQ ID NOS: 1 and 2) (see Chantry et al., J. Biol. Chem., 272: 19236-41 (1997)) was subcloned using standard recombinant DNA techniques into the BamH1-Xba1 site of the insect cell expression vector pFastbac HTb (Life Technologies, Gaithersburg, Md.), such that the clone was in frame with the His tag of the vector. The FLAG® system is described in U.S. Pat. Nos. 4,703,004; 4,782,137; 4,851,341; and 5,011,912, and reagents are available from Eastman Kodak Co.

p110α: Similar to the method used for p110δ, described above, a FLAG®-tagged version of p110α (see Volinia et al., Genomics, 24(3):427-77 (1994)) was subcloned in BamH1-HindIII sites of pFastbac HTb (Life Technologies) such that the clone was in frame with the His tag of the vector.

p110β: A p110β (see Hu et al., Mol. Cell. Biol., 13:7677-88 (1993)) clone was amplified from the human MARATHON® Ready spleen cDNA library (Clontech, Palo Alto Calif.) according to the manufacturer's protocol using the following primers:

```
5' Primer                                (SEQ ID NO: 3)
5'-GATCGAATTCGGCGCCACCATGGACTACAAGGACGACGATGACAAGT

GCTTCAGTTTCATAATGCCTCC-3'

3' Primer                                (SEQ ID NO: 4)
5'-GATCGCGGCCGCTTAAGATCTGTAGTCTTTCCGAACTGTGTG-3'
```

The 5' primer was built to contain a FLAG® tag in frame with the p110β sequence. After amplification, the FLAG®-p110β sequence was subcloned using standard recombinant techniques into the EcoR1-Not1 sites of pFastbac HTa (Life Technologies), such that the clone was in frame with the His tag of the vector.

p110γ: The p110γ cDNA (see Stoyanov et al., Science, 269:690-93 (1995)) was amplified from a human Marathon Ready spleen cDNA library (Clontech) according to the manufacturer's protocol using the following primers:

```
5' Primer                                (SEQ ID NO: 5)
5'-AGAATGCGGCCGCATGGAGCTGGAGAACTATAAACAGCCC-3'

3' Primer                                (SEQ ID NO: 6)
5'-CGCGGATCCTTAGGCTGAATGTTTCTCTCCTTGTTTG-3'
```

A FLAG® tag was subsequently attached to the 5' end of the p110γ sequence and was cloned in the BamH1-Spe1 sites of pFastbac HTb (Life Technologies) using standard recombinant DNA techniques, with the FLAG®-110γ sequence in-frame with the His tag of the vector.

p85α: A BamH1-EcoR1 fragment of FLAG®-tagged p85 cDNA (see Skolnik et al., Cell, 65:83-89 (1991)) was subcloned into the BamH1-EcoR1 sites of the vector pFastbac dual (Life Technologies).

Recombinant baculoviruses containing the above clones were generated using manufacturer's recommended protocol (Life Technologies). Baculoviruses expressing His-tagged p110α, p110β, or p110δ catalytic subunit and p85 subunit were coinfected into Sf21 insect cells. To enrich the heterodimeric enzyme complex, an excess amount of baculovirus expressing p85 subunit was infected, and the His-tagged p110 catalytic subunit complexed with p85 was purified on nickel affinity column. Since p110γ does not associate with p85, Sf21 cells were infected with recombinant baculoviruses expressing His-tagged p110γ only. In an alternate approach, p101 can be cloned into baculovirus, to permit coexpression with its preferred binding partner p110γ.

The 72-hour post-infected Sf21 cells (3 liters) were harvested and homogenized in a hypotonic buffer (20 mM HEPES-KOH, pH 7.8, 5 mM KCl, complete protease inhibitor cocktail (Roche Biochemicals, Indianapolis, Ind.), using a Dounce homogenizer. The homogenates were centrifuged at 1,000×g for 15 min. The supernatants were further centrifuged at 10,000×g for 20 min, followed by ultracentrifugation at 100,000×g for 60 min. The soluble fraction was immediately loaded onto 10 mL of HITRAP® nickel affinity column (Pharmacia, Piscataway, N.J.) equilibrated with 50 mL of Buffer A (50 mM HEPES-KOH, pH 7.8, 0.5 M NaCl, 10 mM imidazole). The column was washed extensively with Buffer A, and eluted with a linear gradient of 10-500 mM imidazole. Free p85 subunit was removed from the column during the washing step and only the heterodimeric enzyme complex eluted at 250 mM imidazole. Aliquots of nickel fractions were analyzed by 10% SDS-polyacrylamide gel electrophoresis (SDS-PAGE), stained with SYPRO® Red (Molecular Probes, Inc., Eugene, Oreg.), and quantitated with STORM® PhosphoImager (Molecular Dynamics, Sunnyvale, Calif.). The active fractions were pooled and directly loaded onto a 5 mL Hi-trap heparin column preequilibrated with Buffer B containing 50 mM HEPES-KOH, pH 7.5, 50 mM NaCl, 2 mM dithiothreitol (DTT). The column was washed with 50 mL of Buffer B and eluted with a linear gradient of 0.05-2 M NaCl. A single peak containing PI3K enzyme complex eluted at 0.8 M NaCl. SDS-polyacrylamide gel analysis showed that the purified PI3K enzyme fractions contained a 1:1 stoichiometric complex of p110 and p85 subunits. The protein profile of the enzyme complex during heparin chromatography corresponded to that of lipid kinase activity. The active fractions were pooled and frozen under liquid nitrogen.

EXAMPLES 2-6

Because PI3Kδ is expressed at significant levels in leukocytes, it is important to study the effects of the PI3Kδ-selective inhibitor on leukocyte functions. Accordingly, the effects of PI3Kδ inhibition in several types of leukocytes were examined. Neutrophils were examined to determine the effects that selective inhibition of PI3Kδ might elicit (Example 2, below). It surprisingly was found that selective inhibition of PI3Kδ activity appears to be significantly associated with inhibition of some but not all functions characteristic of activated neutrophils. In addition, the effects of PI3Kδ inhibition on B cell and T cell function also were tested (Examples 3-4, below). Moreover, as PI3Kδ also is expressed in osteoclasts, the effect of PI3Kδ inhibition on the function of these specialized cells was studied (Example 5, below).

EXAMPLE 2

Characterization of Role of PI3Kδ in Neutrophil Function

The effects of a PI3Kδ inhibitor of the invention on neutrophil functions such as superoxide generation, elastase exocytosis, chemotaxis, and bacterial killing can be tested.

A. Preparation of Neutrophils from Human Blood

Aliquots (8 mL) of heparinized blood from healthy volunteers are layered on 3 mL cushions of 7.3% FICOLL® (Sigma, St. Louis, Mo.) and 15.4% HYPAQUE® (Sigma) and centrifuged at 900 rpm for 30 min at room temperature in a table top centrifuge (Beckman). The neutrophil-rich band just above the FICOLL®-HYPAQUE® cushion is collected and washed with Hanks' balanced salt solution (HBSS) containing 0.1% gelatin. Residual erythrocytes are removed by hypotonic lysis with 0.2% NaCl. The neutrophil preparation is washed twice with HBSS containing 0.1% gelatin and used immediately.

B. Measurement of Superoxide Production from Neutrophils

Superoxide generation is one of the hallmarks of neutrophil activation. A variety of activators potentiate superoxide generation by neutrophils. The effect of a present PI3Kδ inhibitor on superoxide generation by three different agonists: TNF1α, IgG, and fMLP, each representing separate classes of activator, is measured. Superoxide generated by the neutrophils is measured by monitoring a change in absorbance upon reduction of cytochrome C by modification of the method described by Green et al., (pp. 14.5.1-14.5.11 in Supp. 12, Curr. Protocols Immunol. (Eds., Colligan et al.) (1994)), as follows. Individual wells of a 96-well plate are coated overnight at 4° C. with 50 μL of 2 mg/mL solution of human fibrinogen or IgG. The wells are washed with PBS and the following reagents were added to each well: 50 μL of HBSS or superoxide dismutase (1 mg/mL), 50 μL of HBSS or TNFα (50 ng/mL), 50 μL cytochrome C (2.7 mg/mL), and 100 μL of purified human neutrophil suspension ($2\times10^6$ cells/mL). The plate is centrifuged for 2 min at 200 rpm and absorbance at 550 nm was monitored for 2 hr. To measure the relative amounts of superoxide generated, values obtained from the superoxide dismutase-containing wells are subtracted from all, and normalized to the values obtained from the wells without any inhibitor.

Compounds of the present invention inhibit TNF-induced superoxide generation by neutrophils in a concentration dependent manner. In addition, superoxide generation induced by IgG was not significantly inhibited by compounds of the present invention.

The effect of compounds of the present invention on superoxide generation induced by another potent inducer, the bacterial peptide formylated-Met-Leu-Phe (fMLP), also can be studied. Like the TNF-induced superoxide generation, fMLP-induced superoxide generation also is inhibited compounds of the present invention. These results show that the PI3Kδ inhibitor compounds of the present invention can prevent stimulus specific induction of superoxide generation by neutrophils, indicating that PI3Kδ is involved in this process.

C. Measurement of Elastase Exocytosis from Neutrophils

In addition to superoxide generation, activated neutrophils also respond by releasing several proteases that are responsible for the destruction of tissues and cartilage during inflammation. As an indication of protease release, the effect of present compound on elastase exocytosis is measured. Elastase exocytosis is quantitated by modification of the procedure described by Ossanna et al. (J. Clin. Invest., 77:1939-51 (1986)), as follows. Purified human neutrophils ($0.2\times10^6$) (treated with either DMSO or a serial dilution of a present compound in DMSO) are stimulated with fMLP in PBS containing 0.01 mg/mL cytochalasin B, 1.0 μM sodium azide ($NaN_3$), 5 μg/mL L-methionine and 1 μM fMLP for 90 min at 37° C. in a 96-well plate. At the end of the incubation period, the plate is centrifuged for 5 min at 1000 rpm, and 90 μL of the supernatant is transferred to 10 μL of 10 mM solution of an elastase substrate peptide, MeO-suc-Ala-Ala-Pro-Val-pNA, wherein MeO-suc=methoxy-succinyl; pNA=p-nitroanilide (Calbiochem, San Diego, Calif.). Absorbance at 410 nm is monitored for 2 hr in a 96-well plate reader. To measure the relative amounts of elastase excytosed, all absorbance values are normalized to the values without any inhibitor. PI3Kδ inhibitor compounds of the present invention inhibit fMLP-induced elastase exocytosis significantly, and do so in a dose-dependent fashion.

D. Measurement of fMLP-Induced Human Neutrophil Migration

Neutrophils have the intrinsic capacity to migrate through tissues, and are one of the first cell types to arrive at the sites of inflammation or tissue injury. The effect of the present compounds on neutrophil migration towards a concentration gradient of fMLP is measured. The day before the migration assays are performed, 6-well plates are coated with recombinant ICAM-1/Fc fusion protein (Van der Vieren et al., Immunity, 3:683-90 (1995)) (25 μg/mL in bicarbonate buffer, pH 9.3) and left overnight at 4° C. After washing, 1% agarose solution, in RPMI-1640 with 0.5% bovine serum albumin (BSA), is added to wells with or without an inhibitor, and plates are placed into a refrigerator before punching holes in the gelled agarose to create plaques (1 central hole surrounded by 6 peripheral ones per well).

Human neutrophils are obtained as described above, and resuspended in RPMI medium supplemented with 0.5% BSA at $5\times10^6$ cells/mL. After combining equal volumes of neutrophil suspension and medium (either with DMSO or a serial dilution of the test compound in DMSO), neutrophils are aliquoted into the peripheral holes, while the central hole received fMLP (5 μM). Plates are incubated at 37° C. in the presence of 5% $CO_2$ for 4 hr, followed by termination of migration by the addition of 1% glutaraldehyde solution in D-PBS. After removing the agarose layer, wells are washed with distilled water and dried.

Analysis of neutrophil migration is conducted on a Nikon DIAPHOT® inverted microscope (1× objective) video workstation using the NIH 1.61 program. Using Microsoft Excel and Table Curve 4 (SSPS Inc., Chicago Ill.) programs, a migration index is obtained for each of the studied conditions. Migration index is defined as the area under a curve representing number of migrated neutrophils versus the net distance of migration per cell.

PI3Kδ inhibitor compounds of the present invention have an effect on neutrophil migration, inhibiting this activity in a dose-dependent manner.

E. Measurement of Bactericidal Capacity of Neutrophils

Given that the PI3Kδ inhibitor compounds of the present invention affect certain neutrophil functions, whether the compounds affect neutrophil-mediated bacterial killing is of interest. The effect of the compounds on neutrophil-mediated Staphylococcus aureus killing is studied according to the method described by Clark and Nauseef (pp. 7.23.4-7.23.6 in Vol. 2, Supp. 6, Curr. Protocols Immunol. (Eds., Colligan et al.) (1994)). Purified human neutrophils ($5\times10^6$ cells/mL) (treated with either DMSO or a serial dilution of present compound in DMSO) are mixed with autologous serum. Overnight-grown S. aureus cells are washed, resuspended in HBSS, and added to the serum-opsonized neutrophils at a 10:1 ratio. Neutrophils are allowed to internalize the bacteria by phagocytosis by incubation at 37° C. for 20 min. The noninternalized bacteria are killed by 10 units/mL lysostaphin at 37° C. for 5 min and the total mixture is rotated at 37° C. Samples are withdrawn at various times for up to 90 min and the neutrophils are lysed by dilution in water. Viable bacteria are counted by plating appropriate dilutions on trypticase-soy-agar plate and counting the S. aureus colonies after overnight growth.

Neutrophil-mediated killing of S. aureus is similar in samples treated with DMSO (control) and with a present compound. Therefore, a PI3Kδ inhibitor does not significantly affect the ability of neutrophils to kill S. aureus, suggesting that PI3Kδ is not involved in this pathway of neutrophil function.

EXAMPLE 3

Characterization of Role of PI3Kδ in B Lymphocyte Function

The effects of a PI3-kinase inhibitor on B cell functions including classical indices such as antibody production and specific stimulus-induced proliferation also are studied.

A. Preparation and Stimulation of B Cells from Peripheral Human Blood

Heparinized blood (200 mL) from healthy volunteers is mixed with an equal volume of D-PBS, layered on 10×10 mL FICOLL-PAQUE® (Pharmacia), and centrifuged at 1600 rpm for 30 min at room temperature. Peripheral blood mononuclear cells (PBMC) are collected from the FICOLL®/serum interface, overlayed on 10 mL fetal bovine serum (FBS) and centrifuged at 800 rpm for 10 min to remove platelets. After washing, cells are incubated with DYNAL® Antibody Mix (B cell kit) (Dynal Corp., Lake Success, N.Y.) for 20 min at 4-8° C. Following the removal of unbound antibody, PBL are mixed with anti-mouse IgG coated magnetic beads (Dynal) for 20 min at 4-8° C. with gentle shaking followed by elimination of labeled non-B cells on the magnetic bead separator. This procedure is repeated once more. The B cells are resuspended in RPMI-1640 with 10% FBS, and kept on ice until further use.

B. Measurement of Antibody Production by Human B Cells

To study antibody production, B cells are aliquoted at 50-75×$10^3$ cells/well into 96-well plate with or without inhibitor, to which IL-2 (100 U/mL) and PANSORBIN® (Calbiochem) Staphylococcus aureus cells (1:90,000) were added. Part of the media is removed after 24-36 hr, and fresh media (with or without inhibitor) and IL-2 is added. Cultures are incubated at 37° C., in the presence of a $CO_2$ incubator for additional 7 days. Samples from each condition (in triplicate) are removed, and analyzed for IgG and IgM, as measured by ELISA. Briefly, IMMULON® 4 96-well plates are coated (50 μL/well) with either 150 ng/mL donkey antihuman IgG (H+L) (Jackson ImmunoResearch, West Grove Pa.), or 2 μg/mL donkey antihuman IgG+IgM (H+L) (Jackson ImmunoResearch) in bicarbonate buffer, and left overnight at 4° C. After washing three times with phosphate buffered saline containing 0.1% TWEEN®-80 (PBST) (350 μL/well), and blocking with 3% goat serum in PBST (100 μL/well) for 1 hr at room temperature, samples (100 μL/well) of B cell spent media diluted in PBST are added. For IgG plates the dilution range is 1:500 to 1:10000, and for IgM 1:50 to 1:1000. After 1 hr, plates are exposed to biotin-conjugated antihuman IgG (100 ng/mL) or antihuman IgM (200 ng/mL) (Jackson ImmunoResearch) for 30 min, following by streptavidin-HRP (1:20000) for 30 min, and finally, to TMB solution (1:100) with $H_2O_2$ (1:10000) for 5 min, with 3×PBST washing between steps. Color development is stopped by $H_2SO_4$ solution, and plates were read on an ELISA plate reader.

Compounds of the present invention inhibited antibody production.

C. Measurement of B Cell Proliferation in Response to Cell Surface IgM Stimulation In the above experiment, B cells are stimulated using PANSORBIN®. The effect compounds of the present invention on B cell proliferation response when they are stimulated through their cell surface IgM using anti-IgM antibody also was measured. Murine splenocytes (Balb/c) are plated into 96-well microtiter plates at 2×$10^5$ cells per well in 10% FBS/RPMI. Appropriate dilutions of test inhibitor in complete medium are added to the cells and the plates are incubated for 30-60 minutes prior to the addition of stimulus. Following the preincubation with test inhibitor, an $F(ab')_2$ preparation of goat antibody specific for the μ-chain of mouse IgM is added to the wells at a final concentration of 25 μg/mL. The plates are incubated at 37° C. for 3 days and 1 μCi of [$^3$H]-thymidine is added to each well for the final four hours of culture. The plates are harvested onto fiber filters, washed, and the incorporation of radiolabel is determined using a beta counter (Matrix 96, Packard Instrument Co., Downers Grove, Ill.) and expressed as counts per minute (CPM).

Compounds of the present invention inhibit anti-IgM-stimulated B cell proliferation in a dose-dependent manner. Because compounds of the present invention inhibit B cell proliferation, it is envisioned that these compounds and other PI3Kδ inhibitors could be used to suppress undesirable proliferation of B cells in clinical settings. For example, in B cell malignancy, B cells of various stages of differentiation show unregulated proliferation. Based on the results shown above, one can infer that PI3Kδ selective inhibitors could be used to control, limit, or inhibit growth of such cells.

EXAMPLE 4

Characterization of Role of PI3Kδ in T Lymphocyte Function

T cell proliferation in response to costimulation of CD3+CD28 is measured. T cells are purified from healthy human blood by negative selection using antibody coated magnetic beads according to the manufacturer's protocol (Dynal) and resuspended in RPMI. The cells are treated with either DMSO or a serial dilution of a present compound in DMSO and plated at 1×$10^5$ cells/well on a 96-well plate precoated with goat antimouse IgG. Mouse monoclonal anti-CD3 and anti-CD28 antibodies then are added to each well at 0.2 ng/mL and 0.2 μg/mL, respectively. The plate is incubated at 37° C. for 24 hr and [$^3$H]-thymidine (1 μCi/well) is added. After another 18-hr incubation, the cells are harvested with an automatic cell harvester, washed, and the incorporated radioactivity was quantified.

Although the present PI3Kδ inhibitor compounds inhibited anti-CD3- and anti-CD28-induced proliferation of T cells, an effect is not as strong as an effect on B cells or on some of the functions of neutrophils. Accordingly, the present compounds are not toxic to cells in general.

EXAMPLE 5

Characterization of Role of PI3Kδ in Osteoclast Function

To analyze the effect of the present PI3Kδ inhibitor compounds on osteoclasts, mouse bone marrow cells are isolated and differentiated to osteoclasts by treating the cells with Macrophage Colony Stimulating Factor$^{-1}$ (mCSF$^{-1}$) and Osteoprotegerin Ligand (OPGL) in serum-containing medium (αMEM with 10% heat-inactivated FBS; Sigma) for 3 days. On day four, when the osteoclasts had developed, the medium is removed and cells are harvested. The osteoclasts are plated on dentine slices at $10^5$ cells/well in growth medium, i.e., αMEM containing 1% serum and 2% BSA with 55 μg/mL OPGL and 10 ng/mL mCSF$^{-1}$. After 3 hr, the medium is changed to 1% serum and 1% BSA, with or without osteopontin (25 μg/mL) and the PI3K inhibitors (100 nM). The medium is changed every 24 hours with fresh osteopontin and the inhibitors. At 72 hr, the medium is removed, and the dentine surfaces are washed with water to remove cell debris and stained with acid hematoxylin. Excess stain is washed and the pit depths are quantitated using confocal microscopy.

The present PI3-kinase inhibitors had an inhibitory effect on osteoclast function. Both the nonspecific inhibitors LY294002 and wortmannin inhibited osteoclast activity. However, the present PI3Kδ inhibitor compounds had a greater effect, and in some cases almost completely inhibited osteoclast activity.

EXAMPLE 6

Characterization of Role of PI3Kδ in Basophil Function

Assessment of the effect of a compound of the invention on basophil function is tested using a conventional histamine release assay, generally in accordance with the method described in Miura et al., J. Immunol., 162:4198-206 (1999). Briefly, enriched basophils are preincubated with test compounds at several concentrations from 0.1 nM to 1,000 nM for 10 min at 37° C. Then, polyclonal goat antihuman IgE (0.1 μg/mL) or fMLP is added, and allowed to incubate for an additional 30 min. Histamine released into the supernatant is measured using an automated fluorometric technique.

A dose-dependent decrease in histamine release was observed for the present compounds when the basophils are stimulated with anti-IgE. This suppression of histamine release was essentially 100% at 1,000 nM. The present compound did not elicit any effect when the basophils are stimulated with fMLP. For comparison, the nonselective PI3K inhibitor LY294002 is tested at 0.1 nM and 10,000 nM, showing close to 100% inhibition of histamine release at the highest concentration.

This indicates that the present inhibitors of PI3Kδ activity can be used to suppress release of histamine, which is one of the mediators of allergy. Since the activity of various PI 3-kinases are required for protein trafficking, secretion, and exocytosis in many cell types, the above suggests that histamine release by other cells, such as mast cells, also can be disrupted by PI 3-kinase delta-selective inhibitors.

CHEMICAL SYNTHESIS EXAMPLES

Specific nonlimiting examples of compounds of the invention are provided below. It is understood in the art that protecting groups can be employed where necessary in accordance with general principles of synthetic chemistry. These protecting groups are removed in the final steps of the synthesis under basic, acidic, or hydrogenolytic conditions readily apparent to persons skilled in the art. By employing appropriate manipulation and protection of any chemical functionalities, synthesis of compounds of structural formulae (I) or (II) not specifically set forth herein can be accomplished by methods analogous to the schemes and demonstrated synthetic procedures set forth below.

Unless otherwise noted, all starting materials were obtained from commercial suppliers and used without further purification. All reactions and chromatography fractions were analyzed by thin-layer chromatography (TLC) on 250 mm silica gel plates, visualized with ultraviolet (UV) light or iodine ($I_2$) stain. Products and intermediates were typically purified by flash chromatography or reverse-phase high performance liquid chromatography.

The following abbreviations are used in the synthetic examples: aq (aqueous), h (hour), min (minutes), sat'd (saturated), eq (equivalents), THF (tetrahydrofuran), RT (room temperature), $Et_3N$ (triethylamine), Zn (zinc dust metal), n-BuOH (n-butyl alcohol), n-BuLi (n-butyl lithium), t-BuOH (tertiary butyl alcohol), NaCl (sodium chloride), $MgSO_4$ (magnesium sulfate), BOC(C(=O)OtBu), $CDCl_3$ (deuterated chloroform), MtBe (methyl tert-butyl ether), $H_2O$ (water), $CHCl_3$ (chloroform), HCl (hydrochloric acid), MeOH (methanol), NaOH (sodium hydroxide), NaOMe (sodium methoxide), TFA (trifluoroacetic acid), $K_2CO_3$ (potassium carbonate), $SOCl_2$ (thionyl chloride), $CH_2Cl_2$ (methylene chloride), EtOAC (ethyl acetate), DMF (dimethylformamide), EtOH (ethanol), DMSO (dimethyl sulfoxide), $NaHCO_3$ (sodium bicarbonate), TLC (thin layer chromatography), HPLC (high performance liquid chromatography), electrospray ionization-mass spectrometry (ESI-MS) or MS (ES), HOBT (hydroxybenzotriazole), EDC (ethyldiethylaminopropylcarbodiimide), DIEA (diisopropylethylamine), HOAc (acetic acid), ACCUFLUOR® NFSi (N-fluorobis (phenylsulfonyl)amine) and other, similar standard abbreviations are used herein.

EXAMPLE 7

Preparation of Intermediate Compounds

4-chloro-5-fluoro-7H-pyrrolo[2,3-d]pyrimidine (1)

A solution of 4-chloro-5-bromo-7H-pyrrolo[2,3-d]pyrimidine (800 mg, 3.45 mmol) in THF (50 mL) at −78° C. was treated with n-BuLi (1.6 M in hexane, 2.2 eq, 7.6 mmol, 4.7 mL) dropwise, and stirred for 30 minutes at the same temperature. The mixture was treated with a solution of ACCUFLUOR® NFSi (2.0 eq, 7 mmol, 2.2 g) in THF (10 mL). The reaction mixture was allowed to warm to room temperature, was stirred for 10 h, and then concentrated to dryness. The residue was dissolved in EtOAc (100 mL), washed with water (3×15 mL) and brine (15 mL), dried with $Na_2SO_4$, and purified by reverse phase HPLC (10×250 mm C18 Luna column, 4.7 mL/min, 10-90% acetonitrile in water over 20 min) to provide intermediate compound 1. ESI-MS m/z=172.1 ($MH^+$).

The reaction described above and intermediate compound 1 are shown below.

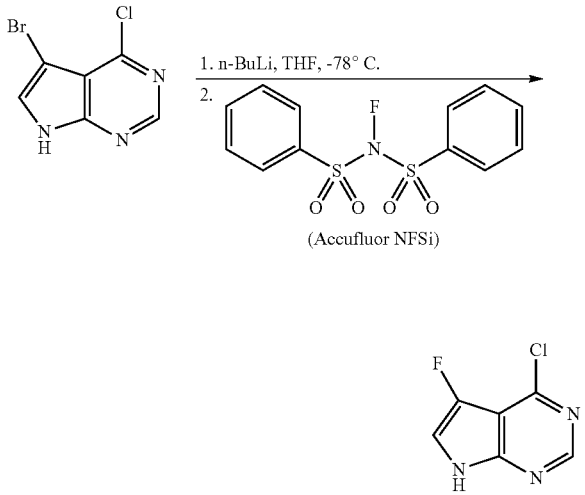

2-amino-6-morpholin-4-ylmethyl-N-phenyl-benzamide (2)

Intermediate compound 2 was prepared according to the procedures set forth in steps A-F below.

6-nitro-benzoic acid methyl ester (3)

Step A: A solution of 6-nitro-benzoic acid in benzene was treated with thionyl chloride (2.5 eq) and stirred at reflux for 8 h. After evaporation, the residue was dissolved in chloroform and then treated with methanol. After stirring at reflux for 3 h, the mixture was evaporated to afford compound 3.

2-bromomethyl-6-nitro-benzoic acid methyl ester (4)

Step B: A mixture of compound 3 (2 g), N-bromosuccinimide (1.93 g), and benzoyl peroxide (0.124 g) in carbon tetrachloride (30 mL) was stirred at reflux overnight. After cooling, solids were filtered off and the filtrate was concentrated to yield compound 4 as a crude, yellow oil.

2-morpholin-4-ylmethyl-6-nitro-benzoic acid methyl ester (5)

Step C: A mixture of compound 4 (3.5 g, crude material), morpholine (0.99 g), potassium carbonate (2.89 g), and potassium iodide (1.66 g) in DMF (22 mL) was stirred at room temperature overnight. The reaction mixture was poured into water (30 mL) and extracted with ethyl acetate (3×30 mL). The combined organic extracts were washed with brine (30 mL), dried over sodium sulfate, and concentrated to a residue. The crude material was purified by flash chromatography (silica gel, 30-50% ethyl acetate/hexanes) to yield compound 5 as a yellow solid.

2-morpholin-4-ylmethyl-6-nitro-benzoic acid (6)

Step D: A solution of compound 5 (0.85 g) and NaOH (0.304 g) in a mixture of water (9 mL), methanol (5 mL), and THF (45 mL) was stirred at reflux for 24 h and concentrated to dryness. The residue was dissolved in water, and the solution was cooled to 0° C. and adjusted to pH 7 with 10% potassium hydrogen sulfate. The mixture was concentrated to dryness, the residue was treated with methanol, and filtered to remove solids. The filtrate was concentrated to yield compound 6 as a yellow solid.

2-morpholin-4-ylmethyl-6-nitro-N-phenyl-benzamide (7)

Step E: A solution of compound 6 (0.62 g, 2.3 mmol) in THF (50 mL) was treated with thionyl chloride (0.94 mL), stirred at room temperature for 4 h, and evaporated to dryness. The residue was dissolved in THF (50 mL) and treated with aniline (0.58 mL, 6.4 mmol) and diisopropylethylamine (1.12 mL, 6.4 mmol). The reaction mixture was stirred for 4 h, concentrated, dissolved in dichloromethane (50 mL), washed with saturated aqueous sodium bicarbonate (25 mL) and brine (25 mL), dried with sodium sulfate, and concentrated. The crude residue of compound 7 then was purified by flash chromatography (5% methanol in dichloromethane).

2-amino-6-morpholin-4-ylmethyl-N-phenyl-benzamide (2)

Step F: A solution of compound 7 (0.3 g) and 10% Pd/C (30 mg) in methanol (35 mL) was stirred under hydrogen (1 atm) for 1.5 h. The mixture was filtered through a bed of CELITE® and the filtrate was concentrated to provide a yellow solid product, intermediate compound 2. ESI-MS m/z=312 ($MH^+$).

Steps A-F and compounds 2-7 are shown in the reaction scheme below.

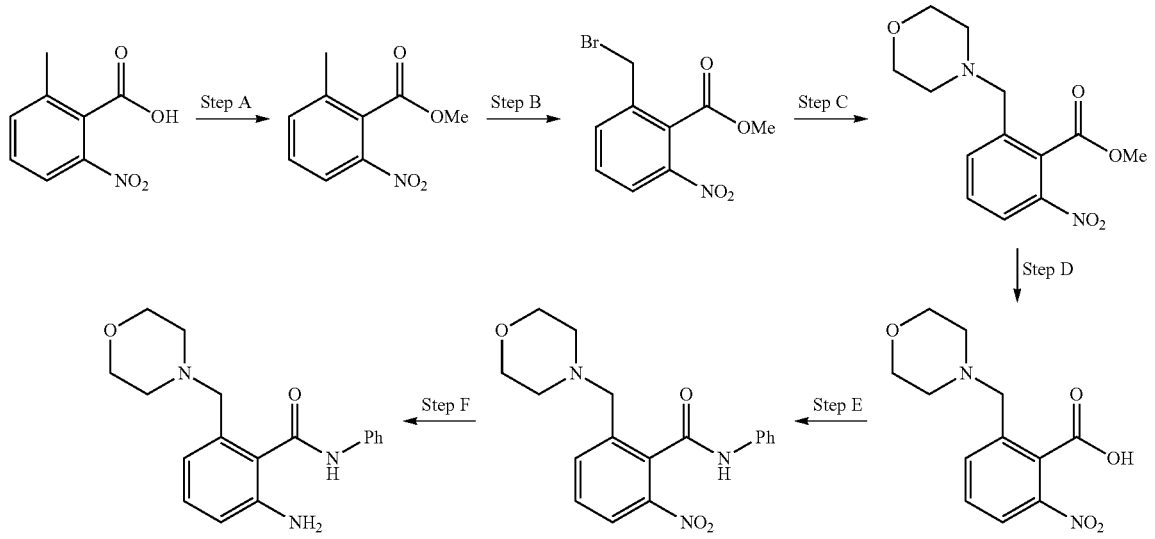

3-morpholin-4-ylmethyl-phenylamine (8)

Intermediate compound 8 (shown below) was prepared according to the procedures set forth in steps A and B.

4-(3-nitrobenzyl)morpholine (9)

Step A: A 250 mL, one-neck, round bottomed flask equipped with a magnetic stirrer and reflux condenser was charged with 1-chloromethyl-3-nitrobenzene (10.0 g, 58.3 mmol), morpholine (15.0 g, 175 mmol) and toluene (75 mL), and the solution was heated at reflux for 2.5 h. The reaction mixture was allowed to cool to ambient temperature then washed with 1N aqueous sodium hydroxide (2×50 mL). The aqueous layer was extracted with ethyl acetate (3×50 mL), and the combined extracts were dried over sodium sulfate and concentrated under reduced pressure to afford compound 9 as an off-white solid. $^1$H NMR ($CDCl_3$) δ (ppm) 8.22 (s, 1H), 8.12 (d, 1H, J=8.2 Hz), 7.68 (d, 1H, J=7.6 Hz), 7.49 (t, 1H, J=7.9 Hz), 3.73 (m, 4H), 3.59 (s, 2H), 2.46 (m, 4H).

3-morpholin-4-ylmethyl-phenylamine (8)

Step B: A 250-mL, three-neck, round bottomed flask equipped with a mechanical stirrer and reflux condensor was charged with compound 9 (12.7 g, 57.4 mmol), iron powder (40.0 g, 71.7 mmol), 2N hydrochloric acid (20 mL) and ethanol (75 mL). The resulting suspension was heated at reflux for 2 h. After this time the mixture was allowed to cool and filtered through a pad of CELITE® 521. The filtrate was concentrated under reduced pressure, the residue diluted with water (100 mL) and basified with solid potassium carbonate to pH 10. The mixture was extracted with ethyl acetate (3×75 mL) and the combined organic extracts were dried over anhydrous sodium sulfate and concentrated under reduced pressure to yield compound 8 as a dark viscous oil. $^1$H NMR ($CDCl_3$) δ(ppm) 7.09 (t, 1H, J=8.1 Hz), 6.70 (m, 2H), 6.58 (m, 1H), 3.70 (m, 4H), 3.40 (bs, 2H), 2.44 (m, 4H). Intermediate compound 8 is shown below.

(8)

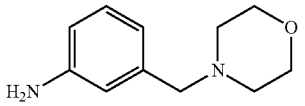

6-bromo-9-(2-trimethylsilanyl-ethoxymethyl)-9H-purine (10)

A 500-mL, one-neck, round bottomed flask equipped with a magnetic stirrer was charged with 6-bromopurine (10.4 g, 52.0 mmol), potassium carbonate (21.5 g, 156 mmol), 4 Å molecular sieves (22.6 g), dimethylformamide (200 mL) and 2-(trimethylsilyl)ethoxymethyl chloride (13.2 g, 78.0 mmol). The reaction mixture was stirred for 18 h at ambient temperature, then filtered with the aid of CELITE®521. Concentration of the filtrate under high vacuum followed by column chromatography gave a 57% yield of intermediate compound 10 as an off-white solid. m.p. 49-52° C.; $^1$H NMR (DMSO-$d_6$) δ (ppm) 8.95 (s, 1H), 8.86 (s, 1H), 3.69 (t, 2H, J=8.0 Hz), 0.93 (t, 2H, J=8.2 Hz), 0.08 (s, 9H); m/z=330 (M+H). Intermediate compound 10 is shown below.

(10)

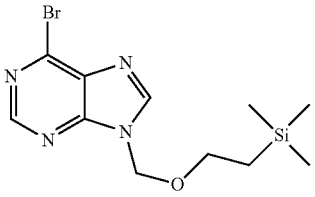

2-amino-6-bromo-9-(2-trimethylsilylethoxy)methyl-9H-purine (11)

Intermediate compound 11 was prepared using the method described above with respect to intermediate compound 10, but 2-amino-6-bromopurine was used in place of 6-bromopurine. Intermediate compound 11 is shown below.

(11)

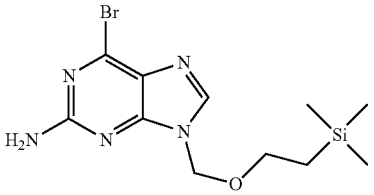

2-di-tert-butyloxycarbonylamino-6-bromo-9-(2-trimethylsilylethoxy)methyl-9H-purine (12)

A 250-mL, one-neck, round bottomed flask equipped with a magnetic stirrer was purged with nitrogen and charged with intermediate compound 11 (11.7 g, 34.0 mmol), di-tert-butyl dicarbonate (22.2 g, 102 mmol), DMAP (581 mg, 4.76 mmol) and anhydrous tetrahydrofuran (150 mL). The reaction mixture was stirred for 18 h at ambient temperature and then evaporated to dryness. Column chromatography of the resulting residue yielded intermediate compound 12 as a white solid. m.p 93-95° C.; $^1$H NMR (DMSO-$d_6$) δ (ppm) 8.99 (s, 1H), 5.71 (s, 2H), 3.66 (t, 2H, J=8.0 Hz), 1.47 (s, 18H), 0.92 (t, 2H, J=8.2 Hz); m/z=546 (M+H). Intermediate compound 12 is shown below.

(12)

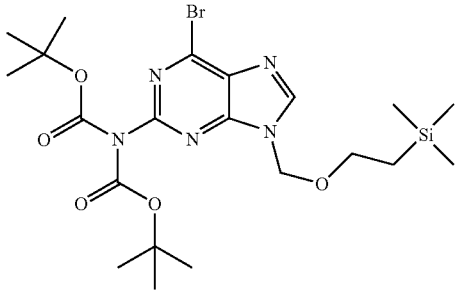

6-chloro-9-(2-trimethylsilanyl-ethoxymethyl)-9H-purine (13)

Intermediate compound 13 was prepared using the method described above with respect to intermediate compound 10, but 6-chloropurine was used in place of 6-bromopurine. Intermediate compound 13 is shown below.

(13)

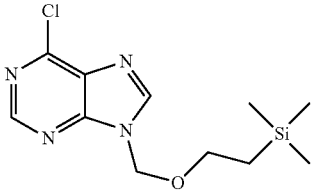

General Procedures

The compounds of the present invention can be prepared by the following methods. Additional compounds are prepared using one of the following methods and selecting appropriate starting materials and reagents. General procedures and specific procedures for synthesizing the present compounds also are set forth in U.S. Pat. No. 6,518,277, incorporated herein by reference.

EXAMPLE 8

Compound Preparation

Compounds in accordance with general formula I (shown above) have been prepared according to the exemplary synthetic procedures described below.

5-methyl-3-phenyl-2-[1-(9H-purin-6-ylamino)-propyl]-3H-quinazolin-4-one (14)

Compound (14) was prepared according to the procedures set forth in steps A-D below.

2-amino-6-methyl-N-phenyl-benzamide (15)

Step A: Thionyl chloride (14.5 mL, 198 mmol) was added to a solution of 2-amino-6-methylbenzoic acid (10.0 g, 66.1 mmol) in benzene (250 mL). The resulting suspension was heated to reflux and stirred overnight. After cooling, the reaction was concentrated in vacuo, and the resulting residue was dissolved in chloroform (300 mL). Aniline (15 mL, 165 mmol) was added, and the mixture heated to reflux. After three hours, the reaction was allowed to cool and the resulting suspension was filtered. The filtrate was subjected to flash chromatography, and the crude product recrystallized from isopropanol to provide compound 15 as a yellow crystalline solid. MS (ES): m/z 227 (M+H), 134. 1H NMR (300 MHz, DMSO-d6) δ 10.26 (s, 1H), 7.75 (d, 2H, J=7.9 Hz), 7.32 (t, 2H, J=7.8 Hz), 7.07 (t, 1H, J=7.3 Hz), 7.00 (t, 1H, J=7.8 Hz), 6.58 (d, 1H, J=8.1 Hz), 6.46 (d, 1H, J=7.4 Hz), 4.98 (br. s, 2H), 2.21 (s, 3H). The reaction described above and compound 15 are shown below.

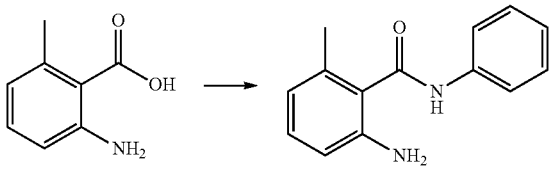

[1-(5-methyl-4-oxo-3-phenyl-3,4-dihydroquinazolin-2-yl)propyl]-carbamic acid benzyl ester (16)

Step B: Compound 15 (1.20 g, 5.30 mmol) was combined with 2-benzyloxycarbonylaminobutyric acid 2,5-dioxo-pyrrolidin-1-yl ester (2.13 g, 6.36 mmol), dimethylaminopyridine (915 mg, 7.49 mmol), and diisopropylethylamine (1.10 mL, 6.36 mmol) in toluene (15 mL). The mixture was heated to 110° C. and stirred at that temperature for 22 hours. After cooling, the reaction was purified by flash chromatography to provide the quinazolinone (16) as a pale yellow solid. MS (ES): m/z 428 (M+H). $^1$H NMR (300 MHz, DMSO-d6) δ 10.26 (s, 1H), 7.75 (d, 2H, J=7.9 Hz), 7.32 (t, 2H, J=7.8 Hz), 7.07 (t, 1H, J=7.3 Hz), 7.00 (t, 1H, J=7.8 Hz), 6.58 (d, 1H, J=8.1 Hz), 6.46 (d, 1H, J=7.4 Hz), 4.98 (br. s, 2H), 2.21 (s, 3H). The reaction described above and compound 16 are shown below.

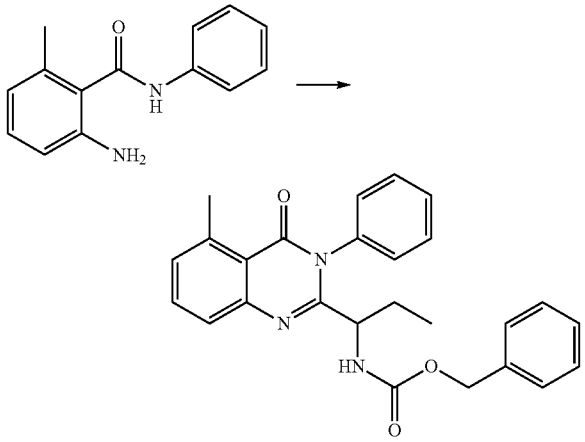

2-(1-amino-propyl)-5-methyl-3-phenyl-3H-quinazolin-4-one (17)

Step C: A catalytic amount of 10% Pd/C was added to a solution of compound 16 (691 mg, 1.62 mmol) in ethanol (8 mL). The resulting mixture was placed under a hydrogen atmosphere (balloon pressure) and allowed to stir at ambient temperature overnight. The reaction was filtered, and the filtrate concentrated in vacuo. The resulting crude residue was purified by flash chromatography to afford the free amine, compound 17, as a pale yellow oil. (ES): m/z 294 (M+H), 237. $^1$H NMR (300 MHz, DMSO-d6) δ 7.68 (t, 1H, J=7.7 Hz), 7.49-7.63 (m, 3H), 7.43-7.49 (m, 1H), 7.36-7.43 (m, 1H), 7.19-7.34 (m, 2H), 4.03-4.19 (m, 1H), 2.72 (s, 3H), 2.04 (br. s, 2H), 1.63-1.79 (m, 1H), 1.29-1.44 (m, 1H), 0.68 (t, 3H, J=7.3 Hz). The reaction described above and compound 17 are shown below.

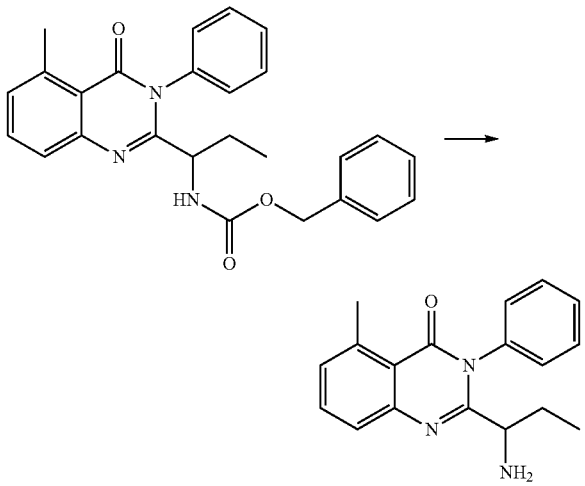

Step C (alternative procedure): Trifluoroacetic acid was added to a solution of the Boc-protected amine compound 16 in dichloromethane. The resulting solution was allowed to stir at ambient temperature until LCMS or TLC indicated complete consumption of starting material. The reaction was concentrated in vacuo, and the residue purified by flash chromatography to provide the free amine 17.

5-methyl-3-phenyl-2-[1-(9H-purin-6-ylamino)-propyl]-3H-quinazolin-4-one (14)

Step D: Compound 17 (100 mg, 0.341 mmol) was combined with 6-bromo purine (75 mg, 0.375 mmol) and diisopropylethylamine (65 uL, 0.375 mmol) in n-butanol (1.0 mL). The reaction was sealed, heated to 120° C., and stirred for 18 hours. The solution was allowed to cool, then concentrated in vacuo. The resulting residue was purified by prep HPLC to provide compound 14 as an olive solid. (ES): m/z 412 (M+H), 206. $^1$H NMR (300 MHz, DMSO-d6) δ 8.96-9.06 (br. m, 1H), 8.53 (br. s, 1H), 8.51 (s, 1H), 7.68 (t, 1H, J=7.8 Hz), 7.45-7.62 (m, 6H), 7.31 (d, 1H, J=7.3 Hz), 4.76-4.86 (m, 1H), 2.73 (s, 3H), 1.98-2.11 (m, 1H), 1.76-1.94 (m, 1H), 0.79 (t, 3H, J=7.2 Hz). The reaction described above and compound 14 are shown below.

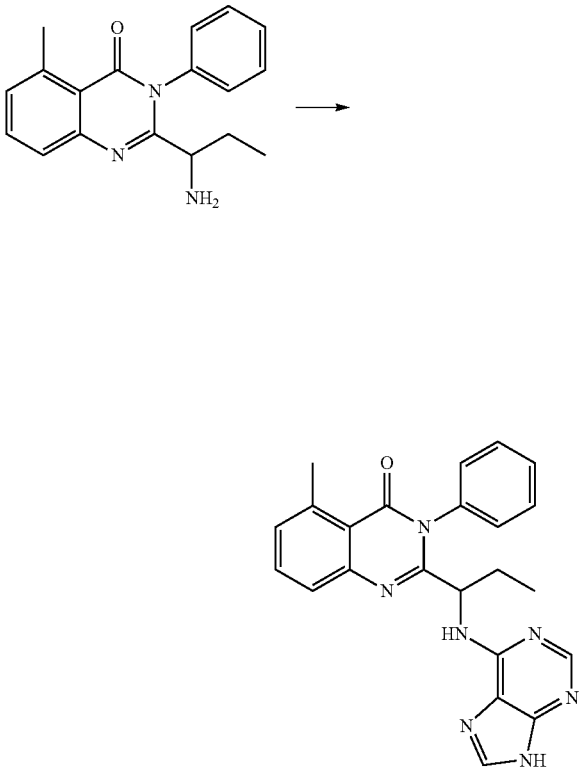

2-[1-(2-fluoro-9H-purin-6-ylamino)-ethyl]-5-methyl-3-phenyl-3H-quinazolin-4-one (18)

Compound 18 was prepared using the general procedure described above with respect to compound 14, but 2-fluoro-6-chloropurine was used in place of 6-bromopurine in step D. ESI-MS m/z 416.1 (MH$^+$). Compound 18 is shown below.

(18)

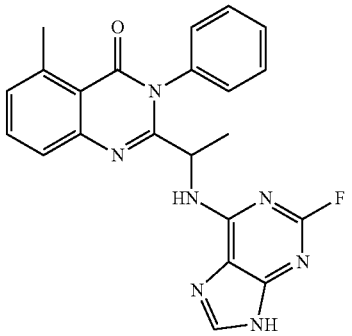

3-(2,6-difluoro-phenyl)-5-methyl-2-[1-(9H-purin-6-ylamino)-ethyl]-3H-quinazolin-4-one (19)

Compound 19 was prepared using the general procedure described above with respect to compound 14, but 2,6-difluorolaniline was used in place of aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 434.1 (MH$^+$). Compound 19 is shown below.

(19)

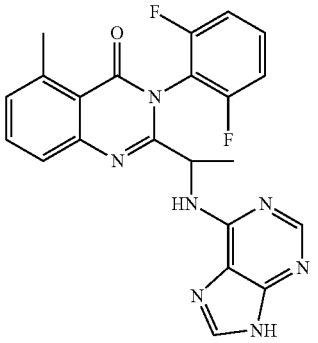

2-[1-(2-amino-9H-purin-6-ylamino)-ethyl]-3-(2,6-difluoro-phenyl)-5-methyl-3H-quinazolin-4-one (20)

Compound 20 was prepared using the general procedure described above with respect to compound 14, but 2,6-difluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. ESI-MS m/z 449.5 (MH$^+$). Compound 20 is shown below.

(20)

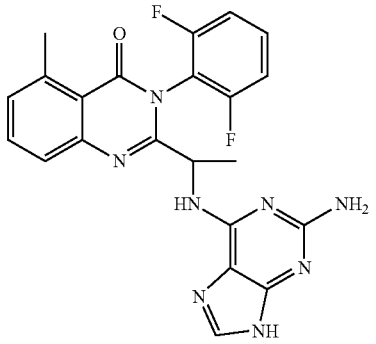

3-(2,6-difluoro-phenyl)-2-[1-(2-fluoro-9H-purin-6-ylamino)-ethyl]-5-methyl-3H-quinazolin-4-one (21)

Compound 21 was prepared using the general procedure described above with respect to compound 14, but 2,6-difluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-fluoro-6-chloropurine was substituted for 6-bromopurine in step D. $^1$HNMR (MeOH-d4): δ 8.22-8.17 (m, 1H); 7.76-7.62 (m, 2H); 7.47-7.45 (m, 1H); 7.38-7.33 (m, 1.2H); 7.30-7.17 (m, 1H); 6.88-6.75 (m, 1H); 5.30-5.27 (m, 0.5H); 5.09-5.07 (m, 0.5H); 2.778 (s, 3H); 1.62-1.50 (m, 3H). Compound 21 is shown below.

(21)

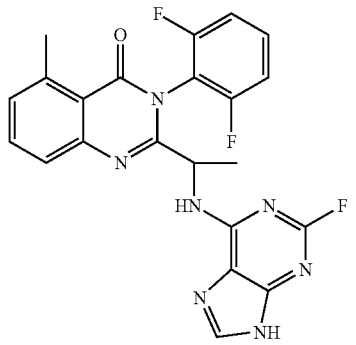

3-(2,6-difluoro-phenyl)-5-methyl-2-[1-(7H-pyrrolo[2,3-d]pyrimidin-4-ylamino)-ethyl]-3H-quinazolin-4-one (22)

Compound 22 was prepared using the general procedure described above with respect to compound 14, but 2,6-difluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 4-chloro-7H-pyrrolo[2,3-d]pyrimidine was substituted for 6-bromopurine in step D. ESI-MS m/z 433 ($MH^+$). Compound 22 is shown below.

(22)

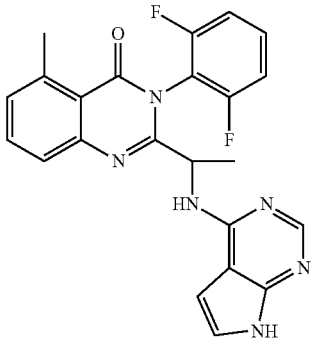

2-[1-(2-amino-9H-purin-6-ylamino)-propyl]-5-methyl-3-phenyl-3H-quinazolin-4-one (23)

Compound 23 was prepared using the general procedure described above with respect to compound 14, but 2-amino-6-bromopurine was substituted for 6-bromopurine in step D. MS (ES): m/z 427 (M+H), 214. Compound 23 is shown below.

(23)

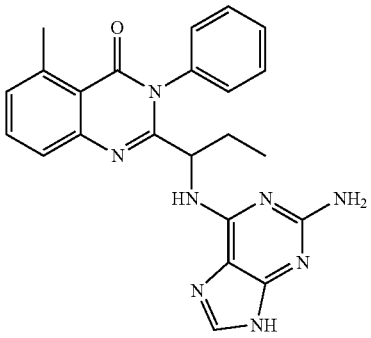

5-methyl-3-phenyl-2-[1-(7H-pyrrolo[2,3-d]pyrimidin-4-ylamino)-propyl]-3H-quinazolin-4-one (24)

Compound 24 was prepared using the general procedure described above with respect to compound 14, but 7-deaza-6-chloropurine was substituted for 6-bromopurine in step D. MS (ES): m/z 411 (M+H), 206. Compound 24 is shown below.

(24)

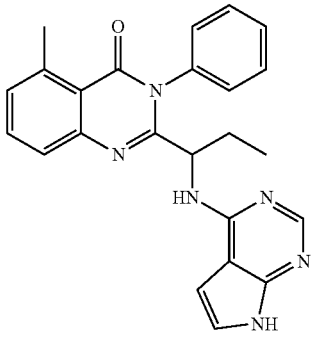

2-[1-(2-fluoro-9H-purin-6-ylamino)-propyl]-5-methyl-3-phenyl-3H-quinazolin-4-one (25)

Compound 25 was prepared using the general procedure described above with respect to compound 14, but 2-fluoro-6-chloropurine was substituted for 6-bromopurine in step D. MS (ES): m/z 430 (M+H), 446. Compound 25 is shown below.

(25)

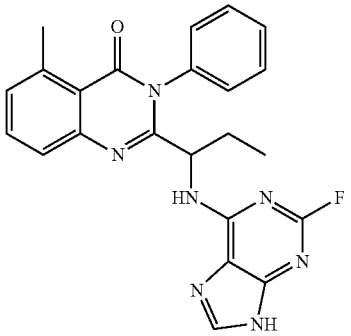

5-methyl-3-phenyl-2-[1-(9H-purin-6-ylamino)-ethyl]-3H-quinazolin-4-one (26)

Compound 26 was prepared using the general procedure described above with respect to compound 14, but 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. MS (ES): m/z 398 (M+H). Compound 26 is shown below.

(26)

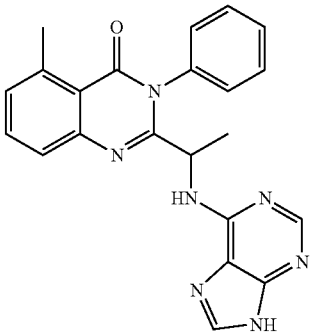

2-[1-(2-amino-9H-purin-6-ylamino)-ethyl]-5-methyl-3-phenyl-3H-quinazolin-4-one (27)

Compound 27 was prepared using the general procedure described above with respect to compound 14, but 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. ESI-MS m/z 413.1 ($MH^+$). Compound 27 is shown below.

(27)

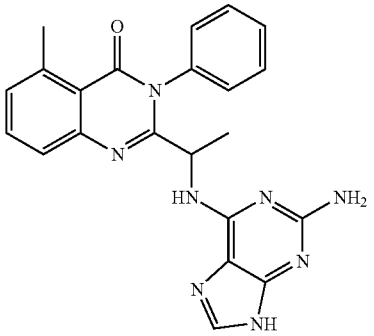

2-[2-benzyloxy-1-(9H-purin-6-ylamino)-ethyl]-5-methyl-3-phenyl-3H-quinazolin-4-one (28)

Compound 28 was prepared using the general procedure described above with respect to compound 14, but 3-benzyloxy-2-tert-butoxycarbonylaminopropionic acid 2,5-dioxo-pyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. MS (ES): m/z 504 (M+H), 396, 261. Compound 28 is shown below.

(28)

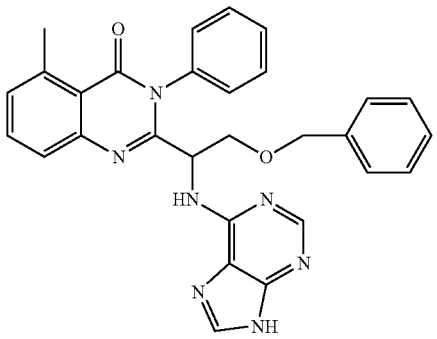

2-[1-(2-amino-9H-purin-6-ylamino)-2-benzyloxy-ethyl]-5-methyl-3-phenyl-3H-quinazolin-4-one (29)

Compound 29 was prepared using the general procedure described above with respect to compound 14, but 3-benzyloxy-2-tert-butoxycarbonylaminopropionic acid 2,5-dioxo-pyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. MS (ES): m/z 519 (M+H), 411, 261. Compound 29 is shown below.

(29)

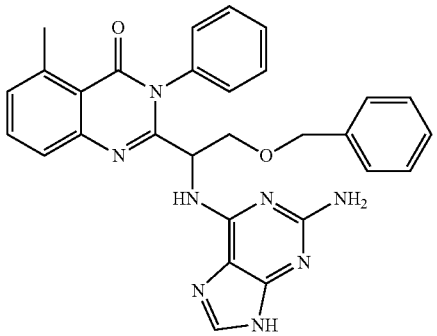

2-[2-benzyloxy-1-(7H-pyrrolo[2,3-d]pyrimidin-4-ylamino)-ethyl]-5-methyl-3-phenyl-3H-quinazolin-4-one (30)

Compound 30 was prepared using the general procedure described above with respect to compound 14, but 3-benzyloxy-2-tert-butoxycarbonylaminopropionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 4-chloro-7H-pyrrolo[2,3-d]pyrimidine was substituted for 6-bromopurine in step D. MS (ES): m/z 503 (M+H), 395. Compound 30 is shown below.

(30)

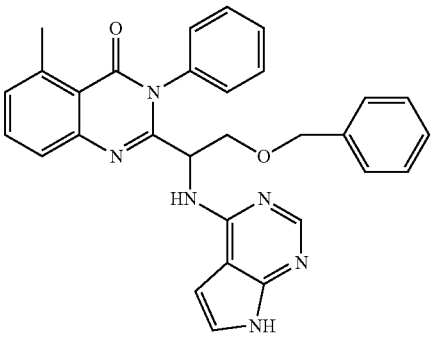

2-[2-benzyloxy-1-(2-fluoro-9H-purin-6-ylamino)-ethyl]-5-methyl-3-phenyl-3H-quinazolin-4-one (31)

Compound 31 was prepared using the general procedure described above with respect to compound 14, but 3-benzyloxy-2-tert-butoxycarbonylaminopropionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-fluoro-6-chloropurine was substituted for 6-bromopurine in step D. MS (ES): m/z 522 (M+H), 414, 261. Compound 31 is shown below.

(31)

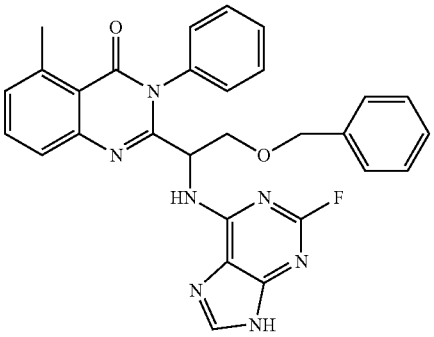

3-(4-fluoro-phenyl)-5-methyl-2-[1-(9H-purin-6-ylamino)-ethyl]-3H-quinazolin-4-one (32)

Compound 32 was prepared using the general procedure described above with respect to compound 14, but, with the following changes: 4-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 416.1 ($MH^+$). Compound 32 is shown below.

(32)

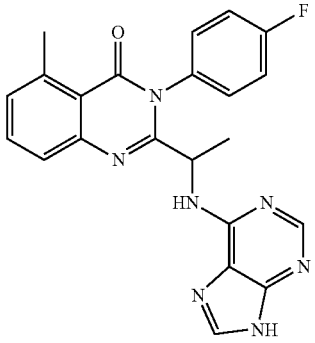

2-[1-(2-amino-9H-purin-6-ylamino)-ethyl]-3-(4-fluoro-phenyl)-5-methyl-3H-quinazolin-4-one (33)

Compound 33 was prepared using the general procedure described above with respect to compound 14, but 4-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. ESI-MS m/z 431.1 ($MH^+$). Compound 33 is shown below.

(33)

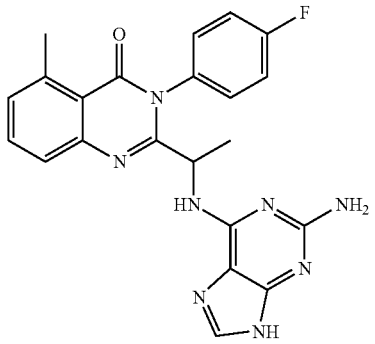

3-(4-fluoro-phenyl)-2-[1-(2-fluoro-9H-purin-6-ylamino)-ethyl]-5-methyl-3H-quinazolin-4-one (34)

Compound 34 was prepared using the general procedure described above with respect to compound 14, but, 4-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-fluoro-6-chloropurine was substituted for 6-bromopurine in step D. ESI-MS m/z 434.1 ($MH^+$). Compound 34 is shown below.

(34)

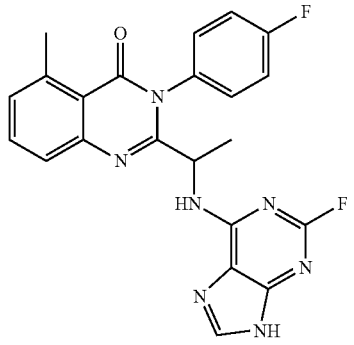

3-(4-fluoro-phenyl)-5-methyl-2-[1-(7H-pyrrolo[2,3-d]pyrimidin-4-ylamino)-ethyl]-3H-quinazolin-4-one (35)

Compound 35 was prepared using the general procedure described above with respect to compound 14, but 4-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 4-chloro-7H-pyrrolo[2,3-d]pyrimidine was substituted for 6-bromopurine in step D. ESI-MS m/z 415.1 ($MH^+$). Compound 35 is shown below.

(35)

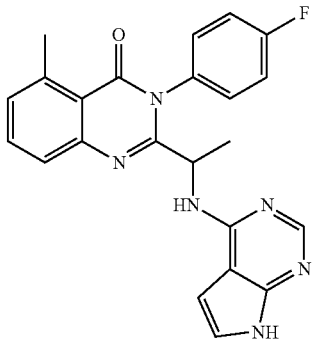

5-methyl-3-phenyl-2-[1-(7H-pyrrolo[2,3-d]pyrimidin-4-ylamino)-ethyl]-3H-quinazolin-4-one (36)

Compound 36 was prepared using the general procedure described above with respect to compound 14, but 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 4-chloro-7H-pyrrolo[2,3-d]pyrimidine was substituted for 6-bromopurine in step D. ESI-MS m/z 397 ($MH^+$). Compound 36 is shown below.

(36)

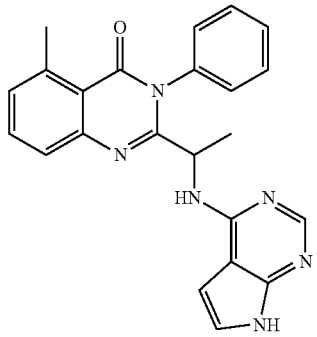

3-(3-fluoro-phenyl)-5-methyl-2-[1-(9H-purin-6-ylamino)-ethyl]-3H-quinazolin-4-one (37)

Compound 37 was prepared using the general procedure described above with respect to compound 14, but 3-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. $^1$HNMR (dmso-d6): 8.30-8.28 (m, 2H); 7.70-7.49 (m, 3H); 7.44-7.30 (m, 4H); 4.91-4.88 (m, 1H); 2.72-2.68 (m, 3h); 1.50-1.48 (m, 3H). Compound 37 is shown below.

(37)

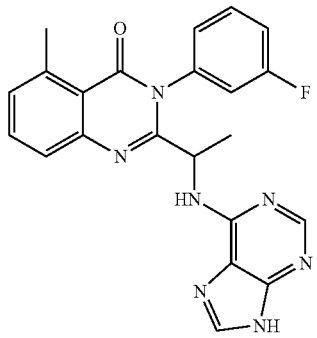

2-[1-(2-amino-9H-purin-6-ylamino)-ethyl]-3-(3-fluoro-phenyl)-5-methyl-3H-quinazolin-4-one (38)

Compound 38 was prepared using the general procedure described above with respect to compound 14, but 3-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. $^1$H NMR (dmso-d6): 8.16-8.12 (m, 1H); 7.74-7.69 (m, 1H); 7.62-7.53 (m, 2H); 7.46-7.12 (m, 6H); 4.96 (bs, 1H); 2.74-2.67 (m, 3H); 1.47-1.45 (m, 3H). Compound 38 is shown below.

(38)

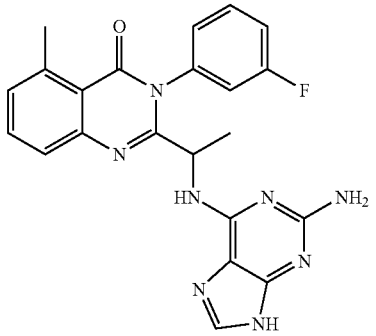

3-(3-fluoro-phenyl)-5-methyl-2-[1-(7H-pyrrolo[2,3-d]pyrimidin-4-ylamino)-ethyl]-3H-quinazolin-4-one (39)

Compound 39 was prepared using the general procedure described above with respect to compound 14, but 3-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 4-chloro-7H-pyrrolo[2,3-d]pyrimidine was substituted for 6-bromopurine in step D. ESI-MS m/z 415.1 ($MH^+$). Compound 39 is shown below.

(39)

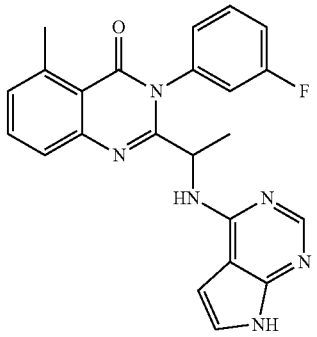

5-methyl-3-phenyl-2-[1-(9H-purin-6-yl)-pyrrolidin-2-yl]-3H-quinazolin-4-one (40)

Compound 40 was prepared using the general procedure described above with respect to compound 14, but pyrrolidine-1,2-dicarboxylic acid 1-tert-butyl ester 2-(2,5-dioxo-pyrrolidin-1-yl) ester was substituted for 2-benzyloxycarbonylaminobutyric acid 2,5-dioxo-pyrrolidin-1-yl ester in step B, and the alternate procedure (TFA deprotection) was used in step C. MS (ES): m/z 424 (M+H), 212. Compound 40 is shown below.

(40)

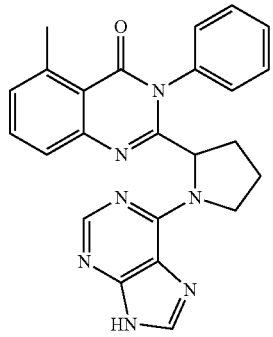

2-[2-hydroxy-1-(9H-purin-6-ylamino)-ethyl]-5-methyl-3-phenyl-3H-quinazolin-4-one (41)

A suspension of compound 28 (60 mg, 0.097 mmol), $Pd(OH)_2$ (cat.), and aqueous $Na_2CO_3$ (0.5 mL) in ethanol (2.5 mL) was hydrogenated at 45 psi for 14 days. The mixture was filtered to removed solvents, and the resulting filtrate was purified by HPLC to provide the product 41 as a white solid. MS (ES): m/z 414 (M+H), 396, 261. Compound 41 is shown below.

(41)

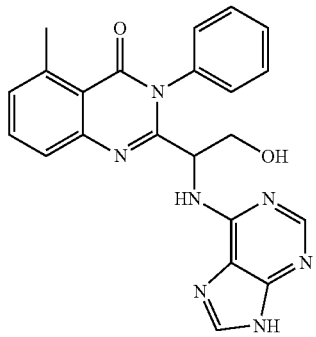

5-methyl-3-phenyl-2-[phenyl-(9H-purin-6-ylamino)-methyl]-3H-quinazolin-4-one (42)

Compound 42 was prepared using the general procedure described above with respect to compound 14, but tert-butoxycarbonylamino-phenyl-acetic acid 2,5-dioxo-pyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. MS (ES): m/z 460 (M+H), 325. Compound 42 is shown below.

(42)

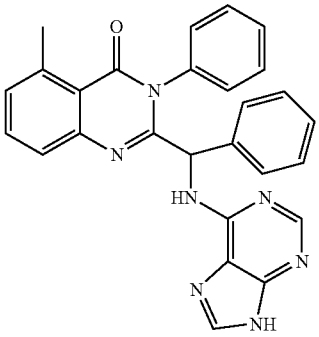

2-[(2-amino-9H-purin-6-ylamino)-phenyl-methyl]-5-methyl-3-phenyl-3H-quinazolin-4-one (43)

Compound 43 was prepared using the general procedure described above with respect to compound 14, but tert-butoxycarbonylamino-phenyl-acetic acid 2,5-dioxo-pyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. MS (ES): m/z 475 (M+H). Compound 43 is shown below.

(43)

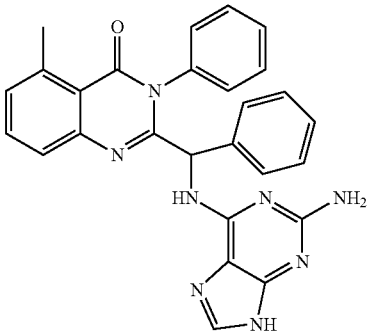

2-[(2-fluoro-9H-purin-6-ylamino)-phenyl-methyl]-5-methyl-3-phenyl-3H-quinazolin-4-one (44)

Compound 44 was prepared using the general procedure described above with respect to compound 14, but tert-butoxycarbonylamino-phenyl-acetic acid 2,5-dioxo-pyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-fluoro-6-chloropurine was substituted for 6-bromopurine in step D. MS (ES): m/z 478 (M+H), 325. Compound 44 is shown below.

(44)

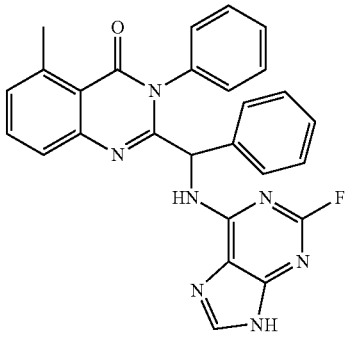

5-methyl-3-phenyl-2-[phenyl-(7H-pyrrolo[2,3-d] pyrimidin-4-ylamino)-methyl]-3H-quinazolin-4-one (45)

Compound 45 was prepared using the general procedure described above with respect to compound 14, but tert-butoxycarbonylamino-phenyl-acetic acid 2,5-dioxo-pyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 4-chloro-7H-pyrrolo[2,3-d]pyrimidine was substituted for 6-bromopurine in step D. MS (ES): m/z 459 (M+H), 230. Compound 45 is shown below.

(45)

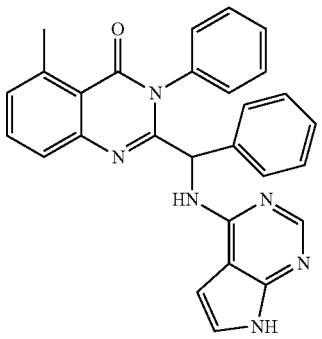

5-fluoro-3-phenyl-2-[1-(9H-purin-6-ylamino)-ethyl]-3H-quinazolin-4-one (46)

Compound 46 was prepared using the general procedure described above with respect to compound 14, but 2-amino-6-fluoro-benzoic acid was substituted for 2-amino-6-methyl-benzoic acid in step A, 2-tert-butoxycarbonylamino-propionic acid 2,5-dioxopyrrolidin-1-yl ester was substituted for 2-benzyloxycarbonylaminobutyric acid 2,5-dioxo-pyrroli din-1-yl ester in step B, and the alternate procedure (TFA deprotection) was used in step C. ESI-MS m/z 402.3 ($MH^+$). Compound 46 is shown below.

(46)

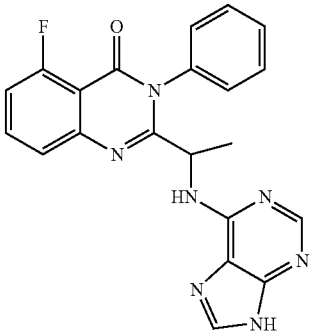

2-[1-(2-amino-9H-purin-6-ylamino)-ethyl]-5-fluoro-3-phenyl-3H-quinazolin-4-one (47)

Compound 47 was prepared using the general procedure described above with respect to compound 14, but 2-amino-6-fluoro-benzoic acid was substituted for 2-amino-6-methyl-benzoic acid in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. ESI-MS m/z 417.2 ($MH^+$). Compound 47 is shown below.

(47)

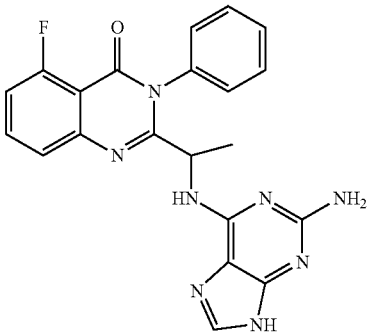

2-[1-(2-amino-9H-purin-6-ylamino)-ethyl]-5-chloro-3-phenyl-3H-quinazolin-4-one (48)

Compound 48 was prepared using the general procedure described above with respect to compound 14, but 2-amino-6-chlorobenzoic acid was substituted for 2-amino-6-methyl-benzoic acid in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. MS (ES): m/z 433 (M+H), 177. Compound 48 is shown below.

(48)

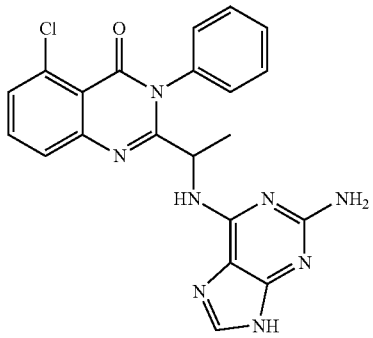

[5-(5-methyl-4-oxo-3-phenyl-3,4-dihydro-quinazolin-2-yl)-5-(9H-purin-6-ylamino)-pentyl]-carbamic acid benzyl ester (49)

Compound 49 was prepared using the general procedure described above with respect to compound 14, but 6-benzyloxycarbonylamino-2-tert-butoxycarbonylamino-hexanoic acid 2,5-dioxo-pyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 589 ($MH^+$). Compound 49 is shown below.

(49)

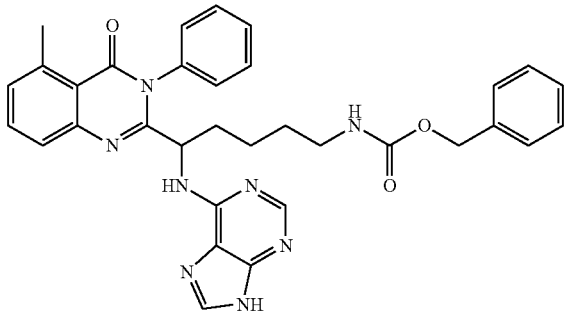

[5-(2-amino-9H-purin-6-ylamino)-5-(5-methyl-4-oxo-3-phenyl-3,4-dihydro-quinazolin-2-yl)-pentyl]-carbamic acid benzyl ester (50)

Compound 50 was prepared using the general procedure described above with respect to compound 14, but 6-benzyloxycarbonylamino-2-tert-butoxycarbonylamino-hexanoic acid 2,5-dioxo-pyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. ESI-MS m/z 604 ($MH^+$). Compound 50 is shown below.

(50)

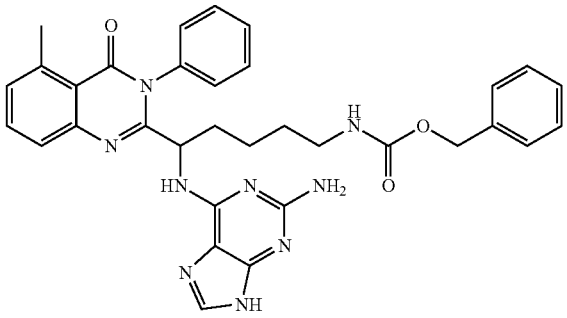

[4-(5-methyl-4-oxo-3-phenyl-3,4-dihydro-quinazolin-2-yl)-4-(9H-purin-6-ylamino)-butyl]-carbamic acid benzyl ester (51)

Compound 51 was prepared using the general procedure described above with respect to compound 14, but 6-benzyloxycarbonylamino-2-tert-butoxycarbonylamino-pentanoic acid 2,5-dioxo-pyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 575 ($MH^+$). Compound 51 is shown below.

(51)

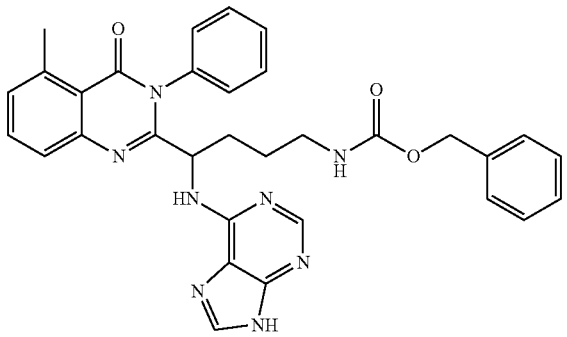

[4-(2-amino-9H-purin-6-ylamino)-4-(5-methyl-4-oxo-3-phenyl-3,4-dihydro-quinazolin-2-yl)-butyl]-carbamic acid benzyl ester (52)

Compound 52 was prepared using the general procedure described above with respect to compound 14, but 6-benzyloxycarbonylamino-2-tert-butoxycarbonylamino-pentanoic acid 2,5-dioxo-pyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. ESI-MS m/z 590 ($MH^+$). Compound 52 is shown below.

(52)

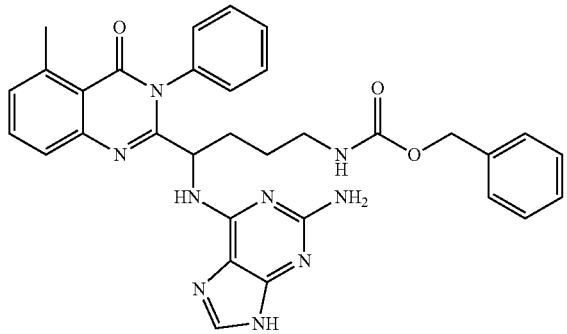

3-phenyl-2-[1-(9H-purin-6-ylamino)-ethyl]-3H-quinazolin-4-one (53)

Compound 53 was prepared using the general procedure described above with respect to compound 14, but anthranilic acid was substituted for 2-amino-6-methylbenzoic acid in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. MS (ES): m/z 384.1 (M+H). Compound 53 is shown below.

(53)

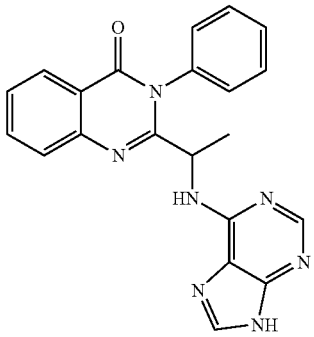

2-[5-amino-1-(9H-purin-6-ylamino)-pentyl]-5-methyl-3-phenyl-3H-quinazolin-4-one) (54)

A mixture of compound 49 (28.5 mg) and palladium on carbon (10 mg, 10% Pd) in ethanol (2 mL) was shaken with hydrogen (40 psi) for 48 h. The mixture was filtered through CELITE® and the filtrate was concentrated to afford the product 54. ESI-MS m/z 455 ($MH^+$). Compound 54 is shown below.

(54)

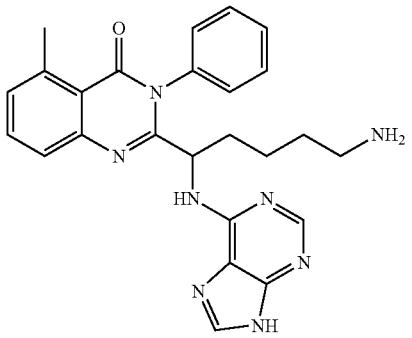

2-[5-amino-1-(2-amino-9H-purin-6-ylamino)-pentyl]-5-methyl-3-phenyl-3H-quinazolin-4-one (55)

Compound 55 was prepared using the general procedure described above with respect to compound 54, but compound 50 was substituted for compound 49. ESI-MS m/z 470 ($MH^+$). Compound 55 is shown below.

(55)

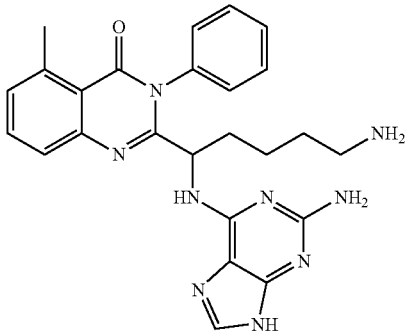

2-[1-(2-amino-9H-purin-6-ylamino)-ethyl]-3-(2,6-Dimethyl-phenyl)-5-methyl-3H-quinazolin-4-one (56)

Compound 56 was prepared using the general procedure described above with respect to compound 14, but 2,6-dimethylaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. ESI-MS m/z 441 ($MH^+$). Compound 56 is shown below.

(56)

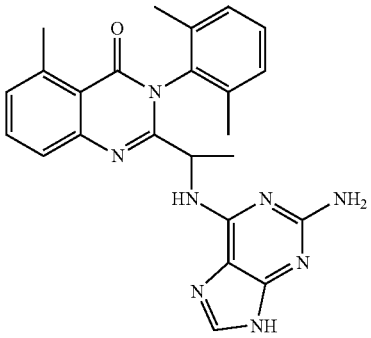

3-(2,6-dimethyl-phenyl)-5-methyl-2-[1-(9H-purin-6-ylamino)-ethyl]-3H-quinazolin-4-one (57)

Compound 57 was prepared using the general procedure described above with respect to compound 14, but 2,6-dimethylaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 426 ($MH^+$). Compound 57 is shown below.

(57)

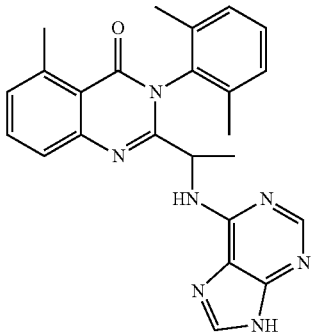

5-morpholin-4-ylmethyl-3-phenyl-2-[1-(9H-purin-6-ylamino)-ethyl]-3H-quinazolin-4-one (58)

Compound 58 was prepared using steps B, C, and D of the general procedure described above with respect to compound 14, but intermediate compound 2 was substituted for the product of step A in step B (step A was thus not needed), 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 483 ($MH^+$). Compound 58 is shown below.

(58)

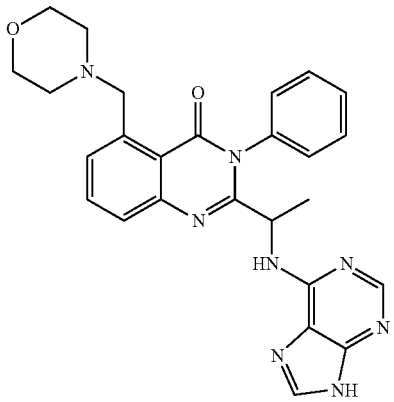

2-[1-(2-amino-9H-purin-6-ylamino)-ethyl]-5-morpholin-4ylmethyl-3-phenyl-3H-quinazolin-4-one (59)

Compound 59 was prepared using the general procedure described above with respect to compound 58, but 2-amino-6-bromopurine was substituted for 6-bromopurine in step D. ESI-MS m/z 498 ($MH^+$). Compound 59 is shown below.

(59)

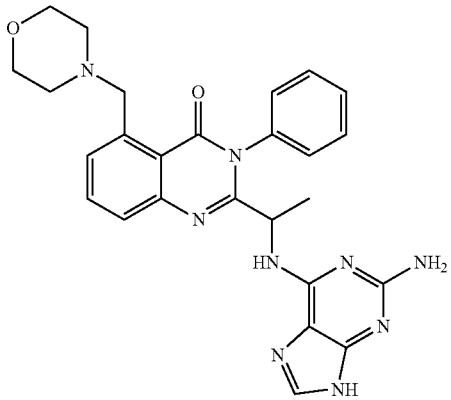

2-[4-amino-1-(2-amino-9H-purin-6-ylamino)-butyl]-5-methyl-3-phenyl-3H-quinazolin-4-one (60)

Compound 60 was prepared using the general procedure described above with respect to compound 54, but compound 52 was substituted for compound 49. ESI-MS m/z 456 ($MH^+$). Compound 60 is shown below.

(60)

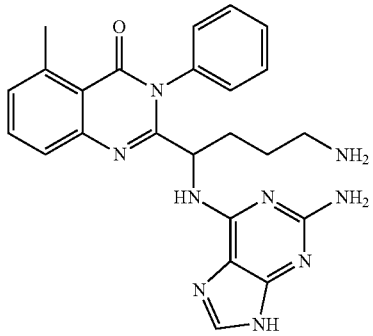

6-fluoro-3-phenyl-2-[1-(9H-purin-6-ylamino)-ethyl]-3H-quinazolin-4-one (61)

Compound 61 was prepared using the general procedure described above with respect to compound 14, but 2-amino-5-fluorobenzoic acid was substituted for 2-amino-5-methylbenzoic acid in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step C, and the alternate procedure (TFA deprotection) was used in step C. ESI-MS m/z 402 ($MH^+$). Compound 61 is shown below.

(61)

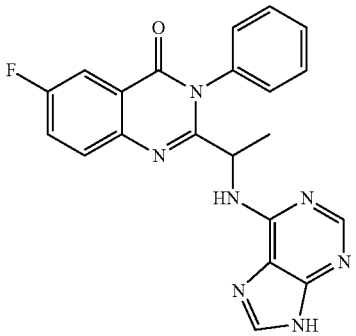

2-[1-(2-amino-9H-purin-6-ylamino)-ethyl]-6-fluoro-3-phenyl-3H-quinazolin-4-one (62)

Compound 62 was prepared using the general procedure described above with respect to compound 61, but 2-amino-6-bromopurine was substituted for 6-bromopurine in step D. ESI-MS m/z 417 ($MH^+$). Compound 62 is shown below.

(62)

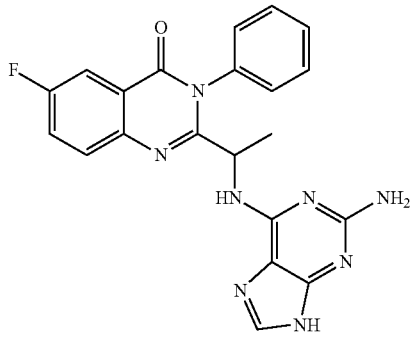

2-[2-tert-butoxy-1-(9H-purin-6-ylamino)-ethyl]-5-methyl-3-phenyl-3H-quinazolin-4-one (63)

Compound 63 was prepared using the general procedure described above with respect to compound 14, but 2-benzyloxycarbonylamino-3-tert-butoxy-propionic acid 2,5-dioxopyrrolidin-1-yl ester was substituted for 2-benzyloxycarbonylaminobutyric acid 2,5-dioxo-pyrrolidin-1-yl ester in step B. MS (ES): m/z 470 (M+H), 396, 261. Compound 63 is shown below.

(63)

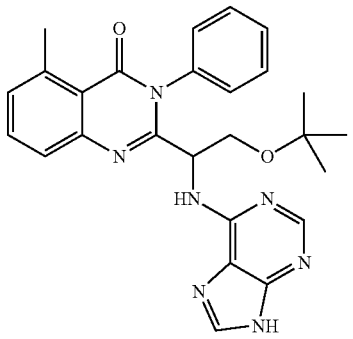

3-(3-methyl-phenyl)-5-methyl-2-[1-(9H-purin-6-ylamino)-ethyl]-3H-quinazolin-4-one (64)

Compound 64 was prepared using the general procedure described above with respect to compound 14, but m-toluidine was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. $^1$H NMR (dmso-d6): 8.41-8.36 (m, 2H); 7.71-7.66 (m, 1H); 7.53-7.51 (m, 5H); 4.97 (m, 1H); 2.72 (s, 3H); 2.39 (s, 1.5H); 2.09 (s, 1.5H); 1.50-1.48 (m, 3H). Compound 64 is shown below.

(64)

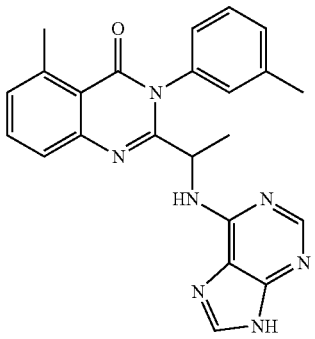

2-[1-(2-amino-9H-purin-6-ylamino)-ethyl]-3-(3-methyl-phenyl)-5-methyl-3H-quinazolin-4-one (65)

Compound 65 was prepared using the general procedure described above with respect to compound 14, but m-toluidine was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. $^1$H NMR (dmso): 8.94-8.92 (m, 1H); 8.18 (s, 1H); 7.75-7.68 (m, 1H); 7.58-7.51 (m, 1H); 5.07-4.96 (m, 1H); 2.79-2.73 (m, 3H); 2.40 (s, 1.5H); 1.91 (s, 1.5H); 1.48-1.43 (m, 3H). Compound 65 is shown below.

(65)

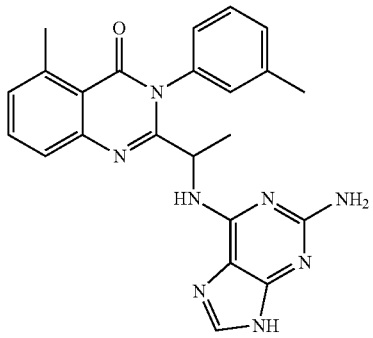

3-(3-chloro-phenyl)-5-methyl-2-[1-(9H-purin-6-ylamino)-ethyl]-3H-quinazolin-4-one (66)

Compound 66 was prepared using the general procedure described above with respect to compound 14, but 3-chloroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. $^1$H NMR (dmso-d6): 8.40-8.31 (m, 2H); 7.73-7.66 (m, 1H); 7.55-7.32 (m, 6H); 5.04-4.86 (m, 1H); 2.72 (s, 3H); 1.52-1.50 (m, 3H). Compound 66 is shown below.

(66)

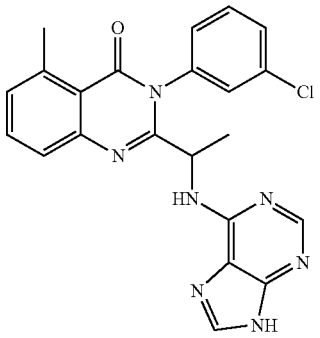

2-[1-(2-amino-9H-purin-6-ylamino)-ethyl]-3-(3-chloro-phenyl)-5-methyl-3H-quinazolin-4-one (67)

Compound 67 was prepared using the general procedure described above with respect to compound 66, but 2-amino-6-bromopurine was substituted for 6-bromopurine in step D. ESI-MS m/z 447.2 ($MH^+$). Compound 67 is shown below.

(67)

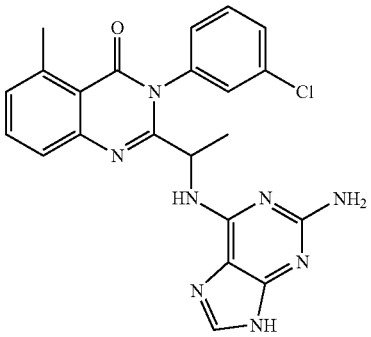

2-[1-(2-amino-9H-purin-6-ylamino)-2-hydroxy-ethyl]-5-methyl-3-phenyl-3H-quinazolin-4-one (68)

Compound 68 was prepared using the general procedure described above with respect to compound 14, but 2-benzyloxycarbonylamino-3-tert-butoxy-propionic acid 2,5-dioxo-pyrrolidin-1-yl ester was substituted for 2-benzyloxycarbonylaminobutyric acid 2,5-dioxo-pyrrolidin-1-yl ester in step B, and 2-amino-6-bromopurine was substituted for 6-bromopurine in step D. The obtained 2-[1-(2-amino-9H-purin-6-ylamino)-2-tert-butoxy-ethyl]-5-methyl-3-phenyl-3H-quinazolin-4-one was then dissolved in trifluoroacetic acid and allowed to stir at ambient temperature for 5 hours. Purification by LC provided the product 68 as a white solid. MS (ES): m/z 429 (M+H), 215, 206, 151. Compound 68 is shown below.

(68)

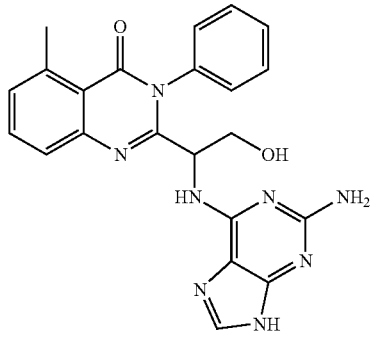

2-[1-(2-amino-9H-purin-6-ylamino)-ethyl]-3-(3-fluoro-phenyl)-3H-quinazolin-4-one (69)

Compound 69 was prepared using the general procedure described above with respect to compound 14, but 3-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. ESI-MS m/z 417.1 ($MH^+$). Compound 69 is shown below.

(69)

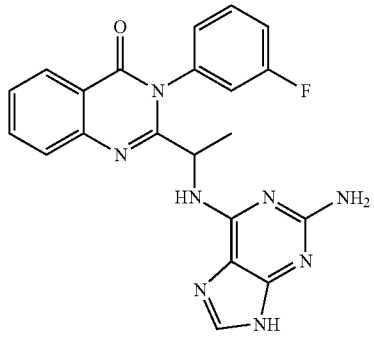

2-[1-(2-amino-9H-purin-6-ylamino)-ethyl]-3-(2,6-difluoro-phenyl)-3H-quinazolin-4-one (70)

Compound 70 was prepared using the general procedure described above with respect to compound 14, but 2,6-difluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. ESI-MS m/z 435.1 ($MH^+$). Compound 70 is shown below.

(70)

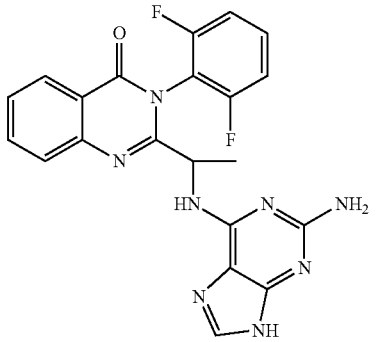

2-[1-(2-amino-9H-purin-6-ylamino)-propyl]-5-fluoro-3-phenyl-3H-quinazolin-4-one (71)

Compound 71 was prepared using the general procedure described above with respect to compound 14, but 2-amino-5-fluorobenzoic acid was substituted for 2-amino-5-methyl-benzoic acid in step A, and 2-amino-6-bromopurine was substituted for 6-bromopurine in step D. ESI-MS m/z 431 ($MH^+$). Compound 71 is shown below.

(71)

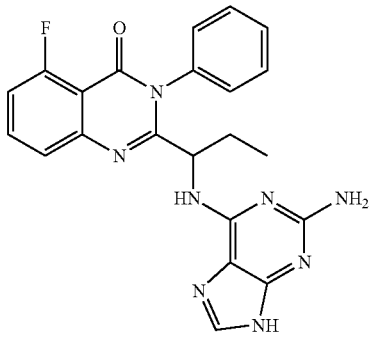

5-chloro-3-(3-fluoro-phenyl)-2-[1-(9H-purin-6-ylamino)-ethyl]-3H-quinazolin-4-one (72)

Compound 72 was prepared using the general procedure described above with respect to compound 14, but 2-amino-6-chlorobenzoic acid was substituted for 2-amino-6-methyl-benzoic acid and 3-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 436.1 ($MH^+$). Compound 72 is shown below.

(72)

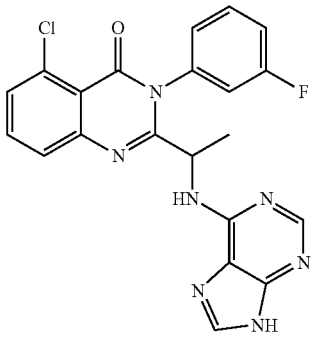

2-[1-(2-amino-9H-purin-6-ylamino)-ethyl]-5-chloro-3-(3-fluoro-phenyl)-3H-quinazolin-4-one (73)

Compound 73 was prepared using the general procedure described above with respect to compound 14, but 2-amino-6-chlorobenzoic acid was substituted for 2-amino-6-methyl-benzoic acid, and 3-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 2-amino-6-bromopurine was substituted for 6-bromopurine in step D. ESI-MS m/z 451.1 ($MH^+$). Compound 73 is shown below.

(73)

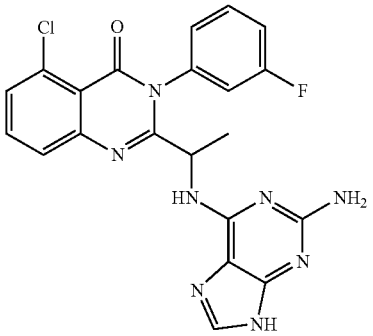

3-phenyl-2-[1-(9H-purin-6-ylamino)-ethyl]-5-trifluoromethyl-3H-quinazolin-4-one (74)

Compound 74 was prepared using the general procedure described above with respect to compound 14, but 2-amino-N-phenyl-6-trifluoromethyl-benzamide was used in place of compound 15 in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used. MS (ES): m/z 452 (M+H). Compound 74 is shown below.

(74)

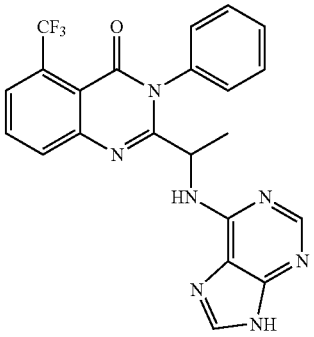

2-amino-N-phenyl-6-trifluoromethyl-benzamide was prepared by addition of aniline (1.0 eq.) to a suspension of 2-amino-6-(trifluoromethyl)-benzoic acid trihydrate (1.0 g, 4.0 mmol, 1.3 eq.) and polystyrene-carbodiimide (3.6 g, 1.1-1.7 eq.) in THF (40 mL). The reaction was stirred at ambient temperature for 18 hours, then filtered. The filtrate was concentrated in vacuo and purified by flash chromatography to provide 2-amino-N-phenyl-6-trifluoromethyl-benzamide as a yellow solid.

3-(2,6-difluoro-phenyl)-5-methyl-2-[1-(9H-purin-6-ylamino)-propyl]-3H-quinazolin-4-one (75)

Compound 75 was prepared using the general procedure described above with respect to compound 14, but 2,6-difluoroaniline was substituted for aniline in step A. ESI-MS m/z 448 ($MH^+$). Compound 75 is shown below.

(75)

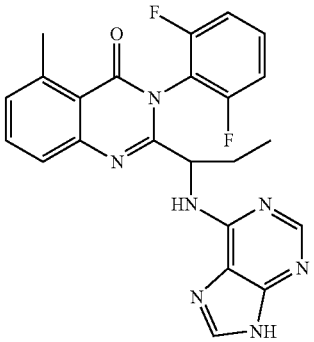

3-(2,6-difluoro-phenyl)-5-methyl-2-[1-(9H-purin-6-ylamino)-ethyl]-3H-quinazolin-4-one (76)

Compound 76 was prepared using the general procedure described above with respect to compound 14, but 2,6-difluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 434.1 ($MH^+$). Compound 76 is shown below.

(76)

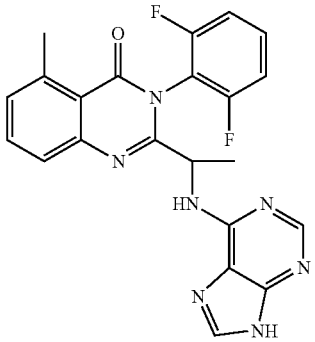

2-[1-(2-amino-9H-purin-6-ylamino)-propyl]-3-(2,6-difluoro-phenyl)-5-methyl-3H-quinazolin-4-one (77)

Compound 77 was prepared using the general procedure described above with respect to compound 75, but 2-amino-6-bromopurine was substituted for 6-bromopurine in step D. ESI-MS m/z 463 ($MH^+$). Compound 77 is shown below.

(77)

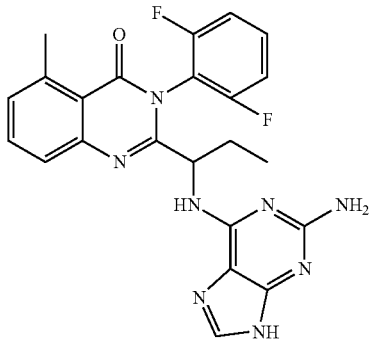

2-[1-(2-amino-9H-purin-6-ylamino)-ethyl]-3-(2,6-difluoro-phenyl)-5-methyl-3H-quinazolin-4-one (78)

Compound 78 was prepared using the general procedure described above with respect to compound 76, but 2-amino-6-bromopurine was substituted for 6-bromopurine in step D. ESI-MS m/z 449 ($MH^+$). Compound 78 is shown below.

(78)

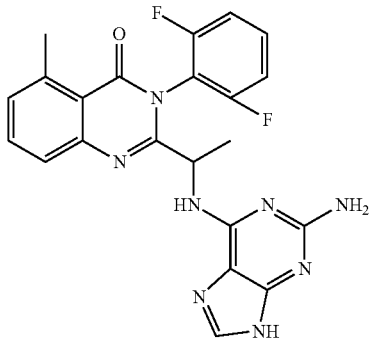

3-(3,5-dichloro-phenyl)-5-methyl-2-[1-(9H-purin-6-ylamino)-ethyl]-3H-quinazolin-4-one (79)

Compound 79 was prepared using the general procedure described above with respect to compound 14, but 3,5-dichloroaniline was substituted for aniline in step 1, and 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 467 ($MH^+$). Compound 79 is shown below.

(79)

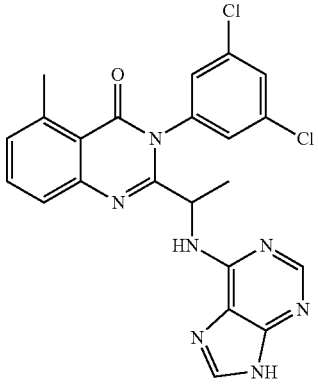

3-(2,6-dichloro-phenyl)-5-methyl-2-[1-(9H-purin-6-ylamino)-ethyl]-3H-quinazolin-4-one (80)

Compound 80 was prepared using the general procedure described above with respect to compound 14, but 2,6-dichloroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 467 ($MH^+$). Compound 80 is shown below.

(80)

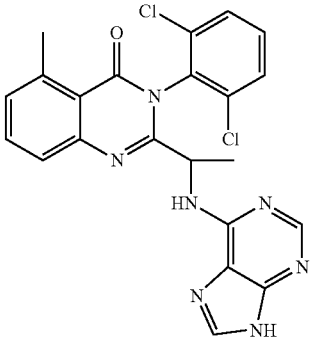

2-[1-(2-amino-9H-purin-6-ylamino)-ethyl]-3-(2,6-dichloro-phenyl)-5-methyl-3H-quinazolin-4-one (81)

Compound 81 was prepared using the general procedure described above with respect to compound 80, but 2-amino-6-bromopurine was substituted for 6-bromopurine in step D. ESI-MS m/z 482 ($MH^+$). Compound 81 is shown below.

(78)

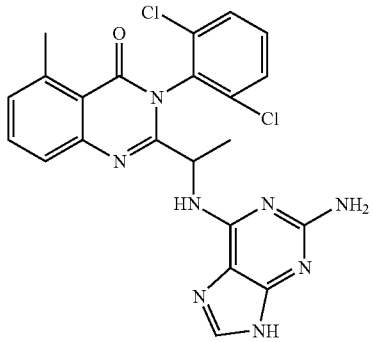

5-chloro-3-phenyl-2-[1-(9H-purin-6-ylamino)-propyl]-3H-quinazolin-4-one (82)

Compound 82 was prepared using the general procedure described above with respect to compound 14, but 2-amino-6-chloro-benzoic acid was substituted for 2-amino-6-methyl-benzoic acid in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 432 ($MH^+$). Compound 82 is shown below.

(82)

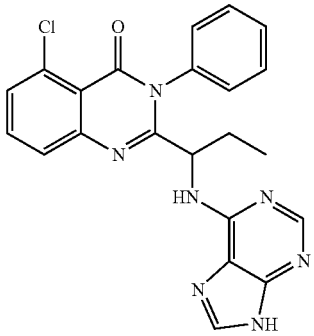

2-[1-(2-amino-9H-purin-6-ylamino)-propyl]-5-chloro-3-phenyl-3H-quinazolin-4-one (83)

Compound 83 was prepared using the general procedure described above with respect to compound 14, but 2-amino-6-bromopurine was substituted for 6-bromopurine in step D. ESI-MS m/z 447 ($MH^+$). Compound 83 is shown below.

(83)

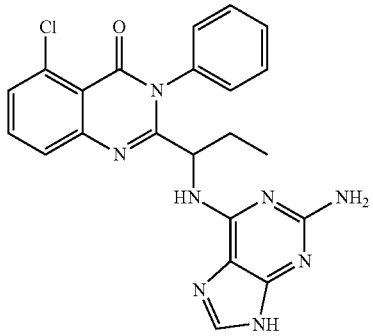

5-methyl-3-phenyl-2-[1-(9H-purin-6-ylamino)-butyl]-3H-quinazolin-4-one (84)

Compound 84 was prepared using the general procedure described above with respect to compound 14, but 2-benzyloxycarbonylamino-pentanoic acid 2,5-dioxo-pyrrolidin-1-yl ester was substituted for 2-benzyloxycarbonylaminobutyric acid 2,5-dioxo-pyrrolidin-1-yl ester in step B. MS (ES): m/z 426 (M+H), 213. Compound 84 is shown below.

(84)

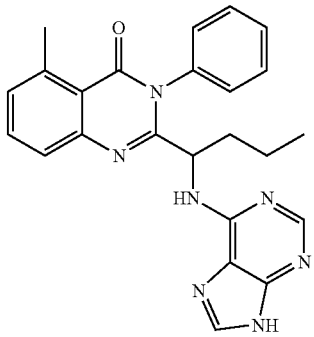

2-[1-(2-amino-9H-purin-6-ylamino)-butyl]-5-methyl-3-phenyl-3H-quinazolin-4-one (85)

Compound 85 was prepared using the general procedure described above with respect to compound 14, but 2-benzyloxycarbonylamino-pentanoic acid 2,5-dioxo-pyrrolidin-1-yl ester was substituted for 2-benzyloxycarbonylaminobutyric acid 2,5-dioxo-pyrrolidin-1-yl ester in step B, and 2-amino-6-bromopurine was substituted for 6-bromopurine in step D. MS (ES): m/z 441 (M+H), 221. Compound 85 is shown below.

(85)

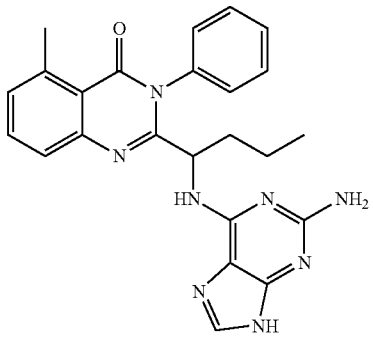

2-[1-(2-amino-9H-purin-6-ylamino)-ethyl]-3-(3,5-dichloro-phenyl)-5-methyl-3H-quinazolin-4-one (86)

Compound 86 was prepared using the general procedure described above with respect to compound 14, but 2-amino-6-bromopurine was substituted for 6-bromopurine in step D. ESI-MS m/z 482 ($MH^+$). Compound 86 is shown below.

(86)

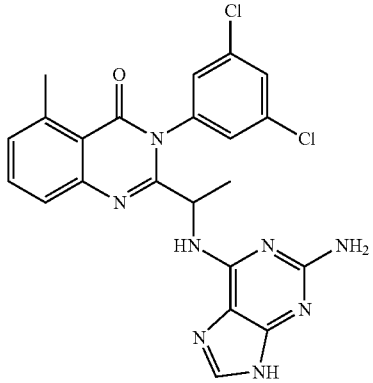

5-methyl-3-(3-morpholin-4-ylmethyl-phenyl)-2-[1-(9H-purin-6-ylamino)-ethyl]-3H-quinazolin-4-one (87)

Compound 87 was prepared using the general procedure described above with respect to compound 14, but intermediate compound 8 was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 497 ($MH^+$). Compound 87 is shown below.

(87)

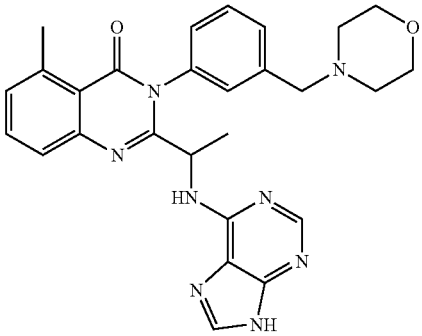

2-[1-(2-amino-9H-purin-6-ylamino)-ethyl]-5-methyl-3-(3-morpholin-4-ylmethyl-phenyl)-3H-quinazolin-4-one (88)

Compound 88 was prepared using the general procedure described above with respect to compound 87, but 2-amino-6-bromopurine was substituted for 6-bromopurine in step D. ESI-MS m/z 49.8 ($MH^+$). Compound 88 is shown below.

(88)

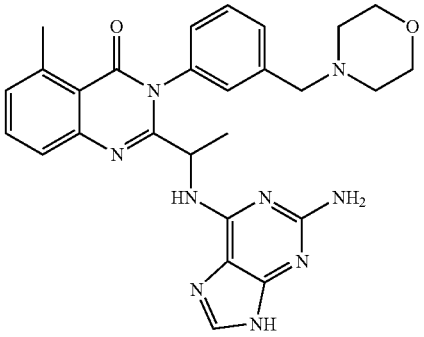

2-[1-(5-bromo-7H-pyrrolo[2,3-d]pyrimidin-4-ylamino)-ethyl]-5-methyl-3-phenyl-3H-quinazolin-4-one (89)

Compound 89 was prepared using the general procedure described above with respect to compound 14, but 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 4-chloro-5-bromo-7H-pyrrolo[2,3-d]pyrimidine (prepared as in J. Med. Chem. 1988, 31, 2086-2092) was substituted for 6-bromopurine in step D. ESI-MS m/z 411.1 ($MH^+$). Compound 89 is shown below.

(89)

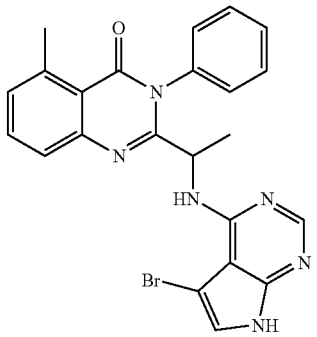

5-methyl-2-[1-(5-methyl-7H-pyrrolo[2,3-d]pyrimidin-4-ylamino)-ethyl]-3-phenyl-3H-quinazolin-4-one (90)

Compound 90 was prepared using the general procedure described above with respect to compound 14, but 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and 4-chloro-5-methyl-7H-pyrrolo[2,3-d]pyrimidine (prepared as in J. Med. Chem. 1990, 33, 1984-1992) was substituted for 6-bromopurine in step D. ESI-MS m/z 411.1 ($MH^+$). Compound 90 is shown below.

(90)

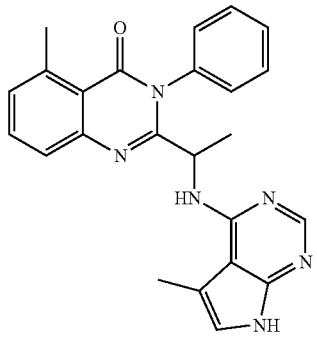

2-[1-(5-fluoro-7H-pyrrolo[2,3-d]pyrimidin-4-ylamino)-ethyl]-5-methyl-3-phenyl-3H-quinazolin-4-one (91)

Compound 91 was prepared using the general procedure described above with respect to compound 14, but 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, the alternate procedure (TFA deprotection) was used in step C, and intermediate compound 1 was substituted for 6-bromopurine. ESI-MS m/z 415.1 ($MH^+$). Compound 91 is shown below.

(91)

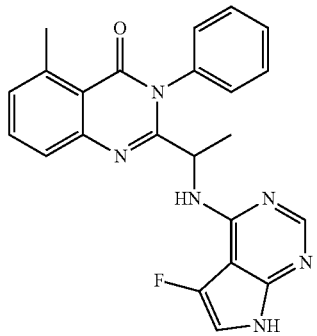

2-[2-hydroxy-1-(9H-purin-6-ylamino)-ethyl]-3-phenyl-3H-quinazolin-4-one (92)

Compound 92 was prepared by adding trifluoroacetic acid to a solution of 2-[2-tert-butoxy-1-(9H-purin-6-ylamino)-ethyl]-3-phenyl-3H-quinazolin-4-one in dichloromethane. The reaction was stirred at ambient temperature for 18 hours, then concentrated in vacuo. Purification by LC provided the product as a white solid. MS (ES): m/z 400 (M+H), 382, 200, 136. Compound 92 is shown below.

(92)

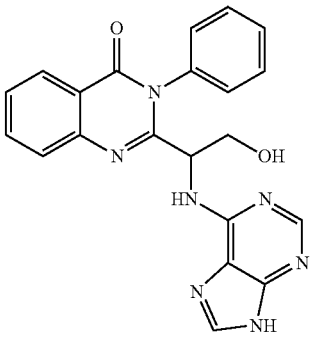

2-[2-tert-butoxy-1-(9H-purin-6-ylamino)-ethyl]-3-phenyl-3H-quinazolin-4-one was prepared using the general procedure described above with respect to compound 14, but 2-amino-6-chlorobenzoic acid was substituted for 2-amino-6-methylbenzoic acid in step A, 2-benzyloxycarbonylamino-3-tert-butoxy-propionic acid 2,5-dioxo-pyrrolidin-1-yl ester was substituted for 2-benzyloxycarbonylaminobutyric acid 2,5-dioxo-pyrrolidin-1-yl ester in step B, and the conditions used in step C removed both the benzyl protecting group and the A-Ring chloro substituent.

3-(3,5-difluoro-phenyl)-5-methyl-2-[1-(9H-purin-6-ylamino)-propyl]-3H-quinazolin-4-one (93)

Compound 93 was prepared using the general procedure described above with respect to compound 14, but 3,5-difluoroaniline was substituted for aniline in step A. ESI-MS m/z 448 ($MH^+$). Compound 93 is shown below.

(93)

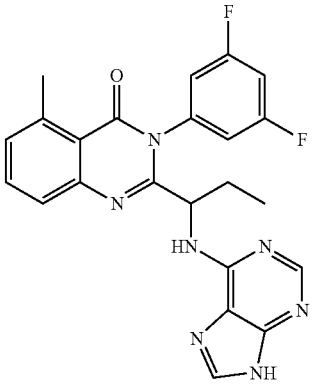

2-[1-(2-amino-9H-purin-6-ylamino)-propyl]-3-(3,5-difluoro-phenyl)-5-methyl-3H-quinazolin-4-one (94)

Compound 94 was prepared using the general procedure described above with respect to compound 90, but 2-amino-6-bromopurine was substituted for 6-bromopurine in step D. ESI-MS m/z 463 ($MH^+$). Compound 94 is shown below.

(94)

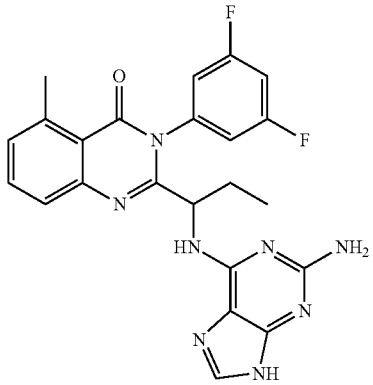

3-(3,5-difluoro-phenyl)-2-[1-(9H-purin-6-ylamino)-ethyl]-3H-quinazolin-4-one (95)

Compound 95 was prepared using the general procedure described above with respect to compound 14, but anthranilic acid was substituted for 2-amino-6-methylbenzoic acid and 3,5-difluoroaniline for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 420 ($MH^+$). Compound 95 is shown below.

(95)

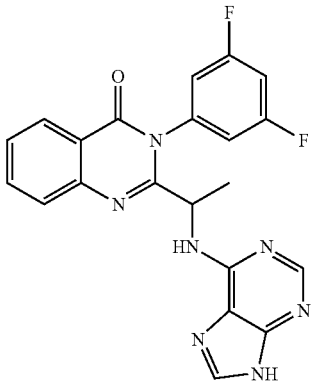

2-[1-(5-bromo-7H-pyrrolo[2,3-d]pyrimidin-4-ylamino)-ethyl]-3-(3-fluoro-phenyl)-5-methyl-3H-quinazolin-4-one (96)

Compound 96 was prepared using the general procedure described above with respect to compound 14, but 3-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 494 ($MH^+$). Compound 96 is shown below.

(96)

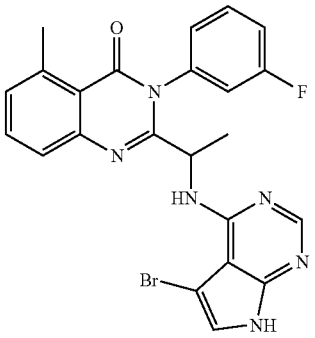

3-(3-fluoro-phenyl)-5-methyl-2-[1-(5-methyl-7H-pyrrolo[2,3-d]pyrimidin-4-ylamino)-ethyl]-3H-quinazolin-4-one (97)

Compound 97 was prepared using the general procedure described above with respect to compound 14, but 3-fluoroaniline was substituted for aniline in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 429 ($MH^+$). Compound 97 is shown below.

(97)

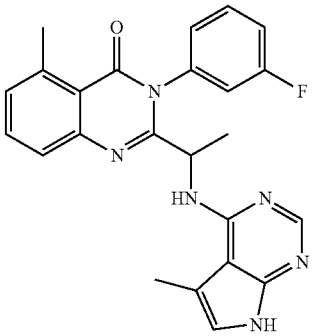

3-phenyl-2-[1-(9H-purin-6-ylamino)-propyl]-3H-quinazolin-4-one (98)

Compound 98 was prepared using the general procedure described above with respect to compound 14, but anthranilic acid was substituted for 2-amino-6-methyl-benzoic acid in step A. MS (ES): m/z 398 (M+H), 199. Compound 98 is shown below.

(98)

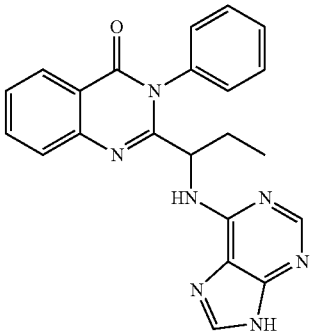

2-[1-(2-amino-9H-purin-6-ylamino)-ethyl]-3-(3,5-difluoro-phenyl)-3H-quinazolin-4-one (99)

Compound 99 was prepared using the general procedure described above with respect to compound 95, but 2-amino-6-bromopurine was substituted for 6-bromopurine in step D. ESI-MS m/z 435 ($MH^+$). Compound 96 is shown below.

(99)

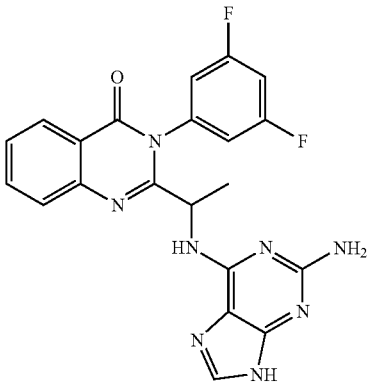

2-[1-(2-amino-9H-purin-6-ylamino)-propyl]-3-phenyl-3H-quinazolin-4-one (100)

Compound 100 was prepared using the general procedure described above with respect to compound 14, but anthranilic acid was substituted for 2-amino-6-methyl-benzoic acid in step A, and 2-amino-6-bromopurine was substituted for 6-bromopurine in step D. MS (ES): m/z 413 (M+H), 207. Compound 100 is shown below.

(100)

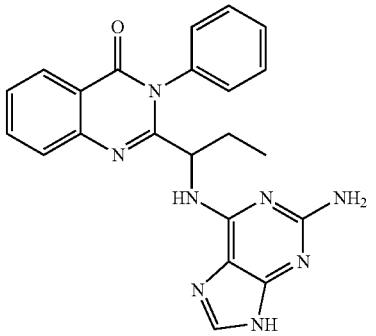

6,7-difluoro-3-phenyl-2-[1-(9H-purin-6-ylamino)-ethyl]-3H-quinazolin-4-one (101)

Compound 101 was prepared using the general procedure described above with respect to compound 14, but 2-amino-4,5-difluoro-benzoic acid was substituted for 2-amino-6-methyl-benzoic acid in step A, 2-tert-butoxycarbonylamino-propionic acid 2,5-dioxopyrrolidin-1-yl ester was substituted for 2-benzyloxycarbonylaminobutyric acid 2,5-dioxo-pyrroli din-1-yl ester in step B, and the alternate procedure (TFA deprotection) was used in step C. ESI-MS m/z 420 ($MH^+$). Compound 101 is shown below.

(101)

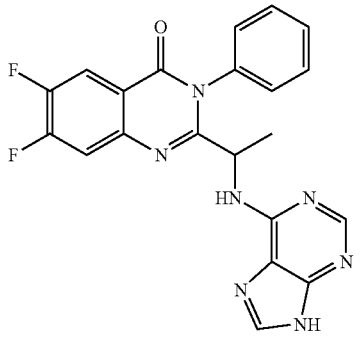

6-fluoro-3-(3-fluoro-phenyl)-2-[1-(9H-purin-6-ylamino)-ethyl]-3H-quinazolin-4-one (102)

Compound 102 was prepared using the general procedure described above with respect to compound 14, but 2-amino-5-fluoro-benzoic acid was substituted for 2-amino-6-methyl-benzoic acid in step A, 2-tert-butoxycarbonylamino-propionic acid 2,5-dioxopyrrolidin-1-yl ester was substituted for 2-benzyloxycarbonylaminobutyric acid 2,5-dioxo-pyrrolidin-1-yl ester in step B, and the alternate procedure (TFA deprotection) was used in step C. ESI-MS m/z 420 ($MH^+$). Compound 102 is shown below.

(102)

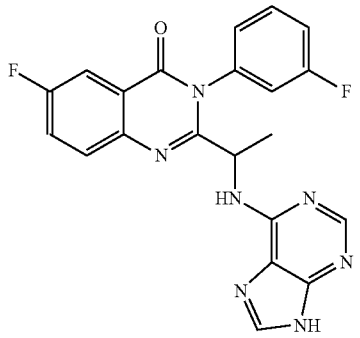

2-[4-diethylamino-1-(9H-purin-6-ylamino)-butyl]-5-methyl-3-phenyl-3H-quinazolin-4-one (103)

Compound 103 was prepared following steps A-D below.

[4-amino-1-(5-methyl-4-oxo-3-phenyl-3,4-dihydro-quinazolin-2-yl)-butyl]-carbamic acid tert-butyl ester (104)

Step A: A 10-mL, one-neck, round bottomed flask equipped with a magnetic stirrer was purged with nitrogen and charged with 10% palladium on carbon (30 mg, 50% wet). A solution of [4-benzyloxycarbonylamino-1-(5-methyl-4-oxo-3-phenyl-3,4-dihydro-quinazolin-2-yl)-butyl]-carbamic acid tert-butyl ester (product from step B of procedure for compound 51) (100 mg, 0.18 mmol) in ethanol (2 mL) and polymethylhydrosiloxane (130 mg) were then added sequentially. The reaction mixture was stirred at 50° C. for 3 h, and then cooled to room temperature. The mixture was filtered through a pad of CELITE® and the filtrate evaporated to dryness Subsequent purification of the resulting crude product by column chromatography afforded a 62% yield of compound 101 as a white solid. $^1H$ NMR ($CD_3OD$) δ 7.55-7.69 (m, 5H), 7.33-7.49 (m, 2H), 7.30 (d, 1H, J=7.3 Hz), 4.29 (m, 1H), 2.77 (s, 3H), 2.38-2.47 (m, 2H), 1.72-1.88 (m, 1H), 1.57-1.79 (m, 1H), 1.13-1.55 (m, 4H), 1.40 (s, 9H). The reaction described above and compound 104 are shown below.

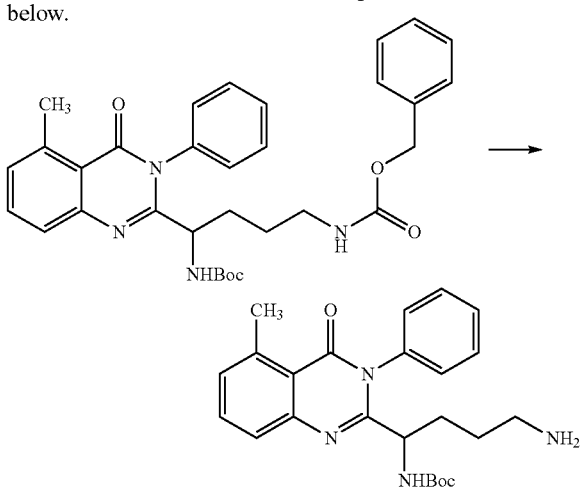

[4-Diethylamino-1-(5-methyl-4-oxo-3-phenyl-3,4-dihydro-quinazolin-2-yl)-butyl]-carbamic acid tert-butyl ester (105)

Step B: A 10-mL, one-neck, round bottomed flask equipped with a magnetic stirrer was purged with nitrogen, and then charged with the compound 104 (100 mg, 0.24 mmol) and 1,2-dichloroethane (2 mL). Acetaldehyde (42 mg, 0.85 mmol) and sodium triacetoxyborohydride (400 mg, 1.90 mmol) were subsequently added. The reaction mixture was stirred for 18 h at ambient temperature, evaporated to dryness, and the resulting residue was dissolved in methanol (20 mL). This methanolic solution was treated with 10% palladium on carbon (5 mg, 50% wet), stirred for 30 min, evaporated to dryness, and partitioned between 10% aqueous potassium carbonate (20 mL) and methylene chloride (20 mL). The organic layer was separated and dried over sodium sulfate. Filtration of the organic layer followed by concentration gave the compound 105 as a yellow oil, which was used without any further purification. $^1H$ NMR ($CDCl_3$) δ 7.51-7.63 (m, 5H), 7.41 (d, 1H, J=7.4 Hz), 7.29 (d, 1H, J=7.15 Hz), 7.22 (d, 1H, J=7.1 Hz), 6.10 (d, 1H, J=8.8 Hz), 4.38-4.52 (m, 1H), 2.81 (s, 3H), 2.32-2.50 (m, 4H), 2.08-2.27 (m, 2H), 1.47-1.73 (m, 4H), 1.42 (s, 9H, 1.25-1.38 (m, 1H), 0.96 (t, 6H, J=7.2 Hz); ESI-MS m/z=479 ($MH^+$). The reaction described above and compound 105 are shown below.

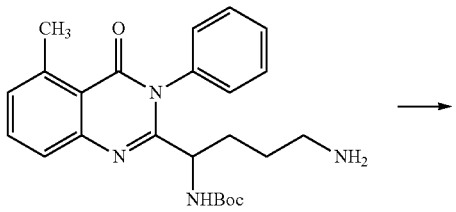

-continued

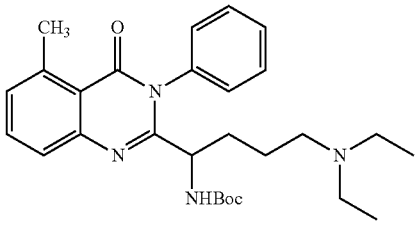

2-(1-amino-4-diethylamino-butyl)-5-methyl-3-phenyl-3H-quinazolin-4-one (106)

The alternative deprotection procedure described above with respect to the preparation of compound 14 (and specifically the preparation of compound 17) was used to deprotect compound 105. The reaction and compound 106 are shown below.

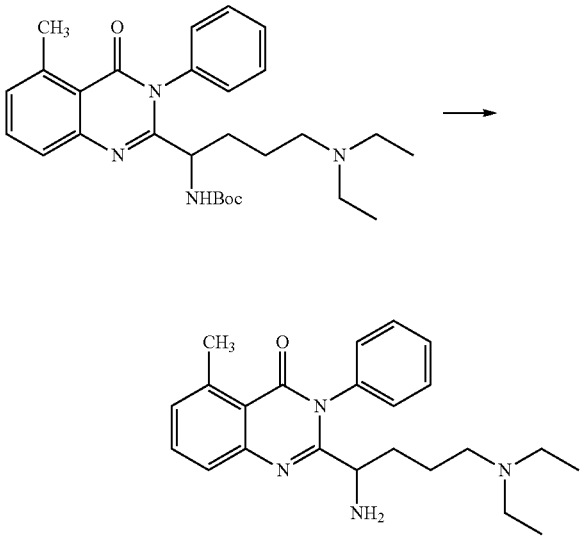

2-[4-Diethylamino-1-(9H-purin-6-ylamino)-butyl]-5-methyl-3-phenyl-3H-quinazolin-4-one (103)

Compound 103 was then prepared following the general procedure provided above in step D of the procedure for compound 14, but compound 106 was used as the free amine. ESI-MS m/z 497 ($MH^+$). The reaction and compound 103 are shown below.

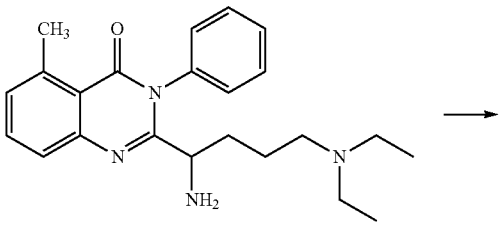

-continued

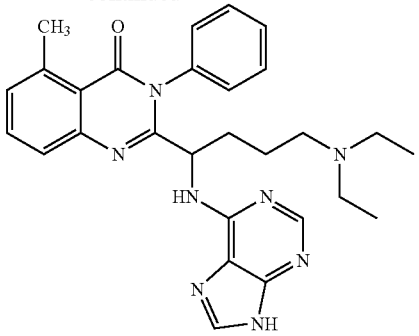

EXAMPLE 9

Compound Preparation

Compounds in accordance with general formula I (shown above), including chiral compounds having general formula II (shown above), have been prepared in accordance with steps A-E of the synthetic scheme shown below.

Step A

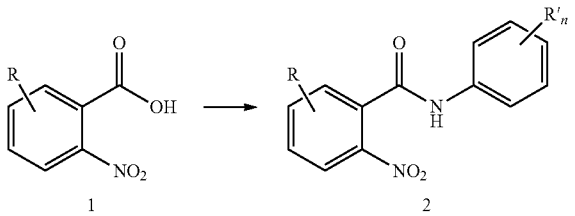

Step B

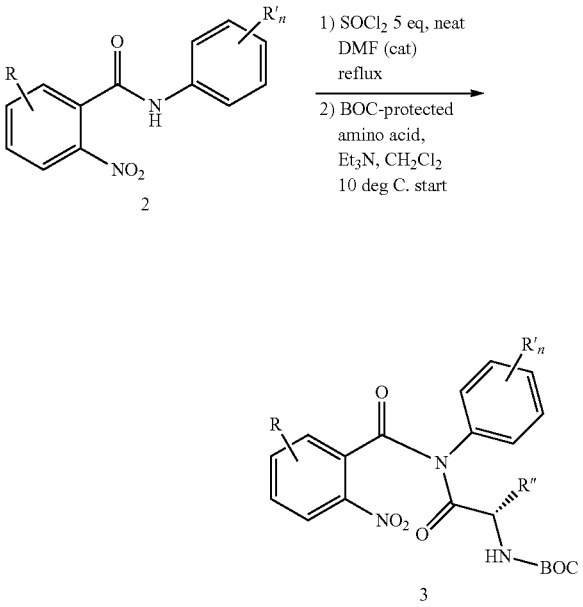

-continued

Step C

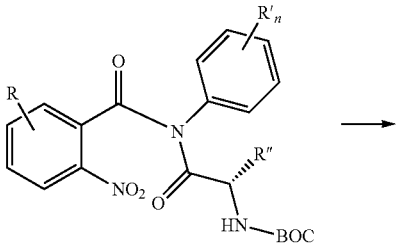

3

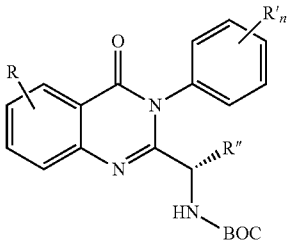

4

Step D

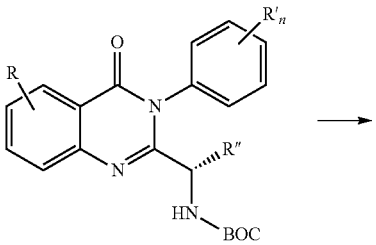

4

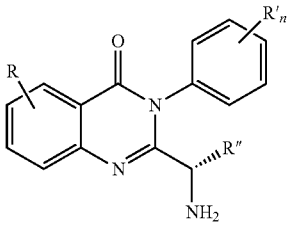

5

Step E

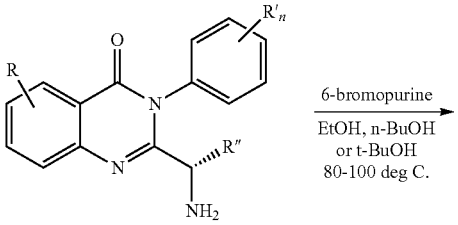

5

-continued

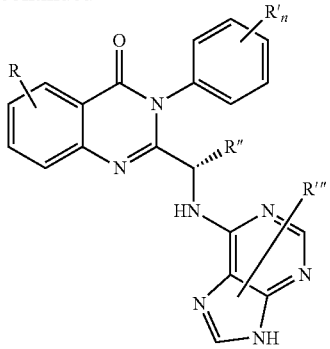

6

(S)-5-fluoro-3-phenyl-2-[1-(9H-purin-6-ylamino)-propyl]-3H-quinazolin-4-one (107)

The synthesis of a compound in accordance with formula I is first exemplified using steps A-E below, which provide a synthetic procedure for compound 107, the structure of which is shown below.

(107)

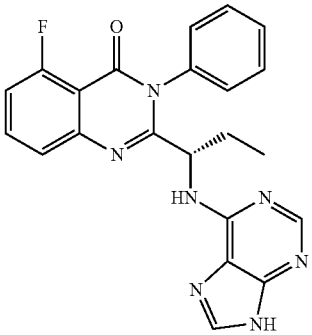

2-fluoro-6-nitro-N-phenyl-benzamide (108)

Step A: A solution of 2-fluoro-6-nitrobenzoic acid (100 g, 0.54 mol) and dimethylformamide (5 mL) in dichloromethane (600 mL) was treated dropwise with oxalyl chloride (2 M in dichloromethane, 410 mL, 0.8 mol, 1.5 eq) over 30 min. After stirring 2 h at room temperature, the reaction was concentrated to an orange syrup with some solids present. The syrup was dissolved in dry dioxane (80 mL) and slowly added to a suspension of aniline (49 mL, 0.54 mol, 1 eq) and sodium bicarbonate (90 g, 1.08 mol, 2 eq) in a mixture of dioxane (250 mL) and water (250 mL) at 6° C. The temperature reached 27° C. at the end of the addition. After 30 min, the reaction mixture was treated with water (1.2 L). The precipitate was collected by vacuum filtration, washed with water (300 mL), air dried in the funnel, and dried in vacuo at 50° C. for 24 h to afford an off-white solid product (139 g, 99%). $^1$H NMR (300 MHz, DMSO-d6) δ 10.82 (s, 1H), 8.12 (d, J=7.7 Hz, 1H), 7.91-7.77 (m, 2H), 7.64 (d, J=7.7 Hz, 2H), 7.38 (t, J=7.9 Hz, 2H), 7.15 (t, J=7.4 Hz, 1H), ESI-MS m/z 261 ($MH^+$). The reaction described above and compound 108 are shown below.

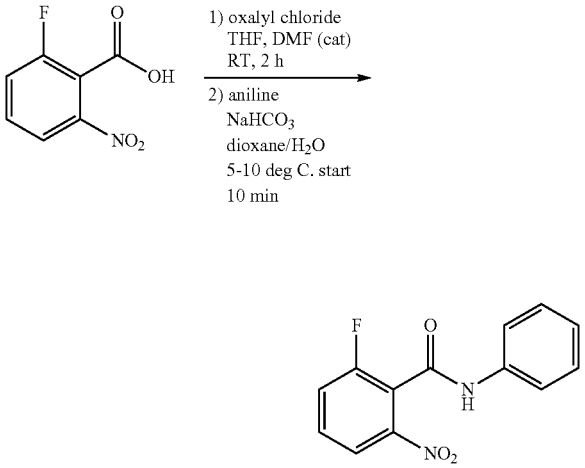

(S)-[1-(2-fluoro-6-nitro-benzoyl)-phenyl-aminocarbonyl]-propyl-carbamic acid tert-butyl ester (109)

Step B: A suspension of compound 108 (0.5 mol) and dimethylformamide (5 mL) in thionyl chloride (256 mL, 2.5 mol, 5 eq) was stirred at 85° C. for 5 hours. The reaction mixture was concentrated in vacuo to a brown syrup. The syrup was dissolved in dichloromethane (200 mL) and was slowly added to a solution of N—BOC-L-2-aminobutyric acid (112 g, 0.55 mol, 1.1 eq) and triethylamine (77 mL, 0.55 mol, 1.1 eq) in dichloromethane (600 mL) at 10° C. After stirring at room temperature for 3 h, salts were removed by filtration, and the solution was washed with 100 mL of water, saturated sodium bicarbonate, water, 5% citric acid, and saturated sodium chloride. The organic phase was dried with magnesium sulfate and concentrated to a red syrup. The syrup was dissolved in dichloromethane (450 mL) and purified by flash chromatography on a silica gel plug (15×22 cm, 4 L dry silica) eluted with hexanes/ethyl acetate (10%, 8 L; 15%, 8 L; 20%, 8 L; 25%, 4 L) to yield the compound 109 as an off-white solid (147 g, 66%). $^1$H NMR (300 MHz, DMSO-d6) δ 8.13 (d, J=8.0 Hz, 1H), 7.84 (t, J=8.6 Hz, 1H), 7.78-7.67 (m, 1H), 7.65-7.49 (m, 3H), 7.40-7.28 (m, 2H), 7.19 (d, J=7.5 Hz, 1H), 4.05 (broad s, 1H), 1.75-1.30 (m, 2H), 1.34 (s, 9H), 0.93 (broad s, 3H). ESI-MS m/z 446.3 ($MH^+$). The reaction described above and compound 109 are shown below.

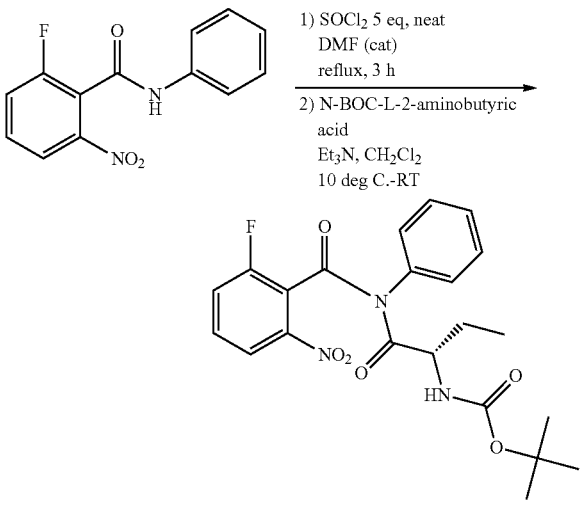

(S)-[1-(5-fluoro-4-oxo-3-phenyl-3,4-dihydro-quinazolin-2-yl)-propyl]-carbamic acid tert-butyl ester (110)

Step C: A solution of compound 109 (125 mmol, 1 eq) in acetic acid (500 mL) was treated with zinc dust (48.4 g, 740 mmol, 6 eq) added in 3 portions, and the reaction mixture was allowed to cool to below 35° C. between additions. After stirring for 2 h at ambient temperature, solids were filtered off by vacuum filtration and washed with acetic acid (50 mL). The filtrate was concentrated in vacuo, dissolved in EtOAc (400 mL), washed with water (300 mL), and the water layer was extracted with EtOAc (300 mL). The combined organic layers were washed with water (200 mL), sat'd sodium bicarbonate (2×200 mL), sat'd NaCl (100 mL), dried with $MgSO_4$, and concentrated to a syrup. The syrup was dissolved in toluene (200 mL) and purified by flash chromatography on a silica gel plug (13×15 cm, 2 L dry silica) eluted with hexanes/ethyl acetate (10%, 4 L; 15%, 4 L; 17.5%, 8 L; 25%, 4 L) to yield compound 110 as an off-white foamy solid (33.6 g, 69%). $^1$H NMR (300 MHz, DMSO-d6) δ 7.83 (td, J=8.2, 5.7 Hz, 1H), 7.64-7.48 (m, 5H), 7.39 (broad d, J=7.6 Hz, 1H), 7.30 (dd, J=8.3 Hz, 1H), 7.23 (d, J=7.6 Hz, 1H), 4.02-3.90 (m, 1H), 1.76-1.66 (m, 1H), 1.62-1.46 (m, 1H), 1.33 (s, 9H), 0.63 (t, J=7.3 Hz, 3H). ESI-MS m/z 398.3 ($MH^+$). The reaction described above and compound 110 are shown below.

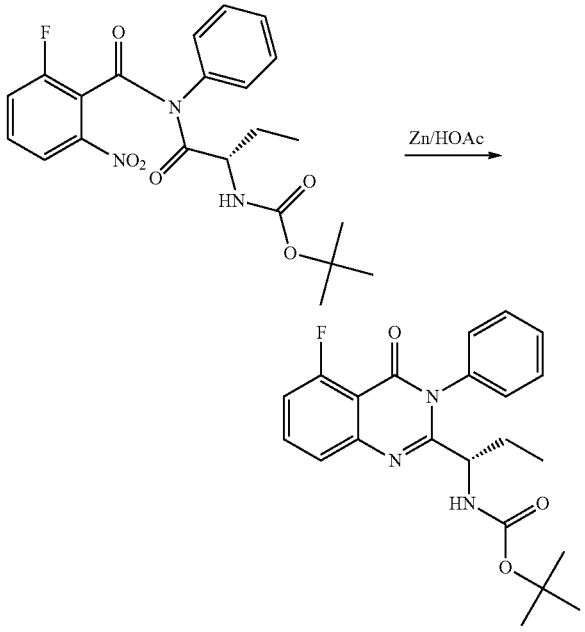

(S)-2-(1-amino-propyl)-5-fluoro-3-phenyl-3H-quinazolin-4-one (111)

Step D: A solution of compound 110 (85 mmol) in dichloromethane (60 mL) was treated with trifluoroacetic acid (60 mL). The reaction mixture was stirred for 1 h, concentrated in vacuo, and partitioned between dichloromethane (150 mL) and 10% $K_2CO_3$ (sufficient amount to keep the pH greater than 10). The aqueous layer was extracted with additional dichloromethane (100 mL), and the combined organic layers were washed with water (50 mL) and brine (50 mL). After drying with Mg $SO_4$, the solution was concentrated to provide compound III as an off-white solid (22 g, 88%). $^1$H NMR (300 MHz, $CDCl_3$) δ 7.73-7.65 (m, 1H), 7.62-7.49 (m, 4H), 7.32-7.22 (m, 2H), 7.13-7.06 (m, 1H), 3.42 (dd, J=7.5, 5.2 Hz, 1H), 1.87-1.70 (m, 1H), 1.58-1.43 (m, 1H), 0.80 (t, J=7.4 Hz, 3H). ESI-MS m/z 298.2 ($MH^+$). The reaction described above and compound III are shown below.

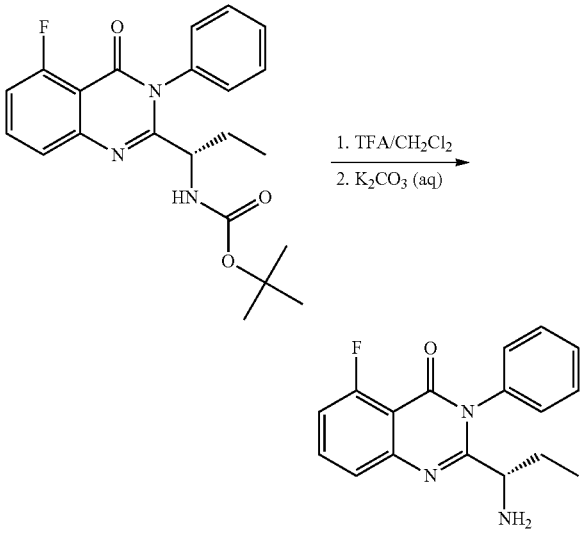

(S)-5-fluoro-3-phenyl-2-[1-(9H-purin-6-ylamino)-propyl]-3H-quinazolin-4-one (107)

Step E: A suspension of compound 111 (65.6 mmol, 1 eq), 6-bromopurine (14.6 g, 73.4 mmol, 1.1 eq), and DIEA (24.3 mL, 140 mmol, 2 eq) in tert-butanol (40 mL) was stirred for 24 h at 80° C. The reaction mixture was concentrated in vacuo and treated with water to yield a solid crude product that was collected by vacuum filtration, washed with water, and air dried. Half of the obtained solid crude product was dissolved in MeOH (600 mL), concentrated onto silica gel (300 mL dry), and purified by flash chromatography (7.5×36 cm, eluted with 10 L of 4% $MeOH/CH_2Cl_2$) to yield a solid product. The solid product was then dissolved in EtOH (250 mL) and concentrated in vacuo to compound 107 as a light yellow solid (7.2 g, 50%). $^1H$ NMR (300 MHz, 80° C., DMSO-d6) δ 12.66 (broad s, 1H), 8.11 (s, 1H), 8.02 (broad s, 1H), 7.81-7.73 (m, 1H), 7.60-7.42 (m, 6H), 7.25-7.15 (m, 2H), 4.97 (broad s, 1H), 2.02-1.73 (m, 2H), 0.79 (t, J=7.3 Hz, 3H). ESI-MS m/z 416.2 ($MH^+$). C, H, N elemental analysis ($C_{22}H_{18}N_7OF.EtOH.0.4H_2O$). Chiral purity 99.8:0.2 (S:R) using chiral HPLC (4.6×250 mm Chiralpak ODH column, 20° C., 85:15 hexanes:EtOH, 1 mL/min, sample loaded at a concentration of 1 mg/mL in EtOH). The reaction described above and compound 107 are shown below.

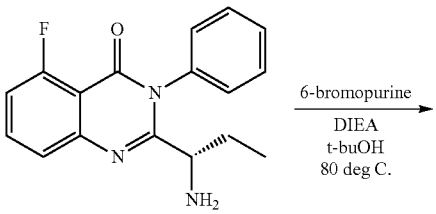

-continued

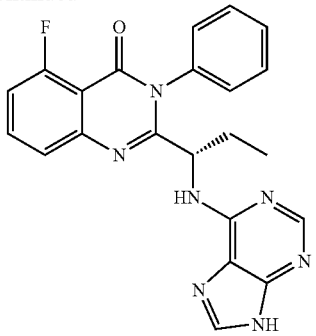

(S)-3-phenyl-2-[1-(9H-purin-6-ylamino)-ethyl]-3H-quinazolin-4-one (112)

Compound 112 was prepared using the general procedure described above with respect to compound 107, but 2-nitrobenzoic acid was substituted for 2-fluoro-6-nitrobenzoic acid in step A, and N—BOC-L-alanine was substituted for N—BOC-L-2-aminobutyric acid in step B. ESI-MS m/z 384.3 ($MH^+$). Chiral purity 99.5:0.5 (S:R). Compound 112 is shown below.

(112)

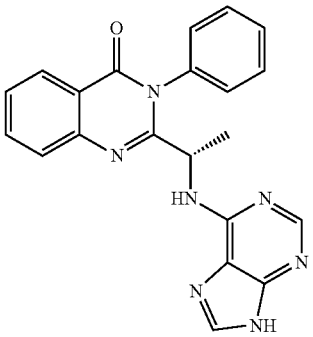

(S)-6-fluoro-3-phenyl-2-[1-(9H-purin-6-ylamino)-ethyl]-3H-quinazolin-4-one (113)

Compound 113 was prepared using the general procedure described above with respect to compound 107, but 2-nitro-5-fluorobenzoic acid was substituted for 2-fluoro-6-nitrobenzoic acid in step A, and N—BOC-L-alanine was substituted for N—BOC-L-2-aminobutyric acid in step B. ESI-MS m/z 402.3 ($MH^+$). Chiral purity 99.9:0.1 (S:R). Compound 113 is shown below.

(113)

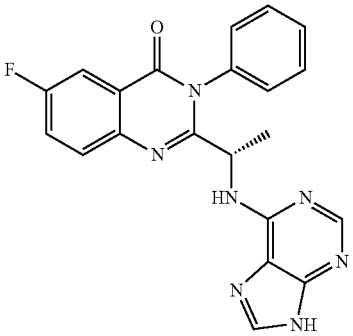

(S)-3-(3,5-difluoro-phenyl)-5-methyl-2-[1-(9H-purin-6-ylamino)-ethyl]-3H-quinazolin-4-one (114)

Compound 114 was prepared using the general procedure described above with respect to compound 107, but 2-nitro-5-methylbenzoic acid was substituted for 2-fluoro-6-nitrobenzoic acid and 3,5-difluoroaniline was substituted for aniline in step A, and N—BOC-L-alanine was substituted for N—BOC-L-2-aminobutyric acid in step B. ESI-MS m/z 434.3 ($MH^+$). Compound 114 is shown below.

(114)

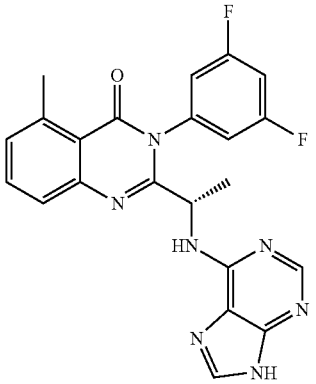

(S)-5-fluoro-2-[1-(2-fluoro-9H-purin-6-ylamino)-ethyl]-3-phenyl-3H-quinazolin-4-one (115)

Compound 115 was prepared using the general procedure described above with respect to compound 107, but 2-nitro-6-fluorobenzoic acid was substituted for 2-fluoro-6-nitrobenzoic acid in step A, N—BOC-L-alanine was substituted for N—BOC-L-2-aminobutyric acid in step B, and 6-chloro-2-fluoropurine was substituted for 6-bromopurine in step E. ESI-MS m/z 420.3 ($MH^+$). Chiral purity 100:0 (S:R). Compound 115 is shown below.

(115)

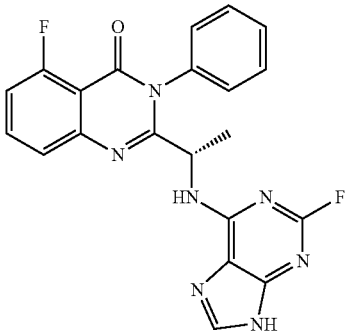

(S)-3-(3-fluoro-phenyl)-2-[1-(9H-purin-6-ylamino)-ethyl]-3H-quinazolin-4-one (116)

Compound 116 was prepared using the general procedure described above with respect to compound 107, but 2-nitrobenzoic acid was substituted for 2-fluoro-6-nitrobenzoic acid and 3-fluoroaniline was substituted for aniline in step A, and N—BOC-L-alanine was substituted for N—BOC-L-2-aminobutyric acid in step B. ESI-MS m/z 402.3 ($MH^+$). Chiral purity 96:4 (S:R). Compound 116 is shown below.

(116)

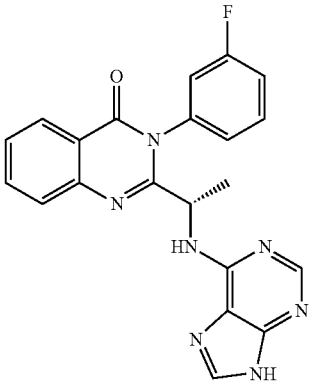

(S)-5-chloro-3-(3,5-difluoro-phenyl)-2-[1-(9H-purin-6-ylamino)-propyl]-3H-quinazolin-4-one (117)

Compound 117 was prepared using the general procedure described above with respect to compound 107, but 2-nitro-5-chlorobenzoic acid was substituted for 2-fluoro-6-nitrobenzoic acid, and 3,5-difluoroaniline was substituted for aniline in step A. ESI-MS m/z 468.3 ($MH^+$). Chiral purity 100:0 (S:R). Compound 117 is shown below.

(117)

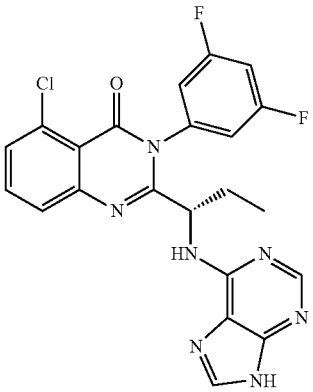

(S)-3-(2,6-difluoro-phenyl)-5-methyl-2-[1-(9H-purin-6-ylamino)-ethyl]-3H-quinazolin-4-one (118)

Compound 118 was prepared using an alternative step B relative to the preparation of compound 107, but the general procedure described above for compound 107 was otherwise generally followed for each of steps A, C, and D.

N-(2,6-difluoro-phenyl)-2-methyl-6-nitro-benzamide (118a)

Step A: Compound 118a was prepared following the preparation procedure described above with respect to compound 107, but 2-nitro-5-methylbenzoic acid was substituted for 2-fluoro-6-nitrobenzoic acid and 2,6-difluoroaniline was substituted for aniline.

L-{2-[(2,6-difluoro-phenyl)-(2-methyl-6-nitro-benzoyl)-amino]-1-methyl-2-oxo-ethyl}-carbamic acid tert-butyl ester (118b)

Step B: Compound 118b was prepared by treating a solution of compound 118a (13.8 g, 47 mmol) in THF (200 mL) dropwise with a solution of potassium hexamethyldisilazide (KHMDS) (0.5 M in toluene, 95 mL, 47 mmol, 1 eq) at 0° C. and stirring the reaction mixture for 30 min at the same temperature. The reaction mixture was then treated with L-2-tert-butoxycarbonylamino-propionic acid 2,5-dioxo-pyrrolidin-1-yl ester (13.5 g, 47 mmol, 1 eq) and stirred at the same temperature for an additional 30 min. The reaction mixture was quenched with water (50 mL) and concentrated in vacuo. The residue was dissolved in ethyl acetate (300 mL), and washed with 100 mL of each of the following: (1) water, (2) sat'd sodium bicarbonate, (3) water, (4) 5% citric acid, (5) water, and (6) brine. The organic layer was dried with $MgSO_4$ and concentrated to a syrup. The crude material was dissolved in dichloromethane (75 mL) and purified by flash chromatography on silica gel (7.5×40 cm), eluted with 20% EtOAc in hexanes (10 L of 20%, then 6 L of 33%).

Steps C and D were performed as described relative to the preparation of compound 107. ESI-MS m/z 434.3 ($MH^+$). Chiral purity 100:0 (S:R). Compound 118 is shown below.

(118)

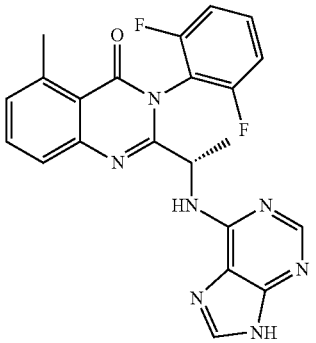

(S)-3-(2,6-difluoro-phenyl)-2-[1-(9H-purin-6-ylamino)-ethyl]-3H-quinazolin-4-one (119)

Compound 119 was prepared using the general procedure described above with respect to compound 118, but 2-nitrobenzoic acid was substituted for 2-nitro-5-methylbenzoic acid. ESI-MS m/z 420.3 ($MH^+$). Chiral purity 100:0 (S:R). Compound 119 is shown below.

(119)

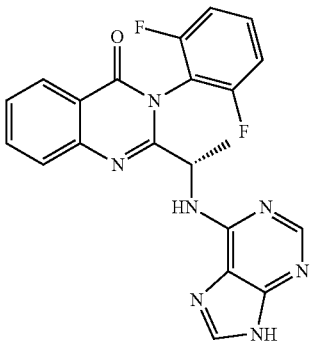

5-Methyl-3-phenyl-2-[3,3,3-trifluoro-1-(9H-purin-6-ylamino)-propyl]-3H-quinazolin-4-one (120)

Compound 120 was prepared using the general procedure described above with respect to compound 107, but 2-methyl-6-nitro-benzoic acid was substituted for 2-fluoro-6-nitro-benzoic acid in step A and 2-tert-butoxycarbonylamino-4,4,4-trifluoro-butyric acid was substituted for 2-tert-butoxycarbonylamino-butyric acid in step B. ESI-MS m/z 466 ($MH^+$). Compound 120 is shown below.

(120)

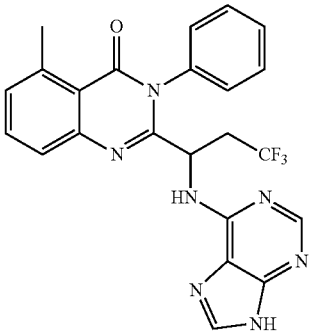

EXAMPLE 10

Compound Preparation

Compounds having general formula I (shown above) have been prepared in accordance with steps A-D of the synthetic scheme entitled "Procedure C" shown below. An alternative synthetic scheme entitled "Scheme D" illustrates additional synthetic routes to compounds having formula I.

Procedure C:

Step A:

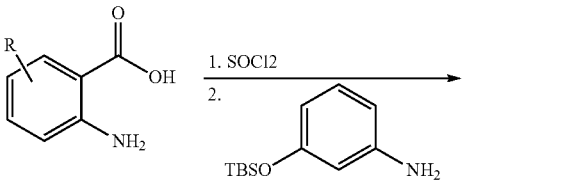

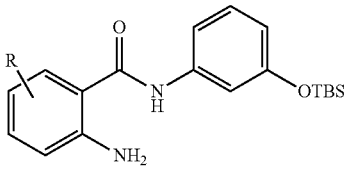

Step B:

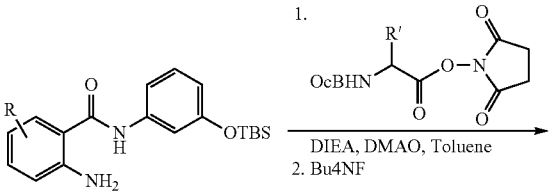

-continued
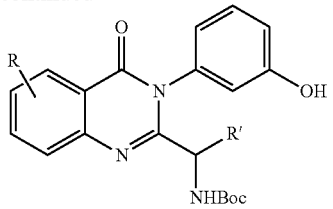
Step C
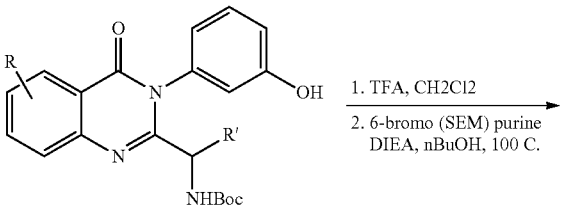
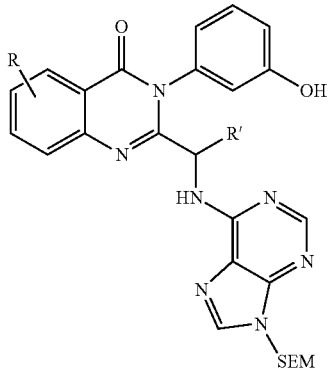
Step D:
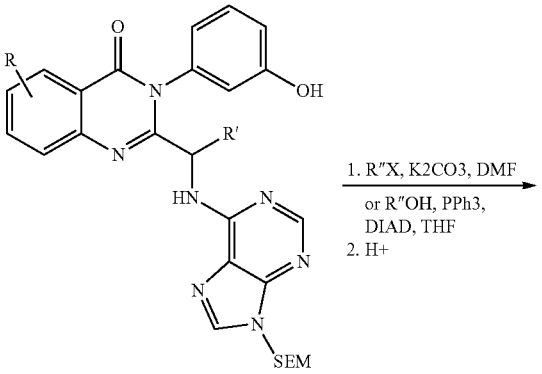
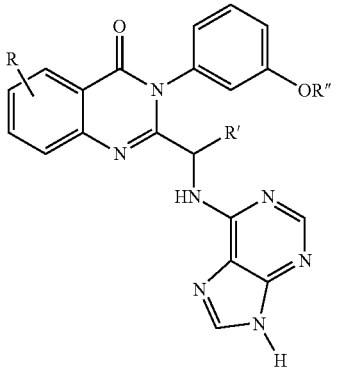
Scheme D
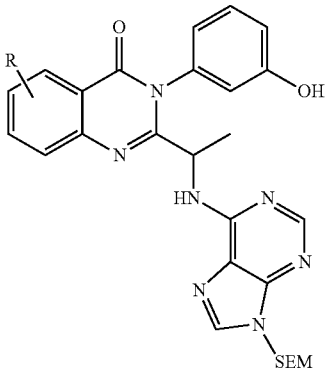
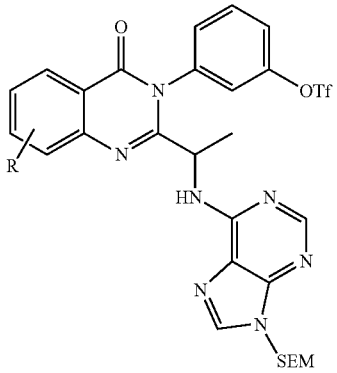
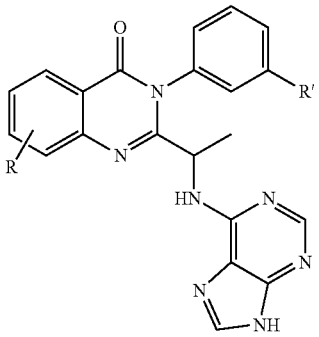
The synthesis of compounds in accordance with Procedure C and Scheme D is first exemplified by the synthetic procedure for 3-(3-hydroxy-phenyl)-5-methyl-2-[1-(9H-purin-6-ylamino)-ethyl]-3H-quinazolin-4-one, also referred to as compound 121, the structure of which is shown below.

(121)

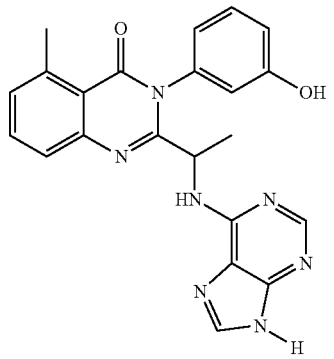

3-(3-Hydroxy-phenyl)-5-methyl-2-[1-(9H-purin-6-ylamino)-ethyl]-3H-quinazolin-4-one Compound 121 was prepared following steps A-D below, and using compound 122 (below) in step A.

3-(tert-butyl dimethylsilyloxy)phenylamine (122)

A 250 mL, three-neck, round bottomed flask equipped with a magnetic stirrer was purged with nitrogen and charged with tert-butyldimethylsilyl chloride (12.5 g, 82.8 mmol), imidazole (7.64 g, 112 mmol), and anhydrous DMF (60 mL). 3-aminophenol (10.0 g, 91.7 mmol) was added to the resulting solution. After stirring for 12 h at ambient temperature, the reaction mixture was poured into water (300 mL). The resulting suspension was extracted with hexanes (3×300 mL), and the extracts were combined, dried over sodium sulfate, and filtered. Concentration of the filtrate followed by column chromatography gave compound 122 as a light yellow oil. $^1$H NMR (DMSO-$d_6$) δ (ppm), 6.84 (t, 1H, J=7.9 Hz), 6.16 (d, 1H, J=6.7 Hz), 6.10 (m, 1H), 5.97 (d, 1H, J=9.1 Hz), 4.98 (s, 2H), 0.95 (s, 9H), 0.16 (s, 6H); m/z=224 (M+H).

2-amino-6-methyl-N-[(3-tert-butyl-dimethyl-silan-oxy)-phenyl]-benzamide (123)

Step A: A 5-L, three-neck, round bottomed flask equipped with a gas bubbler, mechanical stirrer and reflux condenser was charged with 6-amino-2-methylbenzoic acid (25 g, 16.8 mmol), toluene (300 mL), and thionyl chloride (50 mL). The reaction mixture was refluxed for 1 h until evolution of gas ceased. The resulting mixture was then cooled and concentrated under reduced pressure at 50° C. Anhydrous THF (400 mL) and DIEA (90 mL) were added to the resulting residue, followed by compound 122 (37 g, 1.0 eq). The resulting reaction mixture was stirred at ambient temperature for 2 hours, then quenched by the addition of 20% aqueous potassium carbonate (250 mL). The organic layer was separated and concentrated to dryness under reduced pressure. Trituration of the residue with MTBE (70 mL), filtration and drying afforded compound 123. The preparation of compound 123 is generally shown above as step A of Procedure C.

1-{[3-(3-Hydroxy-phenyl)-5-methyl-4-oxo-3,4-dihydro-quinazolin-2-yl]-ethyl}-carbamic acid-tert butyl ester (124)

Step B: A 100-mL, three-neck, round bottomed flask equipped with a magnetic stirrer and a reflux condenser was purged with nitrogen and charged with compound 123 (10 g, 28 mmol), N-tert-butyloxycarbonylalanine N-hydroxysuccinimide ester (9.60 g, 1.0 eq), DMAP (1.90 g), DIEA (6 mL), 4 Å molecular sieves (1.20 g), and anhydrous toluene (100 mL). The resulting mixture was heated in an oil bath at 80° C. for 24 h. 1-Hydroxybenzotriazole (3.78 g) was added to the reaction, and heating continued for an additional 48 h. After cooling, toluene (10 mL) and CELITE® (0.70 g) were added to the warm reaction mixture, followed by filtration and evaporation of the filtrate to give a brown residue. The residue was dissolved in $CH_2Cl_2$ (15 mL) and treated with a solution of tetrabutylammonium fluoride (5.12 g) in MeOH (15 mL). After stirring for 1 h at ambient temperature, the reaction mixture was evaporated to dryness under reduced pressure, and the residue purified by column chromatography to give 81% yield of compound 124 as an off-white solid. The preparation of compound 124 is generally shown above as step B of Procedure C.

2-(1-amino-ethyl)-3-(3-hydroxy-phenyl)-5-methyl-3H-quinazolin-4-one (125)

Step C1: A 100-mL, three-neck, round bottomed flask equipped with a magnetic stirrer was charged with compound 124 (4.50 g, 11.18 mmol) in $CH_2Cl_2$ (15 mL) and TFA (15 mL). After stirring for 1 hr at room temperature, the mixture was concentrated under reduced pressure to afford compound 125, which was used as is in the following step.

3-(3-hydroxy-phenyl)-5-methyl-2-{1-[9-(2-trimethylsilanyl-ethoxymethyl)-9H-purin-6-ylamino]-ethyl}-3H-quinazolin-4-one (126)

Step C2: A nitrogen purged, 50-mL one-neck round bottomed flask equipped with a magnetic stirrer and reflux condenser was charged with compound 125 (2.4 g, 8.16 mmol), intermediate compound 10 (2.70 g, 1.0 eq), n-butanol (20 mL), and DIEA (4.2 mL). The mixture was heated at 100° C. for 4 h then cooled to room temperature. Concentration of the reaction mixture under high vacuum followed by column chromatography gave compound as a white solid. The preparation of compound 126 is generally shown above as step C of Procedure C.

3-(3-hydroxy-phenyl)-5-methyl-2-[1-(9H-purin-6-ylamino)-ethyl]-3H-quinazolin-4-one (121)

Step D: A 100-mL, one-neck, round bottomed flask equipped with a magnetic stirrer was charged with compound 126 (294 mg, 0.5 mmol), MeOH (15 mL) and 4N hydrochloric acid (15 mL), and the reaction mixture was heated for 5 h at 40° C. Evaporation of the methanol under reduced pressure followed by basification to pH 10 with 10% aqueous potassium carbonate gave a white precipitate. The precipitate was filtered, washed with water and dried under vacuum overnight at ambient temperature to afford compound 121 as a white solid. m/z=414 (M+H). The preparation of compound 121 is generally shown above as step D of Procedure C.

3-(3-methoxy-phenyl)-5-methyl-2-{1-[9-(2-trimethylsilanyl-ethoxymethyl)-9H-purin-6-ylamino]-ethyl}-3H-quinazolin-4-one (127)

A 100-mL, one-neck, round bottomed flask equipped with a magnetic stirrer was charged with compound 126 (370 mg, 0.68 mmol), potassium carbonate (235 mg, 1.70 mmol), and DMF (4 mL). The resulting mixture was stirred for 5 min, and methyl iodide (435 mg, 3.10 mmol) was then added. After stirring for a further 1 h at ambient temperature, the reaction mixture was evaporated to dryness under reduced pressure. The residue was purified by column chromatography to give an 82% yield of compound 127 as a light yellow oil. $^1$H NMR ($CD_3OD$) δ (ppm) 8.20 (m, 2H), 6.99-7.66 (m, 7H), 5.58 (s, 2H), 5.15 (bs, 1H), 3.62 (dt, 2H, J=1.8, 8.0 Hz), 3.32 (s, 3H), 2.78 (s, 3H), 1.55 (m, 3H), 0.88 (m, 2H), −0.07 (s 9H); m/z=558 (M+H).

3-(3-methoxy-phenyl)-5-methyl-2-{1-[9H-purin-6-ylamino]-ethyl}-3H-quinazolin-4-one (128)

Compound 127 was reacted in accordance with the procedure described above for compound 121 (step D) to provide compound 128. m/z=428 (M+H). The structure of compound 128 is shown below.

(128)

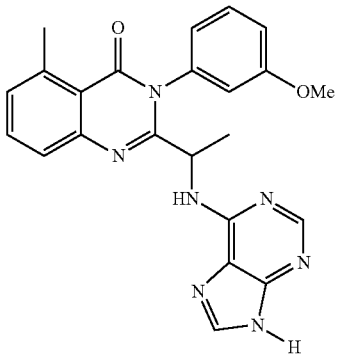

3-(3-Methoxy-phenyl)-5-methyl-2-[1-(9H-purin-6-ylamino)-ethyl]-3H-quinazolin-4-one 3-[3-(2-dimethylamino-ethoxy)-phenyl]-5-methyl-2-{1-[9H-purin-6-ylamino]-ethyl}-3H-quinazolin-4-one (129)

Compound 126 (300 mg, 0.54 mmol) was treated with 2-chloro ethyl dimethylamine hydrochloride salt, at 90° C. for 17 hrs, using the procedure described above for compound 127. The resulting compound was then treated with 4N HCl, in MeOH, using the procedure described for compound 121 (step D). Compound 129 was obtained. m/z=485 (M+H). The structure of compound 129 is shown below.

(129)

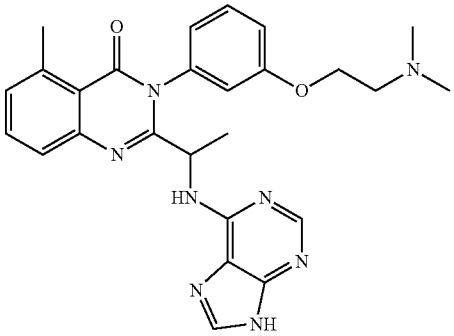

3-[3-(2-Dimethylamino-ethoxy)-phenyl]-5-methyl-2-[1-(9H-purin-6-ylamino)-ethyl]-3H-quinazolin-4-one 3-(3-cyclopropylmethoxy-phenyl)-5-methyl-2-{1-[9H-purin-6-ylamino]-ethyl}-3H-quinazolin-4-one (130)

Compound 126 (300 mgs, 0.54 mmol) was treated with bromomethyl cyclopropane using the procedure outlined for compound 127, at room temperature for 24 hrs. This intermediate was treated with 4N HCl according to the procedure described for compound 121 (step D). m/z=468 (M+H). The structure of compound 130 is shown below.

(130)

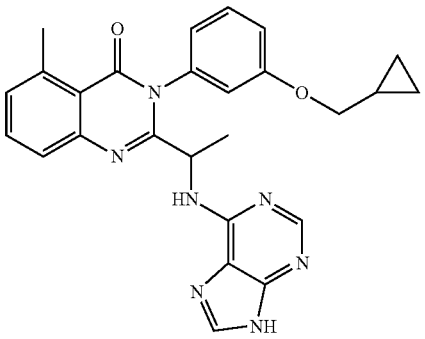

3-(3-Cyclopropylmethoxy-phenyl)-5-methyl-2-[1-(9H-purin-6-ylamino)-ethyl]-3H-quinazolin-4-one 5-methyl-3-(3-prop-2-ynyloxy-phenyl)-2-{1-[9H-purin-6-ylamino]-ethyl}-3H-quinazolin-4-one (131)

Compound 126 (300 mgs, 0.54 mmol) was treated with propargyl bromide at room temperature for 24 hrs using the procedure described above for compound 127. This intermediate was then treated with 4N HCl according to the procedure described for compound 121 (step D). m/z=467 (M+H). The structure of compound 131 is shown below.

(131)

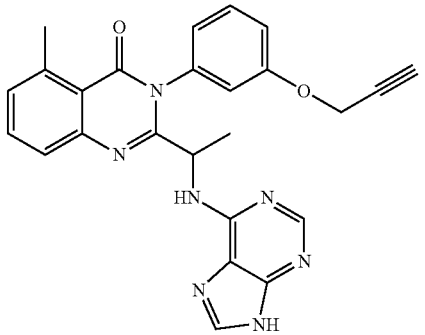

5-Methyl-3-(3-prop-2-ynyloxy-phenyl)-2-[1-(9H-purin-6-ylamino)-ethyl]-3H-quinazolin-4-one 2-{1-[2-amino-9H-purin-6-ylamino]ethyl}-3-(3-hydroxyphenyl)-5-methyl-3H-quinazolin-4-one (132)

Compound 132 was prepared according to the procedures set forth in steps A and B below.

2-{1-[2-di tert-butyloxycarbonylamino-9-(2-trimethylsilylethoxymethyl)-9H-purin-6-ylamino]ethyl}-3-(3-hydroxyphenyl)-5-methyl-3H-quinazolin-4-one (133)

Step A: A nitrogen purged, 50-mL one-neck round bottomed flask equipped with a magnetic stirrer and reflux condenser was charged with compound 125 (3.02 g, 10.2 mmol), intermediate compound 12 (5.56 g, 1.0 eq), n-butanol (20 mL), and DIPEA (6.0 mL). The mixture was heated at 100° C. for 1 h, and then cooled to room temperature. Concentration of the reaction mixture under high vacuum followed by column chromatography gave compound 133 as a white solid.

2-{1-[2-amino-9H-purin-6-ylamino]ethyl}-3-(3-hydroxyphenyl)-5-methyl-3H-quinazolin-4-one (132)

Step B: Compound 133 was dissolved in MeOH (3 mL), treated with 4N HCl (3 mL) and heated at 40° C. for 6 h. The reaction mixture was then concentrated to approximately half the volume and partitioned between water (5 mL) and ethyl acetate (10 mL). The aqueous layer was separated, basified with potassium carbonate to pH 10 and filtered. After washing the filter cake with water (5 mL) and drying under vacuum, compound 132 was obtained as a white solid. m/z=429 (M+H). The structure of compound 132 is shown below.

(132)

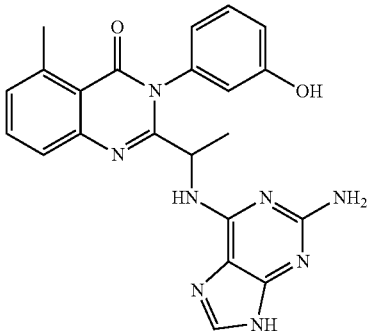

2-[1-(2-Amino-9H-purin-6-ylamino)-ethyl]-3-(3-hydroxy-phenyl)-5-methyl-3H-quinazolin-4-one 2-{1-[2-amino-9H-purin-6-ylamino]ethyl}-3-(3-methoxyphenyl)-5-methyl-3H-quinazolin-4-one (134)

Compound 133 (300 mgs, 0.39 mmol) was treated with methyl iodide using the procedure described above for compound 127. This intermediate was then treated with 4N HCl in methanol according to the procedure described above for compound 132 (step B). m/z=443 (M+H). The structure of compound 134 is shown below.

(134)

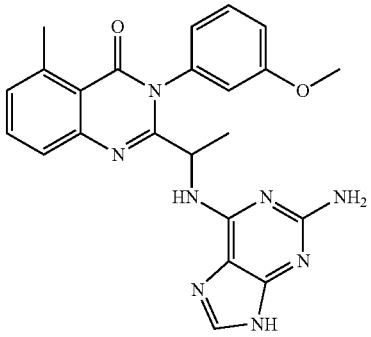

2-[1-(2-Amino-9H-purin-6-ylamino)-ethyl]-3-(3-methoxy-phenyl)-5-methyl-3H-quinazolin-4-one 2-{1-[2-amino-9H-purin-6-ylamino]ethyl}-3-(3-cyclopropylmethoxy-phenyl)-5-methyl-3H-quinazolin-4-one (135)

Compound 133 (231 mgs, 0.30 mmol) was treated with cyclopropyl methyl bromide using the procedure described above for compound 127. The generated intermediate was then treated with 4N HCl in MeOH according to the procedure described above for compound 132 (step B). m/z=483 (M+H). The structure of compound 135 is shown below.

(135)

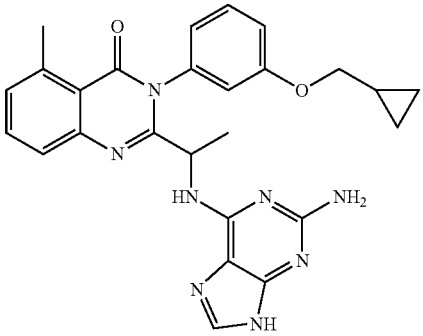

2-[1-(2-Amino-9H-purin-6-ylamino)-ethyl]-3-(3-cyclopropylmethoxy-phenyl)-5-methyl-3H-quinazolin-4-one 2-{1-[2-amino-9H-purin-6-ylamino]ethyl}-5-methyl-3-(3-prop-2-ynyloxy-phenyl)-3H-quinazolin-4-one (136)

Compound 133 (231 mgs, 0.30 mmol) was treated with propargyl bromide using the procedure described above for compound 127. The generated intermediate was then treated with 4N HCl in MeOH according to the procedure described above for compound 132 (step B). m/z=467 (M+H). The structure of compound 136 is shown below.

(136)

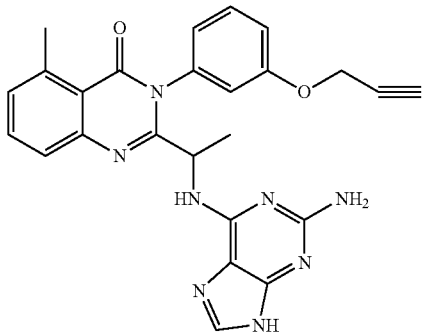

2-[1-(2-Amino-9H-purin-6-ylamino)-ethyl]-5-methyl-3-(3-prop-2-ynyloxy-phenyl)-3H-quinazolin-4-one 3-(3-ethynyl-phenyl)-5-methyl-2-[1-(9H-purin-6-ylamino)-ethyl]-3H-quinazolin-4-one (137)

Compound 137 was prepared according to the procedures set forth in steps A-C below.

Trifluoromethane sulfonic acid 3-(5-methyl-4-oxo-2-{1-[9-(2-trimethylsilanyl-ethoxymethyl)-9H-purin-6-ylamino]-ethyl}-4H-quinazolin-3-yl)-phenyl ester (138)

Step A: A 50-mL, three-neck, round bottomed flask equipped with a magnetic stirrer was purged with nitrogen and charged with compound 126 (500 mg, 0.92 mmol), triethylamine (218 mg, 2.16 mmol), anhydrous methylene chloride (10 mL) and N-phenyltrifluoromethanesulfonimide (496 mg, 1.39 mmol). After stirring for 2 h at ambient temperature, the reaction mixture was partitioned between methylene chloride (50 mL) and 10% aqueous potassium carbonate (50 mL). The organic phase was separated, dried over sodium sulfate and filtered. Concentration of the filtrate followed by column chromatography gave a 77% yield of compound 138 as an off-white solid. $^1$H NMR (DMSO-$d_6$) δ (ppm) 8.32 (bs, 1H), 7.48-8.18 (m, 7H), 7.30 (d, 1H, J=8.0 Hz), 5.51 (s, 2H), 4.75-4.85 (m, 1H), 3.55 (t, 2H, J=8.0 Hz), 2.72 (s, 3H), 1.46 (d, 3H, J=6.6 Hz), 0.83 (dt, 2H, J=1.6, 8.1 Hz), −0.09 (s, 9H).

5-Methyl-2-{1-[9-(2-trimethylsilylethoxymethyl)-9H-purin-6-ylamino]ethyl}-3-(3-trimethylsilylethynylphenyl)-3H-quinazolin-4-one (139)

Step B: A 5-mL reaction vial equipped with a magnetic stirrer was purged with nitrogen and charged with compound 138 (220 mg, 0.33 mmol), dichlorobis(triphenylphosphine) palladium(II) (27.1 mg, 0.039 mmol), and anhydrous DMF (1 mL). Triethylamine (146 mg, 1.44 mmol) and (trimethylsilyl) acetylene (102 mg, 1.04 mmol) were added, and the reaction mixture was stirred for 10 h at 90° C. and an additional 8 h at 100° C. Evaporation of the reaction mixture to dryness followed by column chromatography purification afforded 63% yield of compound 139 as an off-white solid. $^1$H NMR ($CD_3OD$) δ (ppm) 7.43-8.33 (m, 8H), 7.30 (d, 1H, J=6.6 Hz), 5.64 (s, 2H), 5.14 (bs, 1H), 3.68 (t, 2H, J=8.0 Hz), 2.81 (s, 3H), 1.59-1.64 (m, 3H), 0.94 (m, 2H), 0.32 (s, 9H), −0.09 (s, 9H).

3-(3-ethynyl-phenyl)-5-methyl-2-[1-(9H-purin-6-ylamino)-ethyl]-3H-quinazolin-4-one (137)

Step C: Compound 139 (113 mgs, 0.18 mmol) was treated with 4N HCl in MeOH according to the procedure described for compound 121 (step D). This afforded compound 137. m/z=422 (M+H). The structure of compound 137 is shown below.

(137)

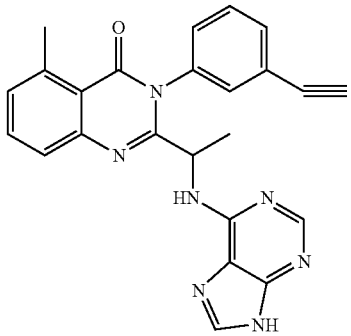

3-(3-Ethynyl-phenyl)-5-methyl-2-[1-(9H-purin-6-ylamino)-ethyl]-3H-quinazolin-4-one 3-{5-methyl-4-oxo-2-[1-(9H-purin-6-ylamino)-ethyl]-4H-quinazolin-3-yl}-benzonitrile (140)

Compound 140 was prepared according to the procedures set forth in steps A and B below.

3-(5-methyl-4-oxo-2-{1-[9-(2-trimethylsilylethoxymethyl)-9H-purin-6-ylamino]ethyl}-4H-quinazolin-3-yl)benzonitrile (141)

Step A: A 5-mL reaction vial equipped with a magnetic stirrer was charged with compound 138 (200 mg, 0.300 mmol), tetrakis(triphenylphosphine)palladium (34.0 mg, 0.029 mmol), zinc cyanide (70 mg, 0.60 mmol) and anhydrous DMF (1 mL). The vial was purged with nitrogen, heated to 120° C. for 3.5 h then cooled to ambient temperature and poured into a saturated aqueous sodium bicarbonate solution (25 mL). The resulting suspension was extracted with methylene chloride (3×20 mL), and the organic extracts were combined, dried over sodium sulfate and filtered. Concentration of the filtrate followed by purification by column chromatography gave a 66% yield of compound 141 as a white solid. $^1$H NMR ($CDCl_3$) δ (ppm) 8.30 (d, 1H, J=6.9 Hz), 7.58-8.02 (m, 7H), 7.30 (d, 1H, J=7.0 Hz), 5.60 (s, 2H), 5.07 (bs, 1H), 3.65 (m, 2H), 2.84 (s, 3H), 1.58 (d, 3H, J=6.7 Hz), 0.96 (m, 2H), 0.02 (s, 9H).

3-{5-Methyl-4-oxo-2-[1-(9H-purin-6-ylamino)-ethyl]-4H-quinazolin-3-yl}-benzonitrile (140)

Step B: Compound 141 was treated with 4N HCL in MeOH for 1 hour using the procedure described for compound 121 (step B) to provide compound 140. m/z=423 (M+H). The structure of compound 140 is shown below.

(140)

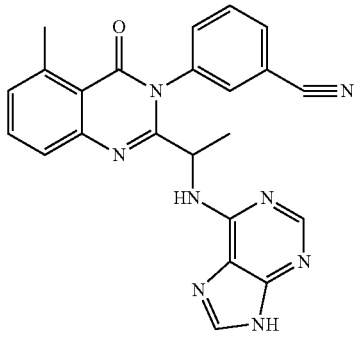

3-{5-methyl-4-oxo-2-[1-(9H-purin-6-ylamino)-ethyl]-4H-quinazolin-3-yl}-benzonitrile 3-{5-Methyl-4-oxo-2-{1-[9H-purin-6-ylamino)-ethyl]-4H-quinazolin-3-yl}-benzamide (142)

Compound 142 was prepared according to the procedures set forth in steps A and B below.

3-(5-Methyl-4-oxo-2-{1-[9-(2-trimethylsilylethoxymethyl)-9H-purin-6-ylamino]ethyl}-4H-quinazolin-3-yl)benzamide (143)

Step A: A 100-mL, three-neck, round bottomed flask equipped with a magnetic stirrer and a reflux condenser was purged with nitrogen and charged with compound 141 (219 mg, 0.40 mmol) and anhydrous methylene chloride (15 mL). N,N-Diethylhydroxylamine (146 mg, 1.64 mmol) was added to the resulting solution, and the reaction mixture was heated for 16 h at 50° C., cooled to ambient temperature, and then evaporated to dryness under reduced pressure. The resulting residue was purified by column chromatography to give a 97% yield of compound 143 as a white solid. m.p. 195-197° C.; $^1$H NMR ($CDCl_3$) δ (ppm) 8.34 (d, 1H, J=10.9 Hz), 7.59-8.06 (m, 7H), 7.28 (m, 1H), 6.95 (bs, 1H), 6.00 (bs, 2H), 5.60 (s, 2H), 5.28 (bs, 1H), 3.62 (t, 2H, J=8.4 Hz), 2.85 (s, 3H), 1.53 (dd, 3H, J=6.7, 10.8 Hz), 0.96 (t, 2H, J=8.3 Hz), 0.01 (s, 9H); m/z=571 (M+H).

3-{5-Methyl-4-oxo-2-{1-[9H-purin-6-ylamino)-ethyl]-4H-quinazolin-3-yl}-benzamide (142)

Step B: Compound 143 was treated with 4N HCL in MeOH for 1.5 hours using the procedure described for compound 121 (step D) to provide compound 142. m/z=441 (M+H). The structure of compound 142 is shown below.

(142)

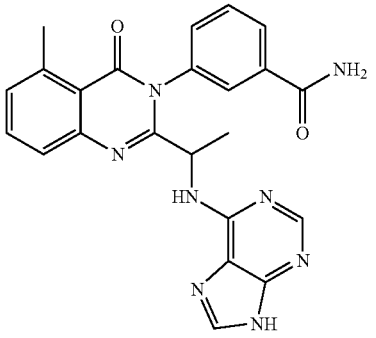

3-{5-Methyl-4-oxo-2-[1-(9H-purin-6-ylamino)-ethyl]-4H-quinazolin-3-yl}-benzamide 3-(3-acetyl-phenyl)-5-methyl-2-{1-[9H-purin-6-ylamino]-ethyl}-3H-quinazolin-4-one (144)

Compound 139 was treated with 4N HCl in MeOH at 70° C. for 16 hours in accordance with the procedure described for compound 121 (step D). This reaction afforded compound 144, the structure of which is shown below. m/z=440 (M+H)

(144)

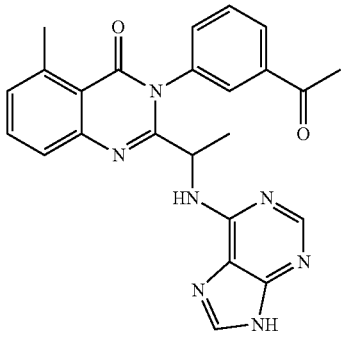

3-(3-Acetyl-phenyl)-5-methyl-2-[1-(9H-purin-6-ylamino)-ethyl]-3H-quinazolin-4-one 2-(3-(5-methyl-4-oxo-2-{1-[9H-purin-6-ylamino]-ethyl}-4H-quinazolin-3-yl-phenoxy acetamide (145)

Compound 126 (300 mgs, 0.54 mmol) was treated with 2 bromo acetamide using the procedure outlined above for compound 127. The reaction was under reflux for 24 hrs in CH3CN. This intermediate was treated with 4N HCl in MeOH for 1 hour, following the procedure described for compound 121 (step D), to provide compound 145. m/z=471 (M+H). The structure of compound 145 is shown below.

(145)

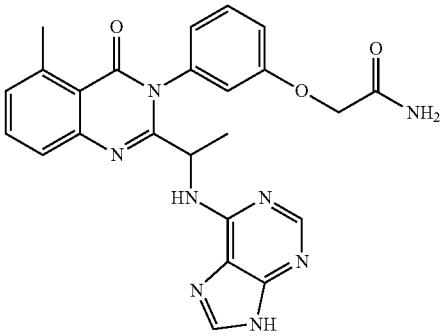

2-(3-{5-Methyl-4-oxo-2-[1-(9H-purin-6-ylamino)-ethyl]-4H-quinazolin-3-yl}-phenoxy)-acetamide 5-methyl-2-{1-[9H-purin-6-ylamino]-ethyl}-3-[3-(tetrahydropuran-4-yloxy)-phenyl]-3H-quinazolin-4-one (146)

A 25-mL, three-neck, round bottomed flask equipped with a magnetic stirrer was purged with nitrogen and charged with compound 126 (270 mgs, 0.5 mmol), tetrahydro pyran-4-ol (60 uL), triphenylphosphine (560 mgs), THF (5 mL), and diethyl azodicarboxylate (340 uL). After stirring for 16 h at ambient temperature, the reaction mixture was evaporated to dryness, and the residue was dissolved in methanol (3 mL), treated with 4N hydrochloric acid (3 mL), and heated at 40° C. for 6 h. The reaction mixture was then concentrated to approximately half the volume and partitioned between water (5 mL) and ethyl acetate (10 mL). The aqueous layer was separated, basified with potassium carbonate to pH 10 and filtered. After washing the filter cake with water (5 mL) and drying under vacuum, compound 146 was obtained. m/z=498 (M+H). The structure of compound 146 is shown below.

(146)

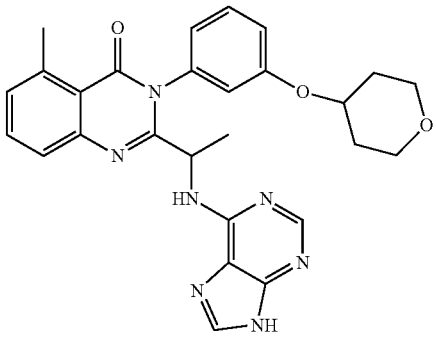

5-Methyl-2-[1-(9H-purin-6-ylamino)-ethyl]-3-[3-(tetrahydro-pyran-4-yloxy)-phenyl]-3H-quinazolin-4-one 3-[3-(2-methoxy-ethoxy)-phenyl]-5-methyl-2-[1-(9H-purin-6-ylamino)-ethyl]-3H-quinazolin-4-one (147)

Compound 126 (300 mgs, 0.54 mmol) was treated with toluene 4-sulfonic acid 2-methoxy ethyl ester at 50 C for 42 hrs using the procedure described above for compound 127. The generated intermediate was then treated with 4N HCl in MeOH, using the procedure described for compound 121 (step D). m/z=487 (M+H).

(147)

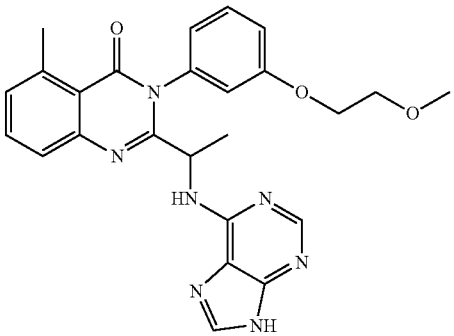

3-[3-(2-Methoxy-ethoxy)-phenyl]-5-methyl-2-[1-(9H-purin-6-ylamino)-ethyl]-3H-quinazolin-4-one 6-fluoro-2-[1-(9H-purin-6-ylamino)ethyl]-3-[3-(tetrahydro-pyran-4-yloxy)-phenyl]-3H-quinazolin-4-one (148)

Compound 148 was prepared according to the procedures set forth in steps A and B below.

6-fluoro-3-(3-hydroxy-phenyl)-2-{1-[9-(2-trimethylsilanyl-ethoxymethyl)-9H-purin-6ylamino-ethyl}-3H-quinazolin-4-one (149)

Step A: Compound 149 was obtained from 6-amino 3-fluoro benzoic acid using the procedures described above for compounds 123, 124, 125, and 126.

6-fluoro-2-[1-(9H-purin-6-ylamino)ethyl]-3-[3-(tetrahydro-pyran-4-yloxy)-phenyl]-3H-quinazolin-4-one (148)

Step B: Compound 148 was obtained from compound 149 using the procedure described for compound 146. m/z=502 (M+H). The structure of compound 148 is shown below.

(148)

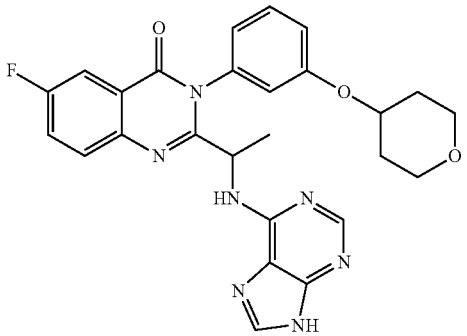

6-Fluoro-2-[1-(9H-purin-6-ylamino)-ethyl]-3-[3-(tetrahydro-pyran-4-yloxy)-phenyl]-3H-quinazolin-4-one 3-[3-(3-dimethylamino-propoxy)-phenyl]-5-methyl-2-[1-(9H-purin-6-ylamino)-ethyl]-3H-quinazolin-4-one (150)

Compound 150 was obtained following the general procedure described for compound 146, but 3-dimethylamino-1-propanol was used in place of tetrahydropyran-4-ol. m/z=499 (M+H). The structure of compound 150 is shown below.

(150)

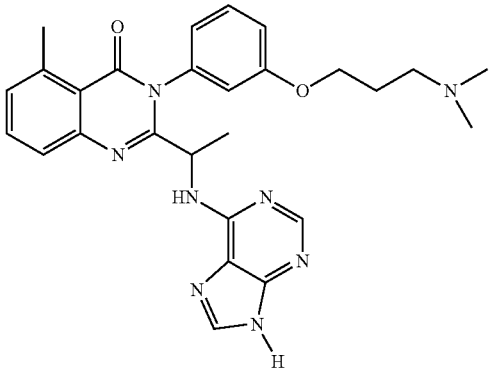

3-[3[(3-Dimethylamino-propoxy)-phenyl]-5-methyl-2-[1-(9H-purin-6-ylamino)-ethyl]-3H-quinazolini-4-one 2-[1-(2-amino-9H-purin-6-ylamino)-ethyl]-3-(3-ethynyl-phenyl)-5-methyl-3H-quinazolin-4-one (151)

Compound 151 was prepared according to the procedures set forth in steps A and B below.

Trifluoromethane sulfonic acid 3-{2-[1-(2-di tert-butyloxycarbonylamino-9-(2-trimethylsilylethoxym-ethyl)-purin-6ylamino)-ethyl]-5-methyl-4-oxo-4H-quinazolin-3-yl}-phenyl ester (152)

Step A: Compound 152 was obtained from compound 133, which was reacted in accordance with the procedure described for compound 138.

2-[1-(2-amino-9H-purin-6-ylamino)-ethyl]-3-(3-ethynyl-phenyl)-5-methyl-3H-quinazolin-4-one (151)

Step B: Compound 151 was obtained from compound 152, which was reacted in accordance with the procedures for compounds 139 and 137 (step C). m/z=437 (M+H). The structure of compound 151 is shown below.

(151)

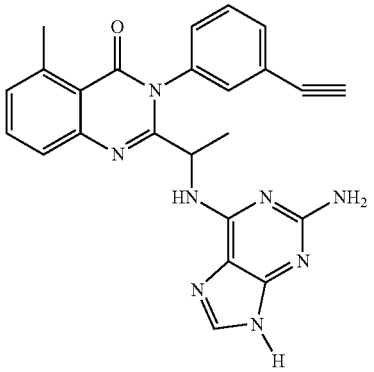

2-[1-(2-Amino-9H-purin-6-ylamino)-ethyl]-3-(3-ethynyl-phenyl)-5-methyl-3H-quinazolin-4-one 3-{2-[1-(2-amino-9H-purin-6-ylamino)-ethyl]-5-methyl-4-oxo-4H-quinazolin-3-yl}-benzonitrile (153)

Compound 153 was obtained from compound 152, which was reacted in accordance with the procedure for compounds 141 and 140 (step D) described above. m/z=438 (M+H). The structure of compound 153 is shown below.

(153)

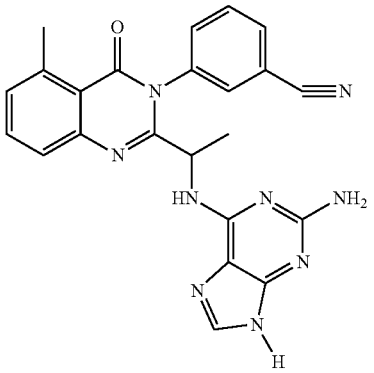

3-{2-[1-(2-Amino-9H-purin-6-ylamino)-ethyl]-5-methyl-4-oxo-4H-quinazolin-3-yl}-benzonitrile 3-{2-[1-(2-amino-9H-purin-6-ylamino)-ethyl]-5-methyl-4-oxo-4H-quinazolin-3-yl}-benzamide (154)

Compound 154 was obtained by first reaction compound 152 in accordance with the procedure for compound 141. This reaction product was then further reacted in accordance with the procedure for compounds 143 and 142 (step B). m/z=456 (M+H). The structure of compound 154 is shown below.

(154)

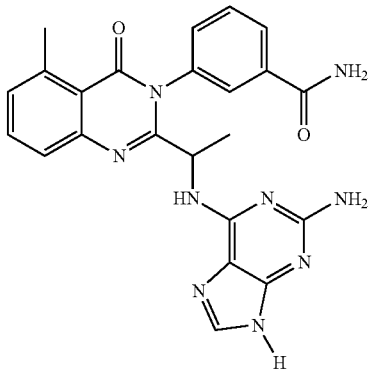

3-{2-[1-(2-Amino-9H-purin-6-ylamino)-ethyl]-5-methyl-4-oxo-4H-quinazolin-3-yl}-benzamide 3-{2-[1-(2-amino-9H-purin-6-ylamino)-ethyl]-5-methyl-4-oxo-4H-quinazolin-3-yl}-benzamide (155)

Compound 155 was obtained by first reacting compound 151 in accordance with the procedure described for compound 139. This reaction product was treated according to the procedure described for compound 144. m/z=455 (M+H). The structure of compound 155 is shown below.

(155)

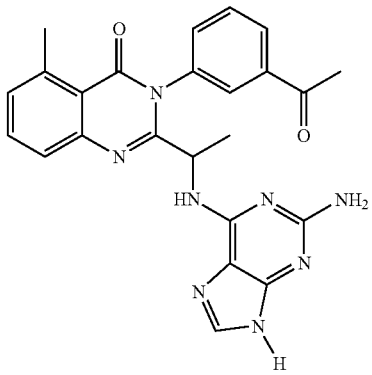

3-3-Acetyl-phenyl)-2-[1-(2-amino-9H-purin-6-ylamino)-ethyl]-5-methyl-3H-quinazolin-4-one 5-methyl-3-(3-morpholin-4-yl-phenyl)-2-[1-(9H-purin-6-ylamino)-ethyl]-3H-quinazolin-4-one (156)

Compound 156 was prepared according to the procedures set forth in steps A and B below.

5-methyl-3-(3-morpholino-4-yl-phenyl)-2-{1-[9-(2-trimethylsilanylethoxymethyl)-9H-purin-6-ylamino]-ethyl}-3H-quinazolin-4-one (157)

Step A: A 3-mL reaction vial was charged with compound 138 (96.1 mg, 0.142 mmol), palladium(II) acetate (3.20 mg, 0.014 mmol), cesium carbonate (84.2 mg, 0.258 mmol) and (+)-BINAP (i.e., 2,2'-bis(diphenylphosphino)-1,1'-binaphthyl) (13.8 mg, 0.022 mmol). The vial was then flushed with nitrogen for 10 min. Toluene (0.3 mL) and morpholine (18 μL) were then added, and the solution was heated at 100° C. for 6 h. Subsequently, the solution was diluted with dichloromethane (5 mL), filtered, and the filtrate was concentrated under reduced pressure. Preparative HPLC of the residue provided compound 157 as a yellow oil. $^1$H NMR ($CH_3OD$) δ (ppm) 8.24-8.30 (m, 2H), 7.48-7.72 (m, 3H), 7.33 (m, 2H), 6.94-7.13 (m, 3H), 5.56 and 5.64 (two s, $CH_2$ rotamer ratio 1:10), 5.15-5.30 (m, 1H), 3.90 (m, 2H), 3.76 (m, 2H), 3.67 (m, 2H), 3.28 (m, 1H), 2.97-3.15 (m, 3H), 2.84 (s, 3H), 1.62 (m, 3H), 0.96 (m, 2H), −0.03 (s, 9H).

5-methyl-3-(3-morpholin-4-yl-phenyl)-2-[1-(9H-purin-6-ylamino)-ethyl]-3H-quinazolin-4-one (156)

Step B: Compound 156 was prepared by reacting compound 157 in accordance with the procedure for the preparation of compound 137 (final step C). m/z=483 (M+H). The structure of compound 156 is shown below.

(156)

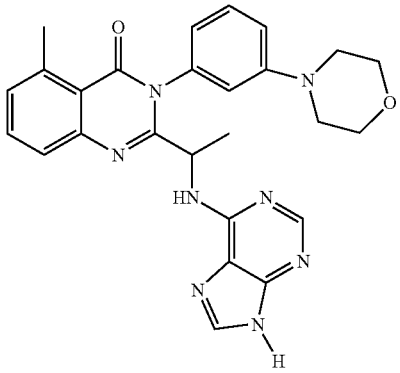

5-Methyl-3-(3-morpholin-4-yl-phenyl)-2-[1-(9H-purin-6-ylamino)-ethyl]-3H-quinazolin-4-one 2-[1-(2-amino-9H-purin-6-ylamino)-ethyl]-5-methyl-3-(3-morpholin-4-yl-phenyl)-3H-quinazolin-4-one (158)

Compound 158 was prepared in accordance with the procedure described for compound 129, but compound 133 was used in place of compound 126. m/z=498 (M+H). The structure of compound 158 is shown below.

(158)

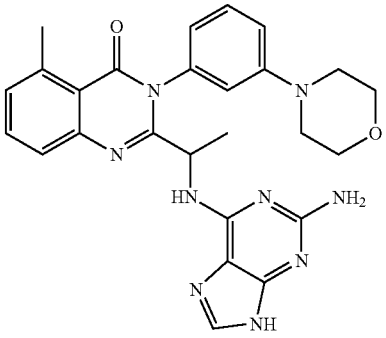

2-[1-(2-Amino-9H-purin-6-ylamino)-ethyl]-5-methyl-3-(3-morpholin-4-yl-phenyl)-3H-quinazolin-4-one 2-[1-(2-amino-9H-purin-6-ylamino)-ethyl]-3-[3-(2-methoxy-ethoxy)-phenyl]-5-methyl-3H-quinazolin-4-one (159)

Compound 159 was prepared by reacting compound 133 in accordance with the procedure for the preparation of compound 147. m/z=487 (M+H). The structure of compound 159 is shown below.

(159)

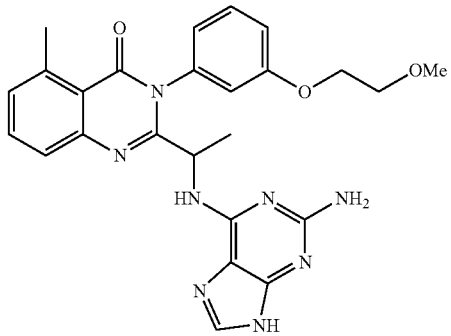

2-[1-(2-Amin-9H-purin-6-ylamino)-ethyl]-3-[3-(2-methoxy-ethoxy)-phenyl]-5-methyl-3H-quinazolin-4-one 2-[1-(2-amino-9H-purin-6-ylamino)-ethyl]-3-[3-(2-dimethylamino-ethoxy)-phenyl]-5-methyl-3H-quinazolin-4-one (160)

Compound 160 was prepared by reacting compound 133 in accordance with the procedure for the preparation of compound 146. m/z=500 (M+H). The structure of compound 160 is shown below.

(160)

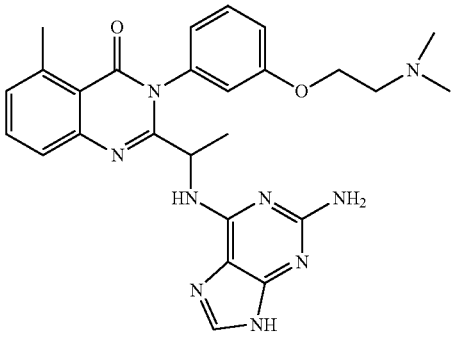

2-[1-(2-Amino-9H-purin-6-ylamino)-ethyl]-3-[3-(2-dimethylamino-ethoxy)-phenyl]-5-methyl-3H-quinazolin-4-one

EXAMPLE 11

Compound Preparation

Compounds having general formula I (shown above) have been prepared in accordance with steps A-D of the synthetic scheme entitled "Procedure E" shown below. Procedure E provides an additional alternative method of preparing compounds with a variety of side chains appended to the linker between the quinazolinone and purine rings of the inventive compounds. Although a propargyl functional group is exemplified, the method illustrated in Procedure E is applicable to many known functional groups.

Procedure E

Step A

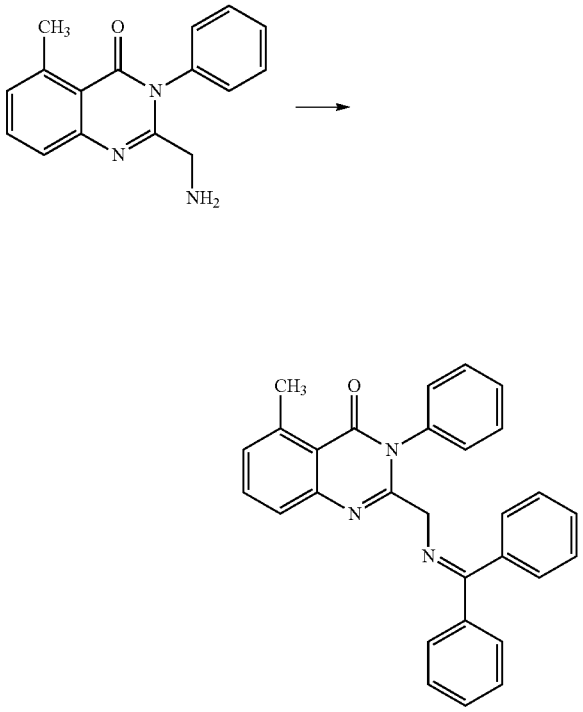

Step B

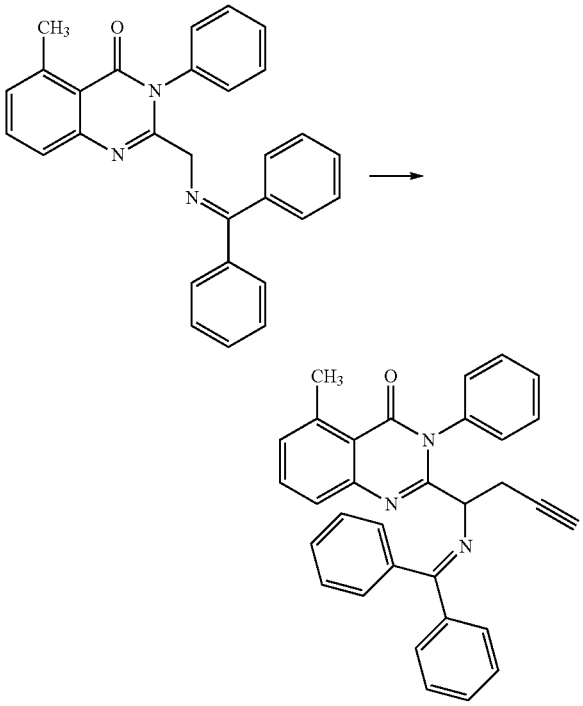

-continued

Step C

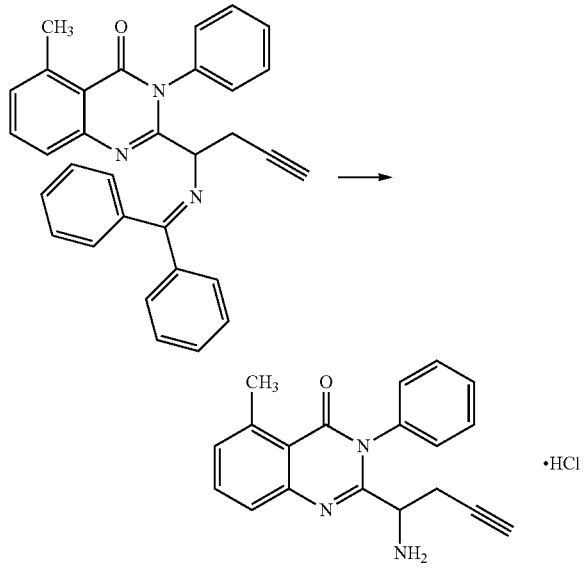

Step D

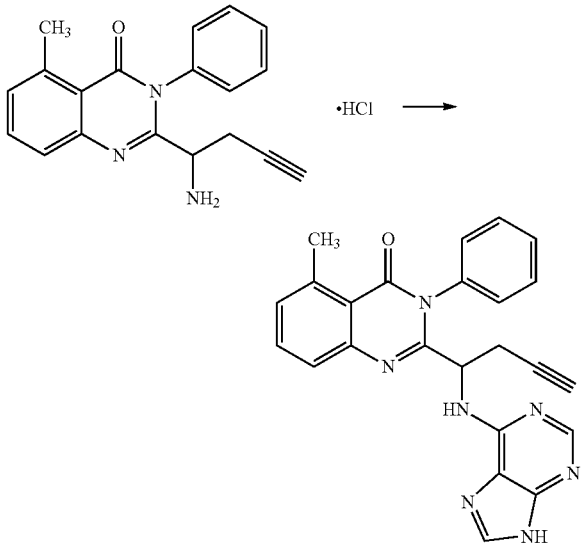

2-[1-(2-amino-9H-purin-6-ylamino)-but-3-ynyl]-5-methyl-3-phenyl-3H-quinazolin-4-one (161)

Compound 161 was prepared according to the procedures set forth in steps A-D below.

2-[(Benzhydrylidene-amino)-methyl]-5-methyl-3-phenyl-3H-quinazolin-4-one (162)

Step A: A 100-mL, one-neck, round bottomed flask equipped with a magnetic stirrer and reflux condenser was charged with 2-aminomethyl-5-methyl-3-phenyl-3H-quinazolin-4-one (2.91 g, 11.0 mmol), benzhydrylideneamine (2.39 g, 13.2 mmol), and 1,2-dichloroethane (15 mL). The reaction mixture was heated at reflux for 4 h under nitrogen atmosphere and then cooled to ambient temperature. Concentration under reduced pressure followed by purification by column chromatography afforded the compound 162 as an orange solid. m.p. 49° C. (dec); $^1$H NMR (DMSO-$d_6$) δ (ppm)

7.22-7.78 (m, 17H), 6.74 (m, 1H), 4.17 (s, 2H), 2.74 (s, 3H); m/z=430 (M+H). The reaction described above and compound 162 are shown below.

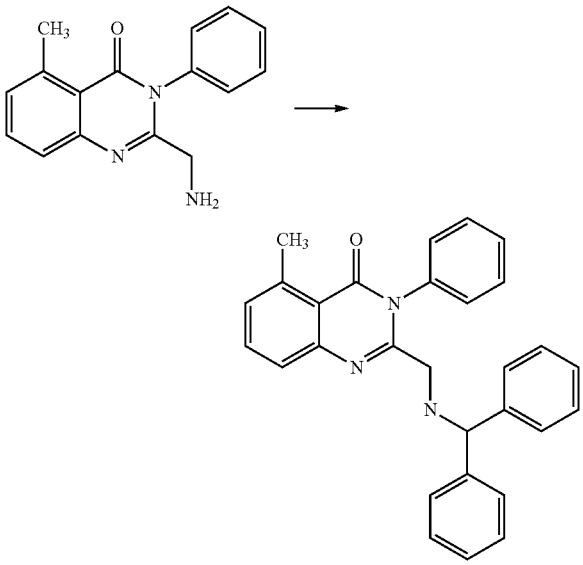

2-[1-(Benzhydrylidene-amino)-but-3-ynyl]-5-methyl-3-phenyl-3H-quinazolin-4-one (163)

Step B: A 25-mL, one-neck, round bottomed flask equipped with a magnetic stirrer was purged with nitrogen and charged with compound 162 (500 mg, 1.20 mmol) and anhydrous THF (4 mL). A 1M solution of potassium tert-butoxide in THF (1.40 mL, 1.40 mmol) was added in one portion. After stirring for 20 min at ambient temperature, an 80% solution of propargyl bromide in toluene (210 μL, 1.89 mmol) was added, and the reaction stirred for an additional 15 min at ambient temperature. Saturated aqueous sodium bicarbonate (5 mL) was then added, the layers separated, and the aqueous layer extracted with ethyl acetate (2×10 mL). The combined organic extracts were dried over sodium sulfate, filtered, and concentrated under reduced pressure. Purification of the residue by column chromatography afforded the product as a yellow solid. $^1$H NMR ($CD_3OD$) δ 7.72 (m, 2H), 7.24-7.67 (m, 3H), 6.77 (m, 3H), 4.61 (t, 1H, J=7.1 Hz), 3.01-3.11 (m, 1H), 2.76 (s, 3H), 2.57 (m, 1H), 2.23 (t, 1H, J=2.5 Hz). The reaction described above and compound 163 are shown below.

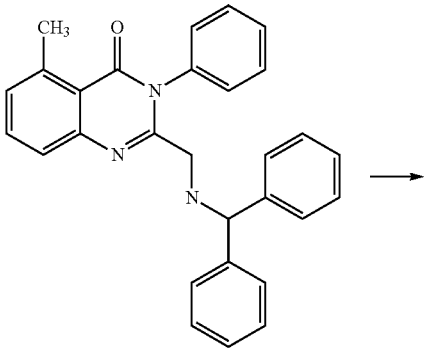

-continued

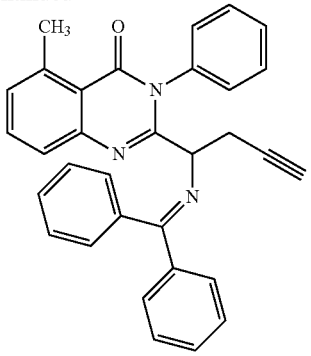

2-(1-amino-but-3-ynyl)-5-methyl-3-phenyl-3H-quinazolin-4-one (164)

Step C: A 50-mL, one-neck, round bottomed flask equipped with a magnetic stirrer was charged with compound 163 (193 mg, 0.41 mmol) and diethyl ether (5 mL). A 2N solution of hydrochloric acid (5 mL) was added in one portion. After stirring for 1.5 h at ambient temperature, sodium chloride (750 mg, 12.8 mmol) was added to the reaction mixture, and stirring was continued for an additional 10 min. The resulting precipitate was filtered, washed sequentially with diethyl ether (0.5 mL), 2N hydrochloric acid (1 mL), and MtBE (2×1 mL). Drying under vacuum at 45° C. for 2 h afforded the product as a pink solid. $^1$H NMR (DMSO-$d_6$) δ 8.82 (s, 3H), 7.79 (t, 1H, J=7.7 Hz), 7.41-7.66 (m, 6H), 7.42 (d, 1H, J=7.3 Hz), 3.91 9s, 1H), 3.11 (m, 1H), 2.87 (m, 1H), 2.75 (s, 3H), 2.54-2.67 (m, 1H). The reaction described above and compound 164 are shown below.

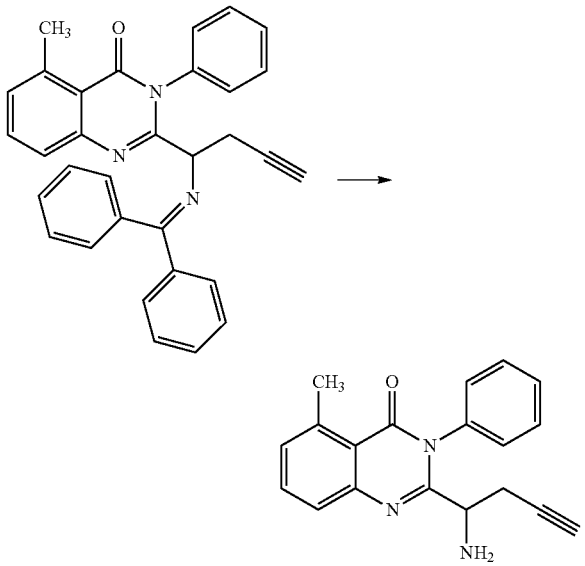

5-methyl-3-phenyl-2-[1-(9H-purin-6-ylamino)-but-3-ynyl]-3H-quinazolin-4-one (161)

Step D: Compound 161 was prepared by reacting compound 164 prepared following the procedure for the preparation of compound 14 (step D) using three equivalents of diisopropylethylamine instead of one. ESI-MS m/z=422 ($MH^+$). The reaction described above and compound 161 are shown below.

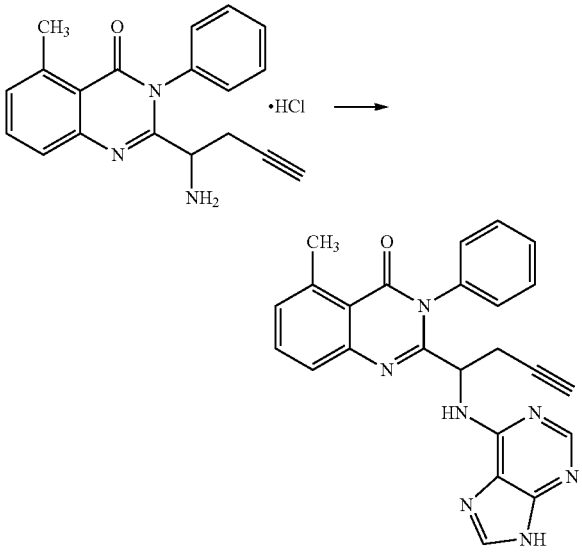

2-[1-(2-amino-9H-purin-6-ylamino)-but-3-ynyl]-5-methyl-3-phenyl-3H-quinazolin-4-one (165)

Compound 165 was prepared following the general procedure described above for the preparation of compound 161, but 2-amino-6-bromopurine was substituted for 6-bromopurine in step D. ESI-MS m/z=437 ($MH^+$).

EXAMPLE 12

Compound Preparation

Compounds having general formula I (shown above) have been prepared in accordance with steps A-E of the synthetic scheme entitled "Procedure K" shown below. Procedure K provides an additional alternative method of preparing such compounds via an oxazine intermediate (step C).

Procedure K

Step A

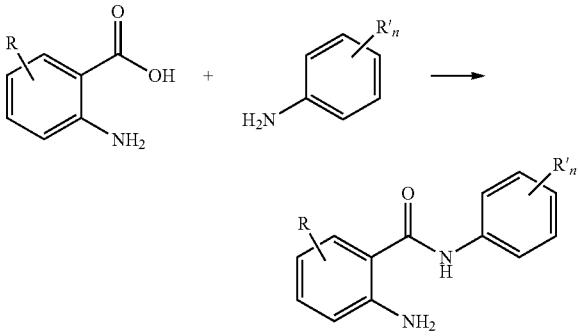

-continued

Step B

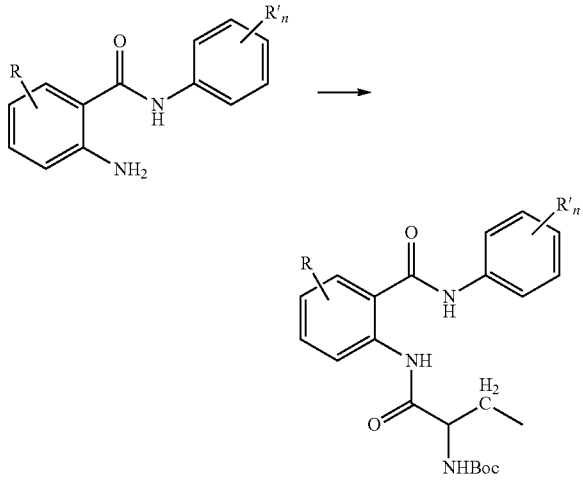

Step C

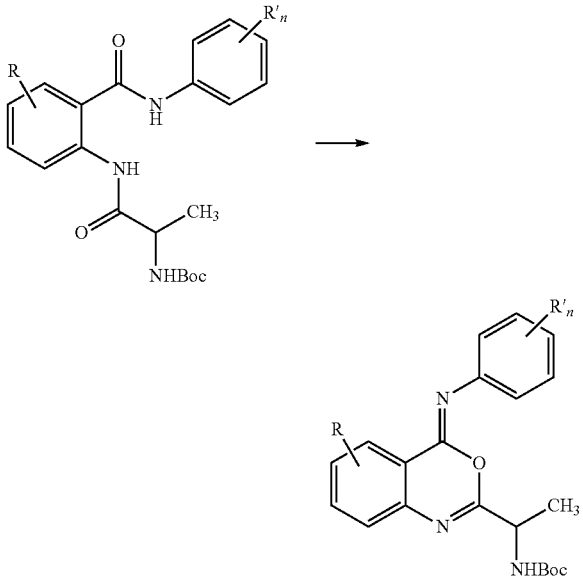

Step D

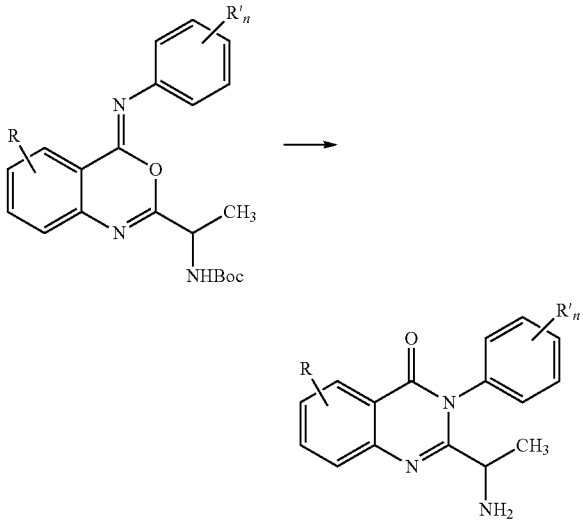

-continued

Step E

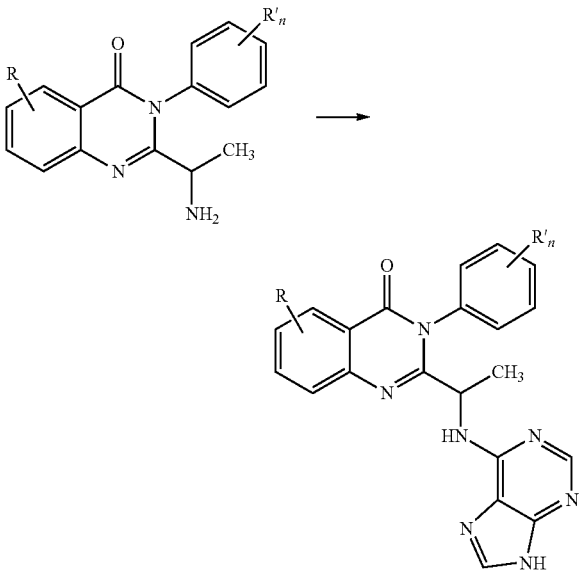

5-chloro-3-(3,5-difluoro-phenyl)-2-[1-(9H-purin-6-ylamino)-ethyl]-3H-quinazolin-4-one (166)

Compound 166 was prepared according to the procedures set forth in steps A-E below.

2-amino-6-chloro-N-(3,5-difluoro-phenyl)-benzamide (167)

Step A: Compound 167 was prepared following the procedure following the procedure for the preparation of compound 15 (step A), but 2-amino-6-chlorobenzoic acid was substituted for 2-amino-6-methylbenzoic acid and 3,5-difluoroaniline was substituted for aniline. The reaction described above and compound 167 are shown below.

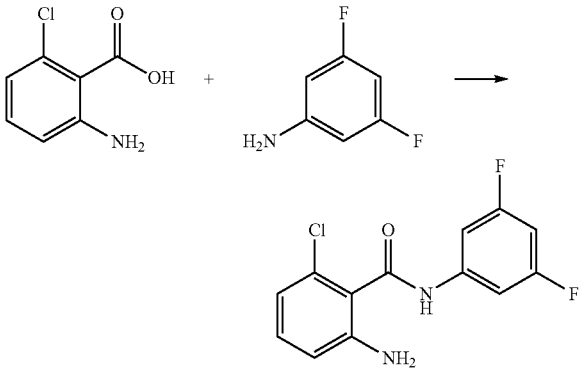

{1-[3-chloro-2-(3,5-difluoro-phenylcarbamoyl)-phenylcarbamoyl]-ethyl}-carbamic acid tert-butyl ester (168)

Step B: A 100-mL, one-neck, round bottomed flask equipped with a magnetic stirrer and reflux condenser was charged with the compound 167 (10.6 mmol), N-tert-butyloxycarbonyl-D,L-alanine N-hydroxysuccinimide ester (3.64 g, 12.7 mmol), 4-N,N-dimethylaminopyridine (710 mg, 5.82 mmol) and 4 Å molecular sieves (3.00 g). The flask was purged with nitrogen, and anhydrous toluene (15 mL) and N,N-diisopropylethylamine (1.64 g, 2.22 mmol) were added. The reaction mixture was heated at 90° C. for 7 h, and the resulting suspension filtered hot. Concentration of the filtrate under reduced pressure afforded a light brown solid, which was purified by column chromatography (silica gel, EtOAc/hexanes). This afforded an 86% yield of compound 168 as a white solid. m.p. 194-196° C. (dec.); $^1$H NMR (DMSO-$d_6$) δ (ppm) 10.96 (s, 1H), 9.46 (s, 1H), 7.84 (d, 1H, J=7.8 Hz), 7.51-7.36 (m, 4H), 7.19 (d, 1H, J=6.8 Hz), 6.99 (t, 1H, J=9.3 Hz), 4.10 (t, 1H, J=7.0 Hz), 1.31 (s, 9H), 1.16 (d, 3H, J=6.9 Hz); m/z=454 (M+H). The reaction described above and compound 168 are shown below.

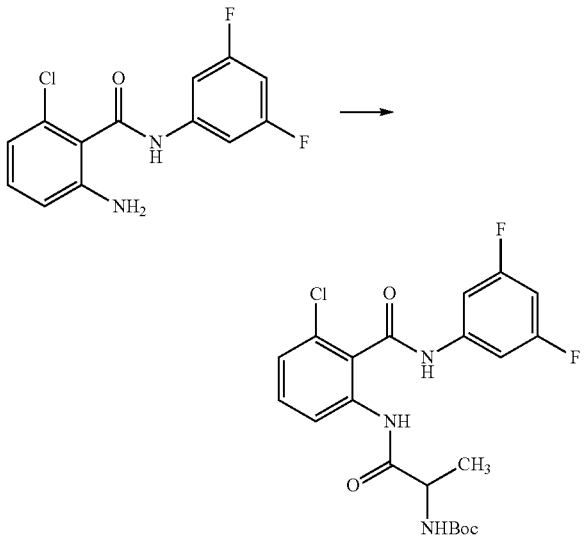

{1-[5-chloro-4-(3,5-difluoro-phenylimino)-4H-benzo[d][1,3]oxazin-2-yl]-ethyl}-carbamic acid tert-butyl ester (169)

Step C: A 100-mL, three-neck, round bottomed flask equipped with a magnetic stirrer and thermometer was purged with nitrogen and charged with compound 168 (3.30 mmol), anhydrous methylene chloride (25 mL), N,N-diisopropylethylamine (4.60 g, 35.7 mmol) and triphenylphosphine (3.98 g, 15.2 mmol). The reaction mixture was then cooled to 0-5° C. in an ice/water bath. Iodine (3.61 g, 14.2 mmol) was then added portion-wise to the reaction mixture over 1 h. Once the addition was complete, the cooling bath was removed, and the mixture was stirred at room temperature for an additional 30 min. The reaction was then quenched with 10% aqueous potassium carbonate (25 mL), the organic layer separated, dried over sodium sulfate, filtered and concentrated under reduced pressure. Column chromatography of the resulting solid (silica gel, EtOAc/hexanes) gave a 52% yield of compound 169 as a white solid. m.p. 117-118° C.; $^1$H NMR (DMSO-$d_6$) δ (ppm) 7.72-7.60 (m, 2H), 7.42 (dd, 1H, J=7.6 Hz, 1.3 Hz), 7.31 (d, 1H, J=7.0 Hz), 6.95 (t, 1H, J=9.3 Hz), 6.82 (m, 2H), 4.27 (m, 1H), 1.33 (s, 9H), 1.28 (d, 3H, J=7.2 Hz); m/z=436 (M+H). The reaction described above and compound 169 are shown below.

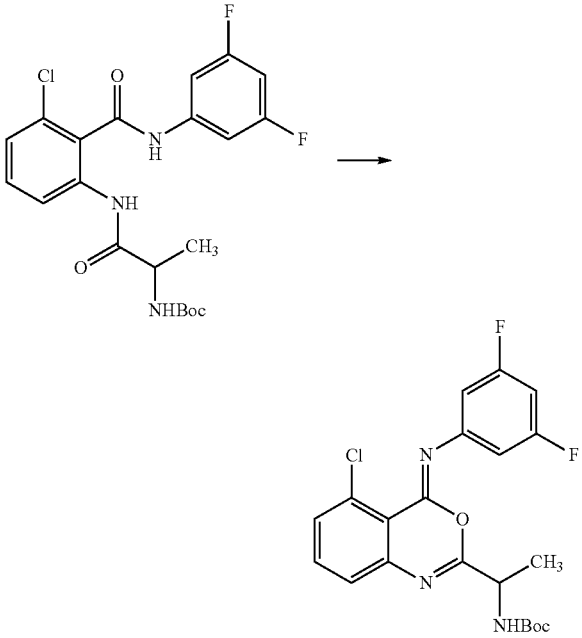

2-(1-amino-ethyl)-5-chloro-3-(3,5-difluoro-phenyl)-3H-quinazolin-4-one (170)

Step D: A solution of compound 169 (1.68 mmol) in piperidine (2 mL) was stirred for 3 h at ambient temperature. Evaporation of the reaction mixture to dryness under high vacuum gave a yellow foam. This foam was dissolved in a 4M solution of hydrogen chloride in 1,4-dioxane (4 mL) and stirred for 17 h at ambient temperature. The reaction mixture was then concentrated to dryness, basified with 10% aqueous potassium carbonate (40 mL) and extracted with MTBE (3×20 mL). Combining the organic extracts, drying over sodium sulfate and concentrating to dryness afforded a solid residue. This residue was dissolved in d-chloroform (5 mL), and warmed for 15 h at 50° C. After cooling to ambient temperature, the reaction mixture was washed with water (3×10 mL), dried over sodium sulfate and evaporated to dryness, affording a 98% yield of compound 170 as a white solid. m.p. 200-202° C.; $^1$H NMR ($CDCl_3$) δ (ppm) 7.65 (m, 2H), 7.49 (m, 1H), 7.01 (t, 1H, J=6.6 Hz), 6.89 (m, 2H), 3.68 (m, 1H), 1.33 (d, 3H, J=6.6 Hz), 1.25 (s, 2H); m/z=336 (M+H). The reaction described above and compound 170 are shown below.

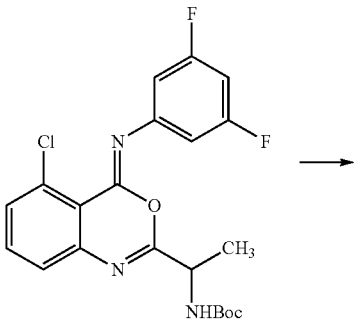

-continued

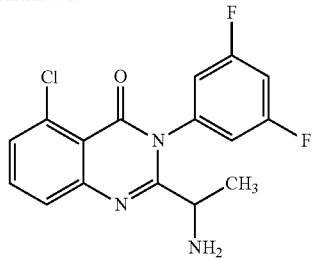

5-chloro-3-(3,5-difluoro-phenyl)-2-[1-(9H-purin-6-ylamino)-ethyl]-3H-quinazolin-4-one (166)

Step E: Compound 166 was prepared by reacting compound 170 in according to the procedure for the preparation of compound 107 (final procedure). ESI-MS m/z 454.3 ($MH^+$). The reaction described above and compound 166 are shown below.

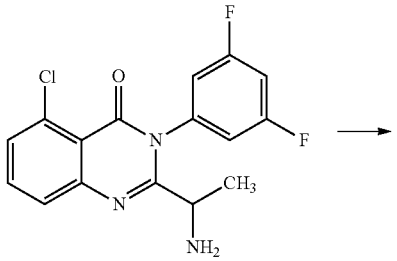

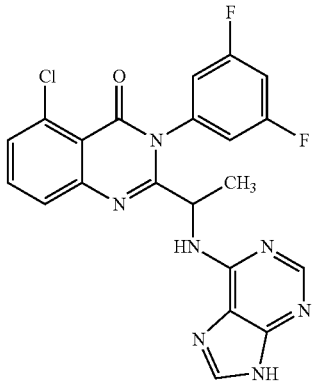

2-[1-(2-amino-9H-purin-6-ylamino)-propyl]-5-chloro-3-(3,5-difluoro-phenyl)-3H-quinazolin-4-one (171)

Compound 171 was prepared following the general procedure for compound 161 (steps A-E), but 2-tert-butoxycarbonylamino-butyric acid 2,5-dioxo-pyrrolidin-1-yl ester was substituted for N-tert-butyloxycarbonyl-D,L-alanine N-hydroxysuccinimide ester in step B, and 2-amino-6-bromopurine was substituted for 6-bromopurine in step E. ESI-MS m/z 454.3 ($MH^+$). The structure of compound 171 is shown below.

(171)

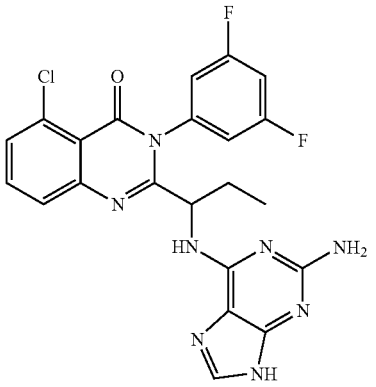

2-[1-(2-amino-9H-purin-6-ylamino)-ethyl]-5-chloro-3-(3,5-difluoro-phenyl)-3H-quinazolin-4-one (172)

Compound 172 was prepared following the general procedure for compound 161 (steps A-E), but 2-amino-6-bromopurine was substituted for 6-bromopurine in step E. The structure of compound 172 is shown below.

(172)

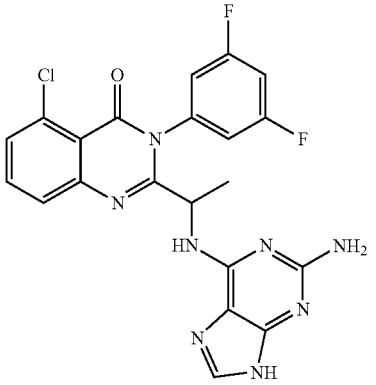

3-(3,5-difluoro-phenyl)-6-fluoro-2-[1-(9H-purin-6-ylamino)-ethyl]-3H-quinazolin-4-one (173)

Compound 173 was prepared following the general procedure for compound 161 (steps A-E), but 2-amino-5-fluorobenzoic acid was substituted for 2-amino-6-chlorobenzoic acid in step A. ESI-MS m/z 438.2 ($MH^+$). The structure of compound 173 is shown below.

(173)

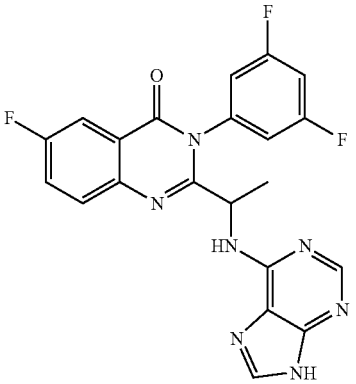

5-chloro-3-(2,6-difluoro-phenyl)-2-[1-(9H-purin-6-ylamino)-propyl]-3H-quinazolin-4-one (174)

Compound 174 was prepared following the general procedure for compound 161 (steps A-E), but 2,6-difluoroaniline was substituted for aniline in step A, and 2-tert-butoxycarbonylamino-butyric acid 2,5-dioxo-pyrrolidin-1-yl ester was substituted for N-tert-butyloxycarbonyl-D,L-alanine N-hydroxysuccinimide ester in step B. ESI-MS m/z 468.2 ($MH^+$). The structure of compound 174 is shown below.

(174)

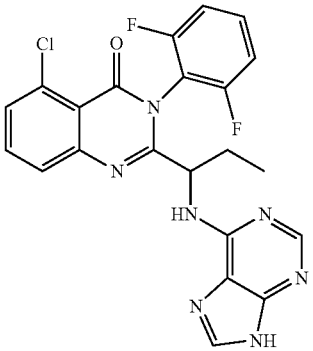

2-[1-(2-amino-9H-purin-6-ylamino)-propyl]-5-chloro-3-(2,6-difluoro-phenyl)-3H-quinazolin-4-one (175)

Compound 175 was prepared following the general procedure for compound 161 (steps A-E), but 2,6-difluoroaniline was substituted for aniline in step A, 2-tert-butoxycarbonylamino-butyric acid 2,5-dioxo-pyrrolidin-1-yl ester was substituted for N-tert-butyloxycarbonyl-D,L-alanine N-hydroxysuccinimide ester in step B, and 2-amino-6-bromopurine was substituted for 6-bromopurine in step E. ESI-MS m/z 483.2 ($MH^+$). The structure of compound 175 is shown below.

(175)

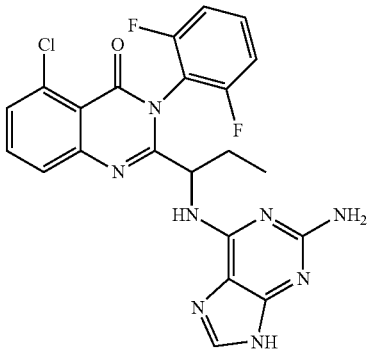

Example 13

Compound Preparation

Compounds having general formula I (shown above) have been prepared in accordance with steps A-G of the synthetic scheme entitled "Procedure L" shown below.

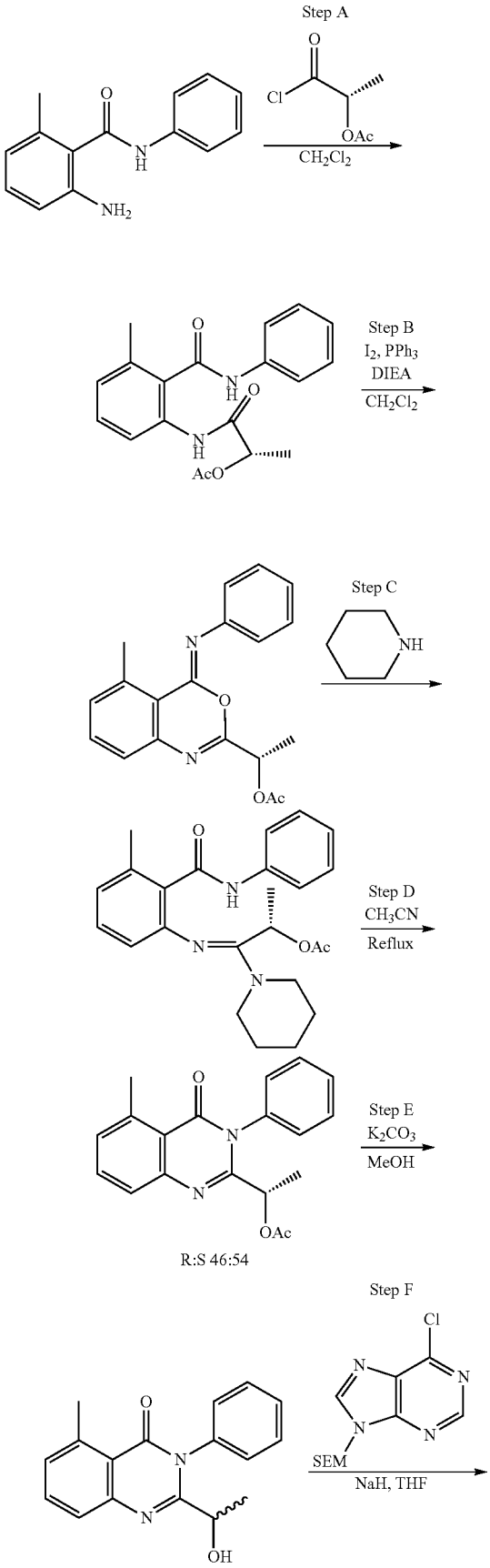

-continued

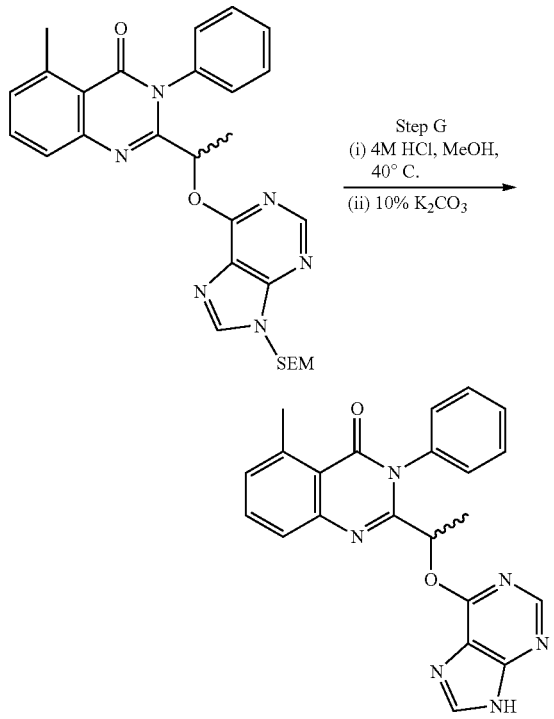

5-methyl-3-phenyl-2-[1-(9H-purin-6-yloxy)-ethyl]-3H-quinazolin-4-one (176)

Compound 176 was prepared according to the procedures set forth in steps A-G below.

acetic acid 1-(3-methyl-2-phenylcarbamoyl-phenyl-carbamoyl)-ethyl ester (177)

Step A: (S)-2-Acetoxypropionyl chloride (5.469 g, 36.32 mmol) was added to a solution of compound 15 (6.788 g, 30 mmol) in dichloromethane (150 mL). A precipitate immediately formed. The reaction was stirred for 25 h and the precipitate was filtered off. The filtrate was washed with saturated sodium bicarbonate solution (3×50 mL) and dried ($MgSO_4$). Filtration and concentration of the filtrate gave a brown solid (7.6 g). Purification by flash chromatography (1:2 EtOAc:hexanes->EtOAc->10:1 EtOAc:MeOH) followed by recrystallization of the impure fractions from EtOAc:hexanes gave compound 177 as a solid. ESI-MS m/z=341 ($MH^+$). The reaction described above and compound 177 are shown below.

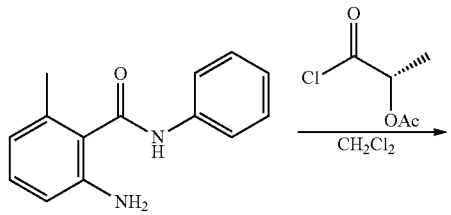

-continued

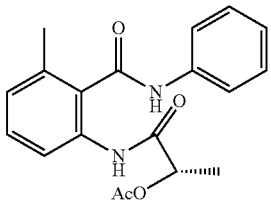

acetic acid 1-(5-methyl-4-phenylimino-4H-benzo[d][1,3]oxazin-2-yl)-ethyl ester (178)

Step B: Compound 177 (0.34 g, 1.0 mmol) was dissolved in dichloromethane (25 mL). Triphenylphosphine (1.311 g, 5 mmol) was added to the solution, followed by iodine (1.269 g, 5 mmol) and DIEA (1.9 mL, 11 mmol). The reaction was capped and stirred for 4 days. The reaction was quenched by addition of saturated aqueous sodium bicarbonate solution (25 mL). The organic layer was separated, dried ($MgSO_4$), filtered, and the filtrate concentrated under reduced pressure to give a dark brown gum (2.886 g). Purification by flash chromatography ($CH_2Cl_2$) gave the imino-1,3-oxazine compound 178 as a yellow oil. ESI-MS m/z=323 ($MH^+$). The reaction described above and compound 178 are shown below.

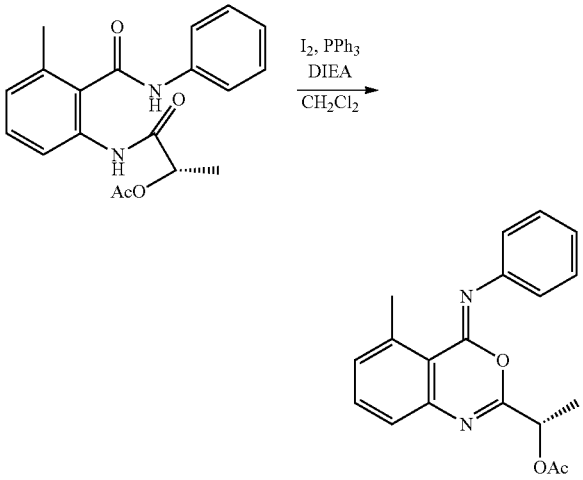

acetic acid 1-methyl-2-(3-methyl-2-phenylcarbamoyl-phenylimino)-2-piperidin-1-yl-ethyl ester (179)

Step C: Piperidine (1 mL) was added to compound 178 (0.161 g, 0.5 mmol) and the reaction mixture was stirred for 19.5 h. The reaction mixture was then concentrated under reduced pressure to give a yellow gum. Trituration with 1:4 EtOAc:hexanes gave a small amount of compound 179 (0.041 g). Flash chromatography (1:4 EtOAc:hexanes) of the filtrate gave only a partially separable mixture of the expected products, the acetoxyquinazolinone compound 179 and the hydroxyquinazolinone (total mass 0.122 g). ESI-MS m/z=408 ($MH^+$). The reaction described above and compound 179 are shown below.

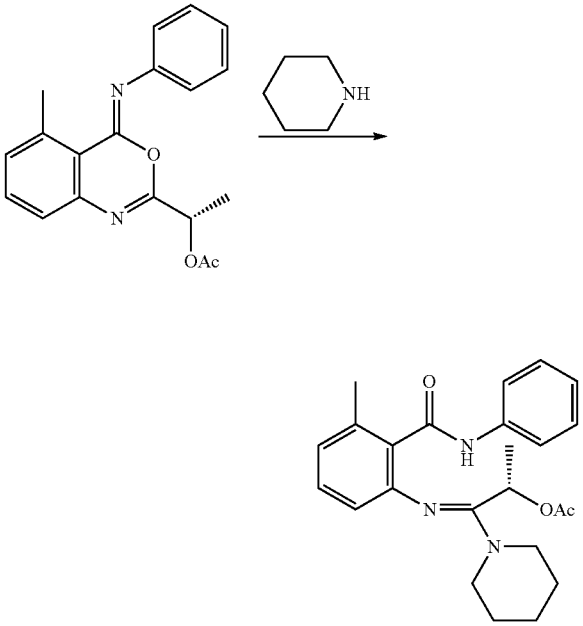

acetic acid 1-(5-methyl-4-oxo-3-phenyl-3,4-dihydro-quinazolin-2-yl)-ethyl ester (180)

Step D: Compound 179 (0.037 g, 0.09 mmol) was dissolved in acetonitrile (10 mL) and the reaction mixture was heated at reflux for 3 h. The solvent was removed under reduced pressure and the residue dissolved in a mixture of ethyl acetate (10 mL) and 1M HCl (5 mL). After separating the aqueous layer, the organic layer was washed with additional 1M HCl (2×5 mL), saturated sodium bicarbonate solution (3×5 mL), water (2×5 mL) and saturated brine (5 mL). The solution was dried ($MgSO_4$), filtered, and the filtrate concentrated under reduced pressure to give compound 180. ESI-MS m/z=323 ($MH^+$). The product had nearly totally racemized at this point (chiral purity was 46:54 S:R). The reaction described above and compound 180 are shown below.

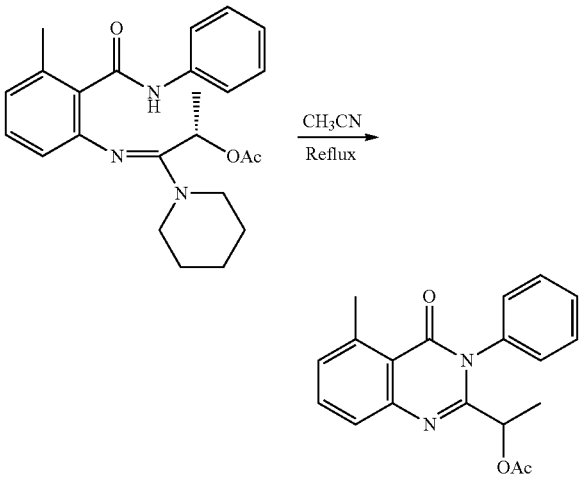

R:S 46:54

2-(1-hydroxy-ethyl)-5-methyl-3-phenyl-3H-quinazolin-4-one (181)

Step E: Compound 180 (0.011 g, 0.034 mmol) was dissolved in methanol (2 mL), and potassium carbonate (0.012 g, 0.085 mmol) was added. The reaction mixture was stirred for 20 min, and then water (20 mL) was added. The mixture was extracted with ethyl acetate (3×10 mL) and the combined organic extracts were washed with saturated brine (10 mL). The organic solution was dried ($MgSO_4$), filtered and concentrated under reduced pressure to give compound 181. ESI-MS m/z=281 ($MH^+$). The reaction described above and compound 181 are shown below.

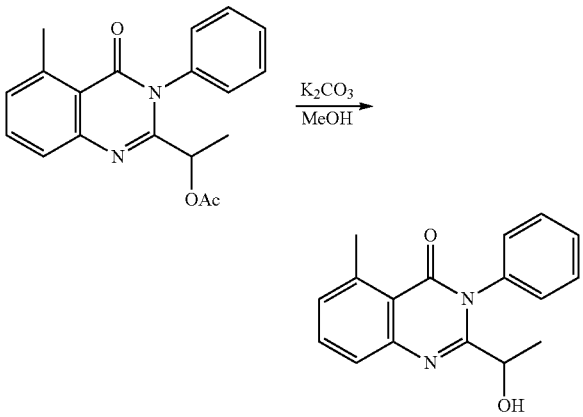

5-methyl-3-phenyl-2-{1-[9-(2-trimethylsilanyl-ethoxymethyl)-9H-purin-6-yloxy]-ethyl}-3H-quinazolin-4-one (182)

Step F: A solution of compound 181 (0.069 g, 0.25 mmol) in THF (5 mL) was treated with sodium hydride (0.007 g, 0.27 mmol) and stirred for 10 min. A solution of intermediate compound 13 (0.077 g, 0.27 mmol) in THF (1 mL) was added to the reaction mixture. The flask originally containing the intermediate compound 13 was washed with additional THF (1 mL) and the washings were also added to the reaction mixture. The reaction was allowed to proceed, and additional sodium hydride (0.005 g, 0.21 mmol) was added at 21.5 h and 23 h. The reaction was quenched after a total of 24 h by addition of saturated ammonium chloride solution (5 mL). The mixture was extracted with dichloromethane (3×5 mL), and the combined organic extracts were dried over $MgSO_4$. After filtration, the filtrate was concentrated under reduced pressure and the residue was purified by flash chromatography (1:1 EtOAc:hexanes->3:2 EtOAc:hexanes) to give compound 182. ESI-MS m/z=529 ($MH^+$). The reaction described above and compound 182 are shown below.

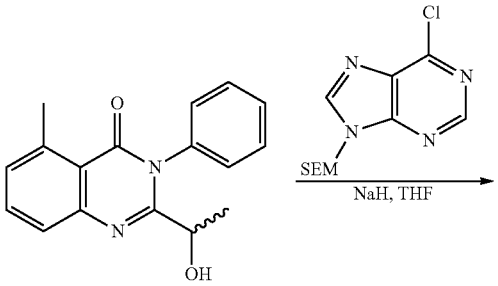

-continued

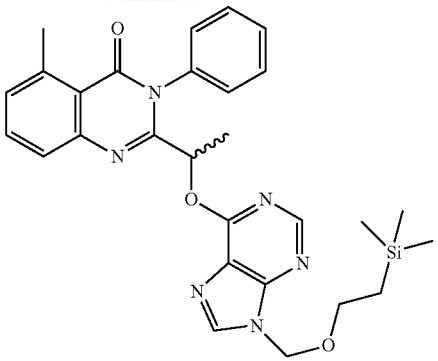

5-Methyl-3-phenyl-2-[1-(9H-purin-6-yloxy)-ethyl]-3H-quinazolin-4-one (176)

Compound 182 (0.053 g, 0.1 mmol) was dissolved in a mixture of methanol (2 mL) and 4M HCl (2 mL). The mixture was stirred and heated to 40° C. for 3 h. The reaction mixture was removed from the heat source and allowed to cool. The reaction mixture was then filtered through a plug of GFA (glass fiber) filter paper and the filtrate concentrated to only remove the methanol. The residue was adjusted to pH 10 by addition of 10% potassium carbonate solution. The resulting solid was collected by filtration and purified by RP-HPLC (C18 Luna column, 10×250 mm, 4.7 mL/min, 10-90% $CH_3CN$ in water in 18 min, with all solvents containing 0.05% formic acid) to give compound 176 as a fluffy white solid after lyophilization. $^1H$ NMR (400 MHz, d6-DMSO) δ 13.40, br s, 1H, 8.40, s, 1H, 8.35, s, 1H, 7.66, t, J=7.8 Hz, 1H, 7.48-7.58, m, 4H, 7.31-7.36, m, 2H, 7.20-7.23, m, 1H, 5.65, q, J=6.6 Hz, 1H, 2.73, s, 3H, 1.65, d, J=6.6 Hz, 3H. ESI-MS m/z=399 ($MH^+$). The reaction described above and compound 176 are shown below.

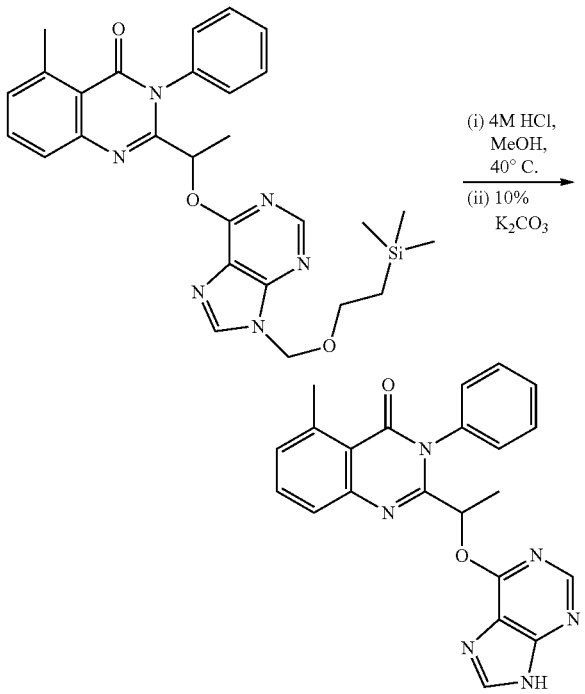

Example 14

Biochemical Assays of PI3K Potency and Selectivity

Biochemical Assay Using 20 μM ATP

Using the method described in Example 2, compounds of the invention were tested for inhibitory activity and potency against PI3Kδ, and for selectivity for PI3Kδ versus other Class I PI3K isozymes. In Table 1, $IC_{50}$ values (μM) are given for PI3Kδ ("Delta"), and may be calculated for the other isoforms using the ratios of $IC_{50}$ values discussed below. To illustrate selectivity of the compounds, the ratios of the $IC_{50}$ values of the compounds for PI3Kα, PI3Kβ, and PI3Kγ relative to PI3Kδ are given, respectively, as "Alpha/Delta Ratio," "Beta/Delta Ratio," and "Gamma/Delta Ratio."

The initial selectivity assays were performed identically to the selectivity assay protocol in Example 2, except using 100 μL Ecoscint for radiolabel detection. Subsequent selectivity assays were done similarly using the same 3× substrate stocks except they contained 0.05 mCi/mL γ[$^{32}$P]ATP and 3 mM PIP2. Subsequent selectivity assays also used the same 3× enzyme stocks, except they now contained 3 nM of any given PI3K isoform.

For all selectivity assays, the test compounds were weighed out and dissolved into 10-50 mM stocks in 100% DMSO (depending on their respective solubilities) and stored at −20° C. Compounds were thawed (to room temperature or 37° C.), diluted to 300 μM in water from which a 3-fold dilution series into water was done. From these dilutions, 20 μL was added into the assay wells alongside water blanks used for the enzyme (positive) control and the no enzyme (background) control. The remainder of the assay was performed essentially according to the selectivity assay protocol in Example 2.

TABLE 1

| | Delta $IC_{50}$ (nM) | Alpha-Delta Ratio | Beta-Delta Ratio | Gamma-Delta Ratio | Human PMN Elastase $EC_{50}$ (nM) | Human B Lymphocyte $EC_{50}$ (nM) |
|---|---|---|---|---|---|---|
| Compound 117 | 12 | 662 | 78 | 67 | 382 | 1.6 |
| Compound 98 | 16 | 608 | 74 | 66 | 84 | 4.6 |
| Compound 107 | 9 | 248 | 49 | 21 | 119 | 6.1 |
| Compound 174 | 45 | 250 | 72 | 38 | 298 | 30.7 |
| Compound 93 | 26 | 721 | 94 | 62 | 584 | |

Example 15

Cell-Based Assay Data for Inhibitors of PI3Kδ Activity

Using the methods described in Example 2, compounds of the invention were tested for inhibitory activity and potency in an assay of neutrophil (PMN) elastase release. Data from these assays are set forth in Table 1. In Table 1, the values shown are effective concentrations of the compound ($EC_{50}$; μM).

All publications and patent documents cited in this specification are incorporated herein by reference for all that they disclose.

While the present invention has been described with specific reference to certain preferred embodiments, further modifications can be practiced within the scope of the invention as it is defined in the claims below. Accordingly, no limitations should be placed on the invention other than those specifically recited in the claims.

SEQUENCE LISTING

```
<160> NUMBER OF SEQ ID NOS: 6

<210> SEQ ID NO 1
<211> LENGTH: 5220
<212> TYPE: DNA
<213> ORGANISM: Artificial Sequence
<220> FEATURE:
<223> OTHER INFORMATION: Human p110delta complete cDNA
<220> FEATURE:
<221> NAME/KEY: CDS
<222> LOCATION: (196)..(3327)

<400> SEQUENCE: 1

cagtcgctcc gagcggccgc gagcagagcc gcccagccct gtcagctgcg ccgggacgat      60

aaggagtcag gccagggcgg gatgacactc attgattcta aagcatcttt aatctgccag     120

gcggaggggg ctttgctggt ctttcttgga ctattccaga gaggacaact gtcatctggg     180

aagtaacaac gcagg atg ccc cct ggg gtg gac tgc ccc atg gaa ttc tgg      231
                 Met Pro Pro Gly Val Asp Cys Pro Met Glu Phe Trp
                 1               5                   10

acc aag gag gag aat cag agc gtt gtg gtt gac ttc ctg ctg ccc aca       279
Thr Lys Glu Glu Asn Gln Ser Val Val Val Asp Phe Leu Leu Pro Thr
        15                  20                  25

ggg gtc tac ctg aac ttc cct gtg tcc cgc aat gcc aac ctc agc acc       327
Gly Val Tyr Leu Asn Phe Pro Val Ser Arg Asn Ala Asn Leu Ser Thr
    30                  35                  40
```

```
atc aag cag ctg ctg tgg cac cgc gcc cag tat gag ccg ctc ttc cac      375
Ile Lys Gln Leu Leu Trp His Arg Ala Gln Tyr Glu Pro Leu Phe His
45                  50                  55                  60

atg ctc agt ggc ccc gag gcc tat gtg ttc acc tgc atc aac cag aca      423
Met Leu Ser Gly Pro Glu Ala Tyr Val Phe Thr Cys Ile Asn Gln Thr
                65                  70                  75

gcg gag cag caa gag ctg gag gac gag caa cgg cgt ctg tgt gac gtg      471
Ala Glu Gln Gln Glu Leu Glu Asp Glu Gln Arg Arg Leu Cys Asp Val
            80                  85                  90

cag ccc ttc ctg ccc gtc ctg cgc ctg gtg gcc cgt gag ggc gac cgc      519
Gln Pro Phe Leu Pro Val Leu Arg Leu Val Ala Arg Glu Gly Asp Arg
        95                  100                 105

gtg aag aag ctc atc aac tca cag atc agc ctc ctc atc ggc aaa ggc      567
Val Lys Lys Leu Ile Asn Ser Gln Ile Ser Leu Leu Ile Gly Lys Gly
    110                 115                 120

ctc cac gag ttt gac tcc ttg tgc gac cca gaa gtg aac gac ttt cgc      615
Leu His Glu Phe Asp Ser Leu Cys Asp Pro Glu Val Asn Asp Phe Arg
125                 130                 135                 140

gcc aag atg tgc caa ttc tgc gag gag gcg gcc gcc cgc cgg cag cag      663
Ala Lys Met Cys Gln Phe Cys Glu Glu Ala Ala Ala Arg Arg Gln Gln
                145                 150                 155

ctg ggc tgg gag gcc tgg ctg cag tac agt ttc ccc ctg cag ctg gag      711
Leu Gly Trp Glu Ala Trp Leu Gln Tyr Ser Phe Pro Leu Gln Leu Glu
            160                 165                 170

ccc tcg gct caa acc tgg ggg cct ggt acc ctg cgg ctc ccg aac cgg      759
Pro Ser Ala Gln Thr Trp Gly Pro Gly Thr Leu Arg Leu Pro Asn Arg
        175                 180                 185

gcc ctt ctg gtc aac gtt aag ttt gag ggc agc gag gag agc ttc acc      807
Ala Leu Leu Val Asn Val Lys Phe Glu Gly Ser Glu Glu Ser Phe Thr
    190                 195                 200

ttc cag gtg tcc acc aag gac gtg ccg ctg gcg ctg atg gcc tgt gcc      855
Phe Gln Val Ser Thr Lys Asp Val Pro Leu Ala Leu Met Ala Cys Ala
205                 210                 215                 220

ctg cgg aag aag gcc aca gtg ttc cgg cag ccg ctg gtg gag cag ccg      903
Leu Arg Lys Lys Ala Thr Val Phe Arg Gln Pro Leu Val Glu Gln Pro
                225                 230                 235

gaa gac tac acg ctg cag gtg aac ggc agg cat gag tac ctg tat ggc      951
Glu Asp Tyr Thr Leu Gln Val Asn Gly Arg His Glu Tyr Leu Tyr Gly
            240                 245                 250

aac tac ccg ctc tgc cag ttc cag tac atc tgc agc tgc ctg cac agt      999
Asn Tyr Pro Leu Cys Gln Phe Gln Tyr Ile Cys Ser Cys Leu His Ser
        255                 260                 265

ggg ttg acc cct cac ctg acc atg gtc cat tcc tcc tcc atc ctc gcc     1047
Gly Leu Thr Pro His Leu Thr Met Val His Ser Ser Ser Ile Leu Ala
    270                 275                 280

atg cgg gat gag cag agc aac cct gcc ccc cag gtc cag aaa ccg cgt     1095
Met Arg Asp Glu Gln Ser Asn Pro Ala Pro Gln Val Gln Lys Pro Arg
285                 290                 295                 300

gcc aaa cca cct ccc att cct gcg aag aag cct tcc tct gtg tcc ctg     1143
Ala Lys Pro Pro Pro Ile Pro Ala Lys Lys Pro Ser Ser Val Ser Leu
                305                 310                 315

tgg tcc ctg gag cag ccg ttc cgc atc gag ctc atc cag ggc agc aaa     1191
Trp Ser Leu Glu Gln Pro Phe Arg Ile Glu Leu Ile Gln Gly Ser Lys
            320                 325                 330

gtg aac gcc gac gag cgg atg aag ctg gtg gtg cag gcc ggg ctt ttc     1239
Val Asn Ala Asp Glu Arg Met Lys Leu Val Val Gln Ala Gly Leu Phe
        335                 340                 345

cac ggc aac gag atg ctg tgc aag acg gtg tcc agc tcg gag gtg agc     1287
His Gly Asn Glu Met Leu Cys Lys Thr Val Ser Ser Ser Glu Val Ser
    350                 355                 360
```

```
gtg tgc tcg gag ccc gtg tgg aag cag cgg ctg gag ttc gac atc aac     1335
Val Cys Ser Glu Pro Val Trp Lys Gln Arg Leu Glu Phe Asp Ile Asn
365                 370                 375                 380

atc tgc gac ctg ccc cgc atg gcc cgt ctc tgc ttt gcg ctg tac gcc     1383
Ile Cys Asp Leu Pro Arg Met Ala Arg Leu Cys Phe Ala Leu Tyr Ala
                385                 390                 395

gtg atc gag aaa gcc aag aag gct cgc tcc acc aag aag aag tcc aag     1431
Val Ile Glu Lys Ala Lys Lys Ala Arg Ser Thr Lys Lys Lys Ser Lys
            400                 405                 410

aag gcg gac tgc ccc att gcc tgg gcc aac ctc atg ctg ttt gac tac     1479
Lys Ala Asp Cys Pro Ile Ala Trp Ala Asn Leu Met Leu Phe Asp Tyr
        415                 420                 425

aag gac cag ctt aag acc ggg gaa cgc tgc ctc tac atg tgg ccc tcc     1527
Lys Asp Gln Leu Lys Thr Gly Glu Arg Cys Leu Tyr Met Trp Pro Ser
    430                 435                 440

gtc cca gat gag aag ggc gag ctg ctg aac ccc acg ggc act gtg cgc     1575
Val Pro Asp Glu Lys Gly Glu Leu Leu Asn Pro Thr Gly Thr Val Arg
445                 450                 455                 460

agt aac ccc aac acg gat agc gcc gct gcc ctg ctc atc tgc ctg ccc     1623
Ser Asn Pro Asn Thr Asp Ser Ala Ala Ala Leu Leu Ile Cys Leu Pro
                465                 470                 475

gag gtg gcc ccg cac ccc gtg tac tac ccc gcc ctg gag aag atc ttg     1671
Glu Val Ala Pro His Pro Val Tyr Tyr Pro Ala Leu Glu Lys Ile Leu
            480                 485                 490

gag ctg ggg cga cac agc gag tgt gtg cat gtc acc gag gag gag cag     1719
Glu Leu Gly Arg His Ser Glu Cys Val His Val Thr Glu Glu Glu Gln
        495                 500                 505

ctg cag ctg cgg gaa atc ctg gag cgg cgg ggg tct ggg gag ctg tat     1767
Leu Gln Leu Arg Glu Ile Leu Glu Arg Arg Gly Ser Gly Glu Leu Tyr
    510                 515                 520

gag cac gag aag gac ctg gtg tgg aag ctg cgg cat gaa gtc cag gag     1815
Glu His Glu Lys Asp Leu Val Trp Lys Leu Arg His Glu Val Gln Glu
525                 530                 535                 540

cac ttc ccg gag gcg cta gcc cgg ctg ctg ctg gtc acc aag tgg aac     1863
His Phe Pro Glu Ala Leu Ala Arg Leu Leu Leu Val Thr Lys Trp Asn
                545                 550                 555

aag cat gag gat gtg gcc cag atg ctc tac ctg ctg tgc tcc tgg ccg     1911
Lys His Glu Asp Val Ala Gln Met Leu Tyr Leu Leu Cys Ser Trp Pro
            560                 565                 570

gag ctg ccc gtc ctg agc gcc ctg gag ctg cta gac ttc agc ttc ccc     1959
Glu Leu Pro Val Leu Ser Ala Leu Glu Leu Leu Asp Phe Ser Phe Pro
        575                 580                 585

gat tgc cac gta ggc tcc ttc gcc atc aag tcg ctg cgg aaa ctg acg     2007
Asp Cys His Val Gly Ser Phe Ala Ile Lys Ser Leu Arg Lys Leu Thr
    590                 595                 600

gac gat gag ctg ttc cag tac ctg ctg cag ctg gtg cag gtg ctc aag     2055
Asp Asp Glu Leu Phe Gln Tyr Leu Leu Gln Leu Val Gln Val Leu Lys
605                 610                 615                 620

tac gag tcc tac ctg gac tgc gag ctg acc aaa ttc ctg ctg gac cgg     2103
Tyr Glu Ser Tyr Leu Asp Cys Glu Leu Thr Lys Phe Leu Leu Asp Arg
                625                 630                 635

gcc ctg gcc aac cgc aag atc ggc cac ttc ctt ttc tgg cac ctc cgc     2151
Ala Leu Ala Asn Arg Lys Ile Gly His Phe Leu Phe Trp His Leu Arg
            640                 645                 650

tcc gag atg cac gtg ccg tcg gtg gcc ctg cgc ttc ggc ctc atc ctg     2199
Ser Glu Met His Val Pro Ser Val Ala Leu Arg Phe Gly Leu Ile Leu
        655                 660                 665

gag gcc tac tgc agg ggc agc acc cac cac atg aag gtg ctg atg aag     2247
Glu Ala Tyr Cys Arg Gly Ser Thr His His Met Lys Val Leu Met Lys
    670                 675                 680
```

```
cag ggg gaa gca ctg agc aaa ctg aag gcc ctg aat gac ttc gtc aag     2295
Gln Gly Glu Ala Leu Ser Lys Leu Lys Ala Leu Asn Asp Phe Val Lys
685                 690                 695                 700

ctg agc tct cag aag acc ccc aag ccc cag acc aag gag ctg atg cac     2343
Leu Ser Ser Gln Lys Thr Pro Lys Pro Gln Thr Lys Glu Leu Met His
                705                 710                 715

ttg tgc atg cgg cag gag gcc tac cta gag gcc ctc tcc cac ctg cag     2391
Leu Cys Met Arg Gln Glu Ala Tyr Leu Glu Ala Leu Ser His Leu Gln
            720                 725                 730

tcc cca ctc gac ccc agc acc ctg ctg gct gaa gtc tgc gtg gag cag     2439
Ser Pro Leu Asp Pro Ser Thr Leu Leu Ala Glu Val Cys Val Glu Gln
        735                 740                 745

tgc acc ttc atg gac tcc aag atg aag ccc ctg tgg atc atg tac agc     2487
Cys Thr Phe Met Asp Ser Lys Met Lys Pro Leu Trp Ile Met Tyr Ser
    750                 755                 760

aac gag gag gca ggc agc ggc ggc agc gtg ggc atc atc ttt aag aac     2535
Asn Glu Glu Ala Gly Ser Gly Gly Ser Val Gly Ile Ile Phe Lys Asn
765                 770                 775                 780

ggg gat gac ctc cgg cag gac atg ctg acc ctg cag atg atc cag ctc     2583
Gly Asp Asp Leu Arg Gln Asp Met Leu Thr Leu Gln Met Ile Gln Leu
                785                 790                 795

atg gac gtc ctg tgg aag cag gag ggg ctg gac ctg agg atg acc ccc     2631
Met Asp Val Leu Trp Lys Gln Glu Gly Leu Asp Leu Arg Met Thr Pro
            800                 805                 810

tat ggc tgc ctc ccc acc ggg gac cgc aca ggc ctc att gag gtg gta     2679
Tyr Gly Cys Leu Pro Thr Gly Asp Arg Thr Gly Leu Ile Glu Val Val
        815                 820                 825

ctc cgt tca gac acc atc gcc aac atc caa ctc aac aag agc aac atg     2727
Leu Arg Ser Asp Thr Ile Ala Asn Ile Gln Leu Asn Lys Ser Asn Met
    830                 835                 840

gca gcc aca gcc gcc ttc aac aag gat gcc ctg ctc aac tgg ctg aag     2775
Ala Ala Thr Ala Ala Phe Asn Lys Asp Ala Leu Leu Asn Trp Leu Lys
845                 850                 855                 860

tcc aag aac ccg ggg gag gcc ctg gat cga gcc att gag gag ttc acc     2823
Ser Lys Asn Pro Gly Glu Ala Leu Asp Arg Ala Ile Glu Glu Phe Thr
                865                 870                 875

ctc tcc tgt gct ggc tat tgt gtg gcc aca tat gtg ctg ggc att ggc     2871
Leu Ser Cys Ala Gly Tyr Cys Val Ala Thr Tyr Val Leu Gly Ile Gly
            880                 885                 890

gat cgg cac agc gac aac atc atg atc cga gag agt ggg cag ctg ttc     2919
Asp Arg His Ser Asp Asn Ile Met Ile Arg Glu Ser Gly Gln Leu Phe
        895                 900                 905

cac att gat ttt ggc cac ttt ctg ggg aat ttc aag acc aag ttt gga     2967
His Ile Asp Phe Gly His Phe Leu Gly Asn Phe Lys Thr Lys Phe Gly
    910                 915                 920

atc aac cgc gag cgt gtc cca ttc atc ctc acc tat gac ttt gtc cat     3015
Ile Asn Arg Glu Arg Val Pro Phe Ile Leu Thr Tyr Asp Phe Val His
925                 930                 935                 940

gtg att cag cag ggg aag act aat aat agt gag aaa ttt gaa cgg ttc     3063
Val Ile Gln Gln Gly Lys Thr Asn Asn Ser Glu Lys Phe Glu Arg Phe
                945                 950                 955

cgg ggc tac tgt gaa agg gcc tac acc atc ctg cgg cgc cac ggg ctt     3111
Arg Gly Tyr Cys Glu Arg Ala Tyr Thr Ile Leu Arg Arg His Gly Leu
            960                 965                 970

ctc ttc ctc cac ctc ttt gcc ctg atg cgg gcg gca ggc ctg cct gag     3159
Leu Phe Leu His Leu Phe Ala Leu Met Arg Ala Ala Gly Leu Pro Glu
        975                 980                 985

ctc agc tgc tcc aaa gac atc cag tat ctc aag gac  tcc ctg gca ctg    3207
Leu Ser Cys Ser Lys Asp Ile Gln Tyr Leu Lys Asp  Ser Leu Ala Leu
    990                 995                 1000
```

```
ggg  aaa aca gag gag gag  gca ctg aag cac ttc  cga gtg aag ttt      3252
Gly  Lys Thr Glu Glu Glu  Ala Leu Lys His Phe  Arg Val Lys Phe
1005                1010                1015

aac  gaa gcc ctc cgt gag  agc tgg aaa acc aaa  gtg aac tgg ctg      3297
Asn  Glu Ala Leu Arg Glu  Ser Trp Lys Thr Lys  Val Asn Trp Leu
1020                1025                1030

gcc  cac aac gtg tcc aaa  gac aac agg cag tagtggctcc tcccagccct     3347
Ala  His Asn Val Ser Lys  Asp Asn Arg Gln
1035                1040

gggcccaaga ggaggcggct gcgggtcgtg gggaccaagc acattggtcc taaaggggct   3407

gaagagcctg aactgcacct aacgggaaag aaccgacatg gctgcctttt gtttacactg   3467

gttatttatt tatgacttga aatagtttaa ggagctaaac agccataaac ggaaacgcct   3527

ccttcattca gcggcggtgc tgggcccccc gaggctgcac ctggctctcg gctgaggatt   3587

gtcaccccaa gtcttccagc tggtggatct gggcccagca aagactgttc tcctcccgag   3647

ggaaccttct tcccaggcct cccgccagac tgcctgggtc ctggcgcctg gcggtcacct   3707

ggtgcctact gtccgacagg atgcctcgat cctcgtgcga cccaccctgt gtatcctccc   3767

tagactgagt tctggcagct ccccgaggca gccggggtac cctctagatt cagggatgct   3827

tgctctccac ttttcaagtg ggtcttgggt acgagaattc cctcatcttt ctctactgta   3887

aagtgatttt gtttgcaggt aagaaaataa tagatgactc accacacctc tacggctggg   3947

gagatcaggc ccagccccat aaaggagaat ctacgctggt cctcaggacg tgttaaagag   4007

atctgggcct catgtagctc accccggtca cgcatgaagg caaaagcagg tcagaagcga   4067

atactctgcc attatctcaa aaatcttttt tttttttttt ttgagatggg gtcttcctct   4127

gttgcccagg ctggagtgca gtggtgcaat cttggctcac tgtaacctcc gcctcccagg   4187

ttcaagtgat tcttcttgcc tcagcctcct gagtagctgg gattacaggt gtgcaccacc   4247

cgtacccagc taatttttgt attttagtag agacgggggt ttcaccatgt tggctgggct   4307

ggtctcgaac tcctgacctc aggtgatcca cccgcctgag cctcccaaag tgctgggatt   4367

acaggcatga gccaccacgc ccggcccact ctgccattgt ctaagccacc tctgaaagca   4427

ggttttaaca aaaggatgag gccagaactc ttccagaacc atcacctttg ggaacctgct   4487

gtgagagtgc tgaggtacca gaagtgtgag aacgaggggg cgtgctggga tctttctctc   4547

tgactatact tagtttgaaa tggtgcaggc ttagtcttaa gcctccaaag gcctggattt   4607

gagcagcttt agaaatgcag gttctagggc ttctcccagc cttcagaagc caactaactc   4667

tgcagatggg gctaggactg tgggctttta gcagcccaca ggtgatccta acatatcagg   4727

ccatggactc aggacctgcc cggtgatgct gttgatttct caaaggtctt ccaaaactca   4787

acagagccag aagtagccgc ccgctcagcg gctcaggtgc cagctctgtt ctgattcacc   4847

aggggtccgt cagtagtcat tgccacccgc ggggcacctc cctggccaca cgcctgttcc   4907

cagcaagtgc tgaaactcac tagaccgtct gcctgtttcg aaatggggaa agccgtgcgt   4967

gcgcgttatt tatttaagtg cgcctgtgtg cgcgggtgtg ggagcacact ttgcaaagcc   5027

acagcgtttc tggttttggg tgtacagtct tgtgtgcctg gcgagaagaa tattttctat   5087

ttttttaagt catttcatgt ttctgtctgg ggaaggcaag ttagttaagt atcactgatg   5147

tgggttgaga ccagcactct gtgaaacctt gaaatgagaa gtaaaggcag atgaaaagaa   5207

aaaaaaaaaa aaa                                                      5220
```

<210> SEQ ID NO 2
<211> LENGTH: 1044
<212> TYPE: PRT

<213> ORGANISM: Artificial Sequence
<220> FEATURE:
<223> OTHER INFORMATION: Human p110delta protein

<400> SEQUENCE: 2

Met Pro Pro Gly Val Asp Cys Pro Met Glu Phe Trp Thr Lys Glu Glu
1 5 10 15

Asn Gln Ser Val Val Val Asp Phe Leu Leu Pro Thr Gly Val Tyr Leu
20 25 30

Asn Phe Pro Val Ser Arg Asn Ala Asn Leu Ser Thr Ile Lys Gln Leu
35 40 45

Leu Trp His Arg Ala Gln Tyr Glu Pro Leu Phe His Met Leu Ser Gly
50 55 60

Pro Glu Ala Tyr Val Phe Thr Cys Ile Asn Gln Thr Ala Glu Gln Gln
65 70 75 80

Glu Leu Glu Asp Glu Gln Arg Arg Leu Cys Asp Val Gln Pro Phe Leu
85 90 95

Pro Val Leu Arg Leu Val Ala Arg Glu Gly Asp Arg Val Lys Lys Leu
100 105 110

Ile Asn Ser Gln Ile Ser Leu Leu Ile Gly Lys Gly Leu His Glu Phe
115 120 125

Asp Ser Leu Cys Asp Pro Glu Val Asn Asp Phe Arg Ala Lys Met Cys
130 135 140

Gln Phe Cys Glu Glu Ala Ala Ala Arg Arg Gln Gln Leu Gly Trp Glu
145 150 155 160

Ala Trp Leu Gln Tyr Ser Phe Pro Leu Gln Leu Glu Pro Ser Ala Gln
165 170 175

Thr Trp Gly Pro Gly Thr Leu Arg Leu Pro Asn Arg Ala Leu Leu Val
180 185 190

Asn Val Lys Phe Glu Gly Ser Glu Glu Ser Phe Thr Phe Gln Val Ser
195 200 205

Thr Lys Asp Val Pro Leu Ala Leu Met Ala Cys Ala Leu Arg Lys Lys
210 215 220

Ala Thr Val Phe Arg Gln Pro Leu Val Glu Gln Pro Glu Asp Tyr Thr
225 230 235 240

Leu Gln Val Asn Gly Arg His Glu Tyr Leu Tyr Gly Asn Tyr Pro Leu
245 250 255

Cys Gln Phe Gln Tyr Ile Cys Ser Cys Leu His Ser Gly Leu Thr Pro
260 265 270

His Leu Thr Met Val His Ser Ser Ser Ile Leu Ala Met Arg Asp Glu
275 280 285

Gln Ser Asn Pro Ala Pro Gln Val Gln Lys Pro Arg Ala Lys Pro Pro
290 295 300

Pro Ile Pro Ala Lys Lys Pro Ser Ser Val Ser Leu Trp Ser Leu Glu
305 310 315 320

Gln Pro Phe Arg Ile Glu Leu Ile Gln Gly Ser Lys Val Asn Ala Asp
325 330 335

Glu Arg Met Lys Leu Val Val Gln Ala Gly Leu Phe His Gly Asn Glu
340 345 350

Met Leu Cys Lys Thr Val Ser Ser Ser Glu Val Ser Val Cys Ser Glu
355 360 365

Pro Val Trp Lys Gln Arg Leu Glu Phe Asp Ile Asn Ile Cys Asp Leu
370 375 380

Pro Arg Met Ala Arg Leu Cys Phe Ala Leu Tyr Ala Val Ile Glu Lys
385 390 395 400

```
Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Thr Gly Thr Val Arg Ser Asn Pro Asn
    450                 455                 460

Thr Asp Ser Ala Ala Ala Leu Leu Ile Cys Leu Pro Glu Val Ala Pro
465                 470                 475                 480

His Pro Val Tyr Tyr Pro Ala Leu Glu Lys Ile Leu Glu Leu Gly Arg
                485                 490                 495

His Ser Glu Cys Val His Val Thr Glu Glu Glu Gln Leu Gln Leu Arg
            500                 505                 510

Glu Ile Leu Glu Arg Arg Gly Ser Gly Glu Leu Tyr Glu His Glu Lys
        515                 520                 525

Asp Leu Val Trp Lys Leu Arg His Glu Val Gln Glu His Phe Pro Glu
    530                 535                 540

Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys His Val
            580                 585                 590

Gly Ser Phe Ala Ile Lys Ser Leu Arg Lys Leu Thr Asp Asp Glu Leu
        595                 600                 605

Phe Gln Tyr Leu Leu Gln Leu Val Gln Val Leu Lys Tyr Glu Ser Tyr
    610                 615                 620

Leu Asp Cys Glu Leu Thr Lys Phe Leu Leu Asp Arg Ala Leu Ala Asn
625                 630                 635                 640

Arg Lys Ile Gly His Phe Leu Phe Trp His Leu Arg Ser Glu Met His
                645                 650                 655

Val Pro Ser Val Ala Leu Arg Phe Gly Leu Ile Leu Glu Ala Tyr Cys
            660                 665                 670

Arg Gly Ser Thr His His Met Lys Val Leu Met Lys Gln Gly Glu Ala
        675                 680                 685

Leu Ser Lys Leu Lys Ala Leu Asn Asp Phe Val Lys Leu Ser Ser Gln
    690                 695                 700

Lys Thr Pro Lys Pro Gln Thr Lys Glu Leu Met His Leu Cys Met Arg
705                 710                 715                 720

Gln Glu Ala Tyr Leu Glu Ala Leu Ser His Leu Gln Ser Pro Leu Asp
                725                 730                 735

Pro Ser Thr Leu Leu Ala Glu Val Cys Val Glu Gln Cys Thr Phe Met
            740                 745                 750

Asp Ser Lys Met Lys Pro Leu Trp Ile Met Tyr Ser Asn Glu Glu Ala
        755                 760                 765

Gly Ser Gly Gly Ser Val Gly Ile Ile Phe Lys Asn Gly Asp Asp Leu
    770                 775                 780

Arg Gln Asp Met Leu Thr Leu Gln Met Ile Gln Leu Met Asp Val Leu
785                 790                 795                 800

Trp Lys Gln Glu Gly Leu Asp Leu Arg Met Thr Pro Tyr Gly Cys Leu
                805                 810                 815

Pro Thr Gly Asp Arg Thr Gly Leu Ile Glu Val Val Leu Arg Ser Asp
```

```
            820                 825                 830

Thr Ile Ala Asn Ile Gln Leu Asn Lys Ser Asn Met Ala Ala Thr Ala
        835                 840                 845

Ala Phe Asn Lys Asp Ala Leu Leu Asn Trp Leu Lys Ser Lys Asn Pro
    850                 855                 860

Gly Glu Ala Leu Asp Arg Ala Ile Glu Glu Phe Thr Leu Ser Cys Ala
865                 870                 875                 880

Gly Tyr Cys Val Ala Thr Tyr Val Leu Gly Ile Gly Asp Arg His Ser
                885                 890                 895

Asp Asn Ile Met Ile Arg Glu Ser Gly Gln Leu Phe His Ile Asp Phe
            900                 905                 910

Gly His Phe Leu Gly Asn Phe Lys Thr Lys Phe Gly Ile Asn Arg Glu
        915                 920                 925

Arg Val Pro Phe Ile Leu Thr Tyr Asp Phe Val His Val Ile Gln Gln
    930                 935                 940

Gly Lys Thr Asn Asn Ser Glu Lys Phe Glu Arg Phe Arg Gly Tyr Cys
945                 950                 955                 960

Glu Arg Ala Tyr Thr Ile Leu Arg Arg His Gly Leu Leu Phe Leu His
                965                 970                 975

Leu Phe Ala Leu Met Arg Ala Ala Gly Leu Pro Glu Leu Ser Cys Ser
            980                 985                 990

Lys Asp Ile Gln Tyr Leu Lys Asp  Ser Leu Ala Leu Gly  Lys Thr Glu
        995                 1000                1005

Glu Glu  Ala Leu Lys His Phe  Arg Val Lys Phe Asn  Glu Ala Leu
    1010                1015                1020

Arg Glu  Ser Trp Lys Thr Lys  Val Asn Trp Leu Ala  His Asn Val
    1025                1030                1035

Ser Lys  Asp Asn Arg Gln
    1040


<210> SEQ ID NO 3
<211> LENGTH: 69
<212> TYPE: DNA
<213> ORGANISM: Artificial sequence
<220> FEATURE:
<223> OTHER INFORMATION: 5' Primer for p110beta

<400> SEQUENCE: 3

gatcgaattc ggcgccacca tggactacaa ggacgacgat gacaagtgct tcagtttcat     60

aatgcctcc                                                             69


<210> SEQ ID NO 4
<211> LENGTH: 42
<212> TYPE: DNA
<213> ORGANISM: Artificial sequence
<220> FEATURE:
<223> OTHER INFORMATION: 3' Primer for p110beta

<400> SEQUENCE: 4

gatcgcggcc gcttaagatc tgtagtcttt ccgaactgtg tg                        42


<210> SEQ ID NO 5
<211> LENGTH: 40
<212> TYPE: DNA
<213> ORGANISM: Artificial Sequence
<220> FEATURE:
<223> OTHER INFORMATION: 5' Primer for p110gamma

<400> SEQUENCE: 5
```

-continued

```
agaatgcggc cgcatggagc tggagaacta taaacagccc                    40


<210> SEQ ID NO 6
<211> LENGTH: 37
<212> TYPE: DNA
<213> ORGANISM: Artificial Sequence
<220> FEATURE:
<223> OTHER INFORMATION: 3' Primer for p110gamma

<400> SEQUENCE: 6

cgcggatcct taggctgaat gtttctctcc ttgtttg                       37
```

The invention claimed is:

1. A method of inhibiting a growth or a proliferation of cancer cells of hematopoietic origin comprising contacting the cancer cells with an effective amount of a compound, wherein said compound is

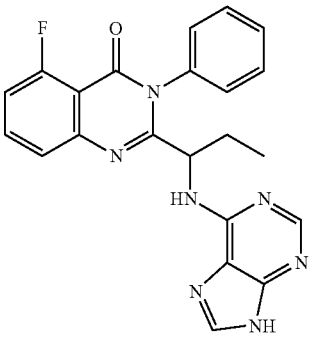

or a pharmaceutically acceptable salt thereof.

2. The method of claim 1, wherein the cancer [of hematopoietic origin is] *cells are* lymphoma, leukemia, or multiple myeloma *cells*.

3. The method of claim 2, wherein the compound or the pharmaceutically acceptable salt thereof is the S-enantiomer.

4. A method of treating a condition in a subject, wherein the condition is lymphoma, leukemia or multiple myeloma, comprising administering to the subject an effective amount of a compound, wherein the compound is [5-fluoro-3-phenyl-2-[1-(9H-purin-6 -ylamino)-propyl]-3H-quinazolin-4-one]

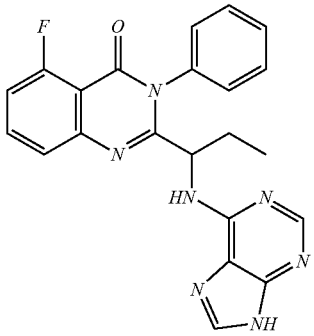

or a pharmaceutically acceptable salt thereof.

5. The method of claim 4, wherein the condition is selected from the group consisting of Burkitt's lymphoma, Hodgkins' lymphoma, non-Hodgkins lymphoma, lymphocytic lymphoma, lymphocytic leukemia, multiple myeloma and chronic myeloid leukemia.

6. The method of claim 4, wherein the compound or the pharmaceutically acceptable salt thereof is the S-enantiomer.

* * * * *